(12) United States Patent
Faustman

(10) Patent No.: US 12,269,891 B2
(45) Date of Patent: Apr. 8, 2025

(54) AGONISTIC ANTI-TUMOR NECROSIS FACTOR RECEPTOR 2 ANTIBODIES

(71) Applicant: The General Hospital Corporation, Boston, MA (US)

(72) Inventor: Denise L. Faustman, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 452 days.

(21) Appl. No.: 17/561,448

(22) Filed: Dec. 23, 2021

(65) Prior Publication Data

US 2022/0112299 A1 Apr. 14, 2022

Related U.S. Application Data

(63) Continuation of application No. 15/755,404, filed as application No. PCT/US2016/049064 on Aug. 26, 2016, now abandoned.

(60) Provisional application No. 62/211,345, filed on Aug. 28, 2015.

(51) Int. Cl.
| | | |
|---|---|---|
| C07K 16/28 | (2006.01) | |
| A61K 38/19 | (2006.01) | |
| A61K 39/395 | (2006.01) | |
| A61P 37/06 | (2006.01) | |
| G01N 33/68 | (2006.01) | |

(52) U.S. Cl.
CPC ........ *C07K 16/2878* (2013.01); *A61K 38/191* (2013.01); *A61K 39/3955* (2013.01); *A61P 37/06* (2018.01); *G01N 33/6854* (2013.01); *C07K 2317/34* (2013.01); *C07K 2317/622* (2013.01); *C07K 2317/75* (2013.01); *C07K 2317/92* (2013.01); *G01N 2333/7151* (2013.01)

(58) Field of Classification Search
None
See application file for complete search history.

(56) References Cited

U.S. PATENT DOCUMENTS

| | | | |
|---|---|---|---|
| 4,309,418 | A | 1/1982 | Green |
| 4,457,916 | A | 7/1984 | Hayashi et al. |
| 4,495,282 | A | 1/1985 | Ohnishi et al. |
| 4,677,063 | A | 6/1987 | Mark et al. |
| 4,677,064 | A | 6/1987 | Mark et al. |
| 4,681,760 | A | 7/1987 | Fathman |
| 4,791,101 | A | 12/1988 | Adolf |
| 4,816,567 | A | 3/1989 | Cabilly et al. |
| 4,879,226 | A | 11/1989 | Wallace et al. |
| 4,963,354 | A | 10/1990 | Shepard et al. |
| 4,985,241 | A | 1/1991 | Zimmerman et al. |
| 5,002,876 | A | 3/1991 | Sreekrishna et al. |
| 5,059,530 | A | 10/1991 | Oshima et al. |
| 5,139,481 | A | 8/1992 | Faustman et al. |
| 5,215,743 | A | 6/1993 | Singh et al. |
| 5,283,058 | A | 2/1994 | Faustman |
| 5,288,852 | A | 2/1994 | Yamada et al. |
| 5,370,870 | A | 12/1994 | Wong |
| 5,487,984 | A | 1/1996 | Allet et al. |
| 5,538,854 | A | 7/1996 | Faustman |
| 5,560,908 | A | 10/1996 | Satoh et al. |
| 5,593,698 | A | 1/1997 | Weiner et al. |
| 5,677,425 | A | 10/1997 | Bodmer et al. |
| 5,783,216 | A | 7/1998 | Faustman |
| 5,821,337 | A | 10/1998 | Carter et al. |
| 5,843,425 | A | 12/1998 | Sachs et al. |
| 5,843,452 | A | 12/1998 | Wiedmann et al. |
| 5,874,306 | A | 2/1999 | Beattie et al. |
| 5,919,452 | A | 7/1999 | Le et al. |
| 5,939,532 | A | 8/1999 | Nakamura et al. |
| 6,046,031 | A | 4/2000 | Ni et al. |
| 6,056,952 | A | 5/2000 | Rosenberg |
| 6,159,461 | A | 12/2000 | Besmer et al. |
| 6,165,737 | A | 12/2000 | Wang et al. |
| 6,177,076 | B1 | 1/2001 | Lattime et al. |
| 6,284,879 | B1 | 9/2001 | Faustman |
| 6,414,218 | B1 | 7/2002 | Faustman et al. |
| 6,420,139 | B1 | 7/2002 | Classen |
| 6,491,908 | B1 | 12/2002 | Rosenberg |
| 6,599,710 | B1 | 7/2003 | Faustman |
| 6,617,171 | B2 | 9/2003 | Faustman et al. |
| 6,660,487 | B2 | 12/2003 | Faustman |
| 6,709,833 | B2 | 3/2004 | Fukui et al. |

(Continued)

FOREIGN PATENT DOCUMENTS

| | | |
|---|---|---|
| CN | 107441491 A | 12/2017 |
| EP | 0612529 A2 | 8/1994 |

(Continued)

OTHER PUBLICATIONS

Hoffmann et al., "Large-scale in vitro expansion of polyclonal human CD4(+)CD25$^{high}$ regulatory T cells," Blood. 104(3):895-903 (2004).

(Continued)

*Primary Examiner* — Ruixiang Li
(74) *Attorney, Agent, or Firm* — Clark & Elbing LLP

(57) ABSTRACT

The invention provides agonistic TNFR2 antibodies and antigen-binding fragments thereof and encompasses the use of these antibodies as therapeutics to promote the proliferation of regulatory T cells (T-reg) for the treatment of immunological diseases. Antibodies of the invention can be used to potentiate the T-reg-mediated deactivation of self- and allergen-reactive T- and B-lymphocytes, and can thus be used to treat a wide variety of indications, including autoimmune diseases, allergic reactions, asthma, graft-versus-host disease, and allograft rejection, among others.

13 Claims, 14 Drawing Sheets

Specification includes a Sequence Listing.

(56) References Cited

U.S. PATENT DOCUMENTS

| | | |
|---|---|---|
| 6,773,705 B1 | 8/2004 | Faustman et al. |
| 6,844,011 B1 | 1/2005 | Faustman |
| 6,866,843 B2 | 3/2005 | Habener et al. |
| 6,923,959 B2 | 8/2005 | Habener et al. |
| 6,984,380 B1 | 1/2006 | Faustman |
| 7,015,037 B1 | 3/2006 | Furcht et al. |
| 7,438,902 B2 | 10/2008 | Habener et al. |
| 7,485,293 B1 | 2/2009 | Faustman |
| 7,510,877 B2 | 3/2009 | Yilmaz et al. |
| 7,537,756 B2 | 5/2009 | Habener et al. |
| 7,582,313 B2 | 9/2009 | Faustman |
| 7,628,988 B2 | 12/2009 | Faustman |
| 8,017,392 B2 | 9/2011 | Faustman |
| 8,021,693 B2 | 9/2011 | Faustman |
| 8,173,129 B2 | 5/2012 | Faustman |
| 8,314,213 B2 | 11/2012 | Bernett et al. |
| 8,697,077 B2 | 4/2014 | Faustman |
| 9,522,181 B2 | 12/2016 | Faustman |
| 9,676,862 B2 | 6/2017 | Ellmark et al. |
| 9,821,010 B2 | 11/2017 | Faustman |
| 10,765,700 B2 | 9/2020 | Faustman |
| 10,906,982 B2 | 2/2021 | Faustman |
| 10,988,543 B2 | 4/2021 | Thompson |
| 11,844,814 B2 | 12/2023 | Faustman |
| 11,859,002 B2 | 1/2024 | Faustman |
| 2002/0106689 A1 | 8/2002 | Faustman et al. |
| 2002/0123472 A1 | 9/2002 | Faustman |
| 2002/0187548 A1 | 12/2002 | Keller et al. |
| 2003/0005469 A1 | 1/2003 | Faustman et al. |
| 2003/0031657 A1 | 2/2003 | Habener et al. |
| 2004/0028658 A1 | 2/2004 | Faustman |
| 2004/0031066 A9 | 2/2004 | Faustman et al. |
| 2004/0229785 A1 | 11/2004 | Faustman |
| 2004/0235160 A1 | 11/2004 | Nishikawa et al. |
| 2005/0043514 A1 | 2/2005 | Fukui et al. |
| 2005/0158288 A1 | 7/2005 | Faustman |
| 2005/0158302 A1 | 7/2005 | Faustman et al. |
| 2005/0181502 A1 | 8/2005 | Furcht et al. |
| 2005/0244386 A1 | 11/2005 | Habener et al. |
| 2006/0062769 A1 | 3/2006 | Habener et al. |
| 2007/0116688 A1 | 5/2007 | Faustman |
| 2008/0102054 A1 | 5/2008 | Faustman |
| 2008/0175830 A1 | 7/2008 | Steinman et al. |
| 2008/0176796 A1 | 7/2008 | Bradley et al. |
| 2009/0028877 A1 | 1/2009 | Iida et al. |
| 2010/0068177 A1 | 3/2010 | Faustman |
| 2010/0298232 A1 | 11/2010 | Liu |
| 2011/0236374 A1 | 9/2011 | Shitara et al. |
| 2012/0045435 A1 | 2/2012 | Deisher |
| 2012/0066777 A1 | 3/2012 | Kawamura et al. |
| 2012/0115739 A1 | 5/2012 | Schmittling et al. |
| 2012/0196919 A1 | 8/2012 | Brown et al. |
| 2013/0064831 A1 | 3/2013 | Humphrey |
| 2014/0096274 A1 | 4/2014 | Quax et al. |
| 2014/0121123 A1 | 5/2014 | Wang et al. |
| 2014/0369973 A1 | 12/2014 | Bernstein et al. |
| 2015/0099707 A1 | 4/2015 | Pastan et al. |
| 2015/0110794 A1 | 4/2015 | Sato et al. |
| 2015/0366909 A1 | 12/2015 | Faustman |
| 2016/0280765 A1 | 9/2016 | Dorvillius et al. |
| 2017/0158771 A1 | 6/2017 | Glennie et al. |
| 2017/0226217 A1 | 8/2017 | Ellmark et al. |
| 2018/0044430 A1 | 2/2018 | Chiu et al. |
| 2019/0135929 A1 | 5/2019 | Faustman |
| 2019/0202925 A1 | 7/2019 | Thompson |
| 2020/0270355 A1 | 8/2020 | Faustman |
| 2021/0301028 A1 | 9/2021 | Thompson |
| 2021/0317221 A1 | 10/2021 | Faustman |
| 2021/0340268 A1 | 11/2021 | Faustman |
| 2022/0002423 A1 | 1/2022 | Faustman |
| 2022/0112299 A1 | 4/2022 | Faustman |
| 2023/0174659 A1 | 6/2023 | Faustman |
| 2023/0295326 A1 | 9/2023 | Faustman |
| 2023/0383003 A1 | 11/2023 | Faustman |

FOREIGN PATENT DOCUMENTS

| | | |
|---|---|---|
| EP | 2295588 A1 | 3/2011 |
| WO | WO-92/04033 A1 | 3/1992 |
| WO | WO-93/02690 A1 | 2/1993 |
| WO | WO-94/09137 A1 | 4/1994 |
| WO | WO-95/24914 A1 | 9/1995 |
| WO | WO-95/25533 A1 | 9/1995 |
| WO | WO-97/08328 A1 | 3/1997 |
| WO | WO-97/13844 A1 | 4/1997 |
| WO | WO-97/21802 A1 | 6/1997 |
| WO | WO-99/53953 A2 | 10/1999 |
| WO | WO-99/59632 A1 | 11/1999 |
| WO | WO-00/53209 A1 | 9/2000 |
| WO | WO-01/44472 A1 | 6/2001 |
| WO | WO-01/91793 A1 | 12/2001 |
| WO | WO-02/26819 A2 | 4/2002 |
| WO | WO-2004/003164 A2 | 1/2004 |
| WO | WO-2004022097 A1 | 3/2004 |
| WO | WO-2005/042727 A2 | 5/2005 |
| WO | WO-2005107802 A2 | 11/2005 |
| WO | WO-2006/038027 A2 | 4/2006 |
| WO | WO-2006/109044 A2 | 10/2006 |
| WO | WO-2006/119107 A2 | 11/2006 |
| WO | WO-2008/157394 A2 | 12/2008 |
| WO | WO-2010/124259 A1 | 10/2010 |
| WO | WO-2011044368 A1 | 4/2011 |
| WO | WO-2011/107989 A1 | 9/2011 |
| WO | WO-2011109789 A2 | 9/2011 |
| WO | WO-2012035141 A1 | 3/2012 |
| WO | WO-2012/122464 A1 | 9/2012 |
| WO | WO-2012/174522 A1 | 12/2012 |
| WO | WO-2013011063 A1 | 1/2013 |
| WO | WO-2014/015101 A1 | 1/2014 |
| WO | WO-2014/124134 A1 | 8/2014 |
| WO | WO-2015/145360 A1 | 10/2015 |
| WO | WO-2016/032547 A1 | 3/2016 |
| WO | WO-2016/187068 A1 | 11/2016 |
| WO | WO-2017/040312 A1 | 3/2017 |
| WO | WO-2017060144 A1 | 4/2017 |
| WO | WO-2017/083525 A1 | 5/2017 |
| WO | WO-2017/197331 A2 | 11/2017 |
| WO | WO-2018/064307 A2 | 4/2018 |
| WO | WO-2018/092907 A1 | 5/2018 |
| WO | WO-2018/115003 A2 | 6/2018 |
| WO | WO-2019/094559 A2 | 5/2019 |
| WO | WO-2020/041361 A1 | 2/2020 |
| WO | WO-2020/193718 A1 | 10/2020 |

OTHER PUBLICATIONS

International Search Report and Written Opinion for International Patent Application No. PCT/US14/15101, mailed Jun. 24, 2014 (14 pages).

EPO Communication Pursuant to Rules 161(2) and 162 EPC for International Application No. PCT/US2014/015101, dated Oct. 15, 2015 (2 pages).

Brod et al., "New clinical trial in newly diagnosed type 1 diabetes," <http://www.diabetesstation.org/articles/brod.htm>, retrieved Jun. 19, 2001 (2 pages).

EPO Communication pursuant to Article 94(3) EPC for European Application No. 00914899.0, dated May 25, 2012 (9 pages).

EPO Invitation pursuant to Article 94(3) and Rule 71(1) EPC for European Application No. 00914899.0, dated Jun. 2, 2014 (4 pages).

EPO Summons to attend oral proceedings pursuant to Rule 115(1) EPC for European Application No. 00914899.0, dated Nov. 12, 2014 (6 pages).

EPO Communication pursuant to Article 94(3) and Rule 71(1) EPC for European Application No. 00914899.0, dated Mar. 6, 2015 (3 pages).

EPO Communication under Rule 71(3) EPC for European Application No. 00914899.0, dated Jun. 23, 2015 (6 pages).

Extended European Search Report for European Application No. 12005556.1, dated Sep. 2, 2014 (8 pages).

(56) References Cited

OTHER PUBLICATIONS

EPO Communication pursuant to Rule 69 EPC for European Application No. 12005556.1, dated Oct. 7, 2014 (2 pages).
EPO Communication pursuant to Article 94(3) EPC for European Application No. 12005556.1, dated Jul. 2, 2015 (7 pages).
EPO Summons to attend oral proceedings pursuant to Rule 115(1) EPC for European Application No. 12005556.1, dated Dec. 18, 2015 (4 pages).
International Search Report for International Application No. PCT/US00/06239, mailed Jul. 31, 2000 (2 pages).
Bleumink et al., "Etanercept-induced subacute cutaneous lupus erythematosus," Rheumatology. 40(11):1317-1319 (2001).
Burnham et al., "Oral BCG vaccine in Crohn's disease," Gut. 20(3):229-233 (1979).
Cairns et al., "New onset systemic lupus erythematosus in a patient receiving etanercept for rheumatoid arthritis," Ann Rheum Dis. 61(11):1031-2 (2002).
Charles et al., "Assessment of antibodies to double-stranded DNA induced in rheumatoid arthritis patients following treatment with infliximab, a monoclonal antibody to tumor necrosis factor alpha: findings in open-label and randomized placebo-controlled trials," Arthritis Rheum. 43(11):2383-90 (2000).
Declaration of Dr. Denise Faustman from U.S. Appl. No. 10/775,487, dated Jun. 14, 2007 (13 pages).
Declaration of Denise Faustman, M.D., Ph.D., from U.S. Appl. No. 10/851,983, dated Jul. 3, 2007 (7 pages).
Engleman et al., "Treatment of NZB/NZW $F_1$ hybrid mice with Mycobacterium bovis strain BCG or type II interferon preparations accelerates autoimmune disease," Arthritis Rheum. 24(11):1396-1402 (1981).
Enayati et al., "Association of anti-tumor necrosis factor therapy with the development of multiple sclerosis," J Clin Gastroenterol. 39(4): 303-6 (2005) (1 page) (Abstract only).
Feldmann et al., "Role of cytokines in rheumatoid arthritis," Annu Rev Immunol. 14:397-440 (1996) (1 page) (Abstract only).
Galaria et al., "Leukocytoclastic vasculitis due to etanercept," J Rheumatol. 27(8):2041-4 (2000) (1 page) (Abstract only).
Jarrett et al., "Anti-tumor necrosis factor-alpha therapy-induced vasculitis: case series," J Rheumatol. 30(10):2287-91 (2003) (1 page) (Abstract only).
Klinkhoff, "Biological agents for rheumatoid arthritis: targeting both physical function and structural damage," Drugs. 64(12):1267-83 (2004) (Abstract only).
Lipsky et al., "Infliximab and methotrexate in the treatment of rheumatoid arthritis," N Engl J Med. 343(22):1594-1602 (2000).
Moreland et al., "Etanercept therapy in rheumatoid arthritis: a randomized, controlled trial," Ann Intern Med. 130(6):478-486 (1999).
Sandborn, "Strategies targeting tumor necrosis factor in Crohn's disease," Acta Gastroenterol Belg. 64(2):170-2 (2001) (1 page) (Abstract only).
Sandborn et al., "Antitumor necrosis factor therapy for inflammatory bowel disease: a review of agents, pharmacology, clinical results, and safety," Inflamm Bowel Dis. 5(2):119-33 (1999) (Abstract only).
Schaible, "Long term safety of infliximab," Can J Gastroenterol. 14(Suppl C):29C-32C (2000) (Abstract only).
Shakoor et al., "Drug-induced systemic lupus erythematosus associated with etanercept therapy," Lancet. 359(9306):579-80 (2002) (Absract only).
Swale et al., "Etanercept-induced systemic lupus erythematosus," Clin Exp Dermatol. 28(6):604-607 (2003).
Thomas et al., "Demyelination during anti-tumor necrosis factor alpha therapy with infliximab for Crohn's disease," Inflamm Bowel Dis. 10(1):28-31 (2004) (Abstract only).
Vermeire et al., "Autoimmunity associated with anti-tumor necrosis factor alpha treatment in Crohn's disease: a prospective cohort study," Gastroenterology. 125(1):32-9 (2003) (1 page) (Abstract only).

Examination Report issued in Australian Patent Application No. 2003247840, dated Jan. 31, 2008 (4 pages).
International Search Report for International Patent Application No. PCT/US03/20578, mailed Apr. 27, 2004 (1 page).
International Search Report for International Patent Application No. PCT/US03/36531, mailed Jul. 14, 2004 (1 page).
Examiner's Report for Canadian Patent Application No. 2,543,745, dated Jul. 15, 2011 (4 pages).
EPO Communication Enclosing Supplementary European Search Report for EP Application No. 03762242.0, dated Jun. 8, 2009 (8 pages).
EPO Communication Pursuant to Article 94(3) EPC issued in European Patent Application No. 03762242.0, dated Oct. 30, 2009 (2 pages).
EPO Communication Pursuant to Article 94(3) EPC issued in European Patent Application No. 03762242.0, dated Dec. 1, 2011 (4 pages).
EPO Communication Pursuant to Article 94(3) EPC issued in European Patent Application No. 04817543.4, dated Jan. 22, 2010 (5 pages).
Extended European Search Report for European Patent Application No. 11008889.5, dated Apr. 12, 2012 (10 pages).
Faustman et al., "Stem cells in the spleen: Therapeutic potential for Sjogren's syndrome, type I diabetes, and other disorders," available in PMC Jul. 21, 2014, published in final edited form as: Int J Biochem Cell Biol. 42(10):1576-9 (2010) (8 pages).
EPO Communication Pursuant to Article 94(3) EPC issued in European Patent Application No. 11008889.5, dated Mar. 4, 2013 (4 pages).
EPO Communication Pursuant to Article 94(3) EPC for European Patent Application No. 11008889.5, dated Mar. 19, 2014 (4 pages).
EPO Communication Pursuant to Article 94(3) EPC for European Patent Application No. 11008889.5, dated Oct. 27, 2014 (5 pages).
Extended European Search Report for European Application No. 14189654.8, dated Feb. 16, 2015 (7 pages).
Bercovici et al., "Systemic administration of agonist peptide blocks the progression of spontaneous CD8-mediated autoimmune diabetes in transgenic mice without bystander damage," J Immunol. 165(1):202-10 (2000) (10 pages).
Faustman et al., "TNF receptor 2 pathway: drug target for autoimmune diseases," Nat Rev Drug Discov. 9(6):482-93 (2010).
Watt et al., "Specific alternative HOX11 transcripts are expressed in paediatric neural tumours and T-cell acute lymphoblastic leukaemia," Gene. 323:89-99 (2003) (1 page) (Abstract only).
Wilson et al., "Bone-marrow haematopoietic-stem-cell niches," Nat Rev Immunol. 6(2):93-106 (2006).
International Preliminary Report on Patentability for International Application No. PCT/US2014/015101, issued Aug. 11, 2015 (9 pages).
Technical Data Sheet for Purified Rat Anti-Human CD120b, BD Pharmingen™ (2011) (2 pages).
Extended European Search Report for European Application No. 14748807.6, dated Jul. 15, 2016 (10 pages).
Communication pursuant to Rules 70(2) and 70a(2) EPC for European Application No. 14748807.6, dated Aug. 2, 2016 (1 page).
Chopra et al., "Exogenous TNFR2 activation protects from acute GvHD via host T reg cell expansion," J Exp Med. 213(9):1881-1900 (Aug. 2016) (21 pages).
Product Data Sheet for TNF RII/TNFRSF1B Inhibition of TNP-alpha-induced Cyotoxicity and Neutralization by Human TNF RII/TNFRSF1B Antibody. Retrieved Aug. 1, 2017. R&D Systems Inc. (3 pages).
Pillay et al., "Antibodies in oncology," N Biotechnol. 28(5):518-529 (2011).
International Search Report and Written Opinion for International Application No. PCT/US17/32513, mailed Oct. 25, 2017 (17 pages).
Kretschmer et al., "Strong antigenic selection shaping the immunoglobulin heavy chain repertoire of B-1a lymphocytes in lambda 2(315) transgenic mice," Eur J Immunol. 32(8):2317-27 (2002).
Sedger et al., "Poxvirus tumor necrosis factor receptor (TNFR)-like T2 proteins contain a conserved preligand assembly domain that inhibits cellular TNFR1-induced cell death," J Virol. 80(18):9300-9 (2006).

(56) References Cited

OTHER PUBLICATIONS

Wagner, "Making and using antibodies," <http://www-users.med.cornell.edu/~jawagne/Antibody_Approaches.html>, accessed Aug. 8, 2016 (7 pages).
Diaw et al., "Structural and affinity studies of IgM polyreactive natural autoantibodies," J Immunol. 158(2):968-76 (1997).
Trad et al., "Clonal Progression during the T Cell-Dependent B Cell Antibody Response Depends on the Immunoglobulin DH Gene Segment Repertoire," Front Immunol. 5(385):1-11 (Aug. 2014).
International Search Report and Written Opinion for International Application No. PCT/US16/32547, mailed Aug. 31, 2016 (24 pages).
Yu et al., "Complex Interplay between Epitope Specificity and Isotype Dictates the Biological Activity of Antihuman CD40 Antibodies," Cancer Cell. 33(4):1-12 (Apr. 2018) (17 pages).
International Preliminary Report on Patentability for International Application No. PCT/US2016/032547, issued Nov. 21, 2017 (16 pages).
International Preliminary Report on Patentability for International Application No. PCT/US2017/032513, mailed Nov. 22, 2018 (8 pages).
Chen et al., "The phenotypic and functional consequences of tumour necrosis factor receptor type 2 expression on CD4(+) FoxP3(+) regulatory T cells," Immunology. 133(4):426-33 (2011).
Ji et al., "Cutting Edge: The Natural Ligand for Glucocorticoid-Induced TNF Receptor-Related Protein Abrogates Regulatory T Cell Suppression," J Immunol. 172(10):5823-7 (2004).
Office Action for Japanese Application No. 2018-127922, mailed May 14, 2019 (5 pgs).
Extended European Search Report for European Application No. 18199457.5, dated May 2, 2019 (7 pages).
Santee et al., "Human tumor necrosis factor receptor p75/80 (CD120b) gene structure and promoter characterization," J Biol Chem. 271(35):21151-9 (1996).
International Search Report and Written Opinion for International Application No. PCT/US18/59779, mailed Apr. 18, 2019 (19 pages).
MacCallum et al., "Antibody-antigen interactions: contact analysis and binding site topography," J Mol Biol. 262(5):732-45 (1996) (14 pages).
Ban et al., "Strategic Internal Covalent Cross-Linking of TNF Produces a Stable TNF Trimer With Improved TNFR2 Signaling," Mol Cell Ther. 3:7 (Aug. 2015) (6 pages).
Torrey et al., "Targeting TNFR2 With Antagonistic Antibodies Inhibits Proliferation of Ovarian Cancer Cells and Tumor-Associated $T_{regs}$," Sci Signal. 10(462):eaaf8608 (2017) (13 pages).
Lamminmäki et al., "Crystal Structure of a Recombinant Anti-Estradiol Fab Fragment in Complex With 17beta-Estradiol," J Biol Chem. 276(39):36687-94 (2001).
Chen et al., "Enhancement and destruction of antibody function by somatic mutation: unequal occurrence is controlled by V gene combinatorial associations," EMBO J. 14(12):2784-94 (1995).
Rudinger, "Characteristics of the amino acids as components of a peptide hormone sequence," in Peptide Hormones, Parsons, ed., University Park Press, Jun. 1976, pp. 1-7.
Extended European Search Report for European Application No. 17796980.5, dated Mar. 5, 2020 (12 pages).
International Preliminary Report on Patentability for International Application No. PCT/US2018/059779, mailed May 22, 2020 (11 pages).
International Search Report and Written Opinion for International Application No. PCT/US2019/047330, mailed Nov. 20, 2019 (15 pages).
International Preliminary Report on Patentability for International Application No. PCT/US2019/047330, issued Feb. 23, 2021 (7 pages).
Yan et al., "Construction of a synthetic phage-displayed Nanobody library with CDR3 regions randomized by trinucleotide cassettes for diagnostic applications," J Transl Med. 12:343 (Dec. 2014) (12 pages).
Williams et al., "Phenotypic screening reveals TNFR2 as a promising target for cancer immunotherapy," Oncotarget. 7(42):68278-68291 (Sep. 2016).
Extended European Search Report for European Application No. 18875602.7, dated Jul. 19, 2021 (12 pages).
International Search Report and Written Opinion for PCT/US2021/032540, mailed Oct. 29, 2021 (15 pages).
Chopra et al., "Tumor necrosis factor receptor 2-dependent homeostasis of regulatory T cells as a player in TNF-induced experimental metastasis," Carcinogenesis. 34(6):1296-303 (Feb. 2013).
Office Action for Japanese Patent Application No. 2020-204143, mailed Dec. 16, 2021 (6 pages).
Extended European Search Report for European Patent Application No. 21175520.2, dated Dec. 10, 2021 (7 pages).
Office Action for Korean Application No. 10-2018-7036235, dated Nov. 29, 2021 (11 pages).
Office Action for Chinese Patent Application No. 201780043276.X, issued Dec. 2, 2021 (17 pages).
Fischer et al., "Selective Targeting of TNF Receptors as a Novel Therapeutic Approach," Front Cell Dev Biol. 8:401 (May 2020) (21 pages).
"Potential New Cancer Therapy Could Target Tumors Two Ways," National Cancer Institute, <https://www.cancer.gov/news-events/cancer-currents-blog/2017/tnfr2-target-tumors>, dated Feb. 15, 2017, retrieved on Mar. 14, 2022 (6 pages).
Stevens et al., "Overcoming the challenges of topical antibody administration for improving healing outcomes: a review of recent laboratory and clinical approaches," Wound Practice Res. 25(4):188-94 (Dec. 2017).
Yang et al., "Optimizing TNFR2 antagonism for immunotherapy with tumor microenvironment specificity," J Leukoc Biol. 107(6):971-980 (Mar. 2020).
Extended European Search Report for European Patent Application No. 19852179.1, dated May 6, 2022 (9 pages).
Morris et al., "Selective Blockade of TNFR1 Improves Clinical Disease and Bronchoconstriction in Experimental RSV Infection," Viruses. 12(10):1176 (Oct. 17, 2020) (20 pages).
Yang et al., "Role of TNF-TNF Receptor 2 Signal in Regulatory T Cells and Its Therapeutic Implications," Front Immunol. 9:784 (Apr. 19, 2018) (11 pages).
Barnes et al., "Susceptibility to Burkholderia pseudomallei is associated with host immune responses involving tumor necrosis factor receptor-1 (TNFR1) and TNF receptor-2 (TNFR2)," FEMS Immunol Med Microbiol. 52(3):379-88 (Feb. 22, 2008).
Liang et al., "Distinct Role of TNFR1 and TNFR2 in Protective Immunity Against Orientia tsutsugamushi Infection in Mice," Front Immunol. 13:867924 (Apr. 11, 2022) (17 pages).
Extended European Search Report for European Application No. 19885048.9, dated Nov. 30, 2022 (12 pages).
English Translation of Office Action for Japanese Patent Application No. 2021-526263, mailed Oct. 31, 2023 (3 pages).
English Translation of Office Action for Chinese Patent Application No. 201980089022.0, mailed Oct. 22, 2023 (9 pages).
Extended European Search Report for European Application No. 21803059.1, dated Apr. 30, 2024 (10 pages).
Lightle et al., "Mutations within a human IgG2 antibody form distinct and homogeneous disulfide isomers but do not affect Fc gamma receptor or C1q binding," Protein Science. 19:753-762 (Jan. 2010).
Al-Awqati et al., "Stem cells in the kidney," Kidney Int. 61(2):387-95 (2002).
Aldrich et al., "Positive selection of self- and alloreactive CD8+ T cells in Tap-1 mutant mice," Proc Natl Acad Sci USA. 91(14):6525-8 (1994).
Alison et al., "Hepatocytes from non-hepatic adult stem cells," Nature. 406(6793):257 (2000).
Allen et al., "Effect of bacillus Calmette-Guerin vaccination on new-onset type 1 diabetes," Diabetes Care. 22(10):1703-7 (1999).
Almoallim et al., "Anti-tumor necrosis factor-alpha induced systemic lupus erythematosus," Open Rheumatol J. 6:315-9 (2012).
Altomonte et al., "Serum levels of interleukin-1b, tumour necrosis factor-a and interleukin-2 in rheumatoid arthritis. Correlation with disease activity," Clin Rheumatol. 11(2):202-205 (1992).

(56) References Cited

OTHER PUBLICATIONS

Anderson et al., "Can stem cells cross lineage boundaries?," Nat Med. 7(4):393-5 (2001).
Anderson et al., "Studies on the cytophilic properties of human beta2 microglobulin," J Immunol. 114(3):997-1000 (1975).
Anderson et al., "The NOD mouse: a model of immune dysregulation," Annu Rev Immunol. 23:447-485 (2005).
Aranda et al., "Analysis of intestinal lymphocytes in mouse colitis mediated by transfer of CD4+, CD45RB$^{high}$ T Cells to SCID recipients," J Immunol. 158(7):3464-3473 (1997).
Aristarkhov et al., "E2-C, a cyclin-selective ubiquitin carrier protein required for the destruction of mitotic cyclins," Proc Natl Acad Sci USA. 93(9):4294-9 (1996).
Ashton-Rickardt et al., "Evidence for a differential avidity model of T cell selection in the thymus," Cell. 76(4):651-63 (1994).
Ashton-Rickardt et al., "Peptide contributes to the specificity of positive selection of CD8+ T Cells in the thymus," Cell. 73(5):1041-9 (1993).
Atkinson et al., "The NOD mouse model of type 1 diabetes: As good as it gets?," Nat Med. 5(6):601-4 (1999).
Baeuerle et al., "NF-kappaB: Ten years after," Cell. 87(1):13-20 (1996).
Baeza et al., "Pancreatic regenerating gene overexpression in the nonobese diabetic mouse during active diabetogenesis," Diabetes. 45(1):67-70 (1996) (5 pages).
Baeza et al., "Reg protein: a potential beta-cell-specific growth factor?," Diabetes Metab. 22(4):229-34 (1996).
Baeza et al., "Specific reg II gene overexpression in the non-obese diabetic mouse pancreas during active diabetogenesis," FEBS Letters. 416(3):364-8 (1997).
Baik et al., "BCG vaccine prevents insulitis in low dose streptozotocin-induced diabetic mice," Diabetes Res Clin Pract. 46(2):91-97 (1999).
Baldwin, "The NF-kappaB and IkappaB proteins: new discoveries and insights," Ann Rev Immunol. 14:649-683 (1996).
Ban et al., "Selective death of autoreactive T Cells in human diabetes by TNF or TNF receptor 2 agonism," Proc Natl Acad Sci USA. 105(36):13644-13649 (2008).
Barres, "A new role for glia: generation of neurons!," Cell. 97(6):667-70 (1999).
Baxter et al., "Mycobacteria precipitate an SLE-like syndrome in diabetes-prone NOD mice," Immunology. 83(2):227-231 (1994).
Beers et al., Disorders of Carbohydrate Metabolism: Diabetes Mellitus. *The Merck Manual of Diagnosis and Therapy*, 17th Ed. Merck Research Laboratories, 165-171 (1999) (5 pages).
Beg et al., "An essential role for NF-kappaB in preventing TNF-alpha-induced cell death," Science. 274(5288):782-784 (1996).
Beilhack et al., "A Selective TNFR2 Agonist Expands Host Treg Cells in Vivo to Protect from Acute Graft-Versus-Host Disease," Blood. 124(21): 1099 (2014) (Abstract only) (5 pages).
Bendelac et al., "Syngeneic transfer of autoimmune diabetes from diabetic NOD mice to healthy neonates. Requirement for both L3T4+ and Lyt-2+ T Cells," J Exp Med. 166(4):823-832 (1987).
Benkler et al., "Parkinson's disease, autoimmunity, and olfaction," Int J Neurosci. 119(12):2133-43 (2009) (Abstract only) (1 page).
Bernabeu et al., "Beta2-microglobulin from serum associates with MHC class I antigens on the surface of cultured cells," Nature. 308:642-645 (1984) (Abstract only) (2 pages).
Bill et al., "Use of soluble MHC class II/peptide multimers to detect antigen-specific T cells in human disease," Arthritis Res. 4:261-265 (2002).
Bjornson et al., "Turning brain into blood: A hematopoietic fate adopted by adult neural stem cells in vivo," Science. 283(5401):534-537 (1999).
Blüml et al., "Antiinflammatory effects of tumor necrosis factor on hematopoietic cells in a murine model of erosive arthritis," Arthritis Rheum. 62(6):1608-19 (2010).
Boches et al., "Role for the adenosine triphosphate-dependent proteolytic pathway in reticulocyte maturation," Science. 215(4535):978-980 (1982).
Brayer et al., "Alleles from chromosomes 1 and 3 of NOD mice combine to influence Sjögren's syndrome-like autoimmune exocrinopathy," J. Rheumatol. 27(8):1896-1904 (2000).
Brazelton et al., "From marrow to brain: expression of neuronal phenotypes in adult mice," Science. 290:1775-1779 (2000).
Brod et al., "Ingested interferon alpha suppresses Type I diabetes in non-obese diabetic mice," Diabetologia. 41(10):1227-1232 (1998).
Brodbeck et al., "Genetic determination of nephrogenesis: the Pax/Eya/Six gene network," Pediatr Nephrol. 19(3):249-255 (2004) (1 page) (Abstract Only).
Brás et al., "Diabetes-prone NOD mice are resistant to *Mycobacterium avium* and the infection prevents autoimmune disease," Immunology. 89:20-25 (1996).
Bunting et al., "Enforced P-glycoprotein pump function in murine bone marrow cells results in expansion of side population stem cells in vitro and repopulating cells in vivo," Blood. 96(3):902-909 (2000).
Caetano et al., "Effect of methotrexate (MTX) on NAD(P)+ dehydrogenases of HeLa cells: malic enzyme, 2-oxoglutarate and isocitrate dehydrogenases," Cell Biochem Funct. 15(4):259-264 (1997).
Cavallo et al., "BCG vaccine with and without nicotinamide in recent onset IDDM: a multicenter randomized trial," Second Congress of the Immunology of Diabetes Society, Canberra, Australia, Dec. 8-11, 1996. Autoimmunity. 24(Suppl. 1):18 (1996).
Cebrián et al., "MHC-I expression renders catecholaminergic neurons susceptible to T-cell-mediated degeneration," Nat Commun. 5:3633 (2014) (Abstract only) (1 page).
Chatenoud et al., "CD3 antibody-induced dominant self tolerance in overtly diabetic NOD mice," J Immunol. 158(6):2947-2954 (1997).
Chen et al., "Contrasting effects of TNF and anti-TNF on the activation of effector T cells and regulatory T cells in autoimmunity," available in PMC Dec. 1, 2012, published in final edited form as: FEBS Lett. 585(23):3611-8 (2011) (16 pages).
Chen et al., "Therapy: Paradoxical effects of targeting TNF signalling in the treatment of autoimmunity," Nat Rev Rheumatol. 12(11):625-6 (2016).
Choi et al., "Prevention of encephalomyocarditis virus-induced diabetes by live recombinant *Mycobacterium bovis* bacillus Calmette-Guérin in susceptible mice," Diabetes. 49 (9):1459-1467 (2000).
Christen et al., "A dual role for TNF-alpha in type 1 diabetes: islet-specific expression abrogates the ongoing autoimmune process when induced late but not early during pathogenesis," J Immunol. 166(12):7023-32 (2001).
Cole et al., "Two ParaHox genes, *SpLox* and *SpCdx*, interact to partition the posterior endoderm in the formation of a functional gut," Development. 136(4):541-549 (2009).
Colucci et al., "Programmed cell death in the pathogenesis of murine IDDM: resistance to apoptosis induced in lymphocytes by cyclophosphamide," J Autoimmunity. 9:271-276 (1996).
Communication pursuant to Article 94(3) EPC for European Patent Application No. 14189654.8, dated Oct. 19, 2016 (5 pages).
Corbett et al., "Nitric oxide mediates cytokine-induced inhibition of insulin secretion by human islets of Langerhans," Proc Natl Acad Sci USA. 90(5):1731-1735 (1993).
Coux et al., "Enzymes catalyzing ubiquitination and proteolytic processing of the p105 precursor of nuclear factor kappaB1," J Biol Chem. 273(15):8820-8828 (1998).
Couzin, "Diabetes studies conflict on power of spleen cells," Science. 311:1694 (2006).
Creasey et al., "Biological effects of recombinant human tumor necrosis factor and its novel muteins on tumor and normal cell lines," Cancer Res. 47(1):145-9 (1987).
D'Andrea, "Add Alzheimer's disease to the list of autoimmune diseases," Med Hypotheses. 64(3):458-63 (2005) (Abstract only) (2 pages).
Darzynkiewicz et al., "Use of flow and laser scanning cytometry to study mechanisms regulating cell cycle and controlling cell death," Clinics in Laboratory Medicine. 21(4):857-873 (2001).
Dear et al., "The *Hox11* gene is essential for cell survival during spleen development," Development. 121(9):2909-2915 (1995).
Declaration of Dr. Denise Faustman under 37 C.F.R. § 1.132 regarding U.S. Appl. No. 10/358,664, dated May 13, 2009 (4 pages).

(56) References Cited

OTHER PUBLICATIONS

Dieguez-Acuna et al., "Characterization of mouse spleen cells by subtractive proteomics," Mol Cell Proteomics. 4(10):1459-1470 (2005).
Dieguez-Acuna et al., "Proteomics identifies multipotent and low oncogenic risk stem cells of the spleen," Int J Biochem Cell Biol. 42(10):1651-60 (2010) (10 pages).
Dilts et al., "Autoimmune diabetes: The involvement of benign and malignant autoimmunity," J Autoimmun. 12:229-232 (1999).
Dinarello, "Interleukin-1, Interleukin-1 receptors and Interleukin-1 receptor antagonist," Intern Rev Immunol. 16:457-499 (1998).
Dong et al., "Essential protective role of tumor necrosis factor receptor 2 in neurodegeneration," Proc Natl Acad Sci USA. 113(43):12304-9 (2016).
Driscoll et al., "The proteasome (multicatalytic protease) is a component of the 1500-kDa proteolytic complex which degrades ubiquitin-conjugated proteins," J Biol Chem. 265(9):4789-4792 (1990).
Durand et al., "Mesenchymal lineage potentials of aorta-gonad-mesonephros stromal clones," Haematologica. 91(9):1172-1179 (2006).
Eglitis et al., "Hematopoietic cells differentiate into both microglia and macroglia in the brains of adult mice," Proc Natl Acad Sci USA. 94:4080-4085 (1997).
Elliott et al., "Effect of bacille Calmette-Guerin vaccination on C-peptide secretion in children newly diagnosed with IDDM," Diabetes Care. 21(10):1691-1693 (1998).
Extended European Search Report for European Patent Application No. 16842699.7, dated May 10, 2019 (10 pages).
Eytan et al., "ATP-dependent incorporation of 20S protease into the 26S complex that degrades proteins conjugated to ubiquitin," Proc Natl Acad Sci USA. 86:7751-7755 (1989).
Fan et al., "Generation of p50 subunit of NF-kappaB by processing of p105 through an ATP-dependent pathway," Nature. 354:395-398 (1991).
Faustman et al., "Abnormal T-lymphocyte subsets in Type I Diabetes," Diabetes. 38:1462-1468 (1989).
Faustman et al., "Linkage of faulty major histocompatibility complex class I to autoimmune diabetes," Science. 254:1756-1761 (1991).
Faustman et al., "Murine pancreatic beta-Cells express H-2K and H-2D but not Ia antigens," J Exp Med. 151(6):1563-1568 (1980).
Faustman et al., "Prevention of xenograft rejection by masking donor HLA class I antigens," Science. 252:1700-1702 (1991).
Faustman et al., "T-lymphocyte changes linked to autoantibodies. Association of insulin autoantibodies with CD4+CD45R+ lymphocyte subpopulation in prediabetic subjects," Diabetes. 40(5):590-597 (1991).
Faustman et al., "TNF Receptor 2 and Disease: Autoimmunity and Regenerative Medicine," Front Immunol. 4:478 (2013) (8 pages).
Feldman et al., "Anti-TNFalpha therapy is useful in rheumatoid arthritis and Crohn's disease: Analysis of the mechanism of action predicts utility in other diseases," Transplant Proc. 30(8):4126-4127 (1998).
Ferrando et al., "Adult T-Cell ALL patients whose lymphoblasts express the HOX11 oncogene have an excellent prognosis when treated with chemotherapy and are not candidates for allogeneic bone marrow transplantation in first remission," Blood. 11: Abstract 578 (2002) (1 page).
Fischer et al., "A TNF receptor 2 selective agonist rescues human neurons from oxidative stress-induced cell death," PloS One. 6(11):e27621 (2011) (11 pages).
Fischer et al., "An improved flow cytometric assay for the determination of cytotoxic T lymphocyte activity," J Immunol Methods. 259:159-169 (2002).
Foulis, "C.L. Oakley lecture (1987). The pathogenesis of beta cell destruction in Type I (insulin-dependent) diabetes mellitus," J Pathol. 152(3):141-148 (1987).
Fu et al., "Antigen processing and autoimmunity: Evaluation of mRNA abundance and function of HLA-Linked genes," Ann NY Acad Sci. 842:138-155 (1998).

Fu et al., "Defective major histocompatibility complex class I expression on lymphoid cells in autoimmunity," J Clin Invest. 91:2301-2307 (1993).
Fukada et al., "Two signals are necessary for cell proliferation induced by a cytokine receptor gp130: Involvement of STAT3 in anti-apoptosis," Immunity. 5:449-460 (1996).
Gage et al., "Multipotent progenitor cells in the adult dentate gyrus," J Neurobiol. 36:249-266 (1998).
Gage, "Mammalian neural stem cells," Science. 287(5457):1433-1438 (2000).
Ganoth et al., "A multicomponent system that degrades proteins conjugated to ubiquitin. Resolution of factors and evidence for ATP-dependent complex formation," J Biol Chem. 263(25):12412-12419 (1988).
Gaur et al., "Induction of islet allotolerance in nonhuman primates," Ann NY Acad Sci. 958:199-203 (2002).
Gazda et al., "Diabetes results from a late change in the autoimmune response of NOD mice," J Autoimmun. 10(3):261-270 (1997).
Gazda et al., "Regulation of autoimmune diabetes: characteristics of non-islet-antigen specific therapies," Immunol Cell Biol. 74: 401-407 (1996).
Genestier et al., "Immunosuppressive properties of methotrexate: Apoptosis and clonal deletion of activated peripheral T Cells," J Clin Invest. 102(2):322-328 (1998).
Gerich et al., "Advances in diabetes for the millennium: Understanding insulin resistance," MedGenMed. 6(3 Suppl.):11 (2004) (9 pages).
Ghosh et al., "Activation in vitro of NF-kappaB by phosphorylation of its inhibitor IkappaB," Nature. 344(6267):678-682 (1990).
Glas et al., "The CD8+ T Cell repertoire in beta2-microglobulin-deficient mice is biased towards reactivity against self-major histocompatibility class I," J Exp Med. 179(2):661-672 (1994).
Goldberg, "Functions of the proteasome: The lysis at the end of the tunnel," Science. 268:522-523 (1995).
Goldberg, "The mechanism and functions of ATP-dependent proteases in bacterial and animal cells," Eur J Biochem. 203:9-23 (1992).
Gottlieb et al., "Cell acidification in apoptosis: Granulocyte colony-stimulating factor delays programmed cell death in neutrophils by up-regulating the vacuolar H+-ATPase," Proc Natl Acad Sci USA. 92(13):5965-5968 (1995).
Graves et al., "Lack of association between early childhood immunizations and beta-cell autoimmunity," Diabetes Care. 22:1694-7 (1999).
Grewal et al., "Local expression of transgene encoded TNFalpha in islets prevents autoimmune diabetes in nonobese diabetic (NOD) mice by preventing the development of auto-reactive islet-specific T Cells," J Exp Med. 184:1963-1974 (1996).
Grilli et al., "Neuroprotection by aspirin and sodium salicylate through blockade of NF-kappaB activation," Science. 274:1383-1385 (1996).
Gronostajski et al., "The ATP dependence of the degradation of short- and long-lived proteins in growing fibroblasts," J Biol Chem. 260(6):3344-3349 (1985).
Gueckel et al., "Mutations in the yeast proteasome beta-Type subunit Pre3 uncover position-dependent effects on proteasomal peptidase activity and in vivo function," J Biol Chem. 273(31):19443-19452 (1998).
Gupta, "Molecular steps of tumor necrosis factor receptor-mediated apoptosis," Curr Mol Med. 1(3):317-324 (2001).
Haas et al., "Pathways of ubiquitin conjugation," FASEB J. 11:1257-1268 (1997).
Hao et al., "Effect of mycophenolate mofetil on islet allografting to chemically induced or spontaneously diabetic animals," Transplant Proc. 24(6):2843-2844 (1992).
Harada et al., "Prevention of overt diabetes and insulitis in NOD mice by a single BCG vaccination," Diabetes Res Clin Pract. 8:85-89 (1990).
Hartwell et al., "Aberrant cytokine regulation in macrophages from young autoimmune-prone mice: Evidence that the intrinsic defect in MRL macrophage IL-1 expression is transcriptionally controlled," Mol Immunol. 32(10):743-751 (1995).

(56) References Cited

OTHER PUBLICATIONS

Hayashi et al., "Essential role of human leukocyte antigen-encoded proteasome subunits in NF-kappaB activation and prevention of tumor necrosis factor-alpha-induced apoptosis," J Biol Chem. 275(7):5238-5247 (2000).
Hayashi et al., "NOD mice are defective in proteasome production and activation of NF-kappaB," Mol Cell Biol. 19(12):8646-8659 (1999).
Hershko et al., "The ubiquitin system for protein degradation," Annu Rev Biochem. 61: 761-807 (1992).
Hester et al., "Studies on the cytophilic properties of human beta2-microglobulin. II. The role of histocompatibility antigens," Scand J Immunol. 9(2):125-134 (1979).
Horsfall et al., "Characterization and specificity of B-cell responses in lupus induced by Mycobacterium bovis in NOD/Lt mice," Immunology. 95(1):8-17 (1998).
Horwitz et al., "Recombinant bacillus Calmette-Guérin (BCG) vaccines expressing the *Mycobacterium tuberculosis* 30-kDa major secretory protein induce greater protective immunity against tuberculosis than conventional BCG vaccines in a highly susceptible animal model," Proc Natl Acad Sci USA. 97(25):13853-13858 (2000).
Hostikka et al., "The mouse Hoxc11 gene: genomic structure and expression pattern," Mech Dev. 70(1-2):133-145 (1998) (Abstract Only).
Hsu et al., "TRADD-TRAF2 and TRADD-FADD interactions define two distinct TNF receptor 1 signal transduction pathways," Cell. 84:299-308 (1996).
Humphreys-Beher et al., "New concepts for the development of autoimmune exocrinopathy derived from studies with the NOD mouse model," Arch Oral Biol. 44(Suppl 1):S21-S25 (1999) (Abstract Only) (2 pages).
Hyafil et al., "Dissociation and exchange of the beta2-microglobulin subunit of HLA-A and HLA-B antigens," Proc Natl Acad Sci USA. 76(11):5834-5838 (1979).
Hycult Biotech, "Certificate of Analysis—Technical Data Sheet," dated Mar. 19, 2018 (2 pages).
Hycult Biotech, "Product Brochure," 2009 (36 pages).
Hymowitz et al., "Toward small-molecule agonists of TNF receptors," Nat Chem Biol. 1(7):353-354 (2005).
International Preliminary Report on Patentability for International Patent Application No. PCT/US2015/030282, mailed Nov. 24, 2016 (12 pages).
International Preliminary Report on Patentability for International Application No. PCT/US2019/061828, mailed May 27, 2021 (12 pages).
International Search Report and Written Opinion for International Application No. PCT/US16/49064, mailed Jan. 5, 2017 (19 pages).
International Search Report and Written Opinion for International Application No. PCT/US19/61828, mailed Mar. 30, 2020 (17 pages).
International Search Report and Written Opinion for International Application No. PCT/US2015/030282, mailed Aug. 17, 2015 (18 pages).
International Search Report for International Application No. PCT/US2004/037998, mailed Feb. 28, 2008 (2 pages).
Jackson et al., "Hematopoietic potential of stem cells isolated from murine skeletal muscle," Proc Natl Acad Sci USA. 96(25):14482-14486 (1999).
Jacob et al., "Monoclonal anti-tumor necrosis factor antibody renders non-obese diabetic mice hypersensitive to irradiation and enhances insulitis development," Int Immunol. 4(5):611-614 (1992).
Jacob et al., "Prevention of diabetes in nonobese diabetic mice by tumor necrosis factor (TNF): Similarities between TNF-alpha and interleukin 1," Proc Natl Acad Sci USA. 87:968-972 (1990).
Jacob et al., "Tumour necrosis factor-alpha in murine autoimmune 'lupus' nephritis," Nature. 331:356-358 (1988).
Jakubowski et al., "Phase I trial of intramuscularly administered tumor necrosis factor in patients with advanced cancer," J Clin Oncol. 7(3):298-303 (1989).
Jiang et al., "Pluripotency of mesenchymal stem cells derived from adult marrow," Nature. 418:41-49 (2002).
Johansson et al., "Identification of a neural stem cell in the adult mammalian central nervous system," Cell. 96:25-34 (1999).
Juang et al., "Beneficial influence of glycemic control upon the growth and function of transplanted islets," Diabetes. 43:1334-1339 (1994).
Kaijzel et al., "Functional analysis of a human tumor necrosis factor alpha (TNF-alpha) promoter polymorphism related to joint damage in rheumatoid arthritis," Mol Med. 4:724-733 (1998).
Kanzler et al., "Hox11 acts cell autonomously in spleen development and its absence results in altered cell fate of mesenchymal spleen precursors," Devel Biol. 234:231-243 (2001).
Kaufman et al., "Patterns of hemopoietic reconstitution in nonobese diabetic mice: dichotomy of allogeneic resistance versus competitive advantage of disease-resistant marrow," J Immunol. 158(5):2435-2442 (1997).
Kawasaki et al., "Prevention of type 1 diabetes: from the view point of beta cell damage," Diabetes Res Clin Pract. 66:S27-S32 (2004).
Khalili et al., "Bone marrow cells are a source of undifferentiated cells to prevent Sjögren's syndrome and to preserve salivary glands function in the non-obese diabetic mice," available in PMC Jun. 13, 2013, published in final edited form as: Int J Biochem Cell Biol. 42(11):1893-9 (2010) (18 pages).
Khalili et al., "Mesenchymal stromal cells improve salivary function and reduce lymphocytic infiltrates in mice with Sjögren's-like disease," PLoS One. 7(6):e38615 (2012) (11 pages).
Khalili et al., "Treatment for salivary gland hypofunction at both initial and advanced stages of Sjögren-like disease: a comparative study of bone marrow therapy versus spleen cell therapy with a 1-year monitoring period," Cytotherapy. 16(3):412-23 (2014).
Kieran et al., "The DNA binding subunit of NF-kappaB is identical to factor KBF1 and homologous to the *rel* oncogene product," Cell. 62:1007-18 (1990).
Kim, "Regulation of Immune Cell Functions by Metabolic Reprogramming," J Immunol Res. 2018:8605471 (2018) (13 pages).
Klingensmith et al., "Vaccination with BCG at diagnosis does not alter the course of IDDM," Diabetes 57th Annual Meeting and Scientific Sessions, June 21-24, Boston MA. 40(Suppl 1):193A, 0744 (1997) (3 pages) (Abstract Only).
Koarada et al., "B Cells lacking RP105, a novel B cell antigen, in systemic lupus erythematosus," Arthritis & Rheumatism. 42(12):2593-600 (1999).
Kodama et al., "Islet regeneration during the reversal of autoimmune diabetes in NOD mice," Science. 302:1223-1227 (2003).
Kodama et al., "Regenerative medicine: A radical reappraisal of the spleen," Trends Mol Med. 11(6):271-276 (2005).
Kodama et al., "The therapeutic potential of tumor necrosis factor for autoimmune disease: A mechanistically based hypothesis," Cell Mol Life Sci. 62:1850-1862 (2005).
Kopp et al., "Inhibition of NF-kappaB by sodium salicylate and aspirin," Science. 265(5174):956-959 (1994).
Kouskoff et al., "Organ-specific disease provoked by systemic autoimmunity," Cell. 87(5):811-22 (1996) (1 page) (Abstract only).
Koyama et al., "Hox11 genes establish synovial joint organization and phylogenetic characteristics in developing mouse zeugopod skeletal elements," Development. 137(22): 3795-800 (2010) (Abstract Only).
Krause et al., "Multi-organ, multi-lineage engraftment by a single bone marrow-derived stem cell," Cell. 105:369-377 (2001).
Kuehnle et al., "The therapeutic potential of stem cells from adults," BMJ. 325(7360):372-6 (2002).
Kwon et al., "Evidence for involvement of the proteasome complex (26S) and NFkappaB in IL-1beta-induced nitric oxide and prostaglandin production by rat islets and RINm5F Cells," Diabetes. 47(4):583-591 (1998).
Kwon et al., "Interleukin-1beta-induced nitric oxide synthase expression by rat pancreatic beta-cells: Evidence for the involvement of nuclear factor kappaB in the signaling mechanism," Endocrinology. 136(11):4790-4795 (1995).
Laakko et al., "Versatility of merocyanine 540 for the flow cytometric detection of apoptosis in human and murine cells," J Immunol Methods. 261(1-2):129-139 (2002).

(56) References Cited

OTHER PUBLICATIONS

Lahav-Baratz et al., "Reversible phosphorylation controls the activity of cyclosome-associated cyclin-ubiquitin ligase," Proc Natl Acad Sci USA. 92:9303-9307 (1995).
Lakey et al., "BCG immunotherapy prevents recurrence of diabetes in islet grafts transplanted into spontaneously diabetic NOD mice," Transplantation. 57(8):1213-1217 (1994).
Lammert et al., "Induction of pancreatic differentiation by signals from blood vessels," Science. 294:564-567 (2001).
Lanza et al., "Transplantation of encapsulated canine islets into spontaneously diabetic BB/Wor rats without immunosuppression," Endocrinology. 131(2):637-642 (1992).
Lapchak et al., "Tumor necrosis factor production is deficient in diabetes-prone BB rats and can be corrected by complete Freund's adjuvant: A possible immunoregulatory role of tumor necrosis factor in the prevention of diabetes," Clin Immunol Immunopathol. 65(2):129-134 (1992).
Lawrence et al., "Differential hepatocyte toxicity of recombinant Apo2L/TRAIL versions," Nat Med. 7(4):383-385 (2001).
Leeuwenberg et al., "Lipopolysaccharide LPS-mediated soluble TNF receptor release and TNF receptor expression by monocytes. Role of CD14, LPS binding protein, and bactericidial/permeability-increasing protein," J Immunol. 152(10):5070-6 (1994) (8 pages).
Lewis et al., "Integrins regulate the apoptotic response to DNA damage through modulation of p53," Proc Natl Acad Sci USA. 99(6):3627-3632 (2002).
Li et al., "Abnormal class I assembly and peptide presentation in the nonobese diabetic mouse," Proc Natl Acad Sci USA. 91(23):11128-11132 (1994).
Li et al., "Reduced expression of peptide-loaded HLA class I molecules on multiple sclerosis lymphocytes," Ann Neurol. 38(2):147-154 (1995).
Li et al., "Use of Donor beta 2-Microglobulin-Deficient Transgenic Mouse Liver Cells for Isografts, Allografts, and Xenografts," Transplantation. 55(4):940-6 (1993).
Ljunggren et al., "MHC class I expression and CD8+ T cell development in TAP1/beta2-microglobulin double mutant mice," Int Immunol. 7(6):975-984 (1995).
Loetscher et al., "Human tumor necrosis factor alpha (TNFalpha) mutants with exclusive specificity for the 55-kDa or 75-kDa TNF receptors," J Biol Chem. 268(35):26350-26357 (1993).
Macchi et al., "Impaired apoptosis in mitogen-stimulated lymphocytes of patients with multiple sclerosis," NeuroReport. 10(25):399-402 (1999).
Madsen et al., "Oligodendroglial TNFR2 mediates membrane TNF-dependent repair in experimental autoimmune encephalomyelitis by promoting oligodendrocyte differentiation and remyelination," J Neurosci. 36(18):5128-43 (2016).
Mak et al., "Signaling for survival and apoptosis in the immune system," Arthritis Res. 4(Suppl 3):S243-S252 (2002).
Markiewicz et al., "Long-term T cell memory requires the surface expression of self-peptide/major histocompatibility complex molecules," Proc Natl Acad Sci USA. 95(6):3065-70 (1998).
Markmann et al., "Indefinite survival of MHC class I-deficient murine pancreatic islet allografts," Transplantation. 54(6):1085-1089 (1992).
Marriott, "TNF-alpha antagonists: Monoclonal antibodies, soluble receptors, thalidomide and other novel approaches," Expert Opin Invest Drugs. 6(8):1105-1108 (1997).
Matsumoto et al., "Liver organogenesis promoted by endothelial cells prior to vascular function," Science. 294(5542):559-563 (2001).
Mayer-Proschel et al., "Isolation of lineage-restricted neuronal precursors from multipotent neuroepithelial stem cells," Neuron. 19(4):773-785 (1997).
McGuire et al., "An enzyme related to the high molecular weight multicatalytic proteinase, macropain, participates in a ubiquitin-mediated, ATP-stimulated proteolytic pathway in soluble extracts of BHK 21/C13 fibroblasts," Biochim Biophys Acta. 967(2):195-203 (1988).
McInerney et al., "Prevention of insulitis and diabetes onset by treatment with complete Freund's adjuvant in NOD mice," Diabetes. 40(6):715-725 (1991).
McKay, "Mammalian deconstruction for stem cell reconstruction," Nat Med. 6(7):747-8 (2000).
Mera et al., "The spleen contributes stem cells to peripheral blood stem cell transplants," J Stem Cell Res Ther. 4(11):1000253 (2014) (4 pages).
Mercurio et al., "p105 and p98 precursor proteins play an active role in NF-kappa B-mediated signal transduction," Genes Dev. 7(4):705-718 (1993).
Mestas et al., "Of mice and not men: Differences between mouse and human immunology," J Immunol. 172(5):2731-2738 (2004).
Mezey et al., "Turning blood into brain: cells bearing neuronal antigens generated in vivo from bone marrow," Science. 290(5497):1779-1782 (2000).
Miller et al., "Both the Lyt-2+ and L3T4+ T cell subsets are required for the transfer of diabetes in nonobese diabetic mice," J Immunol. 140(1):52-8 (1988).
Mittelman et al., "A phase I pharmacokinetic study of recombinant human tumor necrosis factor administered by a 5-day continuous infusion," Invest New Drugs. 10(3):183-190 (1992).
Miyazaki et al., "Predominance of T lymphocytes in pancreatic islets and spleen of pre-diabetic non-obese diabetic (NOD) mice: a longitudinal study," Clin Exp Immunol. 60(3):622-630 (1985).
Morrison, "Stem cell potential: Can anything make anything?" Curr Biol. 11(1):R7-R9 (2001).
Murthi et al., "Novel homeobox genes are differentially expressed in placental microvascular endothelial cells compared with macrovascular cells," Placenta. 29(7):624-630 (2008).
Nomikos et al., "Combined treatment with nicotinamide and desferrioxamine prevents islet allograft destruction in NOD mice," Diabetes. 35(11):1302-1304 (1986).
Offield et al., "PDX-1 is required for pancreatic outgrowth and differentiation of the rostral duodenum," Development. 122(3):983-995 (1996).
Okubo et al., "Homogeneous Expansion of Human T-Regulatory Cells Via Tumor Necrosis Factor Receptor 2," Sci Rep. 3:3153 (2013) (11 pages).
Okubo et al., "Supplemental Information: Homogeneous Expansion of Human T-Regulatory Cells Via Tumor Necrosis Factor Receptor 2," Sci Rep. 3:3153 (2013) (8 pages).
Ono et al., "IDDM in BB rats. Enhanced MHC class I heavy-chain gene expression in pancreatic islets," Diabetes. 37(10):1411-1418 (1988).
Orlowski, "The multicatalytic proteinase complex, a major extralysosomal proteolytic system," Biochemistry. 29(45):10289-10297 (1990).
Osorio et al., "Beta-2 microglobulin gene disruption prolongs murine islet allograft survival in NOD mice," Transplant Proc. 26(2):752 (1994).
Palombella et al., "The ubiquitin-proteasome pathway is required for processing the NF-kappa B1 precursor protein and the activation of NF-kappa B," Cell. 78(5):773-785 (1994).
Paolillo et al., "The effect of Bacille Calmette-Guérin on the evolution of new enhancing lesions to hypointense T1 lesions in relapsing remitting MS," J Neurol. 250(2):247-248 (2003).
Pestano et al., "Inactivation of misselected CD8 T cells by CD8 gene methylation and cell death," Science. 284(5417):1187-91 (1999).
Petersen et al., "Bone marrow as a potential source of hepatic oval cells," Science. 284(5417):1168-70 (1999).
Pontesilli et al., "Circulating lymphocyte populations and autoantibodies in non-obese diabetic (NOD) mice: a longitudinal study," Clin Exp Immunol. 70(1):84-93 (1987).
Pozzilli, "BCG vaccine in insulin-dependent diabetes mellitus," Lancet. 349(9064):1520-1 (1997).
Prieto et al., "Apoptotic rate: A new indicator for the quantification of the incidence of apoptosis in cell cultures," Cytometry. 48(4):185-93 (2002).
Qin et al., "BCG vaccination prevents insulin-dependent diabetes mellitus (IDDM) in NOD mice after disease acceleration with cyclophosphamide," J Autoimmun. 10(3):271-278 (1997).

(56) References Cited

OTHER PUBLICATIONS

Qin et al., "Complete Freund's adjuvant-induced T cells prevent the development and adoptive transfer of diabetes in nonobese diabetic mice," J Immunol. 150(5):2072-80 (1993).
Quintana et al., "Experimental autoimmune myasthenia gravis in naive non-obese diabetic (NOD/LtJ) mice: susceptibility associated with natural IgG antibodies to the acetylcholine receptor," Int Immunol. 15(1):11-16 (2003).
R&D Systems, "Human TNF RII/TNFRSF1B Antibody," dated Jul. 7, 2018 (1 page).
Raab et al., "In vitro evaluation of methotrexate and azathioprine for antipsoriatic activity," Arch Derm Res. 253(1):77-84 (1975).
Rabinovitch et al., "TNF-alpha down-regulates type 1 cytokines and prolongs survival of syngeneic islet grafts in nonobese diabetic mice," J Immunol. 159(12):6298-6303 (1997).
Rabinovitch et al., "Tumor necrosis factor mediates the protective effect of Freund's adjuvant against autoimmune diabetes in BB rats," J Autoimmun. 8(3):357-366 (1995).
Rajagopalan et al., "Pathogenic anti-DNA autoantibody-inducing T helper cell lines from patients with active lupus nephritis: isolation of CD4-8-T helper cell lines that express the gamma delta T-cell antigen receptor," Proc Natl Acad Sci USA. 87(18):7020-7024 (1990).
Raju et al., "Characterization and developmental expression of Tlx-1, the murine homolog of HOX11," Mech Dev. 44(1):51-64 (1993).
Ramiya et al., "Reversal of insulin-dependent diabetes using islets generated in vitro from pancreatic stem cells," Nat Med. 6(3):278-282 (2000).
Rath et al., "TNF-induced signaling in apoptosis," J Clin Immunol. 19(6):350-364 (1999).
Rechsteiner, "Ubiquitin-mediated pathways for intracellular proteolysis," Annu Rev Cell Biol. 3:1-30 (1987).
Rietze et al., "Purification of a pluripotent neural stem cell from the adult mouse brain," Nature. 412(6848):736-739 (2001).
Ristori et al., "Use of Bacille Calmette-Guerin (BCG) in multiple sclerosis," Neurology. 53(7):1588-1589 (1999).
Roberts et al., "Developmental expression of Hox11 and specification of splenic cell fate," Am J Pathol. 146(5):1089-1101 (1995).
Roberts et al., "Hox11 controls the genesis of the spleen," Nature. 368(6473):747-749 (1994).
Robertson et al., "Preservation of insulin mRNA levels and insulin secretion in HIT cells by avoidance of chronic exposure to high glucose concentrations," J Clin Invest. 90(2):320-325 (1992).
Robinson et al., "A novel NOD-derived murine model of primary Sjögren's Syndrome," Arthitis Rheum. 41(1):150-156 (1998).
Robinson et al., "Elevated levels of cysteine protease activity in saliva and salivary glands of the nonobese diabetic (NOD) mouse model for Sjögren Syndrome," Proc Natl Acad Sci USA. 94:5767-5771 (1997).
Rolfe et al., "The ubiquitin-mediated proteolytic pathway as a therapeutic area," J Mol Med. 75(1):5-17 (1997).
Rosenthal, "Prometheus's vulture and the stem-cell promise," N Engl J Med. 349(3):267-74 (2003).
Ryu et al., "Reversal of established autoimmune diabetes by restoration of endogenous beta cell function," J Clin Invest. 108(1):63-72 (2001).
Sadelain et al., "Prevention of type I diabetes in NOD mice by adjuvant immunotherapy," Diabetes. 39(5):583-9 (1990).
Sarin et al., "Cytotoxic effect of TNF and lymphotoxin on T lymphoblasts," J Immunol. 155(8):3716-3718 (1995).
Satoh et al., "Inhibition of type 1 diabetes in BB rats with recombinant human tumor necrosis factor-alpha," J Immunol. 145(5):1395-1399 (1990).
Satoh et al., "Recombinant human tumor necrosis factor alpha suppresses autoimmune diabetes in nonobese diabetic mice," J Clin Invest. 84(4):1345-1348 (1989).
Schatz et al., "Defective inducer T-cell function before the onset of insulin-dependent diabetes mellitus," J Autoimmun. 4(1):125-136 (1991).

Schmidt et al., "Interspecies exchange of beta 2-microglobulin and associated MHC and differentiation antigens," Immunogenetics. 13(6):483-91 (1981).
Schuppan, "Current concepts of celiac disease pathogenesis," Gastroenterology. 119(1):234-242 (2000).
Sears et al., "NF-kappaB p105 processing via the ubiquitin-proteasome pathway," J Biol Chem. 273(3):1409-1419 (1998).
Serrano et al., "Non-HLA associations with autoimmune diseases," Autoimmun Rev. 5(3):209-214 (2006).
Serreze et al., "Th1 to Th2 cytokine shifts in nonobese diabetic mice: Sometimes an outcome, rather than the cause, of diabetes resistance elicited by immunostimulation," J Immunol. 166(2):1352-1359 (2001).
Serup et al., "Islet and stem cell transplantation for treating diabetes," BMJ. 322 (7277):29-32 (2001).
Serup, "Panning for pancreatic stem cells," Nat Genet. 25(2):134-135 (2000).
Shaikh et al., "TNF Receptor Type II as an Emerging Drug Target for the Treatment of Cancer, Autoimmune Diseases, and Graft-Versus-Host Disease: Current Perspectives and In Silico Search for Small Molecule Binders," Front Immunol. 9:1382 (2018) (6 pages).
Shehadeh et al., "Effect of adjuvant therapy on development of diabetes in mouse and man," Lancet. 343(8899):706-707 (1994).
Shehadeh et al., "Repeated BCG vaccination is more effective than a single dose in preventing diabetes in non-obese diabetic (NOD) mice," Isr J Med Sci. 33(11):711-715 (1997).
Shihabuddin et al., "Adult spinal cord stem cells generate neurons after transplantation in the adult dentate gyrus," J Neurosci. 20(23):8727-8735 (2000).
Shohami et al., "Dual role of tumor necrosis factor alpha in brain injury," Cytokine Growth Factor Rev. 10(2):119-130 (1999).
Silva et al., "Prevention of autoimmune diabetes through immunostimulation with Q fever complement-fixing antigen," Ann NY Acad Sci. 1005:423-430 (2003).
Singh et al., "Can progression of IDDM be prevented in newly diagnosed patients by BCG immunotherapy?" Diabetes Metab Rev. 13(4):320-321 (1997).
Slack, "Stem cells in epithelial tissues," Science. 287:1431-1433 (2000).
Song et al., "Tumor necrosis factor-related apoptosis-inducing ligand (TRAIL) is an inhibitor of autoimmune inflammation and cell cycle progression," J Exp Med. 191(7):1095-1103 (2000).
Speiser et al., "Loss of ATP-dependent proteolysis with maturation of reticulocytes and erythrocytes," J Biol Chem. 257(23):14122-14127 (1982).
Sreenan et al., "Increased beta-cell proliferation and reduced mass before diabetes onset in the nonobese diabetic mouse," Diabetes. 48(5):989-996 (1999).
Stephens et al., "Protection of NIT-1 pancreatic beta-cells from immune attack by inhibition of NF-kappaB," J Autoimmun. 10(3):293-298 (1997).
Storms et al., "Hoechst dye efflux reveals a novel CD7+CD34- lymphoid progenitor in human umbilical cord blood," Blood. 96(6):2125-2133 (2000).
Sun et al., "MHC class I multimers," Arthritis Res. 3(5):265-269 (2001).
Supplementary Partial European Search Report for European Application No. 04817543, dated Oct. 6, 2009 (4 pages).
Swirski et al., "Identification of splenic reservoir monocytes and their deployment to inflammatory sites," available in PMC Jan. 7, 2010, published in final edited form as: Science. 325(5940):612-616 (2009) (12 pages).
Szodoray et al., "Programmed cell death in rheumatoid arthritis peripheral blood T-cell subpopulations determined by laser scanning cytometry," Lab Invest. 83(12):1839-1848 (2003).
Tamura et al., "In vivo differentiation of stem cells in the aorta-gonad-mesonephros region of mouse embryo and adult bone marrow," Exp Hematol. 30(8):957-966 (2002) (Abstract Only).
Tartaglia et al., "The two different receptors for tumor necrosis factor mediate distinct cellular responses," Proc Natl Acad Sci USA. 88(20):9292-9296 (1991).

(56) References Cited

OTHER PUBLICATIONS

Tavernier et al., "Analysis of the structure-function relationship of tumour necrosis factor. Human/mouse chimeric TNF proteins: general properties and epitope analysis," J Mol Biol. 211(2):493-501 (1990).
Terada et al., "Bone marrow cells adopt the phenotype of other cells by spontaneous cell fusion," Nature. 416(6880):542-545 (2002).
Toma et al., "Isolation of multipotent adult stem cells from the dermis of mammalian skin," Nat Cell Bio. 3:778-784 (2001).
Totpal et al., "TNF and its receptor antibody agonist differ in mediation of cellular responses," J Immunol. 153:2248-2257 (1994).
Townsley et al., "Dominant-negative cyclin-selective ubiquitin carrier protein E2-C/UbcH10 blocks cells in metaphase," Proc Natl Acad Sci USA. 94:2362-2367 (1997).
Tran et al., "Reversal of Sjögren's-like syndrome in non-obese diabetic mice," Ann Rheum Dis. 66:812-814 (2007).
Trowsdale et al., "Sequences encoded in the class II region of the MHC related to the 'ABC' superfamily of transporters," Nature. 348(6303):741-4 (1990).
Ulaeto et al., "A T-cell dormant state in the autoimmune process of nonobese diabetic mice treated with complete Freund's adjuvant," Proc Natl Acad Sci USA. 89:3927-3931 (1992).
Vagima et al., "MT1-MMP and RECK are involved in human CD34+ progenitor cell retention, egress, and mobilization," J Clin Invest. 119(3):492-503 (2009).
Van der Kooy et al., "Why stem cells?," Science. 287:1439-1441 (2000).
Van Nocker et al., "The multiubiquitin-chain-binding protein Mcb1 is a component of the 26S proteasome in *Saccharomyces cerevisiae* and plays a nonessential, substrate-specific role in protein turnover," Mol Cell Biol. 16(11):6020-6028 (1996).
Van Noort et al., "Cell biology of autoimmune diseases," Int Rev Cytol. 178:127-206 (1998).
Van Zee et al., "A human tumor necrosis factor (TNF) alpha mutant that binds exclusively to the p55 TNF receptor produces toxicity in the baboon," J Exp Med. 179(4):1185-1191 (1994).
Vidal-Puig et al., "Tolerance to peripheral tissue is transient and maintained by tissue-specific class I expression," Transplant Proc. 26(6):3314-6 (1994).
Vogel, "Stem cell research. Studies cast doubt on plasticity of adult cells," Science. 295:1989,1991 (2002).
Von Herrath et al., "In vivo treatment with a MHC class I-restricted blocking peptide can prevent virus-induced autoimmune diabetes," J Immunol. 161:5087-5096 (1998).
Wang et al., "Prevention of recurrence of IDDM in islet-transplanted diabetic NOD mice by adjuvant immunotherapy," Diabetes. 41:114-117 (1992).
Watt et al., "Out of Eden: stem cells and their niches," Science. 287:1427-30 (2000).
Waxman et al., "Demonstration of two distinct high molecular weight proteases in rabbit reticulocytes, one of which degrades ubiquitin conjugates," J Biol Chem. 262(6):2451-2457 (1987).
Weissman, "Translating stem and progenitor cell biology to the clinic: barriers and opportunities," Science. 287:1442-1446 (2000).
Welborn et al., "A human tumor necrosis factor p75 receptor agonist stimulates in vitro T cell proliferation but does not produce inflammation or shock in the baboon," J Exp Med. 184(1):165-171 (1996).
Wellik et al., "Hox11 paralogous genes are essential for metanephric kidney induction," Genes Dev. 16:1423-1432 (2002).
Wellik, "The role of Hox11 paralogous genes in prostate development," Grant Detail. (2009) (1 page)(Abstract only).
Weringer et al., "Identification of T cell subsets and Class I and Class II antigen expression in islet grafts and pancreatic islets of diabetic BioBreeding/Worcester rats," Am J Pathol. 132(2):292-303 (1988).
Wicker et al., "Transfer of autoimmune diabetes mellitus with splenocytes from nonobese diabetic (NOD) mice," Diabetes. 35:855-860 (1986).
Willis et al., "Type 1 Diabetes in insulin-treated adult-onset diabetic subjects," Diabetes Res Clin Pract. 42:49-53 (1998).
Winston, "Embryonic stem cell research: the case for . . . ," Nat Med. 7(4):396-397 (2001).
Wong et al., "Identification of an MHC class I-restricted autoantigen in Type I Diabetes by screening an organ-specific cDNA library," Nat Med. 5(9):1026-1031 (1999).
Written Opinion for International Application No. PCT/US2004/037998, mailed Feb. 28, 2008 (3 pages).
Xu et al., "MHC/peptide tetramer-based studies of T cell function," J Immunol Methods. 268(1):21-28 (2002).
Yagi et al., "Possible mechanism of the preventive effect of BCG against diabetes mellitus in NOD Mouse. I. Generation of suppressor macrophages in spleen cells of BCG-vaccinated mice," Cell Immunol. 138(1):130-141 (1991).
Yagi et al., "Possible mechanism of the preventive effect of BCG against diabetes mellitus in NOD Mouse. II. Suppression of pathogenesis by macrophage transfer from BCG-vaccinated mice," Cell Immunol. 138:142-149 (1991).
Yan et al., "Reduced expression of Tap1 and Lmp2 antigen-processing genes in the nonobese diabetic (NOD) mouse due to a mutation in their shared bidirectional promoter," J Immunol. 159(6):3068-3080 (1997).
Yang et al., "A variant of TNFR2-Fc fusion protein exhibits improved efficacy in treating experimental rheumatoid arthritis," PLoS Comput Biol. 6(2):e1000669 (2010) (7 pages).
Yang et al., "Effect of tumor necrosis factor alpha on insulin-dependent diabetes mellitus in NOD Mice. I. The early development of autoimmunity and the diabetogenic process," J Exp Med. 180(3):995-1004 (1994).
Ying et al., "Changing potency by spontaneous fusion," Nature. 416(6880):545-548 (2002).
Zachs et al., "Noninvasive ultrasound stimulation of the spleen to treat inflammatory arthritis," Nat Commun. 10:951 (2019) (10 pages).
Zulewski et al., "Multipotential nestin-positive stem cells isolated from adult pancreatic islets differentiate ex vivo into pancreatic endocrine, exocrine, and hepatic phenotypes," Diabetes. 50:521-533 (2001).
Zöller et al., "Apoptosis resistance in peripheral blood lymphocytes of alopecia areata patients," Retrieved from Science Direct, published in: J Autoimmun. 23(3):241-256 (2004) (30 pages).
English Translation of Office Action for Korean Application No. 10-2022-7020235, dated Jan. 2, 2023 (6 pages).
Examination Report for Australian Patent Application No. 2017263833, dated Jun. 1, 2023 (3 pages).
Office Action for Canadian Application No. 3,023,930, dated May 17, 2023 (6 pages).
English Translation of Notice of Reasons for Rejection for Japanese Application No. 2021-509865, mailed Aug. 8, 2023 (2 pgs).
Office Action for Canadian Application No. 2,985,816, dated Jun. 22, 2023 (8 pages).
Office Action for Canadian Application No. 3,109,954, dated Oct. 12, 2023 (7 pages).
International Preliminary Report on Patentability for International Application No. PCT/US22/13273, issued Jul. 20, 2023 (8 pages).
International Search Report and Written Opinion for International Application No. PCT/US22/13273, mailed Dec. 13, 2022 (17 pages).
EPO Communication Pursuant to Article 94(3) EPC issued in European Patent Application No. 19852179.1, dated Jan. 18, 2024 (5 pages).
Qiu et al., "Engineering an anti-CD52 antibody for enhance deamidation stability," MAbs. 11(7):1266-75 (Oct. 2019).
English Translation of Office Action for Chinese Application No. 201980068984.8, mailed Mar. 1, 2024 (9 pages).
Peppel et al: "A Tumour Necrosis Factor (TNF) Receptor IGG Heavy Chain Chimeric Protein as a Bivalent Antagonist of TNF Activity", Journal of Experimental Medicine, Rockefeller University Press, US, 174(6), Dec. 1, 1991 (Dec. 1, 1991), pp. 1483-1489.
Vanamee et al: "Structural principles of tumor necrosis factor superfamily signaling", Sci. Signal. 11, Jan. 2, 2018 (12 pages).
Naismith et al: "Crystallographic evidence for dimerization of unliganded tumor necrosis factor receptor", Journal of Biological Chemistry, American Society for Biochemistry and Molecular Biology, US, 270 (22), Jun. 2, 1995, pp. 13303-13307.

(56) References Cited

OTHER PUBLICATIONS

Extended European Search Report for European Application No. 23190358.4, mailed May 15, 2024 (8 pages).

Van der Most et al., "Tumor eradication after cyclophosphamide depends on concurrent depletion of regulatory T cells: a role for cycling TNFR2-expressing effector-suppressor T cells in limiting effective chemotherapy," Cancer Immunol Immunother. 58(8):1219-28 (Aug. 2009) (Epub Dec. 2008).

Chen et al., "TNFR2 is critical for the stabilization of the CD4+ Foxp3+ regulatory T. cell phenotype in the inflammatory environment," J Immunol. 190(3):1076-84 (Feb. 2013) (Epub Dec. 2012) (11 pages).

Turner et al., "Mechanism of TNFa-induced IL-1a, IL-1ß and IL-6 expression in human cardiac fibroblasts: Effects of statins and thiazolidinediones," Cardiovasc Res. 76(1):81-90 (Oct. 2007) (Epub Jun. 2007).

Rudikoff et al., "Single amino acid substitution altering antigen-binding specificity," Immunology, 79, pp. 1979-1983 (1982) (5 pages).

Lee et al., "An antibody engineering platform using amino acid networks: A case study in development of antiviral therapeutics," Antiviral Res. 192:105105 (9 pages) (Aug. 2021).

Janeway et al., Chapter 3: Structure of the Antibody Molecule and Immunoglobulin Genes, *Immunobiology, Third Edition*. Penolope Austin, Eleanor Lawrence, and Miranda Robertson, Current Biology Ltd./Garland Publishing Inc., 3:1-3:11 (1997) (14 pages).

FIG. 1A. Epitopes within TNFR2 bound by MR2-1

```
        10          20          30          40          50
MAPVAVWAAL  AVGLELWAAA  HALPAQVAFT  PYAPEPGSTC  RLREYYDQTA
        60          70          80          90         100
QMCCSKCSPG  QHAKVFCTKT  SDTVCDSCED  STYTQLWNWV  PECLSCGSRC
       110         120         130         140         150
SSDQVETQAC  TREQNRICTC  RPGWYCALSK  QEGCRLCAPL  RKCRPGFGVA
       160         170         180         190         200
RPGTETSDVV  CKPCAPGTFS  NTTSSTDICR  PHQICNVVAI  PGNASMDAVC
       210         220         230         240         250
TSTSPTRSMA  PGAVHLPQPV  STRSQHTQPT  PEPSTAPSTS  FLLPMGPSPP
       260         270         280         290         300
AEGSTGDFAL  PVGLIVGVTA  LGLLIIGVVN  CVIMTQVKKK  PLCLQREAKV
       310         320         330         340         350
PHLPADKARG  TQGPEQQHLL  ITAPSSSSSS  LESSASALDR  RAPTRNQPQA
       360         370         380         390         400
PGVEASGAGE  ARASTGSSDS  SPGGHGTQVN  VTCIVNVCSS  SDHSSQCSSQ
       410         420         430         440         450
ASSTMGDTDS  SPSESPKDEQ  VPFSKEECAF  RSQLETPETL  LGSTEEKPLP
       460
LGVPDAGMKP  S
```

FIG. 1B. Epitopes within TNFR2 bound by 8E6.D1

```
            10          20          30          40          50
    MAPVAVWAAL  AVGLELWAAA  HALPAQVAFT  PYAPEPGSTC  RLREYYDQTA
            60          70          80          90         100
    QMCCSKCSPG  QHAKVFCTKT  SDTVCDSCED  STYTQLWNWV  PECLSCGSRC
           110         120         130         140         150
    SSDQVETQAC  TREQNRICTC  RPGWYCALSK  QEGCRLCAPL  RKCRPGFGVA
           160         170         180         190         200
    RPGTETSDVV  CKPCAPGTFS  NTTSSTDICR  PHQICNVVAI  PGNASMDAVC
           210         220         230         240         250
    TSTSPTRSMA  PGAVHLPQPV  STRSQHTQPT  PEPSTAPSTS  FLLPMGPSPP
           260         270         280         290         300
    AEGSTGDFAL  PVGLIVGVTA  LGLLIIGVVN  CVIMTQVKKK  PLCLQREAKV
           310         320         330         340         350
    PHLPADKARG  TQGPEQQHLL  ITAPSSSSSS  LESSASALDR  RAPTRNQPQA
           360         370         380         390         400
    PGVEASGAGE  ARASTGSSDS  SPGGHGTQVN  VTCIVNVCSS  SDHSSQCSSQ
           410         420         430         440         450
    ASSTMGDTDS  SPSESPKDEQ  VPFSKEECAF  RSQLETPETL  LGSTEEKPLP
           460
    LGVPDAGMKP  S
```

FIG. 2. Conformation-dependent epitope mapping of MR2-1

| SEQ ID NO. | Peptide Sequence | Structural Group | Raw luminescence data |
|---|---|---|---|
| 1 | CRPHQICNVVAIPGN | LIN | 1357 |
| 2 | CRPHQICNVVGAPGN | LIN.AA | 963 |
| 3 | QEGCRLCAPLAACRP | LIN.AA | 882 |
| 4 | TFSNTTSSTDAARPH | LIN.AA | 698 |
| 5 | PSTSFLLPMGPSPPA | LIN | 684 |
| 6 | QVETQACTREQNRIC | LIN | 629 |
| 7 | LWNWVPECLSCGSRC | LIN | 623 |
| 8 | QLWNWVPECLSCGSR | LIN | 619 |
| 9 | QACTREQNRICTCRP | LIN | 606 |
| 10 | TFSNTTSSTDICRPH | LIN | 604 |
| 11 | PGWYCALSKQEGCRL | LIN | 603 |
| 12 | CQLWNWVPEALAGGSRC | LOOP.AA | 594 |
| 13 | LS2GSRCSSDQGGSGGREQNRICT2RP | CYS.S | 584 |
| 14 | WNWVPECLSCAARCS | LIN.AA | 531 |
| 15 | LWNWVPE2LSCGGSGGQACTREQNRI2 | CYS.S | 525 |
| 16 | PLRKCRPGFGVARPG | LIN | 523 |
| 17 | 2GSRCSSDQVEGGSGGREQNRICT2RP | CYS.S | 510 |
| 18 | PE2LS2GSRCGGSGGREQNRICT2RP | CYS.S | 483 |
| 19 | LWNWVPE2LSCGGSGGACTREQNRI2T | CYS.S | 467 |
| 20 | QLWNWVPECLAAGSR | LIN.AA | 462 |
| 21 | CSSDQVETQA2GGSGGREQNRICT2RP | CYS.S | 459 |
| 22 | EQNRICTCRPAAYCA | LIN.AA | 452 |
| 23 | TTSSTDICRPHQICN | LIN | 448 |
| 24 | ACTREQNRICTCRPG | LIN | 447 |
| 25 | CQLWNWVPEALSAGSRC | LOOP | 441 |
| 26 | RPHQICNVVAIPGNA | LIN | 437 |
| 27 | SRCSSDQVETQGGSGGREQNRICT2RP | CYS.S | 435 |
| 28 | GSRCSSDQVETGGSGGREQNRICT2RP | CYS.S | 433 |
| 29 | LS2GSRCSSDQGGSGGEQNRICT2RPG | CYS.S | 433 |
| 30 | QEGCRL2APLRGGSGGCRPGFGVARPG | CYS.S | 428 |
| 31 | FSNTTSSTDICRPHQ | LIN | 421 |
| 32 | LWNWVPECLSAASRC | LIN.AA | 420 |
| 33 | QTAQMCCSKCSPGQH | LIN | 419 |
| 34 | E2LS2GSRCSSGGSGGREQNRICT2RP | CYS.S | 418 |
| 35 | CEQNRI2T2RPGWY2ACNASMDAV2TSTSPTRC | MAT | 413 |
| 36 | VPE2LS2GSRCGGSGGREQNRICT2RP | CYS.S | 410 |
| 37 | WNWVPE2LSCGGSGGQACTREQNRI2 | CYS.S | 403 |
| 38 | LWNWVPE2LSCGGSGGTQACTREQNRI | CYS.S | 400 |
| 39 | VPE2LS2GSRCGGSGGQA2TREQNRIC | CYS.S | 399 |
| 40 | S2GSRCSSDQVGGSGGREQNRICT2RP | CYS.S | 392 |
| 41 | 2GSRCSSDQVEGGSGGEQNRICT2RPG | CYS.S | 389 |
| 42 | ACTREQNRICAARPG | LIN.AA | 389 |
| 43 | S2GSRCSSDQVGGSGGEQNRICT2RPG | CYS.S | 385 |
| 44 | PLRKCRPGFGAGRPG | LIN.AA | 379 |
| 45 | ICRPHQICNVAGIPG | LIN.AA | 376 |
| 46 | GWYCALSKQEGCRLC | LIN | 375 |
| 47 | QACTREQNRIAACRP | LIN.AA | 374 |
| 48 | WNWVPECLSCGSRCS | LIN | 368 |
| 49 | 2LS2GSRCSSDGGSGGQNRICT2RPGW | CYS.S | 366 |
| 50 | VPE2LSCGSR2GGSGGQACTREQNRI2 | CYS.S | 365 |

FIG. 2. (Con't)

| | | | |
|---|---|---|---|
| 51 | 2LS2GSRCSSDGGSGGREQNRICT2RP | CYS.S | 362 |
| 52 | EGCRL2APLRKGGSGGCRPGFGVARPG | CYS.S | 359 |
| 53 | APEPGSTCRLRGGSGGMC2SK2SPGQH | CYS.S | 353 |
| 54 | LWNWVPE2LSCGGSGGCTREQNRI2T2 | CYS.S | 353 |
| 55 | KQEGCRL2APLGGSGGCRPGFGVARPG | CYS.S | 352 |
| 56 | 2ALSKQEGCRLGGSGGCRPGFGVARPG | CYS.S | 351 |
| 57 | WY2ALSKQEGCGGSGGCRPGFGVARPG | CYS.S | 344 |
| 58 | LSKQEGCRL2AGGSGGCRPGFGVARPG | CYS.S | 342 |
| 59 | GSRCSSDQVETGGSGGEQNRICT2RPG | CYS.S | 341 |
| 60 | ALSKQEGCRL2GGSGGCRPGFGVARPG | CYS.S | 337 |
| 61 | RPGWYCALSKQEGCR | LIN | 336 |
| 62 | AFTPYAPEPGSTCRL | LIN | 327 |
| 63 | RCSSDQVETQAGGSGGREQNRICT2RP | CYS.S | 324 |
| 64 | WNWVPE2LSCGGGSGGACTREQNRI2T | CYS.S | 323 |
| 65 | TSDVV2KPCAPGGSGGTTSSTDICRPH | CYS.S | 323 |
| 66 | ICRPHQICNVVAIPG | LIN | 321 |
| 67 | RLCAPLRK2RPGGSGGCKP2APGTFSN | CYS.S | 320 |
| 68 | PTRSMAPGAVHLPQP | LIN | 320 |
| 69 | YAPEPGSTCRLGGSGGMC2SK2SPGQH | CYS.S | 319 |
| 70 | WVPE2LSCGSRGGSGGQACTREQNRI2 | CYS.S | 317 |
| 71 | PE2LS2GSRCSGGSGGA2TREQNRICT | CYS.S | 317 |
| 72 | E2LS2GSRCSSGGSGGEQNRICT2RPG | CYS.S | 314 |
| 73 | PE2LSCGSR2SGGSGGQACTREQNRI2 | CYS.S | 312 |
| 74 | WVPE2LSCGSRGGSGGACTREQNRI2T | CYS.S | 312 |
| 75 | PGSTCRLREYYGGSGGMC2SK2SPGQH | CYS.S | 311 |
| 76 | PSTAPSTSFLLPMGP | LIN | 310 |
| 77 | RCSSDQVETQAGGSGGQNRICT2RPGW | CYS.S | 308 |
| 78 | PE2LS2GSRCSGGSGGQNRICT2RPGW | CYS.S | 305 |
| 79 | CSSDQVETQA2GGSGGEQNRICT2RPG | CYS.S | 304 |
| 80 | PYAPEPGSTCRGGSGGMC2SK2SPGQH | CYS.S | 302 |
| 81 | VPE2LS2GSRCGGSGGA2TREQNRICT | CYS.S | 301 |
| 82 | CSSDQVETQA2TREQNRICT2R | CYS.D | 299 |
| 83 | E2LS2GSRCSSGGSGGQA2TREQNRIC | CYS.S | 299 |
| 84 | LS2GSRCSSDQGGSGGQNRICT2RPGW | CYS.S | 299 |
| 85 | 2ALSKQEGCRLGGSGGL2APLRKCRPG | CYS.S | 299 |
| 86 | PEPGSTCRLREGGSGGMC2SK2SPGQH | CYS.S | 298 |
| 87 | NRI2TCRPGWYCALSKQEG2RL | CYS.D | 296 |
| 88 | VPE2LS2GSRCGGSGGEQNRICT2RPG | CYS.S | 295 |
| 89 | EPGSTCRLREYGGSGGMC2SK2SPGQH | CYS.S | 294 |
| 90 | KPCAPGTFSNTGGSGGTTSSTDICRPH | CYS.S | 294 |
| 91 | SRCSSDQVETQGGSGGEQNRICT2RPG | CYS.S | 293 |
| 92 | CAPLRK2RPGFGGSGGCKP2APGTFSN | CYS.S | 293 |
| 93 | VPE2LSCGSR2GGSGGACTREQNRI2T | CYS.S | 292 |
| 94 | WNWVPE2LSCGGGSGGTQACTREQNRI | CYS.S | 291 |
| 95 | 2LS2GSRCSSDGGSGGQA2TREQNRIC | CYS.S | 288 |
| 96 | SKQEGCRL2APGGSGGCRPGFGVARPG | CYS.S | 288 |
| 97 | LRKCRPGFGVARPGT | LIN | 288 |
| 98 | WVPE2LSCGSRGGSGGCTREQNRI2T2 | CYS.S | 287 |
| 99 | WY2ALSKQEGCGGSGGL2APLRKCRPG | CYS.S | 287 |
| 100 | CG2RL2APLRK2RPGFCNASMDAV2TSTSPTRC | MAT | 287 |
| 101 | CQI2NVVAIPGNASMDCAPLRK2RPGFGVARPC | MAT | 286 |
| 102 | VETQACTREQNRICT | LIN | 284 |
| 103 | NWVPE2LSCGSGGSGGACTREQNRI2T | CYS.S | 283 |

FIG. 2. (Con't)

| | | | |
|---|---|---|---|
| 104 | TCRLREYYDQTGGSGGMC2SK2SPGQH | CYS.S | 280 |
| 105 | PE2LS2GSRCSGGSGGEQNRICT2RPG | CYS.S | 277 |
| 106 | GSRCSSDQVETGGSGGQNRICT2RPGW | CYS.S | 276 |
| 107 | PE2LSCGSR2SGGSGGACTREQNRI2T | CYS.S | 275 |
| 108 | LSCGSR2SSDQGGSGGQACTREQNRI2 | CYS.S | 274 |
| 109 | PCAPGTFSNTTGGSGGTTSSTDICRPH | CYS.S | 274 |
| 110 | CQA2TREQNRI2T2RPCNASMDAV2TSTSPTRC | MAT | 274 |
| 111 | SRCSSDQVETQGGSGGQNRICT2RPGW | CYS.S | 272 |
| 112 | CQAATREQNRIGAARPC | LOOP.AA | 272 |
| 113 | CSSDQVETQA2GGSGGQNRICT2RPGW | CYS.S | 270 |
| 114 | CAFTPYAPEPGST2RLCNASMDAV2TSTSPTRC | MAT | 267 |
| 115 | CRLREYYDQTAGGSGGMC2SK2SPGQH | CYS.S | 265 |
| 116 | EGCRLCAPLRKCRPG | LIN | 265 |
| 117 | AFTPYAPEPGAACRL | LIN.AA | 263 |
| 118 | C2EDSTYTQLWNWVPECQTAQM22SK2SPGQHC | MAT | 263 |
| 119 | E2LSCGSR2SSGGSGGQACTREQNRI2 | CYS.S | 262 |
| 120 | PE2LS2GSRCSGGSGG2TREQNRICT2 | CYS.S | 262 |
| 121 | LCAPLRK2RPGGSGGCKP2APGTFSN | CYS.S | 262 |
| 122 | LWNWVPE2LSCGGSGGETQACTREQNR | CYS.S | 260 |
| 123 | NWVPE2LSCGSGGSGGQACTREQNRI2 | CYS.S | 258 |
| 124 | RCSSDQVETQAGGSGGEQNRICT2RPG | CYS.S | 257 |
| 125 | Y2ALSKQEGCRGGSGGCRPGFGVARPG | CYS.S | 256 |
| 126 | LSKQEGCRL2AGGSGGL2APLRKCRPG | CYS.S | 254 |
| 127 | WY2ALSKQEGCGGSGGKCRPGFGVARP | CYS.S | 254 |
| 128 | CG2RL2APLRK2RPGFCAFTPYAPEPGST2RLC | MAT | 252 |
| 129 | 2LSCGSR2SSDGGSGGQACTREQNRI2 | CYS.S | 251 |
| 130 | CDQVETQA2TREQNRICNASMDAV2TSTSPTRC | MAT | 251 |
| 131 | ALSKQEGCRL2GGSGGL2APLRKCRPG | CYS.S | 250 |
| 132 | WNWVPE2LSCGGGSGGCTREQNRI2T2 | CYS.S | 247 |
| 133 | LSKQEG2RLCAGGSGGCKP2APGTFSN | CYS.S | 247 |
| 134 | CTREQNRICTAAPGW | LIN.AA | 247 |
| 135 | Y2ALSKQEGCRGGSGGL2APLRKCRPG | CYS.S | 245 |
| 136 | 2RLCAPLRK2RGGSGGCKP2APGTFSN | CYS.S | 245 |
| 137 | QNRICTCRPGAACAL | LIN.AA | 244 |
| 138 | CG2RL2APLRK2RPGFCQA2TREQNRI2T2RPC | MAT | 244 |
| 139 | DVV2KPCAPGTGGSGGTTSSTDICRPH | CYS.S | 243 |
| 140 | QNRI2TCRPGWGGSGGYCALSKQEG2R | CYS.S | 242 |
| 141 | PSTSFLLPMGAAPPA | LIN.AA | 240 |
| 142 | EGCRL2APLRKCRPGFGVARPG | CYS.D | 239 |
| 143 | E2LS2GSRCSSGGSGGA2TREQNRICT | CYS.S | 233 |
| 144 | E2LS2GSRCSSGGSGGQNRICT2RPGW | CYS.S | 233 |
| 145 | LS2GSRCSSDQGGSGGQA2TREQNRIC | CYS.S | 232 |
| 146 | GSTCRLREYYDGGSGGMC2SK2SPGQH | CYS.S | 231 |
| 147 | APSTSFLLPMGPSPP | LIN | 231 |
| 148 | NWVPE2LSCGSGGSGGTQACTREQNRI | CYS.S | 229 |
| 149 | NRI2TCRPGWYGGSGGYCALSKQEG2R | CYS.S | 229 |
| 150 | KPCAPGTFSNTGGSGGTSSTDICRPHQ | CYS.S | 228 |
| 151 | CAPLRK2RPGFGVARPCAFTPYAPEPGST2RLC | MAT | 227 |
| 152 | TPYAPEPGSTCGGSGGMC2SK2SPGQH | CYS.S | 226 |
| 153 | LSCGSR2SSDQGGSGGCTREQNRI2T2 | CYS.S | 226 |
| 154 | TAPSTSFLLPMGPSP | LIN | 226 |
| 155 | E2LSCGSR2SSGGSGGACTREQNRI2T | CYS.S | 225 |
| 156 | CSSDQVETQA2GGSGGTREQNRICT2R | CYS.S | 225 |

FIG. 2. (Con't)

| | | | |
|---|---|---|---|
| 157 | PE2LS2GSRCSGGSGGQA2TREQNRIC | CYS.S | 224 |
| 158 | 2GSRCSSDQVEGGSGGQNRICT2RPGW | CYS.S | 224 |
| 159 | SKQEGCRL2APGGSGGL2APLRKCRPG | CYS.S | 224 |
| 160 | CAPGTFSNTTSGGSGGTTSSTDICRPH | CYS.S | 224 |
| 161 | 2GSRCSSDQVEGGSGGTREQNRICT2R | CYS.S | 223 |
| 162 | CAPLRK2RPGFGVARPCAPLRK2RPGFGVARPC | MAT | 223 |
| 163 | VPE2LS2GSRCGGSGGQNRICT2RPGW | CYS.S | 222 |
| 164 | V2KPCAPGTFSGGSGGTTSSTDICRPH | CYS.S | 222 |
| 165 | WNWVPE2LSCGGGSGGETQACTREQNR | CYS.S | 220 |
| 166 | DQVETQACTREQNRI | LIN | 220 |
| 167 | CAPLRK2RPGFGVARPCQA2TREQNRI2T2RPC | MAT | 220 |
| 168 | NWVPECLSCGSRCSS | LIN | 219 |
| 169 | LS2GSRCSSDQGGSGGTREQNRICT2R | CYS.S | 218 |
| 170 | CG2RL2APLRK2RPGFCQA2TREQNRI2T2RPC | MAT | 215 |
| 171 | SNTTSSTDICRPHQI | LIN | 214 |
| 172 | EGCRLCAPLRAARPG | LIN.AA | 213 |
| 173 | CAPEPGST2RLREYYDCNASMDAV2TSTSPTRC | MAT | 213 |
| 174 | REQNRI2TCRPGGSGGYCALSKQEG2R | CYS.S | 210 |
| 175 | CSR2SSDQVETQA2TRCAPLRK2RPGFGVARPC | MAT | 210 |
| 176 | VV2KPCAPGTFGGSGGTSSTDICRPHQ | CYS.S | 209 |
| 177 | 2KPCAPGTFSNTTSSTDICRPH | CYS.D | 208 |
| 178 | TETSDVV2KPCGGSGGTTSSTDICRPH | CYS.S | 208 |
| 179 | RCSSDQVETQAGGSGGQA2TREQNRIC | CYS.S | 207 |
| 180 | CSSDQVETQA2GGSGGQA2TREQNRIC | CYS.S | 206 |
| 181 | VPE2LS2GSRCGGSGG2TREQNRICT2 | CYS.S | 206 |
| 182 | TREQNRI2TCRGGSGGCALSKQEG2RL | CYS.S | 206 |
| 183 | TREQNRI2TCRGGSGGYCALSKQEG2R | CYS.S | 205 |
| 184 | VCTSTSPTRSAGPGA | LIN.AA | 205 |
| 185 | CQA2TREQNRI2T2RPCAPLRK2RPGFGVARPC | MAT | 204 |
| 186 | SDVV2KPCAPGGGSGGTTSSTDICRPH | CYS.S | 203 |
| 187 | CAATREQNRIAAGRPGC | LOOP.AA | 203 |
| 188 | CDQVETQA2TREQNRICAPLRK2RPGFGVARPC | MAT | 201 |
| 189 | SRCSSDQVETQGGSGGTREQNRICT2R | CYS.S | 200 |
| 190 | STAPSTSFLLPMGPS | LIN | 199 |
| 191 | LS2GSRCSSDQGGSGGA2TREQNRICT | CYS.S | 198 |
| 192 | CLSKQEG2RL2APLRKCAFTPYAPEPGST2RLC | MAT | 198 |
| 193 | CNWVPEALSAGPGASSDQVETQAC | BET1 | 197 |
| 194 | ETSDVV2KPCAGGSGGTTSSTDICRPH | CYS.S | 197 |
| 195 | V2KPCAPGTFSGGSGGTTSSTDICRPHQ | CYS.S | 197 |
| 196 | CVAIPGNASMDAV2TSCAPLRK2RPGFGVARPC | MAT | 197 |
| 197 | SDVV2KPCAPGGGSGGTSSTDICRPHQ | CYS.S | 196 |
| 198 | QICNVVAIPGNGGSGGCTSTSPTRSMA | CYS.S | 196 |
| 199 | DICRPHQICNVVAIP | LIN | 196 |
| 200 | CLWNWVPEALSAGSRAC | LOOP | 196 |
| 201 | CAPEPGST2RLREYYDCAPLRK2RPGFGVARPC | MAT | 196 |
| 202 | STCRLREYYDQGGSGGMC2SK2SPGQH | CYS.S | 194 |
| 203 | VPE2LSCGSR2GGSGGTQACTREQNRI | CYS.S | 194 |
| 204 | LSCGSR2SSDQGGSGGACTREQNRI2T | CYS.S | 194 |
| 205 | C2EDSTYTQLWNWVPECQI2NVVAIPGNASMDC | MAT | 194 |
| 206 | SCGSR2SSDQVGGSGGQACTREQNRI2 | CYS.S | 192 |
| 207 | SRCSSDQVETQGGSGGQA2TREQNRIC | CYS.S | 192 |
| 208 | CTSPTRSMAPGAVHLPCAPLRK2RPGFGVARPC | MAT | 192 |
| 209 | S2GSRCSSDQVGGSGGQA2TREQNRIC | CYS.S | 191 |

FIG. 2. (Con't)

| | | | |
|---|---|---|---|
| 210 | KQEGCRL2APLGGSGGL2APLRKCRPG | CYS.S | 191 |
| 211 | CAATREQNRIATARPGC | LOOP | 191 |
| 212 | C22SK2SPGQHAKVF2CAPLRK2RPGFGVARPC | MAT | 191 |
| 213 | CDVV2KP2APGTFSNTCNASMDAV2TSTSPTRC | MAT | 191 |
| 214 | 2LS2GSRCSSDGGSGGA2TREQNRICT | CYS.S | 190 |
| 215 | E2LSCGSR2SSGGSGGTQACTREQNRI | CYS.S | 189 |
| 216 | CYTQLWNWVPE2LS2GCNASMDAV2TSTSPTRC | MAT | 188 |
| 217 | LS2GSRCSSDQGGSGG2TREQNRICT2 | CYS.S | 187 |
| 218 | C2LS2GSR2SSDQVETCAPLRK2RPGFGVARPC | MAT | 187 |
| 219 | WVPE2LSCGSRGGSGGTQACTREQNRI | CYS.S | 186 |
| 220 | 2TREQNRI2TCGGSGGCALSKQEG2RL | CYS.S | 186 |
| 221 | SDQVETQACTREQNR | LIN | 185 |
| 222 | 2GSRCSSDQVEGGSGGQA2TREQNRIC | CYS.S | 184 |
| 223 | NRI2TCRPGWYGGSGGCALSKQEG2RL | CYS.S | 184 |
| 224 | CG2RL2APLRK2RPGFCREYYDQTAQM22SK2C | MAT | 183 |
| 225 | GTFSNTTSSTAACRP | LIN.AA | 182 |
| 226 | CTV2DS2EDSTYTQLWCNASMDAV2TSTSPTRC | MAT | 182 |
| 227 | PGSTCRLREYYGGSGGQMC2SK2SPGQ | CYS.S | 181 |
| 228 | WVPE2LSCGSRGGSGGETQACTREQNR | CYS.S | 181 |
| 229 | LSCGSR2SSDQGGSGGTQACTREQNRI | CYS.S | 181 |
| 230 | E2LS2GSRCSSGGSGG2TREQNRICT2 | CYS.S | 181 |
| 231 | 2LS2GSRCSSDGGSGGTREQNRICT2R | CYS.S | 181 |
| 232 | PYAPEPGSTCRLREY | LIN | 181 |
| 233 | C22SK2SPGQHAKVF2CNASMDAV2TSTSPTRC | MAT | 181 |
| 234 | CTSSTDI2RPHQI2NVCNASMDAV2TSTSPTRC | MAT | 181 |
| 235 | C22SK2SPGQHAKVF2CAV2TSTSPTRSMAPGC | MAT | 181 |
| 236 | PE2LSCGSR2SGGSGGTQACTREQNRI | CYS.S | 180 |
| 237 | GSRCSSDQVETGGSGGTREQNRICT2R | CYS.S | 180 |
| 238 | KQEG2RLCAPLGGSGGCKP2APGTFSN | CYS.S | 180 |
| 239 | PHQICNVVAIPGGSGGCTSTSPTRSMA | CYS.S | 180 |
| 240 | CLPMGPSPPAEGSTGDCAPLRK2RPGFGVARPC | MAT | 180 |
| 241 | 2LSCGSR2SSDGGSGGCTREQNRI2T2 | CYS.S | 179 |
| 242 | 2KPCAPGTFSNGGSGGTTSSTDICRPH | CYS.S | 179 |
| 243 | CQTAQM22SK2SPGQHCAFTPYAPEPGST2RLC | MAT | 179 |
| 244 | TSSTDICRPHQICNV | LIN | 178 |
| 245 | CEGARLAAPLRAGRPGC | LOOP.AA | 178 |
| 246 | CQA2TREQNRI2T2RPCAFTPYAPEPGST2RLC | MAT | 178 |
| 247 | S2GSRCSSDQVGGSGGQNRICT2RPGW | CYS.S | 177 |
| 248 | V2KPCAPGTFSGGSGGDICRPHQI2NV | CYS.S | 177 |
| 249 | 2LSCGSR2SSDGGSGGACTREQNRI2T | CYS.S | 176 |
| 250 | GSRCSSDQVETGGSGGQA2TREQNRIC | CYS.S | 176 |
| 251 | CQTAQM22SK2SPGQHCQA2TREQNRI2T2RPC | MAT | 176 |
| 252 | Y2ALSKQEGCRGGSGGKCRPGFGVARP | CYS.S | 175 |
| 253 | PCAPGTFSNTTGGSGGTDICRPHQI2N | CYS.S | 175 |
| 254 | DI2RPHQICNVGGSGGVCTSTSPTRSM | CYS.S | 174 |
| 255 | CYTQLWNWVPEGASAGC | LOOP.AA | 174 |
| 256 | GSTCRLREYYDGGSGGQMC2SK2SPGQ | CYS.S | 173 |
| 257 | QEGCRL2APLRGGSGGKCRPGFGVARP | CYS.S | 173 |
| 258 | CNASMDAV2TSTSPTRCAPLRK2RPGFGVARPC | MAT | 173 |
| 259 | CREYYDQTAQM22SK2CNASMDAV2TSTSPTRC | MAT | 173 |
| 260 | CGSR2SSDQVEGGSGGQACTREQNRI2 | CYS.S | 172 |
| 261 | CLPAQVAFTPYAPEPGCNASMDAV2TSTSPTRC | MAT | 172 |
| 262 | CLWNWVPEALSPGSRASSDQVETC | BET1 | 171 |

FIG. 2. (Con't)

| | | | |
|---|---|---|---|
| 263 | S2GSRCSSDQVGGSGGA2TREQNRICT | CYS.S | 171 |
| 264 | CSTAPSTSFLLPMGPSC | LOOP | 171 |
| 265 | CQA2TREQNRI2T2RPCAFTPYAPEPGST2RLC | MAT | 171 |
| 266 | CAV2TSTSPTRSMAPGCAPLRK2RPGFGVARPC | MAT | 171 |
| 267 | QNRI2TCRPGWYCALSKQEG2R | CYS.D | 170 |
| 268 | VPE2LS2GSRCGGSGGTREQNRICT2R | CYS.S | 170 |
| 269 | 2KPCAPGTFSNGGSGGTSSTDICRPHQ | CYS.S | 170 |
| 270 | NWVPE2LSCGSGGSGGCTREQNRI2T2 | CYS.S | 168 |
| 271 | CREYYDQTAQM22SK2CAPLRK2RPGFGVARPC | MAT | 168 |
| 272 | 2LS2GSRCSSDGGSGG2TREQNRICT2 | CYS.S | 167 |
| 273 | QEG2RLCAPLRGGSGGCKP2APGTFSN | CYS.S | 167 |
| 274 | CAPLRK2RPGFGVARPCNASMDAV2TSTSPTRC | MAT | 167 |
| 275 | DI2RPHQICNVGGSGGCTSTSPTRSMA | CYS.S | 166 |
| 276 | CQA2TREQNRI2T2RPCQA2TREQNRI2T2RPC | MAT | 166 |
| 277 | CTSSTDI2RPHQI2NVCQA2TREQNRI2T2RPC | MAT | 166 |
| 278 | CLPAQVAFTPYAPEPGCAPLRK2RPGFGVARPC | MAT | 166 |
| 279 | VPE2LSCGSR2GGSGGETQACTREQNR | CYS.S | 165 |
| 280 | CAFTPYAPEPGST2RLCAPLRK2RPGFGVARPC | MAT | 165 |
| 281 | CI2RPHQI2NVVAIPGCAPLRK2RPGFGVARPC | MAT | 165 |
| 282 | CSTSFLLPMGPSPPAECAPLRK2RPGFGVARPC | MAT | 165 |
| 283 | 2TREQNRI2TCGGSGGYCALSKQEG2R | CYS.S | 164 |
| 284 | CAPGTFSNTTSGGSGGTSSTDICRPHQ | CYS.S | 164 |
| 285 | CQTAQM22SK2SPGQHCNASMDAV2TSTSPTRC | MAT | 164 |
| 286 | CNASMDAV2TSTSPTRCNASMDAV2TSTSPTRC | MAT | 164 |
| 287 | CYTQLWNWVPE2LS2GCLSKQEG2RL2APLRKC | MAT | 164 |
| 288 | CRLREYYDQTAGGSGGQMC2SK2SPGQ | CYS.S | 163 |
| 289 | MDAVCTSTSPTRSMA | LIN | 163 |
| 290 | CAVHLPQVSTRSQHTCQA2TREQNRI2T2RPC | MAT | 163 |
| 291 | PE2LS2GSRCSGGSGGTREQNRICT2R | CYS.S | 162 |
| 292 | 2LS2GSRCSSDGGSGGEQNRICT2RPG | CYS.S | 162 |
| 293 | REQNRI2TCRPGGSGGCALSKQEG2RL | CYS.S | 161 |
| 294 | CQTAQM22SK2SPGQHCAPLRK2RPGFGVARPC | MAT | 161 |
| 295 | C2T2RPGWY2ALSKQECAPLRK2RPGFGVARPC | MAT | 161 |
| 296 | CNWVPE2LS2GSR2SSCNASMDAV2TSTSPTRC | MAT | 161 |
| 297 | RCSSDQVETQAGGSGGTREQNRICT2R | CYS.S | 160 |
| 298 | YDQTAQMCCSKCSPG | LIN | 160 |
| 299 | CSPGQHAKVF2TKTSDCAPLRK2RPGFGVARPC | MAT | 160 |
| 300 | CLSKQEG2RL2APLRKCDQVETQA2TREQNRIC | MAT | 160 |
| 301 | CSDQVETQPGTREQNRIC | BET2 | 159 |
| 302 | EQNRI2TCRPGGSGGCALSKQEG2RL | CYS.S | 159 |
| 303 | DVV2KPCAPGTGGSGGTSSTDICRPHQ | CYS.S | 159 |
| 304 | STDI2RPHQICGGSGGCTSTSPTRSMA | CYS.S | 159 |
| 305 | CPSTAPSTSFLLPMGPCNASMDAV2TSTSPTRC | MAT | 159 |
| 306 | GAVHLPQPVSTRSQH | LIN | 158 |
| 307 | CREYYDQTAQM22SK2CQA2TREQNRI2T2RPC | MAT | 158 |
| 308 | C22SK2SPGQHAKVF2CQA2TREQNRI2T2RPC | MAT | 158 |
| 309 | CGWY2ALSKQEG2RL2CQA2TREQNRI2T2RPC | MAT | 158 |
| 310 | CLSKQEG2RL2APLRKCQA2TREQNRI2T2RPC | MAT | 158 |
| 311 | CTSSTDI2RPHQI2NVCAPLRK2RPGFGVARPC | MAT | 158 |
| 312 | 2LSCGSR2SSDGGSGGTQACTREQNRI | CYS.S | 157 |
| 313 | CDQVETQA2TREQNRICAFTPYAPEPGST2RLC | MAT | 157 |
| 314 | CNASMDAV2TSTSPTRCQA2TREQNRI2T2RPC | MAT | 157 |
| 315 | PEPGSTCRLREGGSGGQMC2SK2SPGQ | CYS.S | 156 |

FIG. 2. (Con't)

| | | | |
|---|---|---|---|
| 316 | STCRLREYYDQGGSGGQMC2SK2SPGQ | CYS.S | 156 |
| 317 | LRKCRPGFGVGAPGT | LIN.AA | 156 |
| 318 | CLSKQEG2RL2APLRKCREYYDQTAQM22SK2C | MAT | 156 |
| 319 | CGWY2ALSKQEG2RL2CNASMDAV2TSTSPTRC | MAT | 156 |
| 320 | CTFSNTTSSTDI2RPHCNASMDAV2TSTSPTRC | MAT | 156 |
| 321 | SCGSR2SSDQVGGSGGTQACTREQNRI | CYS.S | 155 |
| 322 | EGCRL2APLRKGGSGGL2APLRKCRPG | CYS.S | 155 |
| 323 | TSSTDICRPHAACNV | LIN.AA | 155 |
| 324 | CRSQHTQPTPEPSTAPCAPLRK2RPGFGVARPC | MAT | 155 |
| 325 | CDQVETQA2TREQNRICQA2TREQNRI2T2RPC | MAT | 154 |
| 326 | CTSPTRSMAPGAVHLPCNASMDAV2TSTSPTRC | MAT | 154 |
| 327 | CGSR2SSDQVETQACTREQNRI | CYS.D | 153 |
| 328 | APEPGSTCRLRGGSGGQMC2SK2SPGQ | CYS.S | 153 |
| 329 | E2LSCGSR2SSGGSGGCTREQNRI2T2 | CYS.S | 153 |
| 330 | ICNVVAIPGNAGGSGGDAVCTSTSPTR | CYS.S | 153 |
| 331 | APSTSFLLPMAASPP | LIN.AA | 153 |
| 332 | CEQNRIATARPAAYAAC | LOOP.AA | 153 |
| 333 | CQVAFTPYPGEPGSTARC | BET2 | 152 |
| 334 | RPHQICNVVAIGGSGGCTSTSPTRSMA | CYS.S | 152 |
| 335 | TRSMAPGAVHLPQPV | LIN | 152 |
| 336 | QNRI2TCRPGWGGSGGCALSKQEG2RL | CYS.S | 151 |
| 337 | ALSKQEG2RLCGGSGGCKP2APGTFSN | CYS.S | 151 |
| 338 | CGVARPGTETSDVV2KCAPLRK2RPGFGVARPC | MAT | 151 |
| 339 | PCAPGTFSNTTGGSGGTSSTDICRPHQ | CYS.S | 150 |
| 340 | CAFTPYAPEPGST2RLCQA2TREQNRI2T2RPC | MAT | 150 |
| 341 | CGTETSDVV2KP2APGCAPLRK2RPGFGVARPC | MAT | 150 |

FIG. 3. Linear epitope mapping of MR2-1

| SEQ ID NO. | TNFR2 Position Nos. | Sequence | Agonist Affinity | Agonist Reading |
|---|---|---|---|---|
| 342 | 45-229 | YYDQTAQMCCSKCSPGQHAKVFCTKTSDTVCDS CEDSTYTQLWNWVPECLSCGSRCSSDQVETQAC TREQNRICTCRPGWYCALSKQEGCRLCAPLRKC RPGFGVARPGTETSDVVCKPCAPGTFSNTTSSTD ICRPHQICNVVAIPGNASMDAVCTSTSPTRSMAPG AVHLPQPVSTRSQHTQP | 4+ | 1.2 |
| 343 | 23-42 | LPAQVAFTPYAPEPGSTCRL | - | 0 |
| 344 | 31-50 | PYAPEPGSTCRLREYYDQTA | - | 0 |
| 345 | 39-58 | TCRLREYYDQTAQMCCSKCS | - | 0 |
| 346 | 48-67 | QTAQMCCSKCSPGQHAKVFC | 1+ | 0 |
| 347 | 56-75 | KCSPGQHAKVFCTKTSDTVC | - | 0 |
| 348 | 64-83 | KVFCTKTSDTVCDSCEDSTY | - | 0 |
| 349 | 72-91 | DTVCDSCEDSTYTQLWNWVP | - | 0 |
| 350 | 80-99 | DSTYTQLWNWVPECLSCGSR | - | 0 |
| 351 | 88-107 | NWVPECLSCGSRCSSDQVET | - | 0 |
| 352 | 96-115 | CGSRCSSDQVETQACTREQN | - | 0 |
| 353 | 104-123 | QVETQACTREQNRICTCRPG | - | 0 |
| 354 | 112-131 | REQNRICTCRPGWYCALSKQ | 2+ | 0 |
| 355 | 120-139 | CRPGWYCALSKQEGCRLCAP | 1+ | 0 |
| 356 | 128-147 | LSKQEGCRLCAPLRKCRPGF | 2+- | 0 |
| 357 | 130-149 | KQEGCRLCAPLRKCRPGFGV | 2+- | 0 |
| 358 | 136-155 | LCAPLRKCRPGFGVARPGTE | - | 0 |
| 359 | 144-163 | RPGFGVARPGTETSDVVCKP | - | 0 |
| 360 | 152-171 | PGTETSDVVCKPCAPGTFSN | - | 0 |
| 361 | 160-179 | VCKPCAPGTFSNTTSSTDIC | - | 0 |
| 362 | 168-187 | TFSNTTSSTDICRPHQICNV | - | 0 |
| 363 | 176-196 | TDICRPHQICNVVAIPGNAS | - | 0 |
| 364 | 187-203 | ICNVVAIPGNASMDAVCTST | - | 0 |
| 365 | 192-211 | GNASMDAVCTSTSPTRSMAP | - | 0 |

FIG. 4. Visualization of epitopes within TNFR2
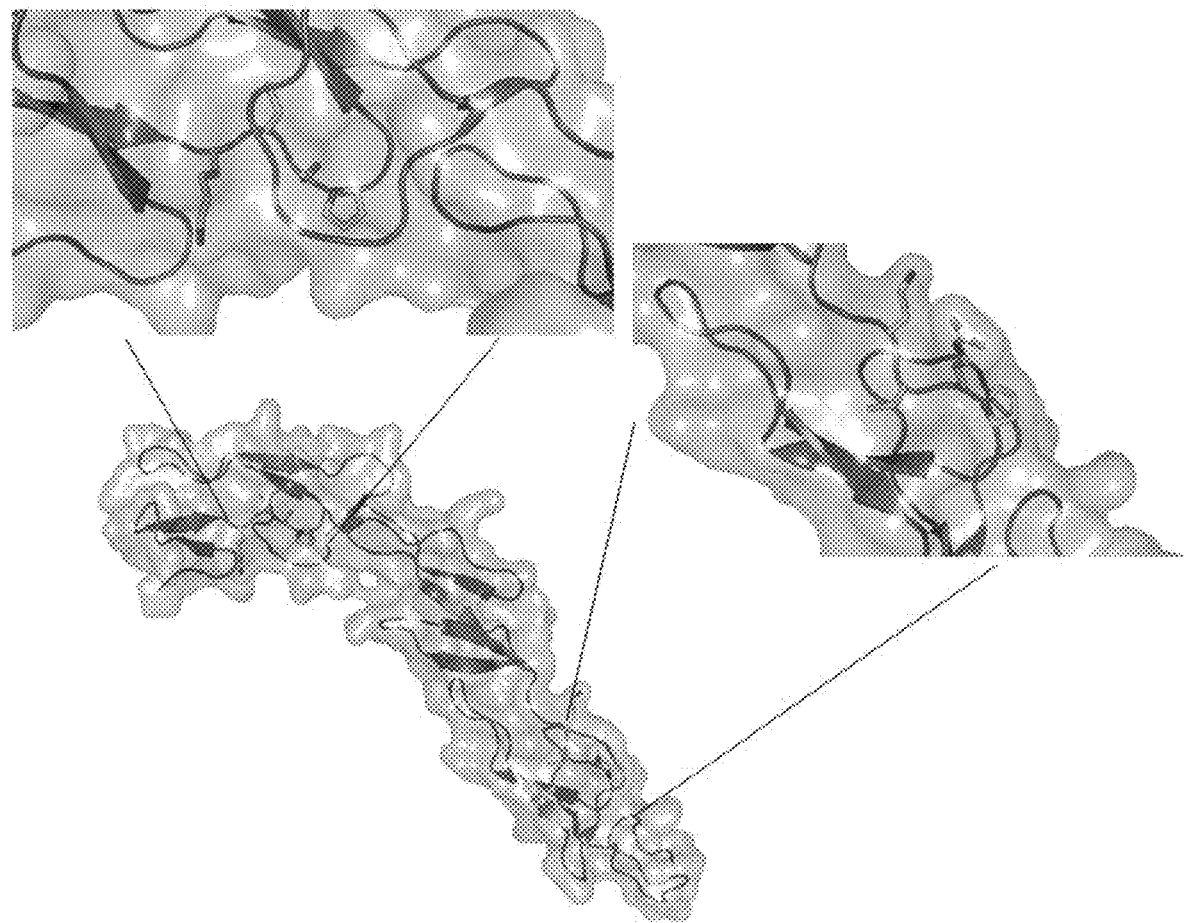

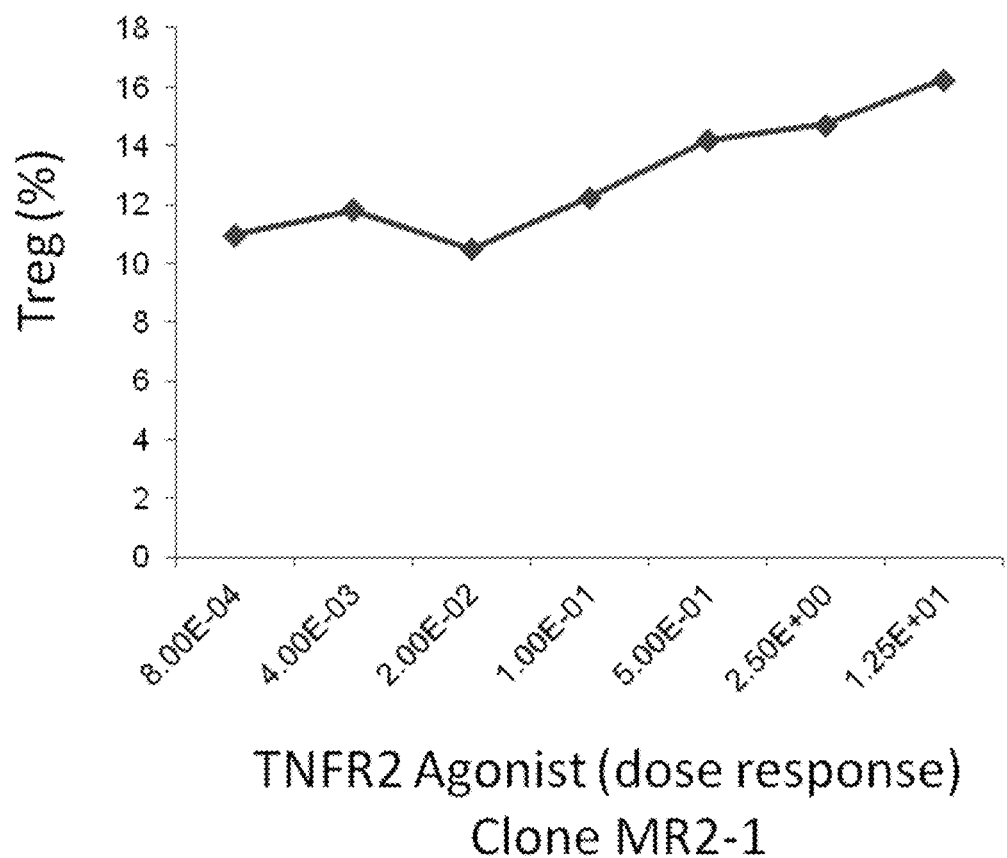
FIG. 5. T-reg induction by MR2-1

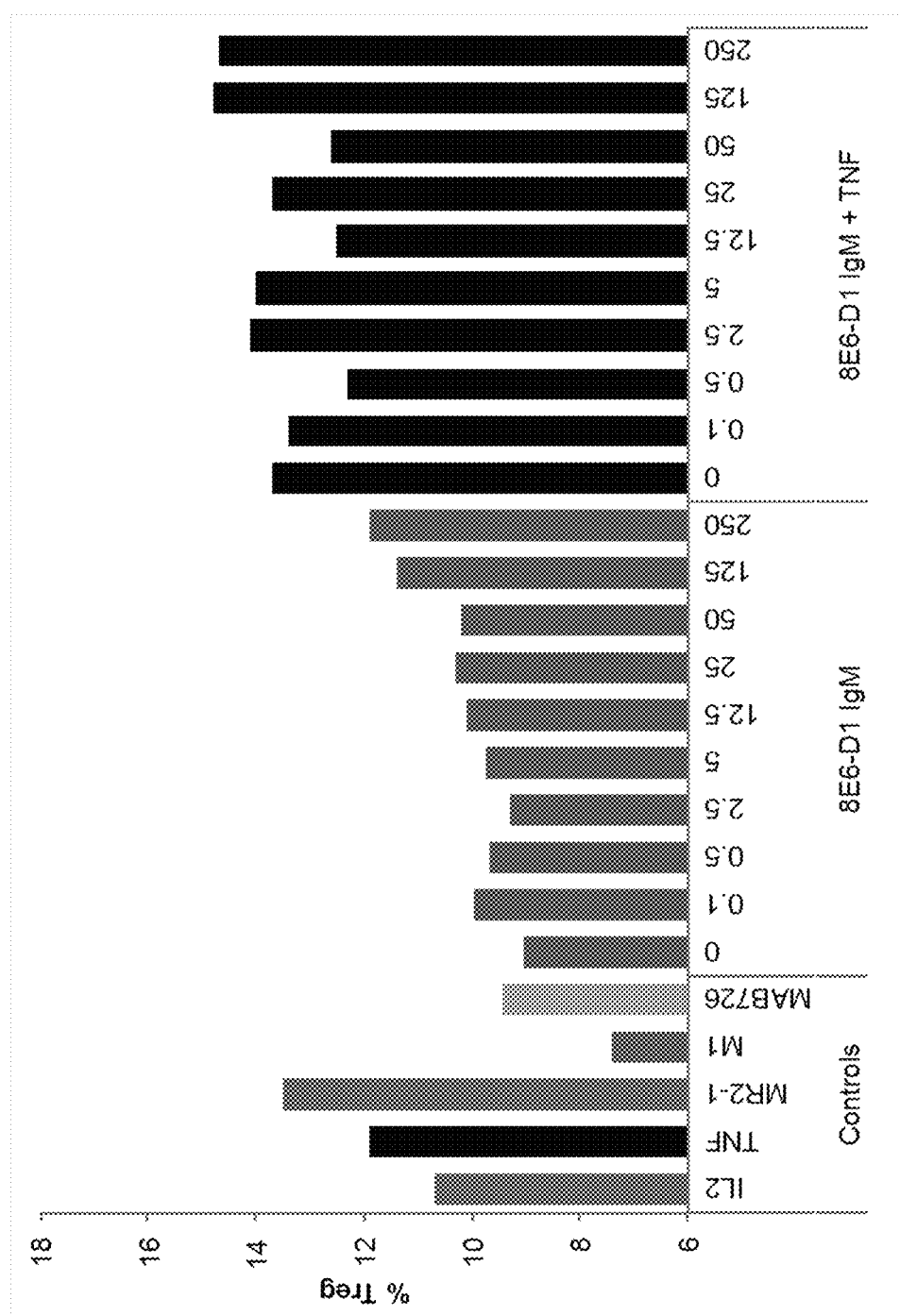
FIG. 6A. T-reg induction by 8E6.D1

AGONISTIC ANTI-TUMOR NECROSIS FACTOR RECEPTOR 2 ANTIBODIES

SEQUENCE LISTING

This application contains a Sequence Listing which has been filed electronically in ASCII format and is hereby incorporated by reference in its entirety. Said ASCII copy, created on Dec. 23, 2021, is named 00786-574003_Sequence_Listing_12_23_21_ST25.txt and is 228,007 bytes in size.

FIELD OF THE INVENTION

The invention relates to antibodies capable of potentiating tumor necrosis factor receptor 2 signalling and their use for modulating the activity of T-reg cells, and provides therapies for immunological disorders or conditions, such as multiple sclerosis, asthma, allergic reactions, graft-versus-host disease, and transplantation graft rejection.

BACKGROUND OF THE INVENTION

Maintaining control of the cell-mediated and humoral immune responses is an important facet of healthy immune system activity. The aberrant regulation of T-cell and B-cell driven immune reactions has been associated with a wide array of human diseases, as the inappropriate mounting of an immune response against various self and foreign antigens plays a causal role in such pathologies as autoimmune disorders, asthma, allergic reactions, graft-versus-host disease, transplantation graft rejection, and a variety of other immunological disorders. These diseases are mediated by T- and B-lymphocytes that exhibit reactivity against self antigens and those derived from non-threatening sources, such as allergens or transplantation allografts. T-reg cells (T-reg cells) have evolved in order to inhibit the activity of immune cells that are cross-reactive with "self" major histocompatability complex (MHC) proteins and other benign antigens. T-reg cells represent a heterogeneous class of T-cells that can be distinguished based on their unique surface protein presentation. The most well-understood populations of T-reg cells include CD4+, CD25+, FoxP3+T-reg cells and CD17+ T-reg cells. The precise mechanisms by which these cells mediate suppression of autoreactive T-cells is the subject of ongoing investigations, though it has been shown that certain classes of T-reg cells inhibit production of the proliferation-inducing cytokine IL-2 in target T-cells and may additionally sequester IL-2 from autoreactive cells by virtue of the affinity of CD25 (a subdomain of the IL-2 receptor) for IL-2 (Josefowicz et al., Ann. Rev. Immun., 30:531-564 (2012)). Moreover, it has been shown that CD4+, CD25+, FoxP3+ T-reg cells are also present in B-cell-rich areas and are capable of directly suppressing immunoglobulin production independent of their ability to attenuate TH2-cell activity (Lim et al., J. Immunol., 175:4180-4183 (2005)).

Tumor necrosis factor receptor (TNFR) subtypes 1 and 2 have been identified on the T-reg cell surface as signal transduction molecules that dictate cell fate. The activation of TNFR1, for instance, potentiates the caspase signaling cascade and terminates in T-reg apoptosis, while activation of TNFR2 induces signaling through the mitogen-activated protein kinase (MAPK) signaling pathway, which orchestrates the TRAF2/3- and $NF_KB$-mediated transcription of genes that promote cell proliferation and escape from apoptosis. Due to its role in directing cell survival and growth, TNFR2 represents an attractive target for expanding populations of T-reg cells as a strategy for treating immunological disorders. There is currently a need for therapies that can augment T-reg cell survival and proliferation for use in treatments targeting such diseases as autoimmune disorders, graft-versus-host disease, allograft rejection, allergic reactions, and asthma, among others.

SUMMARY OF THE INVENTION

The invention provides TNFR2 agonist antibodies and antigen-binding fragments thereof capable of binding TNFR2 and promoting TNFR2 signaling, as well as methods of producing such antibodies and antigen-binding fragments thereof, and methods of treating a subject suffering from an immunological disease by administering such antibodies and antigen-binding fragments thereof.

In a first aspect, the invention provides a TNFR2 agonist antibody or antigen-binding fragment thereof capable of specifically binding TNFR2 (e.g., human TNFR2), e.g., in a human or in a non-human animal. The antibody or antigen-binding fragment thereof specifically binds an epitope containing amino acids 56-60 of SEQ ID NO: 366 (KCSPG) and does not specifically bind an epitope containing amino acids 142-146 of SEQ ID NO: 366 (KCRPG). The antibody or antigen-binding fragment thereof may also lack specific binding for another tumor necrosis factor receptor (TNFR) superfamily member, such as TNFR1, RANK, CD30, CD40, Lymphotoxin beta receptor (LT-βR), OX40, Fas receptor, Decoy receptor 3, CD27, 4-1BB, Death receptor 4, Death receptor 5, Decoy receptor 1, Decoy receptor 2, Osteoprotegrin, TWEAK receptor, TACI, BAFF receptor, Herpesvirus entry mediator, Nerve growth factor receptor, B-cell maturation antigen, Glucocorticoid-induced TNFR-related, TROY, Death receptor 6, Death receptor 3, and Ectodysplasin A2 receptor. TNFR2 agonist antibodies and antigen-binding fragments thereof that specifically bind non-human TNFR2 exhibit specific binding to an epitope containing amino acids KCPPG, but do not specifically bind an epitope containing amino acids KCGPG and/or KCSPG. In addition, TNFR2 agonist antibodies and antigen-binding fragments thereof that specifically bind non-human TNFR2 may also lack specific binding to a TNFR superfamily member other than TNFR2.

In an additional aspect, the invention provides a TNFR2 agonist antibody or antigen-binding fragment thereof capable of specifically binding TNFR2, such as human TNFR2, that specifically binds an epitope containing amino acids 56-60 of SEQ ID NO: 366 (KCSPG) and does not specifically bind another TNFR superfamily member. In certain embodiments, the antibody or antigen-binding fragment thereof does not bind an epitope containing amino acids 142-146 of SEQ ID NO: 366 (KCRPG). In additional cases, the antibody or antigen-binding fragment thereof does not specifically bind any other epitope within TNFR2.

The invention also provides a TNFR2 agonist antibody or antigen-binding fragment thereof capable of specifically binding TNFR2, such as human TNFR2, that specifically binds an epitope containing amino acids 56-60 of SEQ ID NO: 366 (KCSPG) and is capable of promoting the proliferation of a population of T-regulatory (T-reg) cells. In another aspect, the invention encompasses a TNFR2 agonist antibody or antigen-binding fragment thereof capable of specifically binding TNFR2, such as human TNFR2, that specifically binds an epitope containing amino acids 56-60 of SEQ ID NO: 366 (KCSPG) and is capable of promoting the death of one or more CD8+ T-cells. In yet another aspect, the invention provides a TNFR2 agonist antibody or antigen-binding fragment thereof capable of specifically binding TNFR2, such as human TNFR2, that specifically binds an epitope containing amino acids 56-60 of SEQ ID NO: 366 (KCSPG) and is capable of promoting an increase in the level of one or more mRNA molecules encoding a protein selected from the group consisting of cIAP2, TRAF2, Etk, VEGFR2, P13K, Akt, a protein involved in the angiogenic pathway, an IKK complex, RIP, NIK, MAP3K, a protein involved in the NFkB pathway, NIK, JNK, AP-1, a MEK (e.g., MEK1, MEK7), MKK3, NEMO, IL2R, Foxp3, IL2, TNF, and lymphotoxin (e.g., lymphotoxin α and lymphotoxin β). In another aspect, the invention provides a TNFR2 agonist antibody or antigen-binding fragment thereof capable of specifically binding TNFR2, such as human TNFR2, that specifically binds an epitope amino acids 56-60 of SEQ ID NO: 366 (KCSPG) and is capable of promoting an increase in the level of one or more proteins selected from the group consisting of cIAP2, TRAF2, Etk, VEGFR2, P13K, Akt, a protein involved in the angiogenic pathway, an IKK complex, RIP, NIK, MAP3K, a protein involved in the NFkB pathway, NIK, JNK, AP-1, a MEK (e.g., MEK1, MEK7), MKK3, NEMO, IL2R, Foxp3, IL2, TNF, and lymphotoxin (e.g., lymphotoxin α and lymphotoxin β).

The TNFR2 agonist antibody or antigen-binding fragment thereof of the invention specifically binds an epitope within human TNFR2 containing at least five discontinuous or continuous residues within amino acids 96-154 of SEQ ID NO: 366 (CGSRCSSDQVETQACTREQNRICTCRPGWYCALSKQEGCRLCAPLRKCRPGFGVARPGT). Additionally or alternatively, the antibody or antigen-binding fragment thereof binds an epitope within amino acids 111-150 of SEQ ID NO: 366 (TREQNRICTCRPGWYCALSKQEGCRLCAPLRKCRPGFGVA). In other cases, the antibody or antigen-binding fragment thereof binds an epitope within amino acids 115-142 of SEQ ID NO: 366 (NRICTCRPGWYCALSKQEGCRLCAPLRK). Antibodies and antigen-binding fragments of the invention may also bind an epitope within amino acids 122-136 of SEQ ID NO: 366 (PGWYCALSKQEGCRL), and/or an epitope within amino acids 101-107 of SEQ ID NO: 366 (SSDQVET). In further embodiments, the antibody or antigen-binding fragment thereof of the invention binds an epitope within amino acids 48-67 of SEQ ID NO: 366 (QTAQMCCSKCSPGQHAKVFC). In some cases, the antibody or antigen-binding fragment thereof of the invention specifically binds the epitope containing amino acids 56-60 of SEQ ID NO: 366 (KCSPG) with a $K_D$ of less than about 10 nM.

In another aspect, the invention provides a TNFR2 agonist antibody or antigen-binding fragment thereof that specifically binds to an epitope within or containing the amino acid sequence of any one of SEQ ID NOs: 1-341, 346, and 367 and that is capable of specifically binding human TNFR2 but does not specifically bind another TNFR superfamily member.

The TNFR2 agonist antibody or antigen-binding fragment thereof may activate TNFR2 signaling. The antibody or antigen-binding fragment thereof may also bind TNFR2 with a $K_D$ of no greater than about 10 nM (e.g., with a $K_D$ of no greater than about 1 nM). Additionally or alternatively, the antibody or antigen-binding fragment thereof binds TNFR2 to form an antibody-antigen complex with a $k_{on}$ of at least about $10^4$ M$^{-1}$s$^{-1}$ (e.g., with a $k_{on}$ of at least about $10^5$ M$^{-1}$s$^{-1}$). In some cases, the antibody or antigen-binding fragment thereof binds TNFR2 to form an antibody-antigen complex, in which the complex dissociates with a $k_{off}$ of no greater than about $10^{-3}$s$^{-1}$ (e.g., with a $k_{off}$ of no greater than about $10^{-4}$s$^{-1}$). In additional embodiments, the antibody or antigen-binding fragment thereof is capable of promoting the proliferation of a population of T-regulatory (T-reg) cells (e.g., in the presence of TNFα).

In some embodiments, the antibody or antigen-binding fragment thereof has a non-native constant region. For instance, the antibody may be a monoclonal antibody that has a non-native constant region. In some embodiments, the antibody or antigen-binding fragment thereof is an isolated, non-murine antibody.

In another aspect, the invention provides a method of identifying a TNFR2 agonist antibody or antigen-binding fragment thereof, the method including the steps of:
(a) contacting a mixture of antibodies or fragments thereof with at least one peptide having the amino acid sequence of any one of SEQ ID NOs: 1-341, 346, and 367; and
(b) separating antibodies or fragments thereof that specifically bind the peptide from the mixture, thereby producing an enriched antibody mixture comprising at least one TNFR2 agonist antibody or antigen-binding fragment thereof.

In some cases, the method includes the step of determining the amino acid sequence of one or more of the antibodies or antigen-binding fragments thereof in the enriched antibody mixture. In certain embodiments, the peptide is bound to a surface. Additionally or alternatively, the antibody or antigen-binding fragment thereof is expressed on the surface of a phage, bacterial cell, or yeast cell. In other cases, the antibody or antigen-binding fragment thereof is expressed as one or more polypeptide chains non-covalently bound to ribosomes or covalently bound to mRNA or cDNA. The peptide may be conjugated to a detectable label, such as a fluorescent molecule (e.g., green fluorescent protein, cyan fluorescent protein, yellow fluorescent protein, red fluorescent protein, phycoerythrin, allophycocyanin, hoescht, 4',6-diamidino-2-phenylindole (DAPI), propidium iodide, fluorescein, coumarin, rhodamine, tetramethylrhoadmine, and cyanine) or an epitope tag (e.g., maltose-binding protein, glutathione-S-transferase, a poly-histidine tag, a FLAG-tag, a myc-tag, human influenza hemagglutinin (HA) tag, biotin, and streptavidin). In some embodiments, steps (a) and (b) described above are sequentially repeated one or more times.

In additional embodiments of the invention, the method further includes the steps of:
i) exposing the enriched antibody mixture to at least one peptide containing the amino acid sequence of a TNFR superfamily member other than TNFR2; and retaining antibodies or fragments thereof that do not specifically bind the peptide, thereby producing a TNFR2-specific antibody mixture containing at least one TNFR2 agonist antibody or antigen-binding fragment thereof that does not specifically bind a TNFR superfamily member other than TNFR2; and/or
ii) exposing the enriched antibody mixture to at least one peptide containing amino acids 142-146 of SEQ ID NO: 366 (KCRPG); and retaining antibodies or fragments thereof that do not specifically bind the peptide, thereby producing an antibody mixture containing at least one TNFR2 agonist antibody or antigen-binding fragment thereof that does not specifically bind a peptide containing amino acids 142-146 of SEQ ID NO: 366 (KCRPG).

In some cases, the method includes performing steps (i) and (ii) in either order.

In another aspect, the invention provides a method of producing a TNFR2 agonist antibody or antigen-binding fragment thereof by immunizing a non-human mammal with a peptide containing the sequence of any one of SEQ ID NOs: 1-341, 346, and 367 and collecting serum containing the TNFR2 agonist antibody or antigen-binding fragment thereof, such that the antibody or antigen-binding fragment thereof is capable of specifically binding an epitope containing amino acids 56-60 of SEQ ID NO: 366 (KCSPG). In some cases, the non-human mammal is selected from the group consisting of a rabbit, mouse, rat, goat, guinea pig, hamster, horse, primate, and sheep. Additionally or alternatively, the peptide contains the amino acid sequence PGWY-CALSKQEGCRL (SEQ ID NO: 11).

In a further aspect, the invention provides a TNFR2 agonist antibody or antigen-binding fragment thereof produced by any of the above-described methods. In some cases, the antibody or antigen-binding fragment thereof specifically binds an epitope containing amino acids 56-60 of SEQ ID NO: 366 (KCSPG) and does not specifically bind an epitope containing amino acids 142-146 of SEQ ID NO: 366 (KCRPG). Additionally or alternatively, the antibody or antigen-binding fragment thereof specifically binds an epitope containing amino acids 56-60 of SEQ ID NO: 366 (KCSPG) and does not specifically bind a TNFR superfamily member other than TNFR2. In some cases, the antibody or antigen-binding fragment thereof activates TNFR2 signaling. In additional embodiments, the antibody or antigen-binding fragment thereof binds TNFR2 with a $K_D$ of no greater than about 10 nM (e.g., with a $K_D$ of no greater than about 1 nM). Additionally or alternatively, the antibody or antigen-binding fragment thereof binds TNFR2 to form an antibody-antigen complex with a $k_{on}$ of at least about $10^4$ $M^{-1}s^{-1}$ (e.g., with a $k_{on}$ of at least about $10^5$ $M^{-1}s^{-1}$). In some cases, the antibody or antigen-binding fragment thereof binds TNFR2 to form an antibody-antigen complex, in which the complex dissociates with a $k_{off}$ of no greater than about $10^{-3}s^{-1}$ (e.g., with a $k_{off}$ of no greater than about $10^{-4}s^{-1}$). In additional embodiments, the antibody or antigen-binding fragment thereof is capable of promoting the proliferation of a population of T-regulatory (T-reg) cells (e.g., in the presence of TNFα).

In some cases, the TNFR2 agonist antibody or antigen-binding fragment thereof of the invention is a monoclonal antibody or antigen-binding fragment thereof, a polyclonal antibody or antigen-binding fragment thereof, a human antibody or antigen-binding fragment thereof, a humanized antibody or antigen-binding fragment thereof, a primatized antibody or antigen-binding fragment thereof, a bispecific antibody or antigen-binding fragment thereof, or a multispecific antibody or antigen-binding fragment thereof. In other embodiments, the antibody or antigen-binding fragment thereof of the invention is a dual-variable immunoglobulin domain, a monovalent antibody or antigen-binding fragment thereof, a chimeric antibody or antigen-binding fragment thereof, a single-chain Fv molecule (scFv), a diabody, a triabody, a nanobody, an antibody-like protein scaffold, a domain antibody, a Fv fragment, a Fab fragment, a $F(ab')_2$ molecule, or a tandem scFv (taFv).

In further embodiments, the TNFR2 agonist antibody of the invention may contain an immunoglobulin, such as an immunoglobulin of subtype IgG, IgM, IgA, IgD, or IgE.

In some embodiments, the antibody or antigen-binding fragment thereof has a non-native constant region. For instance, the antibody may be a monoclonal antibody that has a non-native constant region. In some embodiments, the antibody or antigen-binding fragment thereof is an isolated, non-murine antibody.

In another aspect, the invention provides a pharmaceutical composition containing a TNFR2 agonist antibody or antigen-binding fragment thereof of the invention and a pharmaceutically acceptable carrier or excipient. The pharmaceutical composition of the invention may also contain an additional therapeutic agent, such as TNFα or BCG, or an immunotherapy agent, such as an anti-CTLA-4 agent, an anti-PD-1 agent, an anti-PD-L1 agent, an anti-PD-L2 agent, a TNF-α cross-linking agent, a TRAIL cross-linking agent, a CD27 agent, a CD30 agent, a CD40 agent, a 4-1BB agent, a GITR agent, an OX40 agent, a TRAILR1 agent, a TRAILR2 agent, or a TWEAKR agent.

The invention also provides a polynucleotide encoding a TNFR2 agonist antibody or antigen-binding fragment thereof of the invention, as well as a vector containing such a polynucleotide. In some embodiments, the vector is an expression vector, such as a eukaryotic expression vector. In other embodiments, the expression vector is a viral vector, such as an adenovirus (Ad, e.g., a serotype 5, 26, 35, or 48 adenovirus), retrovirus (e.g., a γ-retrovirus or a lentivirus), poxvirus, adeno-associated virus, baculovirus, herpes simplex virus, or a vaccinia virus (e.g., a modified vaccinia Ankara (MVA)).

In a further aspect, the invention encompasses a host cell containing a vector of the invention. In some cases, the host cell is a prokaryotic cell. In other embodiments, the vector is a eukaryotic cell, such as a mammalian cell (e.g., a CHO cell, a DHFR CHO cell, a NSO myeloma cell, a COS cell, a 293 cell, or a SP2/0 cell).

The invention additionally provides a method of producing a TNFR2 agonist antibody or antigen-binding fragment described above, the method including the steps of expressing a polynucleotide encoding the antibody or antigen-binding fragment thereof in a host cell and recovering the antibody or antigen-binding fragment thereof from host cell medium.

In another aspect, the invention provides a method of inhibiting an immune response mediated by a B cell or a CD8+ T cell in a subject and a method of treating an immunological disease in a subject, the methods individually including the step of administering to the subject a TNFR2 agonist antibody or antigen binding fragment of the invention, a pharmaceutical composition of the invention, a polynucleotide of the invention, a vector of the invention, or a host cell of the invention.

In some embodiments, the antibody or antigen-binding fragment thereof has a non-native constant region. For instance, the antibody may be a monoclonal antibody that has a non-native constant region. In some embodiments, the antibody or antigen-binding fragment thereof is an isolated, non-murine antibody.

In some cases, the subject is in need of tissue or organ repair or regeneration (e.g., repair or regeneration of a pancreas, salivary gland, pituitary gland, kidney, heart, lung, hematopoietic system, cranial nerves, heart, aorta, olfactory gland, ear, nerves, structures of the head, eye, thymus, tongue, bone, liver, small intestine, large intestine, gut, lung, brain, skin, peripheral nervous system, central nervous system, spinal cord, breast, embryonic structures, embryos, and testes). Administration of a TNFR2 agonist antibody or antigen-binding fragment thereof stimulates or allows repair and/or regeneration of the tissue or organ.

The immunological disease to be treated may be selected from the group consisting of an autoimmune disease, a neurological condition, an allergy, asthma, macular degeneration, muscular atrophy, a disease related to miscarriage, atherosclerosis, bone loss, a musculoskeletal disease, obesity, a graft-versus-host disease, and an allograft rejection. In other embodiments, the autoimmune disease is selected from the group consisting of type I diabetes, Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Essential Mixed Cryoglobulinemia, Fibromyalgia-Fibromyositis, Graves' Disease, Guillain-Barré, Hashimoto's Thyroiditis, Hypothyroidism, Idiopathic Pulmonary Fibrosis, Idiopathic Thrombocytopenia Purpura (ITP), IgA Nephropathy, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, and Wegener's Granulomatosis.

In other embodiments, the neurological condition is selected from the group consisting of a brain tumor, a brain metastasis, a spinal cord injury, schizophrenia, epilepsy, Amyotrophic lateral sclerosis (ALS), Parkinson's disease, Alzheimer's disease, Huntington's disease, and stroke.

In some cases, the allergy is selected from the group consisting of food allergy, seasonal allergy, pet allergy, hives, hay fever, allergic conjunctivitis, poison ivy allergy oak allergy, mold allergy, drug allergy, dust allergy, cosmetic allergy, and chemical allergy.

In other embodiments, the allograft rejection is selected from the group consisting of skin graft rejection, bone graft rejection, vascular tissue graft rejection, ligament graft rejection (e.g., cricothyroid ligament graft rejection, periodontal ligament graft rejection, suspensory ligament of the lens graft rejection, palmar radiocarpal ligament graft rejection, dorsal radiocarpal ligament graft rejection, ulnar collateral ligament graft rejection, radial collateral ligament graft rejection, suspensory ligament of the breast graft rejection, anterior sacroiliac ligament graft rejection, posterior sacroiliac ligament graft rejection, sacrotuberous ligament graft rejection, sacrospinous ligament graft rejection, inferior pubic ligament graft rejection, superior pubic ligament graft rejection, anterior cruciate ligament graft rejection, lateral collateral ligament graft rejection, posterior cruciate ligament graft rejection, medial collateral ligament graft rejection, cranial cruciate ligament graft rejection, caudal cruciate ligament graft rejection, and patellar ligament graft rejection), and organ graft rejection.

In still other embodiments, the graft-versus-host disease arises from a bone marrow transplant or one or more blood cells selected from the group consisting of hematopoietic stem cells, common myeloid progenitor cells, common lymphoid progenitor cells, megakaryocytes, monocytes, basophils, eosinophils, neutrophils, macrophages, T-cells, B-cells, natural killer cells, and dendritic cells.

In some cases, the above-described methods include administering to the subject an additional therapeutic agent, such as TNFα or BCG. Additionally or alternatively, the subject may be administered an immunotherapy agent, such as an anti-CTLA-4 agent, an anti-PD-1 agent, an anti-PD-L1 agent, an anti-PD-L2 agent, a TNF-α cross-linking agent, a TRAIL cross-linking agent, a CD27 agent, a CD30 agent, a CD40 agent, a 4-1BB agent, a GITR agent, an OX40 agent, a TRAILR1 agent, a TRAILR2 agent, or a TWEAKR agent.

In certain embodiments of the above-described methods, the subject is a mammal (e.g., a human). Additionally or alternatively, the antibody may be 8E6.D1 or a humanized antibody or antigen-binding fragment thereof containing one or more (or all) heavy chain and/or light chain CDRs of 8E6.D1.

The invention also provides a kit containing an agent, such as a TNFR2 agonist antibody or antigen binding fragment of the invention, a pharmaceutical composition of the invention, a polynucleotide of the invention, a vector of the invention, and/or a host cell of the invention. In some cases, the kit includes instructions for transfecting a vector of the invention into a host cell. Additionally, the kit may include instructions for expressing a TNFR2 agonist antibody or antigen-binding fragment thereof of the invention in the host cell, and/or a reagent that can be used to express the antibody or antigen-binding fragment thereof in the host cell. In other embodiments, the kit includes instructions for administering the agent to a subject (e.g., a mammalian subject, such as a human) in order to treat an immunological disease. In other embodiments, the kit includes instructions for making or using the agent.

Definitions

As used herein, the term "about" refers to a value that is no more than 10% above or below the value being described. For example, the term "about 5 nM" indicates a range of from 4.5 nM to 5.5 nM.

As used herein, the terms "agonist TNFR2 antibody" and "agonistic TNFR2 antibody" refer to TNFR2 antibodies that are capable of promoting or increasing activation of TNFR2 and/or potentiating one or more signal transduction pathways mediated by TNFR2. For example, agonistic TNFR2 antibodies of the invention can promote or increase the proliferation of a population of T-reg cells. Agonistic TNFR2 antibodies of the invention may promote or increase TNFR2 activation by binding TNFR2, e.g., so as to induce a conformational change that renders the receptor biologically active. For instance, agonistic TNFR2 antibodies may nucleate the trimerization of TNFR2 in a manner similar to the interaction between TNFR2 and its cognate ligand, TNFα, thus inducing TNFR2-mediated signalling. Agonistic TNFR2 antibodies of the invention may be capable of inducing the proliferation of CD4+, CD25+, FOXP3+ T-reg cells. Agonistic TNFR2 antibodies of the invention may also be capable of suppressing the proliferation of cytotoxic T lymphocytes (e.g., CD8+ T-cells), e.g., through activation of immunomodulatory T-reg cells or by directly binding TNFR2 on the surface of an autoreactive cytotoxic T-cell and inducing apoptosis. Unless otherwise noted, the terms "agonist TNFR2 antibody" and "agonistic TNFR2 antibody" also include antibody fragments, e.g., those described below, that retain the ability to bind TNFR2 and potentiate TNFR2 signal transduction. An agonist TNFR2 antibody or fragment thereof may specifically bind TNFR2 without exhibiting specific binding for another receptor of the tumor necrosis factor receptor (TNFR) superfamily.

As used herein, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bi-tri- and quad-specific antibodies, diabodies, triabodies, and tetrabodies), and antigen-binding fragments of antibodies, including e.g., Fab', F(ab')$_2$, Fab, Fv, recombinant IgG (rIgG) fragments, and scFv fragments. Moreover, unless otherwise indicated, the term "monoclonal antibody" (mAb) is meant to include both intact molecules, as well as antibody fragments (such as, for example, Fab and F(ab')$_2$ fragments) that are capable of specifically binding to a target protein. Fab and F(ab')$_2$ fragments lack the Fc fragment of an intact antibody, clear more rapidly from the circulation of the animal, and may have less non-specific tissue binding than an intact antibody (see Wahl et al., J. Nucl. Med. 24:316, 1983; incorporated herein by reference).

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be, e.g., a Fab, F(ab')$_2$, scFv, SMIP, diabody, a triabody, an affibody, a nanobody, an aptamer, or a domain antibody. Examples of binding fragments encompassed by the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., Nature 341:544-546, 1989), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv); see, e.g., Bird et al., Science 242:423-426, 1988, and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the terms "anti-tumor necrosis factor receptor 2 antibody," "TNFR2 antibody," "anti-TNFR2 antibody portion," and/or "anti-TNFR2 antibody fragment" and the like include any protein or peptide-containing molecule that includes at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that is capable of specifically binding to TNFR2. TNFR2 antibodies also include antibody-like protein scaffolds, such as the tenth fibronectin type III domain ($^{10}$Fn3), which contains BC, DE, and FG structural loops similar in structure and solvent accessibility to antibody CDRs. The tertiary structure of the $^{10}$Fn3 domain resembles that of the variable region of the IgG heavy chain, and one of skill in the art can graft, e.g., the CDRs of a TNFR2 monoclonal antibody onto the fibronectin scaffold by replacing residues of the BC, DE, and FG loops of $^{10}$Fn3 with residues from the CDRH-1, CDRH-2, or CDRH-3 regions of a TNFR2 monoclonal antibody. The use of $^{10}$Fn3 domains as scaffolds for epitope grafting is described, e.g., in WO 2000/034784, the disclosure of which is incorporated herein by reference. Additional scaffold proteins encompassed by the term "anti-tumor necrosis factor receptor 2 antibody," "TNFR2 antibody," and the like include peptide-Fc fusion proteins (described, e.g., in WO 2012/122378; as well as in U.S. Pat. No. 8,633,297; the disclosures of each of which are incorporated herein by reference).

As used herein, the term "bispecific antibodies" refers to monoclonal, often human or humanized antibodies that have binding specificities for at least two different antigens. Bispecific TNFR2 antibodies of the invention may have binding specificities that are directed towards TNFR2 and any other antigen, e.g., for a cell-surface protein, receptor, receptor subunit, tissue-specific antigen, virally derived protein, virally encoded envelope protein, bacterially derived protein, or bacterial surface protein, etc. A bispecific antibody may also be an antibody or antigen-binding fragment thereof that includes two separate antigen-binding domains (e.g., two scFvs joined by a linker). The scFvs may bind the same antigen or different antigens.

As used herein, the term "chimeric" antibody refers to an antibody having variable sequences derived from an immunoglobulin of one source organism, such as rat or mouse, and constant regions derived from an immunoglobulin of a different organism (e.g., a human). Methods for producing chimeric antibodies are known in the art. See, e.g., Morrison, 1985, Science 229(4719): 1202-7; Oi et al, 1986, BioTechniques 4:214-221; Gillies et al, 1985, J. Immunol. Methods 125:191-202; U.S. Pat. Nos. 5,807,715; 4,816,567; and 4,816,397; the disclosures of each of which are incorporated herein by reference.

As used herein, the term "complementarity determining region" (CDR) refers to a hypervariable region found both in the light chain and the heavy chain variable domains. The more highly conserved portions of variable domains are called the framework regions (FRs). As is appreciated in the art, the amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The invention includes antibodies comprising modifications in these hybrid hypervariable positions. The variable domains of native heavy and light chains each comprise four framework regions that primarily adopt a β-sheet configuration, connected by three CDRs, which form loops that connect, and in some cases form part of, the β-sheet structure. The CDRs in each chain are held together in close proximity by the FR regions in the order FR1-CDR1-FR2-CDR2-FR3-CDR3-FR4 and, with the CDRs from the other antibody chains, contribute to the formation of the target binding site of antibodies (see Kabat et al, Sequences of Proteins of Immunological Interest (National Institute of Health, Bethesda, Md. 1987; incorporated herein by reference). As used herein, numbering of immunoglobulin amino acid residues is done according to the immunoglobulin amino acid residue numbering system of Kabat et al, unless otherwise indicated.

As used herein, the terms "conservative mutation," "conservative substitution," or "conservative amino acid substitution" refer to a substitution of one or more amino acids for one or more different amino acids that exhibit similar physicochemical properties, such as polarity, electrostatic charge, and/or steric volume. These properties are summarized for each of the twenty naturally-occurring amino acids in Table 1 below.

TABLE 1

Representative physicochemical properties of naturally-occurring amino acids

| Amino Acid | 3 Letter Code | 1 Letter Code | Side-chain Polarity | Charge of side chain at pH of 7.4 | Steric Volume[†] |
|---|---|---|---|---|---|
| Alanine | Ala | A | nonpolar | neutral | small |
| Arginine | Arg | R | polar | positive | large |
| Asparagine | Asn | N | polar | neutral | intermediate |
| Aspartic acid | Asp | D | polar | negative | intermediate |
| Cysteine | Cys | C | nonpolar | neutral | intermediate |
| Glutamic acid | Glu | E | polar | negative | intermediate |
| Glutamine | Gln | Q | polar | neutral | intermediate |
| Glycine | Gly | G | nonpolar | neutral | small |
| Histidine | His | H | polar | neutral (90%) | large |
| Isoleucine | Ile | I | nonpolar | neutral | large |
| Leucine | Leu | L | nonpolar | neutral | large |
| Lysine | Lys | K | polar | positive | large |
| Methionine | Met | M | nonpolar | neutral | large |
| Phenylalanine | Phe | F | nonpolar | neutral | large |
| Proline | Pro | P | nonpolar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

[†]based on volume in $Å^3$: 50-100 is small, 100-150 is intermediate, 150-200 is large, and >200 is bulky From this table it is appreciated that the conservative amino acid families include (i) G, A, V, L and I; (ii) D and E; (iii) A, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the term "conjugate" refers to a compound formed by the chemical bonding of a reactive functional group of one molecule with an appropriately reactive functional group of another molecule. Conjugates may additionally be produced, e.g., as two polypeptide domains covalently bound to one another as part of a single polypeptide chain that is synthesized by the translation of a single RNA transcript encoding both polypeptides in frame with one another.

As used herein, the term "derivatized antibodies" refers to antibodies that are modified by a chemical reaction so as to cleave residues or add chemical moieties not native to an isolated antibody. Derivatized antibodies can be obtained, e.g., by glycosylation, acetylation, pegylation, phosphorylation, amidation, derivatization by addition of known chemical protecting/blocking groups, proteolytic cleavage, linkage to a cellular ligand or other protein. Any of a variety of chemical modifications can be carried out by known techniques, including, without limitation, specific chemical cleavage, acetylation, formylation, metabolic synthesis of tunicamycin, etc. using established procedures. Additionally, the derivative can contain one or more non-natural amino acids, e.g., using amber suppression technology (see, e.g., U.S. Pat. No. 6,964,859; incorporated herein by reference). In certain cases, it may be desirable to include one or more non-natural amino acids within an antibody of the invention in order to provide a reactive functional group that can be used to conjugate the antibody to another molecule. Examples of unnatural amino acids that exhibit this functionality include those that contain, e.g., one or more azide, alkyne, ketone, aniline, alkene, tetrazole, 1,2-aminothiol, phosphine, norbornene, or tetrazine moieties. The reactivity of these functional groups is known to those of skill in the art and is described, e.g., in US 2015/0005481; U.S. Pat. No. 7,807,619; de Araiújo, et al., Chemistry 12:6095-6109 (2006); and Kohn, et al., Angew Chem Int Ed Engl, 43:3106-3116 (2004); the disclosures of each of which are incorporated herein by reference. Other examples of non-natural amino acids that may desirably be incorporated into an antibody of the invention include D-amino acids and other those containing other non-natural side-chain moieties so as to reduce the susceptibility of the antibody to proteolytic degradation by evading recognition by endogenous proteases and endopeptidases.

As used herein, the term "diabodies" refers to bivalent antibodies comprising two polypeptide chains, in which each polypeptide chain includes $V_H$ and $V_L$ domains joined by a linker that is too short (e.g., a linker composed of five amino acids) to allow for intramolecular association of $V_H$ and $V_L$ domains on the same peptide chain. This configuration forces each domain to pair with a complementary domain on another polypeptide chain so as to form a homodimeric structure. Accordingly, the term "triabodies" refers to trivalent antibodies comprising three peptide chains, each of which contains one $V_H$ domain and one $V_L$ domain joined by a linker that is exceedingly short (e.g., a linker composed of 1-2 amino acids) to permit intramolecular association of $V_H$ and $V_L$ domains within the same peptide chain. In order to fold into their native structure, peptides configured in this way typically trimerize so as to position the $V_H$ and $V_L$ domains of neighboring peptide chains spatially proximal to one another to permit proper folding (see Holliger et al., Proc. Natl. Acad. Sci. USA 90:6444-48, 1993; incorporated herein by reference).

As used herein, a "dual variable domain immunoglobulin" ("DVD-Ig") refers to an antibody that combines the target-binding variable domains of two monoclonal antibodies via linkers to create a tetravalent, dual-targeting single agent. (Gu et al., Meth. Enzymol., 502:25-41, 2012; incorporated by reference herein). Suitable linkers for use in the light chains of the DVDs of the invention include those identified on Table 2.1 on page 30 of Gu et al.: the short K chain linkers ADAAP (SEQ ID NO: 380) (murine) and TVAAP (SEQ ID NO: 381) (human); the long K chain linkers ADAAPTVSIFP (SEQ ID NO: 382) (murine) and TVAAPSVFIFPP (SEQ ID NO: 383) (human); the short A chain linker QPKAAP (SEQ ID NO: 384) (human); the long A chain linker QPKAAPSVTLFPP (SEQ ID NO: 385) (human); the GS-short linker GGSGG (SEQ ID NO: 386), the GS-medium linker GGSGGGGSG (SEQ ID NO: 387), and the GS-long linker GGSGGGGSGGGS (SEQ ID NO: 388) (all GS linkers are murine and human). Suitable linkers for use in the heavy chains of the DVDs include those identified on Table 2.1 on page 30 of Gu & Ghayur, 2012, Methods in Enzymology 502:25-41, incorporated by reference herein: the short linkers AKTTAP (SEQ ID NO: 389) (murine) and ASTKGP (SEQ ID NO: 390) (human); the long linkers AKTTAPSVYPLAP (SEQ ID NO: 391) (murine) and ASTKGPSVFPLAP (SEQ ID NO: 392) (human); the GS-short linker GGGGSG (SEQ ID NO: 393), the GS-medium linker GGGGSGGGGS (SEQ ID NO: 394), and the GS-long linker GGGGSGGGGSGGGG (SEQ ID NO: 395) (all GS linkers are murine and human).

As used herein, the term "endogenous" describes a molecule (e.g., a polypeptide, protein, antibody, enzyme, cofactor, or nucleic acid) that is found naturally in a particular organism (e.g., a human) or in a particular location within an organism (e.g., an organ, a tissue, or a cell, such as a human cell).

As used herein, the term "exogenous" describes a molecule (e.g., a polypeptide, protein, antibody, enzyme, cofactor, or nucleic acid) that is not found naturally in a particular organism (e.g., a human) or in a particular location within an organism (e.g., an organ, a tissue, or a cell, such as a human cell). Exogenous materials include those that are provided from an external source to an organism or to cultured matter extracted there from.

As used herein, the term "framework region" or "FR" includes amino acid residues that are adjacent to the CDRs. FR residues may be present in, for example, human antibodies, rodent-derived antibodies (e.g., murine antibodies), humanized antibodies, primatized antibodies, chimeric antibodies, antibody fragments (e.g., Fab fragments), single chain antibody fragments (e.g., scFv fragments), antibody domains, and bispecific antibodies, among others.

As used herein, the term "fusion protein" refers to a protein that is joined via a covalent bond to another molecule. A fusion protein can be chemically synthesized by, e.g., an amide-bond forming reaction between the N-terminus of one protein to the C-terminus of another protein. Alternatively, a fusion protein containing one protein or protein domain covalently bound to another protein or protein domain can be expressed recombinantly in a cell (e.g., a eukaryotic cell or prokaryotic cell) by expression of a polynucleotide encoding the fusion protein, for example, from a vector or the genome of the cell. A fusion protein may contain one protein that is covalently bound to a linker, which in turn is covalently bound to another molecule. Examples of linkers that can be used for the formation of a fusion protein include peptide-containing linkers, such as those that contain naturally occurring or non-naturally occurring amino acids. In certain cases, it may be desirable to include D-amino acids in the linker, as these residues are not present in naturally-occurring proteins and are thus more resistant to degradation by endogenous proteases. Linkers can be prepared using a variety of strategies that are well known in the art, and depending on the reactive components of the linker, can be cleaved by enzymatic hydrolysis, photolysis, hydrolysis under acidic conditions, hydrolysis under basic conditions, oxidation, disulfide reduction, nucleophilic cleavage, or organometallic cleavage. These and other linker modalities are described, e.g., in Leriche et al., Bioorg. Med. Chem., 20:571-582, (2012), the disclosure of which is incorporated herein by reference.

As used herein, the term "heterospecific antibodies" refers to monoclonal, preferably human or humanized, antibodies that have binding specificities for at least two different antigens. Traditionally, the recombinant production of heterospecific antibodies is based on the co-expression of two immunoglobulin heavy chain-light chain pairs, where the two heavy chains have different specificities (as described, e.g., in Milstein et al., Nature 305:537, (1983), the disclosure of which is incorporated herein by reference). Similar procedures for generating heterospecific antibodies are disclosed, e.g., in WO 93/08829; WO 91/00360, WO 92/00373; EP 03089; U.S. Pat. Nos. 6,210,668; 6,193,967; 6,132,992; 6,106,833; 6,060,285; 6,037,453; 6,010,902; 5,989,530; 5,959,084; 5,959,083; 5,932,448; 5,833,985; 5,821,333; 5,807,706; 5,643,759, 5,601,819; 5,582,996; 5,496,549; 4,676,980; as well as in Traunecker et al., EMBO J. 10:3655 (1991); and Suresh et al., Methods in Enzymology 121:210 (1986); the disclosures of each of which are incorporated herein by reference. Heterospecific antibodies can include Fc mutations that enforce correct chain association in multispecific antibodies, as described, e.g., by Klein et al, mAbs 4(6):653-663, (2012); the disclosure of which is incorporated herein by reference.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is derived from a human germline immonglobulin sequence. A human antibody can be produced in a human cell (e.g., by recombinant expression), or by a non-human animal or a prokaryotic or eukaryotic cell that is capable of expressing functionally rearranged human immunoglobulin (e.g., heavy chain and/or light chain) genes. Human antibodies can be made by a variety of methods known in the art including phage display methods using antibody libraries derived from human immunoglobulin sequences. See U.S. Pat. Nos. 4,444,887 and 4,716,111; and PCT publications WO 1998/46645; WO 1998/50433; WO 1998/24893; WO 1998/16654; WO 1996/34096; WO 1996/33735; and WO 1991/10741; the disclosure of each of which is incorporated herein by reference. Human antibodies can also be produced using transgenic mice that are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598; the disclosure of each of which is incorporated by reference herein.

As used herein, the term "humanized" antibodies refers to forms of non-human (e.g., primate, murine, rabbit, goat, rodent, or other non-human mammal) antibodies that are chimeric immunoglobulins, immunoglobulin chains or fragments thereof (such as Fv, Fab, Fab', F(ab')$_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin. All or substantially all of the FR regions may also be those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., Nature 332:323-7, 1988; U.S. Pat. Nos. 5,530,101; 5,585,089; 5,693,761; 5,693,762; and 6,180,370 to Queen et al; EP239400; PCT publication WO 91/09967; U.S. Pat. No. 5,225,539; EP592106; and EP519596; incorporated herein by reference.

As used herein, the term "monoclonal antibody" refers to an antibody that is derived from a single clone, including any eukaryotic, prokaryotic, or phage clone, and not the method by which it is produced.

As used herein, the term "multi-specific antibodies" refers to antibodies that exhibit affinity for more than one target antigen. Multi-specific antibodies can have structures similar to full immunoglobulin molecules and include Fc regions, for example IgG Fc regions. Such structures can include, but not limited to, IgG-Fv, IgG-(scFv)$_2$, DVD-Ig, (scFv)$_2$-(scFv)$_2$-Fc and (scFv)$_2$-Fc-(scFv)$_2$. In case of IgG-(scFv)$_2$, the scFv can be attached to either the N-terminal or the C-terminal end of either the heavy chain or the light chain. Exemplary multi-specific molecules that include Fc regions and into which TNFR2 antibodies or antigen-binding fragments thereof can be incorporated have been reviewed, e.g., by Kontermann, 2012, mAbs 4(2):182-197, Yazaki et al, 2013, Protein Engineering, Design & Selection 26(3):187-193, and Grote et al, 2012, in Proetzel & Ebersbach (eds.), Antibody Methods and Protocols, Methods in Molecular Biology vol. 901, chapter 16:247-263; incorporated herein by reference. In certain cases, antibody fragments can be components of multi-specific molecules without Fc regions, based on fragments of IgG or DVD or scFv. Exemplary multi-specific molecules that lack Fc regions and into which antibodies or antibody fragments can be incorporated include scFv dimers (diabodies), trimers (triabodies) and tetramers (tetrabodies), Fab dimers (conjugates by adhesive polypeptide or protein domains) and Fab trimers (chemically conjugated), are described by Hudson and Souriau, 2003, Nature Medicine 9:129-134; incorporated herein by reference.

As used herein, the term "non-native constant region" refers to an antibody constant region that is derived from a source that is different from that of the antibody variable region or that is a human-generated synthetic polypeptide having an amino sequence that is different from the native antibody constant region sequence. For instance, an antibody containing a non-native constant region may have a variable region derived from a non-human source (e.g., a mouse, rat, or rabbit) and a constant region derived from a human source (e.g., a human antibody constant region).

As used herein, the term "percent (%) sequence identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, for example, at least 30%, (e.g., 30%, 40%, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As used herein, the term "primatized antibody" refers to an antibody comprising framework regions from primate-derived antibodies and other regions, such as CDRs and constant regions, from antibodies of a non-primate source. Methods for producing primatized antibodies are known in the art. See e.g., U.S. Pat. Nos. 5,658,570; 5,681,722; and 5,693,780; incorporated herein by reference.

As used herein, the term "operatively linked" in the context of a polynucleotide fragment is intended to mean that the two polynucleotide fragments are joined such that the amino acid sequences encoded by the two polynucleotide fragments remain in-frame.

As used herein, the term "pharmacokinetic profile" refers to the absorption, distribution, metabolism, and clearance of a drug (e.g., an antibody) over time following administration of the drug to a patient.

As used herein, the term "regulatory sequence" includes promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, CA, 1990); incorporated herein by reference.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain (VL) (e.g., CDR-L1, CDR-L2, and/or CDR-L3) and the variable region of an antibody heavy chain (VH) (e.g., CDR-H1, CDR-H2, and/or CDR-H3) separated by a linker. The linker that joins the VL and VH regions of a scFv fragment can be a peptide linker composed of proteinogenic amino acids. Alternative linkers can be used to so as to increase the resistance of the scFv fragment to proteolytic degradation (e.g., linkers containing D-amino acids), in order to enhance the solubility of the scFv fragment (e.g., hydrophilic linkers such as polyethylene glycol-containing linkers or polypeptides containing repeating glycine and serine residues), to improve the biophysical stability of the molecule (e.g., a linker containing cysteine residues that form intramolecular or intermolecular disulfide bonds), or to attenuate the immunogenicity of the scFv fragment (e.g., linkers containing glycosylation sites). scFv molecules are known in the art and are described, e.g., in U.S. Pat. No. 5,892,019; Flo et al., (Gene 77:51, 1989); Bird et al., (Science 242:423, 1988); Pantoliano et al., (Biochemistry 30:10117, 1991); Milenic et al., (Cancer Research 51:6363, 1991); and Takkinen et al., (Protein Engineering 4:837, 1991). The VL and VH domains of an scFv molecule can be derived from one or more antibody molecules. It will also be understood by one of ordinary skill in the art that the variable regions of the scFv molecules of the invention can be modified such that they vary in amino acid sequence from the antibody molecule from which they were derived. For example, in one embodiment, nucleotide or amino acid substitutions leading to conservative substitutions or changes at amino acid residues can be made (e.g., in CDR and/or framework residues). Alternatively or in addition, mutations are made to CDR amino acid residues to optimize antigen-binding using art-recognized techniques. ScFv fragments are described, for example, in WO 2011/084714; incorporated herein by reference.

As used herein, a small modular immunopharmaceutical (SMIP) protein refers to a protein that contains one or more of the following immunoglobulin domains: an antigen-binding domain, an immunoglobulin hinge region or a domain derived there from, an immunoglobulin heavy chain $C_H2$ constant region or a domain derived there from, and an immunoglobulin heavy chain $C_H3$ constant region or a domain derived there from. Polypeptides containing one or more of these domains can be obtained using methods known in the art or described herein, e.g., by recombinant expression of a polynucleotide encoding one or more of these domains or by chemical synthesis techniques (e.g., solid phase peptide synthesis, see Solid Phase Peptide Synthesis, 2nd ed., 1984 The Pierce Chemical Co., Rockford, 111; the disclosure of which is incorporated herein by reference in its entirety).

As used herein, the phrase "specifically binds" refers to a binding reaction which is determinative of the presence of an antigen in a heterogeneous population of proteins and other biological molecules that is recognized, e.g., by an antibody or antigen-binding fragment thereof, with particularity. An antibody or antigen-binding fragment thereof that specifically binds to an antigen will bind to the antigen or an epitope(s) thereof with a $K_D$ of less than 100 nM (e.g., between 1 pM and 100 nM). An antibody or antigen-binding fragment thereof that does not exhibit specific binding to a particular antigen or epitope thereof will exhibit a $K_D$ of greater than 100 nM (e.g., greater than 500 nM, 1 µM, 100 µM, 500 µM, or 1 mM) for that particular antigen or epitope thereof. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, e.g., Harlow & Lane, Antibodies, A Laboratory Manual, Cold Spring Harbor Press, New York (1988); and Harlow & Lane, Using Antibodies, A Laboratory Manual, Cold Spring Harbor Press, New York (1999), for a description of immunoassay formats and conditions that can be used to determine specific immunoreactivity.

As used herein, the terms "subject" and "patient" refer to an organism that receives treatment (e.g., by administration of an agonistic TNFR2 antibody or antigen-binding fragment thereof of the invention) for a particular disease or condition as described herein (such as an immunological disorder, e.g., an autoimmune disease). Examples of subjects and patients include mammals, such as humans, primates, pigs, goats, rabbits, hamsters, cats, dogs, guinea pigs, members of the bovidae family (such as cattle, bison, buffalo, and yaks, among others), cows, sheep, horses, and bison, among others, receiving treatment for diseases or conditions, for example, immunological disorders, such as autoimmune disorders, graft-versus-host disease, allograft rejection, allergic reactions, and asthma, among others. A patient that is eligible for treatment with the compositions and methods of the invention may have an established disease (e.g., an established immunological disorder, such as an autoimmune disease), in which case the patient has been diagnosed as having the disease and has shown symptoms of the disease for a prolonged period of time (e.g., over the course of days, weeks, months, or years). Alternatively, a patient may be symptomatic for a particular disease, such as an immunological disorder described herein, but has yet to be diagnosed with the disease by a physician. Other patients eligible for treatment with the compositions and methods of the invention include those that have been diagnosed as having an immunological disorder, and may or may not be showing symptoms of the disease as of yet. For example, a patient eligible for treatment with the compositions and methods of the invention may be described as diagnosed but asymptomatic if the patient has received a diagnosis of an immunological disorder, such as multiple sclerosis, e.g., by detection of depleted myelin sheath around one or more neurons of the patient due to the activity of autoreactive T-cells, even though the patient may not yet be showing symptoms of multiple sclerosis (e.g., lack of balance, reduced cognitive performance, blurred vision, or attenuated coordination, among others). Another example of a patient that has been diagnosed with an immunological condition but is asymptomatic as of yet includes a patient that has been diagnosed with rheumatoid arthritis, e.g., by the detection of autoreactive T-cells in a lymph sample isolated from the patient, even though the patient has not yet presented with the symptoms associated with this disease, such as joint pain, joint stiffness, and a decrease in the muscle range or movement, among others.

As used herein, the terms "tumor necrosis factor receptor superfamily," "TNFR superfamily," or "TNFRSF" refer to a group of type I transmembrane proteins, with a carboxy-terminal intracellular domain and an amino-terminal extracellular domain characterized by a common cysteine rich domain (CRD). The TNFR superfamily includes receptors that mediate cellular signaling as a consequence of binding to one or more ligands in the TNF superfamily. The TNFR superfamily can be divided into two subgroups: receptors containing the intracellular death domain and those lacking this domain. The death domain is an 80 amino acid motif that propagates apoptotic signal transduction cascades following receptor activation. Exemplary TNFR super family members that contain the intracellular death domain include TNFR1, while TNFR2 represents a TNFR super family protein that does not contain this domain. Members of the TNFR superfamily include TNFR1, TNFR2, RANK, CD30, CD40, Lymphotoxin beta receptor (LT-βR), OX40, Fas receptor, Decoy receptor 3, CD27, 4-1 BB, Death receptor 4, Death receptor 5, Decoy receptor 1, Decoy receptor 2, Osteoprotegrin, TWEAK receptor, TACI, BAFF receptor, Herpesvirus entry mediator, Nerve growth factor receptor, B-cell maturation antigen, Glucocorticoid-induced TNFR-related, TROY, Death receptor 6, Death receptor 3, and Ectodysplasin A2 receptor.

As used herein, the term "transfection" refers to any of a wide variety of techniques commonly used for the introduction of exogenous DNA into a prokaryotic or eukaryotic host cell, e.g., electroporation, heat shock, lipofection, calcium phosphate precipitation, DEAE-dextran transfection and the like.

As used herein, the terms "treat" or "treatment" refer to therapeutic treatment, in which the object is to inhibit or slow down (lessen) an undesired physiological change or disorder, such as an immunological disorder (e.g., autoimmune disease, allergic reaction, graft-versus-host disease, or allograft rejection). Beneficial or desired clinical results of treatment include, without limitation, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder, as well as those prone to have the condition or disorder or those in which the condition or disorder is to be inhibited.

As used herein the term "variable region CDR" includes amino acids in a CDR or complementarity determining region as identified using sequence- or structure-based methods. As used herein, the term "CDR" or "complementarity determining region" refers to the noncontiguous antigen-binding sites found within the variable regions of both heavy and light chain polypeptides. These particular regions have been described by Kabat et al., J. Biol. Chem. 252:6609-6616 (1977); Kabat, et al., Sequences of Proteins of Immunological Interest, Fifth Edition, U.S. Department of Health and Human Services, NIH Publication No. 91-3242, 1991; Chothia et al., J. Mol. Biol. 196:901-917 (1987); and by MacCallum et al., J. Mol. Biol. 262:732-745 (1996); the disclosures of each of which are incorporated herein by reference. For agonistic TNFR2 antibodies of the invention, a CDR, as defined by Kabat, may be based on sequence comparisons.

As used herein, the term "vector" includes a nucleic acid vector, e.g., a DNA vector, such as a plasmid, a RNA vector, virus or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO 1994/11026, the disclosure of which is incorporated herein by reference. Expression vectors of the invention contain a polynucleotide sequence, as well as, e.g., additional sequence elements used for the expression of proteins and/or the integration of these polynucleotide sequences into the genome of a cell, such as a mammalian cell (e.g., a human cell). Vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements include, e.g., 5' and 3' untranslated regions, an internal ribosomal entry site (IRES), and polyadenylation signal site in order to direct efficient transcription of the gene carried on the expression vector. The expression vectors of the invention may also contain a polynucleotide encoding a marker for selection of cells that contain such a vector. Examples of a suitable marker include genes that encode resistance to antibiotics, such as ampicillin, chloramphenicol, kanamycin, or nourseothricin.

As used herein, the term "VH" refers to the variable region of an immunoglobulin heavy chain of an antibody, including, e.g., the heavy chain of an Fv, scFv, Fab, F(ab')$_2$, Fd, scFv, SMIP, diabody, triabody, affibody, or nanobody. References to "VL" refer to the variable region of an immunoglobulin light chain, including, e.g., the light chain of an Fv, scFv, Fab, F(ab')$_2$, Fd, scFv, SMIP, diabody, triabody, affibody, or nanobody. Antibodies and immunoglobulins are glycoproteins having the same structural characteristics. While antibodies exhibit binding specificity to a specific target, immunoglobulins include both antibodies and other antibody-like molecules which lack target specificity. Native antibodies and immunoglobulins are typically heterotetrameric glycoproteins of about 150,000 Daltons, composed of two identical light (L) chains and two identical heavy (H) chains. Each heavy chain of a native antibody has at the amino terminus a variable domain (VH) followed by a number of constant domains. Each light chain of a native antibody has a variable domain at the amino terminus (VL) and a constant domain at the carboxy terminus.

BRIEF DESCRIPTION OF THE FIGURES

FIGS. 1A and 1B is the amino acid sequence of human TNFR2 (SEQ ID NO: 366). Notably, human TNFR2 is numbered herein starting with an N-terminal methionine at position 1 and concluding with a C-terminal serine at position 461. All references to amino acid positions within TNFR2 are made in the context of the TNFR2 numbering scheme shown in FIGS. 1A and 1B and recited in SEQ ID NO: 366. (FIG. 1A) Shaded residues KCSPG (SEQ ID NO: 367) define an epitope within TNFR2 that is specifically bound by the agonistic TNFR2 antibody MR2-1. MR2-1 additionally binds an epitope that includes shaded residues SSDQVET (SEQ ID NO: 368) and an epitope that includes TREQNRICTCRPGWYCALSKQEGCRLCA-PLRKCRPGFGVA (SEQ ID NO: 370). Though these residues are not consecutive in primary sequence with the KCSPG motif, they are spatially proximal in the three dimensional tertiary structure of TNFR2 and, for MR2-1, may form a discontinuous epitope that is appropriately positioned for interaction with other agonistic TNFR2 antibodies of the invention (see FIG. 4). Agonistic TNFR2 antibodies of the invention bind the KCSPG epitope and may bind one or more of the residues within these other regions. (FIG. 1B) Agonistic TNFR2 antibody 8E6.D1 binds an epitope containing the KCSPG motif within TNFR2 (shown as shaded residues). Significantly, agonistic 8E6.D.1 does not bind an epitope containing the KCRPG motif (SEQ ID NO: 375), shown as underlined residues.

FIG. 2 is a table showing the raw data obtained from enzyme-linked immunosorbant assay (ELISA) experiments that were conducted to determine the affinity of agonistic TNFR2 antibody MR2-1 for various continuous and discontinuous epitopes within TNFR2 (see Example 1). Raw luminescence values are shown in the fourth column of the table (right). Peptide sequences represent those that contain a portion of a conformational epitope within TNFR2 that interacts with MR2-1. Amino acid residues with the single-digit code "2" designate cysteine residues that were chemically protected at the thiol position with an acetamidomethyl (ACM) moiety. These residues are not reactive with bromomethyl-containing electrophiles and were therefore not cross-linked during the cyclization and bicyclization phases of peptide synthesis. The third column in the table indicates the general structure of the peptide scaffold. "LIN" indicates a linear 15-residue peptide that was not subject to an intramolecular cross-linking reaction. "LIN.AA" indicates a linear 15-residue peptide equivalent to the "LIN" group, except residues at positions 10 and 11 of the peptide were substituted with alanine. Where alanine occurred at these positions in the native TNFR2 sequence, these residues were substituted with glycine. "LOOP" indicates a 17-residue peptide in which cysteine residues were inserted at positions 1 and 17 of the peptide chain and were cross-linked by reaction with 2,6-bis(bromomethyl)pyridine. "LOOP.AA" indicates a peptide that is equivalent to the "LOOP" group, except residues at positions 12 and 13 were substituted with alanine. Where alanine occurred at these positions in the native TNFR2 sequence, these residues were substituted with glycine. "MAT" indicates a peptide in which cysteine residues were inserted at positions 1, 17, and 33 and were subsequently cross-linked by reaction with 1,3,5-bis(bromomethyl)benzene. Positions 2-16 and 18-32 represent 15-residue peptides derived from TNFR2. "BET1" indicates a 24-residue peptide derived from TNFR2. Cys residues were inserted into these peptides at positions 1 and 24 and were subsequently cross-linked by reaction with 2,6-bis(bromomethyl)pyridine. Proline and glycine were incorporated into these peptides at positions 9 and 10 in order to nucleate a β-turn, and native cysteine residues were substituted with alanine residues. "BET2" indicates an 18-residue peptide derived from TNFR2. Cys residues were inserted into these peptides at positions 1 and 18 and were subsequently cross-linked by reaction with 2,6-bis(bromomethyl) pyridine. Proline and glycine were incorporated into these peptides at positions 9 and 10 in order to nucleate a β-turn, and native cysteine residues were substituted with alanine residues. "CYS.S" indicates a 27-residue peptide in which positions 1-11 and 17-27 represent 11-residue peptides derived from TNFR2 that contain cysteine residues that form disulfide bridges in the native protein based on information available for UniProt entry P20333. The sequence Gly-Gly-Ser-Gly-Gly was incorporated into positions 12-16 of peptides of this group. Native Cys residues that do not form disulfide bridges were protected with acetamidomethyl (ACM) protecting groups and are designated with the single-digit code "2". "CYS.D" indicates a 22-residue peptide derived from TNFR2 that contains cysteine residues that form disulfide bridges in the native protein based on information available for UniProt entry P20333. Native Cys residues that do not form disulfide bridges were protected with acetamidomethyl (ACM) protecting groups and are designated with the single-digit code "2".

FIG. 3 is a table showing the results of an ELISA-based assay used to screen a series of linear peptides derived from the human TNFR2 sequence for those that bind agonistic antibody MR2-1 with high affinity. Column two of the table shows the positions within the human TNFR2 sequence from which the synthetic peptides were derived. The relative affinity of each of the screened linear peptides is shown in the fourth column of the table, and raw luminescence values are provided in column five.

FIG. 4 is a schematic illustrating the conformational epitopes within TNFR2 that may interact with agonistic TNFR2 antibodies of the invention, as well as residues that do not interact with particular agonistic TNFR2 antibodies. The KCSPG motif is shown in the expansion at the top left of the figure; the KCRPG motif is shown in the expansion at the right of the figure. Exterior surface of the protein designates the van der Waals surface of TNFR2. FIG. 4 is a rendering of a monomer of TNFR2 isolated from the X-ray crystal structure of TNFR2 (PDB ID: 3ALQ, Mukai, et al., Sci. Signal., 3:ra83 (2010)).

FIG. 5 is a graph showing the results of a T-reg induction assay conducted in order to determine the effect of agonistic TNFR2 antibody MR2-1 on the proliferation of T-reg cells. Values shown on the y-axis represent the percent change in the quantity of cultured T-reg cells as a function of MR2-1 concentration (shown in μg/mL). This experiment demonstrates a dose-dependent ability of agonistic TNFR2 antibodies to induce the expansion of T-reg cells.

FIGS. 6A and 6B are graphs showing the results of T-reg induction assays conducted in order to determine the effect of agonistic TNFR2 antibodies on the proliferation of T-reg cells. FIG. 6A is a graph showing the effect of antibody MR2-1 on the induction of T-reg cell growth. Values shown on the y-axis represent the percent change in the quantity of cultured T-reg cells over a 48 hour period in response to incubation of populations of these cells with various external agents. Shown on the left of the graph are the effects of IL-2, TNF, MR2-1, M1 (a negative control that does not bind TNFR2), and MAB726 (a negative control that functions as an antagonist of TNFR2). Bars shown in the center of the figure demonstrate the effect of increasing 8E6-D1 titer on the proliferation of T-reg cells, as this agonistic TNFR2 antibody is capable of inducing T-reg expansion in a dose-dependent fashion. The bars on the right of the chart illustrate the effect of co-incubation of 8E6-D1 and TNF on T-reg induction. FIG. 6B is a graph showing the effect of antibody 8E6.D1 on the induction of T-reg cell growth. Values shown on the y-axis represent the percent change in the quantity of cultured T-reg cells, as measured by FACS analysis, over a 48 hour period in response to incubation of populations of these cells with various external agents. Shown on the left of the graph are the effects of IL-2, TNF, MR2-1, M1, and MAB726. Bars shown in the center of the figure demonstrate the effect of increasing 8E6-D1 titer on the proliferation of T-reg cells, as this agonistic TNFR2 antibody is capable of inducing T-reg expansion in a dose-dependent fashion. The bars on the right of the chart illustrate the effect of co-incubation of 8E6-D1 and TNF on T-reg induction. Taken together, these data demonstrate the agonistic TNFR2 antibody 8E6-D1 is not only capable of inducing T-reg expansion, but can also synergize with the cognate TNFR2 ligand, TNF, to promote robust T-reg proliferation.

DETAILED DESCRIPTION

Figure 6B:
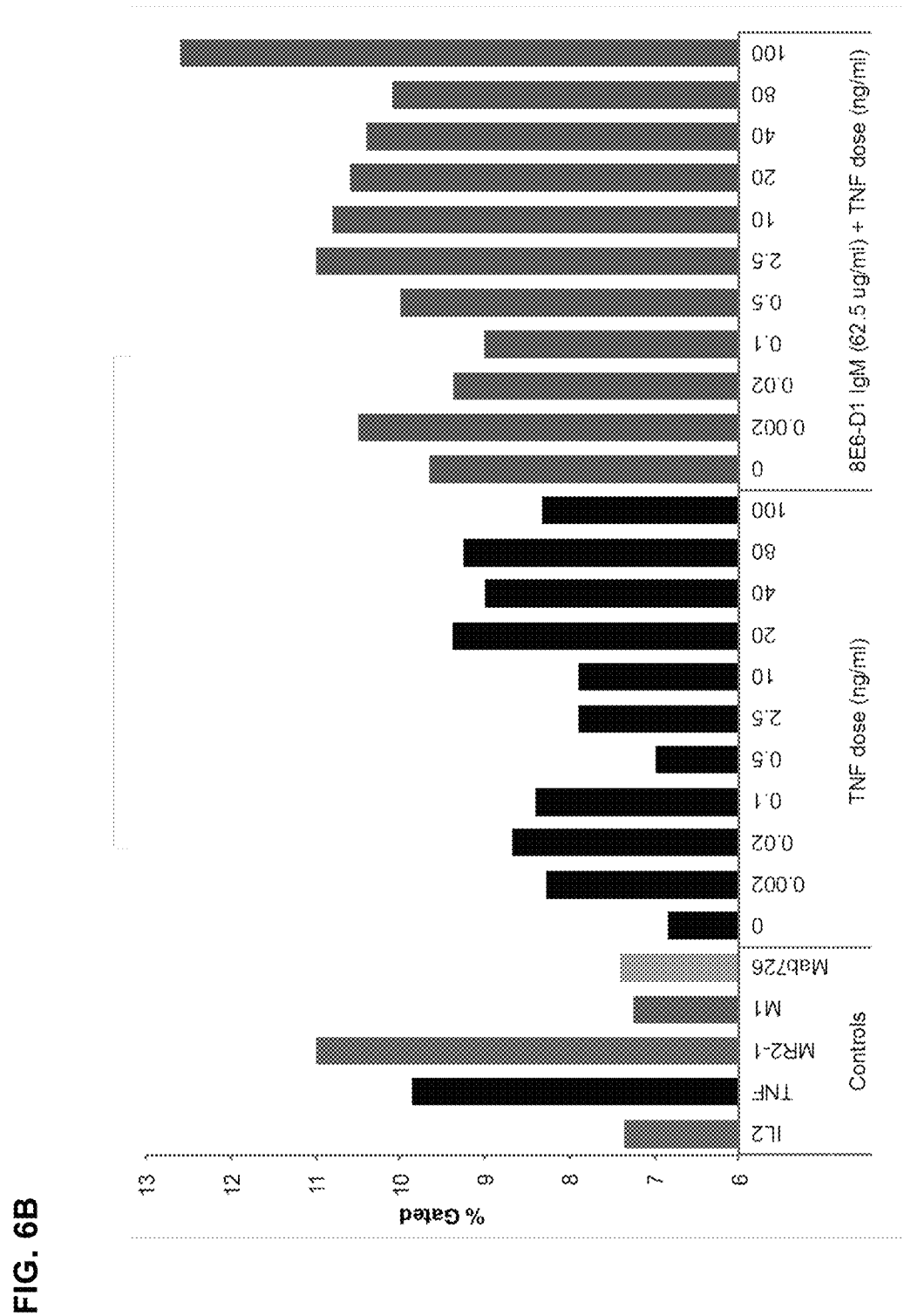

Agonistic TNFR2 antibodies or antigen-binding fragments thereof of the invention potentiate the activation of TNFR2 by binding this receptor (e.g., on the exterior surface of a T-reg cell) and inducing a TNFR2-mediated signal transduction cascade. Agonistic TNFR2 antibodies may promote TNFR2 signaling by nucleating a trimer of TNFR2 proteins at the T-reg cell surface. This is the spatial configuration induced by binding of TNFR2 to its cognate ligand, TNFα. This trimerization event brings individual TNFR2 proteins into close proximity and initiates signaling via the MAPK/NF$_K$B/TRAF2/3 pathway, which ultimately leads to cell growth and escape from apoptosis. Agonistic TNFR2 antibodies of the invention may emulate the TNFR2-TNFα interaction by binding the receptor and triggering this structural change.

Antibodies or antigen-binding fragments thereof of the invention can be used to promote the proliferation of a population of T-reg cells and thus enhance the immunomodulatory activity of these cells. Agonistic TNFR2 antibodies and antigen-binding fragments thereof can therefore be used to attenuate an aberrant cell-mediated or humoral immune response associated with a variety of human diseases, such as autoimmune disorders, asthma, allergic reactions, and diseases associated with allograft tolerance. For instance, agonistic TNFR2 antibodies of the invention may be administered to suppress cytotoxic T-cell and B-cell activity, thereby attenuating the response of a patient to a self or benign antigen. Agonistic TNFR2 antibodies and antigen-binding fragments thereof can be administered to a mammalian subject, such as a human (e.g., by any of a number of routes of administration described herein) in order to attenuate an aberrant immune response, such as a response against a self or non-threatening antigen. Alternatively, agonistic TNFR2 antibodies of the invention can be used to expand a population of T-reg cells ex vivo that have been extracted, e.g., from a patient or an MHC-matched donor. After inducing proliferation of these T-reg cells in culture by treatment with an agonistic TNFR2 antibody or antigen-binding fragment thereof of the invention, these cells can subsequently be administered to a patient, e.g., using standard cellular administration techniques known in the art or described herein. In this way, agonistic TNFR2 antibodies of the invention may synergize with existing techniques to suppress humoral and cell-mediated immune responses as a treatment modality for patients suffering from a variety of immunological disorders.

Agonistic TNFR2 Antibodies

Agonistic TNFR2 antibodies of the invention include antigen-binding fragments, such as an scFv, Fab, F(ab')$_2$, diabody, triabody, or antibody-like scaffold protein as described above, and may be of any immunoglobulin subtype, such as IgG, IgM, IgA, IgD, and IgE. The anti-TNFR2 antibodies of the invention are capable of interacting with and promoting signal transduction events mediated by TNFR2. Thus, the TNFR2 antibodies of the invention can selectively potentiate TNFR2-mediated T-reg cell growth. Without being limited to any particular mechanism, this phenotype may be achieved due to the ability of an agonistic TNFR2 antibody or antigen-binding fragment thereof of the invention to induce conformational changes within TNFR2 that lead to receptor trimerization. This spatial configuration has been shown to render TNFR2 active for MAPK/TRAF 2/3 signal transduction, which subsequently leads to activation of NF$_K$B-mediated transcription of genes involved in T-reg cell growth and escape from apoptosis (Faustman, et al., Nat. Rev. Drug Disc., 9:482-493 (2010), the disclosure of which is incorporated herein by reference).

Agonistic TNFR2 antibodies and antigen-binding fragments thereof of the invention may be capable of inducing the proliferation of a population of T-reg cells, (e.g., levels of CD4+, CD25+, FOXP3+ T cells) e.g., by 0.00001 to 100.0% (e.g., 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008%, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 20.0%, 30.0%, 40.0%, 50.0%, 60.0%, 70.0%, 80.0%, 90.0%, or 100%), e.g., in vivo in a subject administered the antibody or antigen-binding fragment thereof, or in vitro in a sample containing the T-reg cells that are contacted with the antibody or antigen-binding fragment thereof, as measured, e.g., by FACS analysis, relative to a subject or sample containing a population of cells not treated with an agonistic TNFR2 antibody or fragment thereof of the invention.

Agonistic TNFR2 antibodies and antigen-binding fragments thereof of the invention can therefore be used to promote T-reg cell proliferation and can be administered to a mammalian subject, such as a human patient, with an autoimmune disorder, in order to attenuate the magnitude and duration of an immune response (e.g., quantity of CD8+ cytotoxic T lymphocytes produced in vivo in response to a self or non-threatening foreign antigen) in the patient. For instance, administration of an agonistic TNFR2 antibody or antigen-binding fragment thereof of the invention to a human patient, or a population of T-reg cells expanded ex vivo by treatment with the antibody or antigen-binding fragment thereof of the invention, can cause a reduction in the amount of secreted immunoglobulin (e.g., IgG) that is cross-reactive with a self or non-threatening antigen, e.g., by 0.00001 mg/mL to 10.0 mg/mL (e.g., 0.00001 mg/mL, 0.0001 mg/mL, 0.001 mg/mL, 0.01 mg/mL, 0.1 mg/mL, 1.0 mg/mL, or 10.0 mg/mL), or by 0.001 to 1.0 mg/mL (e.g., 0.001 mg/mL, 0.005 mg/mL, 0.010 mg/mL, 0.050 mg/mL, 0.10 mg/mL, 0.20 mg/mL, 0.30 mg/mL, 0.40 mg/mL, 0.50 mg/mL, 0.60 mg/mL, 0.70 mg/mL, 0.80 mg/mL, 0.90 mg/mL, or 1.0 mg/mL) relative to a subject not treated with an agonistic TNFR2 antibody or antigen-binding fragment thereof of the invention. Additionally or alternatively, agonistic TNFR2 antibodies or antigen-binding fragments thereof of the invention may be capable of diminishing cytotoxic T-cell counts (e.g., levels of CD8+ T cells) e.g., by 0.00001 to 100.0% (e.g., 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008%, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 20.0%, 30.0%, 40.0%, 50.0%, 60.0%, 70.0%, 80.0%, 90.0%, or 100%) in a subject as measured, e.g., by FACS analysis relative to a subject not treated with an agonistic TNFR2 antibody or antigen-binding fragment thereof of the invention. For instance, an agonistic TNFR2 antibody or antigen-binding fragment thereof of the invention can be administered to a subject (e.g., a mammalian subject, such as a human) in order to treat, e.g., an immunological disease described herein. Treatment of a subject in this manner may reduce the quantity of autoreactive CD8+ T-cells within the subject.

Agonistic TNFR2 antibodies of the invention may additionally attenuate the secretion of IFNγ, an immunostimulatory cytokine, in a subject, e.g., by 0.00001 mg/mL to 10.0 mg/mL (e.g., 0.00001 mg/mL, 0.0001 mg/mL, 0.001 mg/mL, 0.01 mg/mL, 0.1 mg/mL, 1.0 mg/mL, or 10.0 mg/mL), or by 0.001 to 1.0 mg/mL (e.g., 0.001 mg/mL, 0.005 mg/mL, 0.010 mg/mL, 0.050 mg/mL, 0.10 mg/mL, 0.20 mg/mL, 0.30 mg/mL, 0.40 mg/mL, 0.50 mg/mL, 0.60 mg/mL, 0.70 mg/mL, 0.80 mg/mL, 0.90 mg/mL, or 1.0 mg/mL) relative to a subject not treated with an agonistic TNFR2 antibody of the invention.

Additionally or alternatively, agonistic TNFR2 antibodies or antigen-binding fragments thereof of the invention may be capable of stimulating the transcription of various genes. For instance, an agonistic TNFR2 antibody or antigen-binding fragment thereof may induce the expression of one or more of cIAP2, TRAF2, Etk, VEGFR2, P13K, Akt, genes encoding proteins involved in the angiogenic pathway, IKK complexes, RIP, NIK, MAP3K, genes encoding proteins involved in the NFkB pathway, NIK, JNK, AP-1, a MEK (e.g., MEK1, MEK7), MKK3, NEMO, IL2R, Foxp3, IL2, TNF, and lymphotoxin (e.g., lymphotoxin α and lymphotoxin β). For instance, an agonistic TNFR2 antibody or antigen-binding fragment thereof of the invention may be capable of inducing the transcription of one or more of these genes, thus resulting in an increase in the level of the mRNA transcripts derived from the one or more genes and/or an increase in the level of protein encoded by the one or more genes. The increase in expression of these genes can be detected using established molecular biology techniques known in the art, e.g., by detecting an increase in mRNA levels by Northern blot analysis or reverse-transcription PCT (RT-PCR) methods, or by detecting an increase in protein levels by immunoblot analysis or ELISA-based techniques. Additionally or alternatively, an agonistic TNFR2 antibody or antigen-binding fragment thereof of the invention may be capable of promoting the activity of one or more proteins associated with the TNFR2 signal transduction cascade (or related signaling pathways that are activated as a result of TNFR2 signaling). For instance, an agonistic TNFR2 antibody or antigen-binding fragment thereof of the invention may be capable of promoting an increase in the phosphorylation of one or more proteins, such as cIAP2, TRAF2, Etk, VEGFR2, P13K, Akt, genes encoding proteins involved in the angiogenic pathway, IKK complexes, RIP, NIK, MAP3K, genes encoding proteins involved in the NFkB pathway, NIK, JNK, AP-1, a MEK (e.g., MEK1, MEK7), MKK3, NEMO, IL2R, Foxp3, IL2, TNF, and lymphotoxin (e.g., lymphotoxin α and lymphotoxin β). An increase in the phosphorylation of one or more proteins that occurs, e.g., as a result of treatment of a subject or of a sample of cells isolated from a subject can be detected using standard molecular biology techniques known in the art, such as by immunoblot analysis or ELISA-based techniques.

Agonistic TNFR2 antibodies of the invention are capable of discriminating among the members of the tumor necrosis factor receptor superfamily (TNFRSF). Preferred agonistic TNFR2 antibodies and antigen-binding fragments thereof are those that do not specifically bind a TNFRSF member other than TNFR2. The TNFR superfamily includes receptors that mediate cellular signaling as a consequence of binding to one or more ligands in the TNF superfamily. The TNFR superfamily can be divided categorically into two types of receptors on the basis of whether the receptor contains an intracellular death domain, an 80-amino acid motif that propagates apoptotic signal transduction cascades following receptor activation. Exemplary TNFR super family members that contain the intracellular death domain include TNFR1, while TNFR2 represents a TNFR super family protein that does not contain this domain. Members of the TNFR superfamily include TNFR1, TNFR2, RANK, CD30, CD40, Lymphotoxin beta receptor (LT-βR), OX40, Fas receptor, Decoy receptor 3, CD27, 4-1 BB, Death receptor 4, Death receptor 5, Decoy receptor 1, Decoy receptor 2, Osteoprotegrin, TWEAK receptor, TACI, BAFF receptor, Herpesvirus entry mediator, Nerve growth factor receptor, B-cell maturation antigen, Glucocorticoid-induced TNFR-related, TROY, Death receptor 6, Death receptor 3, and Ectodysplasin A2 receptor.

Agonistic TNFR2 antibodies and antigen-binding fragments thereof of the invention can be assessed to determine whether they lack specific binding for another TNFR superfamily member using a variety of in vitro binding assays, such as ELISA-based methods. For instance, agonistic TNFR2 antibodies or antigen-binding fragments thereof of the invention may specifically bind human TNFR2 or a TNFR2-derived peptide, such as the peptide fragment defined by residues 48-67 of SEQ ID NO: 366 within human TNFR2 (QTAQMCCSKCSPGQHAKVFC, SEQ ID NO: 346), with an affinity that is, e.g., at least 5-fold greater (e.g., 5-fold greater, 6-fold greater, 7-fold greater, 8-fold greater, 9-fold greater, 10-fold greater, 20-fold greater, 30-fold greater, 40-fold greater, 50-fold greater, 60-fold greater, 60-fold greater, 70-fold greater, 80-fold greater, 90-fold greater, 100-fold greater, 200-fold greater, 300-fold greater, 400-fold greater, 500-fold greater, 600-fold greater, 700-fold greater, 800-fold greater, 900-fold greater, 1,000-fold greater, 2,000-fold greater, 3,000-fold greater, 4,000-fold greater, 5,000-fold greater, 6,000-fold greater, 7,000-fold greater, 8,000-fold greater, 9,000-fold greater, 10,000-fold greater, or more) than the affinity of the same antibody for another TNFR superfamily member. For instance, agonistic TNFR2 antibodies or antigen-binding fragments thereof of the invention may bind the peptide defined by SEQ ID NO: 346 with an affinity that is, e.g., 5-fold greater, 6-fold greater, 7-fold greater, 8-fold greater, 9-fold greater, 10-fold greater, 20-fold greater, 30-fold greater, 40-fold greater, 50-fold greater, 60-fold greater, 60-fold greater, 70-fold greater, 80-fold greater, 90-fold greater, 100-fold greater, 200-fold greater, 300-fold greater, 400-fold greater, 500-fold greater, 600-fold greater, 700-fold greater, 800-fold greater, 900-fold greater, 1,000-fold greater, 2,000-fold greater, 3,000-fold greater, 4,000-fold greater, 5,000-fold greater, 6,000-fold greater, 7,000-fold greater, 8,000-fold greater, 9,000-fold greater, or 10,000-fold greater than the affinity of the same antibody for another TNFR superfamily member, such as TNFR1, RANK, CD30, CD40, Lymphotoxin beta receptor (LT-βR), OX40, Fas receptor, Decoy receptor 3, CD27, 4-1BB, Death receptor 4, Death receptor 5, Decoy receptor 1, Decoy receptor 2, Osteoprotegrin, TWEAK receptor, TACI, BAFF receptor, Herpesvirus entry mediator, Nerve growth factor receptor, B-cell maturation antigen, Glucocorticoid-induced TNFR-related, TROY, Death receptor 6, Death receptor 3, or Ectodysplasin A2 receptor.

Additionally, agonistic TNFR2 antibodies and antigen-binding fragments of the invention may, but preferably do not, bind an epitope containing residues 142-146 of SEQ ID NO: 366 within human TNFR2 (KCRPG, SEQ ID NO: 375). For instance, agonistic TNFR2 antibodies of the invention may bind an epitope containing residues 130-149 of SEQ ID NO: 366 (KQEGCRLCAPLRKCRPGFGV, SEQ ID NO: 357).

Preferred agonistic TNFR2 antibodies and antigen-binding fragments of the invention are those that specifically bind the KCSPG epitope of TNFR2, but do not specifically bind the KCRPG epitope of TNFR2 (i.e., the agonistic TNFR2 antibodies and antigen-binding fragments can distinguish between these two epitopes). For instance, an agonistic TNFR2 antibody or antigen-binding fragment of the invention may bind an epitope containing one or more residues within the KCSPG motif of TNFR2 with an affinity that is, e.g., 5-fold greater, 6-fold greater, 7-fold greater, 8-fold greater, 9-fold greater, 10-fold greater, 20-fold greater, 30-fold greater, 40-fold greater, 50-fold greater, 60-fold greater, 60-fold greater, 70-fold greater, 80-fold greater, 90-fold greater, 100-fold greater, 200-fold greater, 300-fold greater, 400-fold greater, 500-fold greater, 600-fold greater, 700-fold greater, 800-fold greater, 900-fold greater, 1,000-fold greater, 2,000-fold greater, 3,000-fold greater, 4,000-fold greater, 5,000-fold greater, 6,000-fold greater, 7,000-fold greater, 8,000-fold greater, 9,000-fold greater, or 10,000-fold greater than the affinity of the same antibody or antigen-binding fragment for a peptide that contains the KCRPG sequence of human TNFR2 (SEQ ID NO: 375). For example, agonistic TNFR2 antibodies and antigen-binding fragments of the invention may bind an epitope containing one or more residues of the KCSPG motif, such as the peptide defined by residues 48-67 of human TNFR2 (QTAQMCCSKCSPGQHAKVFC, SEQ ID NO: 346) with an affinity that is, e.g., 5-fold greater, 6-fold greater, 7-fold greater, 8-fold greater, 9-fold greater, 10-fold greater, 20-fold greater, 30-fold greater, 40-fold greater, 50-fold greater, 60-fold greater, 60-fold greater, 70-fold greater, 80-fold greater, 90-fold greater, 100-fold greater, 200-fold greater, 300-fold greater, 400-fold greater, 500-fold greater, 600-fold greater, 700-fold greater, 800-fold greater, 900-fold greater, 1,000-fold greater, 2,000-fold greater, 3,000-fold greater, 4,000-fold greater, 5,000-fold greater, 6,000-fold greater, 7,000-fold greater, 8,000-fold greater, 9,000-fold greater, or 10,000-fold greater than the affinity of the same antibody or antigen-binding fragment for a peptide that contains the KCRPG sequence (SEQ ID NO: 375) of human TNFR2, such as a peptide defined by residues 130-149 of SEQ ID NO: 366 (KQEGCRLCAPLRKCRPGFGV, SEQ ID NO: 357).

Specific Binding Properties of Agonistic TNFR2 Antibodies

The specific binding of an antibody or antibody fragment of the invention to TNFR2 (e.g., human TNFR2) can be determined by any of a variety of established methods. The affinity can be represented quantitatively by various metrics, including the concentration of antibody needed to achieve half-maximal potentiation of TNFR2 signalling in vitro ($EC_{50}$) and the equilibrium constant ($K_Dn$) of the antibody-TNFR2 complex dissociation. The equilibrium constant, $K_D$, which describes the interaction of TNFR2 with an antibody or antigen-binding fragment thereof of the invention is the chemical equilibrium constant for the dissociation reaction of a TNFR2-antibody complex into solvent-separated TNFR2 and antibody molecules that do not interact with one another.

Antibodies of the invention are those that specifically bind to TNFR2 with a $K_{on}$ value of less than 100 nM (e.g., 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 4 nM, 3 nM, 2 nM, or 1 nM). In certain cases, antibodies of the invention are those that specifically bind to TNFR2 with a $K_D$ value of less than 1 nM (e.g., 990 pM, 980 pM, 970 pM, 960 pM, 950 pM, 940 pM, 930 pM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM, 770 pM, 760 pM, 750 pM, 740 pM, 730 pM, 720 pM, 710 pM, 700 pM, 690 pM, 680 pM, 670 pM, 660 pM, 650 pM, 640 pM, 630 pM, 620 pM, 610 pM, 600 pM, 590 pM, 580 pM, 570 pM, 560 pM, 550 pM, 540 pM, 530 pM, 520 pM, 510 pM, 500 pM, 490 pM, 480 pM, 470 pM, 460 pM, 450 pM, 440 pM, 430 pM, 420 pM, 410 pM, 400 pM, 390 pM, 380 pM, 370 pM, 360 pM, 350 pM, 340 pM, 330 pM, 320 pM, 310 pM, 300 pM, 290 pM, 280 pM, 270 pM, 260 pM, 250 pM, 240 pM, 230 pM, 220 pM, 210 pM, 200 pM, 190 pM, 180 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM, 10 pM, 5 pM, or 1 pM).

Antibodies of the invention can also be characterized by a variety of in vitro binding assays. Examples of experiments that can be used to determine the $K_D$ or $EC_{50}$ of a TNFR2 antibody include, e.g., surface plasmon resonance, isothermal titration calorimetry, fluorescence anisotropy, and ELISA-based assays, among others. ELISA represents a particularly useful method for analyzing antibody activity, as such assays typically require minimal concentrations of antibodies. A common signal that is analyzed in a typical ELISA assay is luminescence, which is typically the result of the activity of a peroxidase conjugated to a secondary antibody that specifically binds a primary antibody (e.g., a TNFR2 antibody of the invention). Antibodies of the invention are capable of binding TNFR2 and epitopes derived thereof, such as epitopes containing one or more, or all, of residues 56-60 of SEQ ID NO: 366 within human TNFR2 (KCSPG, SEQ ID NO: 367), as well as isolated peptides derived from TNFR2 that structurally pre-organize various residues in a manner that may simulate the conformation of these amino acids in the native protein. For instance, antibodies of the invention may bind peptides containing one or more, or all, amino acids of this KCSPG motif and one or more additional amino acids of residues 48-67 of SEQ ID NO: 366 within human TNFR2 (SEQ ID NO: 346). Such peptides may pre-dispose one or more residues of the KCSPG motif towards binding an agonistic TNFR2 antibody or antigen-binding fragment thereof, e.g., by selectively presenting a conformation of the KCSPG epitope that is similar to the conformation this epitope exhibits in native human TNFR2. Exemplary peptides capable of stabilizing short sequence motifs include cyclic and bicyclic peptides, e.g., that feature an amide bond between the N- and C-terminal residues of the peptide and/or intramolecular cross-links formed by reaction of a side-chain functional group (e.g., a cysteine thiolate) with a scaffolding molecule (e.g., a multivalent electrophile, such as 2,6-bis(bromomethyl)pyridine or 1,3,5-tris(bromomethyl)benzene). Other intramolecular cross-links, such as olefin-containing linkers formed by ring-closing metathesis, saturated alkyl linkers formed by olefin reduction, disulfide bridges formed by cysteine oxidation, and triazole-containing linkers formed by azide-alkyne cycloaddition reactions are known in the art and can be used to produce a peptide that restricts the conformation of an epitope within TNFR2, such as the KCSPG motif, to that which is presented in the native protein (see, e.g., WO 2014/190257; WO 2008/040833; WO 2012/057624; U.S. Pat. Nos. 7,999,068; and 8,778,844; the disclosures of each of which are incorporated herein by reference).

The binding of an agonistic TNFR2 antibody or antigen-binding fragment thereof of the invention to TNFR2 or a constrained peptide containing one or more, or all, of the residues of the KCSPG motif can be quantified, e.g., via an ELISA-based technique. For instance, one can determine whether a TNFR2 antibody binds to a particular epitope within TNFR2 by analyzing the luminescence that occurs upon incubation of an HRP substrate (e.g., 2,2'-azino-di-3-ethylbenzthiazoline sulfonate) with a complex containing an antigen (e.g., a TNFR2-derived peptide) and a TNFR2 antibody when the complex is bound to a HRP-conjugated secondary antibody. For instance, TNFR2 antibodies of the invention may induce a luminescence response of about 150 absorbance units or more when incubated with surface-immobilized antigen and a HRP-conjugated secondary antibody in the presence of an HRP substrate. In certain cases, the luminescence observed can be from about 150 to about 1,400 absorbance units (e.g., 200-1,000 absorbance units, 300-900 absorbance units, or 400-800 absorbance units). In particular cases, the luminescence observed can be from about 150 to about 300 absorbance units (e.g., 150-200 absorbance units or 200-250 absorbance units).

Agonistic TNFR2 Antibodies that Bind TNFR2 from Non-Human Animals

In addition to binding one or more, or all, of the residues of the KCSPG motif, or polypeptides containing the KCSPG motif, agonistic TNFR2 antibodies and antigen-binding fragments thereof of the invention also include those that specifically bind epitopes containing the equivalent TNFR2 motif of non-human animals, such as non-human mammals, e.g., in a cow, bison, boar, mouse, or rat, among others. In these non-human mammals, the TNFR2 sequence features a KCPPG motif (SEQ ID NO: 396) in place of a KCSPG motif. Agonistic TNFR2 antibodies and antigen-binding fragments of the invention also include those that are capable of specifically binding epitopes that contain one or more, or all, of the residues KCPPG in TNFR2 derived from a non-human animal. These agonistic TNFR2 antibodies and antigen-binding fragments may be administered, e.g., to non-human mammals.

Sequences within non-human TNFR2 that are equivalent to the KCSPG motif in human TNFR2 are shown in Table 2 below.

TABLE 2

Location of sequences equivalent to
KCSPG in TNFR2 from non-human mammals

| Source of TNFR2 | Sequence equivalent to KCSPG | Amino acid positions of equivalent sequence within TNFR2 | SEQ ID NO. of full-length TNFR2 sequence | Genbank Accession No. of full-length TNFR2 sequence |
|---|---|---|---|---|
| Human | KCSPG | 56-60 | 366 | P20333.3 |
| Cattle | KCPPG | 56-60 | 397 | AAI05223 |
| Bison | KCPPG | 56-60 | 398 | XP_010848145 |
| Boar | KCPPG | 58-62 | 399 | ABV02767.1 |
| Mouse | KCPPG | 57-61 | 400 | AAA39752.1 |
| Rat | KCPPG | 57-61 | 401 | Q80WY6 |

Agonistic TNFR2 antibodies and antigen-binding fragments thereof of the invention may be capable of binding epitopes surrounding the KCPPG motif in TNFR2 derived from non-human animals. For instance, agonistic TNFR2 antibodies and antigen-binding fragments thereof may be capable of binding epitopes such as QKIQMCCSKCPPGYRVQSLC in TNFR2 derived from cattle (SEQ ID NO: 402), HKIQMCCSKCPPGYRVQSLC in TNFR2 derived from bison (SEQ ID NO: 403), TKAQMCCSKCPPGFRIQTSC in TNFR2 derived from boar (SEQ ID NO: 404), RKAQMCCAKCPPGQYVKHFC in TNFR2 derived from a mouse (SEQ ID NO: 405), and/or KKAQMCCAKCPPGQYAKHFC in TNFR2 derived from a rat (SEQ ID NO: 406), as well as sequences that exhibit at least 85% sequence identity (e.g., 85%, 90%, 95%, 97%, 99%, or 100% sequence identity) to these sequences and epitopes that contain conservative amino acid substitutions relative to these sequences (e.g., so long as the amino acids KCPPG are present in the epitope).

Agonistic TNFR2 antibodies and antigen-binding fragments thereof of the invention may be capable of binding epitopes surrounding downstream of the KCPPG motif in TNFR2 derived from non-human animals. For instance, agonistic TNFR2 antibodies and antigen-binding fragments thereof may be capable of binding epitopes such as SSDQVET in TNFR2 derived from cattle, bison, and boar (SEQ ID NO: 368), TTDQVEI in TNFR2 derived from mice (SEQ ID NO: 407), and/or SDDQVET in TNFR2 derived from rats (SEQ ID NO: 408), as well as sequences that exhibit at least 85% sequence identity (e.g., 85%, 90%, 95%, 97%, 99%, or 100% sequence identity) to these sequences and epitopes that contain conservative amino acid substitutions relative to these sequences.

Agonistic TNFR2 antibodies and antigen-binding fragments thereof of the invention may be capable of binding additional epitopes downstream of the KCPPG motif in TNFR2 derived from non-human animals. For instance, agonistic TNFR2 antibodies and antigen-binding fragments thereof may be capable of binding epitopes such as TTKQNRICTCKPGWYCTLGRQEGCRLCVALRKCGPGFGVA in TNFR2 derived from cattle and bison (SEQ ID NO: 409), TPKQNRICSCKPGWYCTLGRQEGCRLCMALRKCSPGFGVT in TNFR2 derived from boar (SEQ ID NO: 410), TKQQNRVCACEAGRYCALKTHSGSCRQCMRLSKCGPGFGVA in TNFR2 derived from mice (SEQ ID NO: 411), and/or TKKQNRVCACNADSYCALKLHSGNCRQCMKLSKCGPGFGVA in TNFR2 derived from rats (SEQ ID NO: 412), as well as sequences that exhibit at least 85% sequence identity (e.g., 85%, 90%, 95%, 97%, 99%, or 100% sequence identity) to these sequences and epitopes that contain conservative amino acid substitutions relative to these sequences.

In certain cases, agonistic TNFR2 antibodies and antigen-binding fragments thereof of the invention are capable of specifically binding epitopes that contain one or more, or all of the residues KCPPG in TNFR2 derived from a non-human animal and do not specifically bind a member of the TNFR superfamily other than TNFR2 (e.g., TNFR1, RANK, CD30, CD40, Lymphotoxin beta receptor (LT-βR), OX40, Fas receptor, Decoy receptor 3, CD27, 4-1BB, Death receptor 4, Death receptor 5, Decoy receptor 1, Decoy receptor 2, Osteoprotegrin, TWEAK receptor, TACI, BAFF receptor, Herpesvirus entry mediator, Nerve growth factor receptor, B-cell maturation antigen, Glucocorticoid-induced TNFR-related, TROY, Death receptor 6, Death receptor 3, and Ectodysplasin A2 receptor).

Additionally or alternatively, agonistic TNFR2 antibodies and antigen-binding fragments thereof of the invention for use in non-human mammals are capable of specifically binding epitopes containing one or more, or all, of the residues KCPPG in TNFR2 derived from a non-human animal, but do not specifically bind an epitope in TNFR2 derived from a non-human animal containing a sequence equivalent to the KCRPG motif present in human TNFR2 (e.g., KCGPG or KCSPG, see Table 3 and sequence alignment below).

Sequences in TNFR2 derived from a non-human animal that are equivalent to the KCRPG motif in human TNFR2 include the KCGPG motif (SEQ ID NO: 413) in cattle, bison, mice, and rats. The sequence in TNFR2 derived from a boar that is equivalent to KCRPG found in human TNFR2 is KCSPG, located at amino acids 144-148 within boar TNFR2. Sequences within TNFR2 derived from non-human animals that are equivalent to the KCRPG motif in human TNFR2 are shown in Table 3 below.

TABLE 3

Location of sequences equivalent to
KCRPG in TNFR2 from non-human mammals

| Source of TNFR2 | Sequence equivalent to KCRPG | Amino acid positions of equivalent sequence within TNFR2 | SEQ ID NO. of full-length TNFR2 sequence | Genbank Accession No. of full-length TNFR2 sequence |
|---|---|---|---|---|
| Human | KCRPG | 142-146 | 366 | P20333.3 |
| Cattle | KCGPG | 142-146 | 397 | AAI05223 |
| Bison | KCGPG | 142-146 | 398 | XP_010848145 |
| Boar | KCSPG | 144-148 | 399 | ABV02767.1 |
| Mouse | KCGPG | 144-148 | 400 | AAA39752.1 |
| Rat | KCGPG | 144-148 | 401 | Q80WY6 |

Epitopes within TNFR2 derived from the non-human mammals discussed above that may be bound by agonistic TNFR2 antibodies and antigen-binding fragments thereof of the invention are summarized in the sequence alignment below. This sequence alignment shows partial sequences of TNFR2 derived from human, cattle, bison, boar, mouse, and rat, as well as epitopes (highlighted in grey) that may be bound by agonistic TNFR2 antibodies and antigen-binding fragments thereof of the invention.

Alignment of partial TNFR2 sequences derived from human and select non-human mammals
```
Human:    1  MAPVAVWAALAVGLELWAAAHALPAQVAFTPYAPEPGSTCRL--REYYDQTAQMCCSKCSPGQHAKVECTKTSDTVCDSC   78
Cattle:   1  MAPTAFWAALAVGLQFWAAGRAVPAQAVFTPYIPEPGSSCRQ--QEYYNQKIQMCCSKCPPGYRVQSLCNMTLDTICASC   78
Bison:    1  MAPTAFWAALAVGLQFWAAGRAVPAQAVFTPYIPEPGSSCRQ--QEYYNHKIQMCCSKCPPGYRVQSLCNTTLDTICASC   78
Boar:     1  MAPAAVWAALTVGLQLWAAGRAVPSQAVEMPYAPELGSSCRLPLKEYYDTKAQMCCSKCPPGFRIQTSCNRTSDTVCGSC   80
Mouse:    1  MAPAALWVALVFELQLWATGHTVPAQVVLTPYKPEPGYECQIS-QEYYDRKAQMCCAKCPPGQYVKHFCNKTSDTVCADC   79
Rat:      1  MAPAALWVALVVELQLWATGHTVPAKVVLTPYKPEPGNQCQIS-QEYYDKKAQMCCAKCPPGQYAKHFCNKTSDTVCADC   79 invention are capable of localizing to the surface of a TNFR2-expressing cell (e.g., a T-reg cell) and rapidly associating with TNFR2, thereby inducing receptor activation, e.g., in a fashion similar to that of TNFα. Moreover, the slow dissociation of the antibody-TNFR2 complex can be indicative of a long half-life of the complex in vivo, which results in stable, sustained up-regulation of the growth of the TNFR2-expressing cell (e.g., sustained up-regulation of T-reg growth, such as a CD4+, CD25+, FOXP3+ T-cell). These ideal thermodynamic and kinetic parameters of TNFR2 binding are consistent with the strong intermolecular contacts that are established upon association of antibodies and antibody fragments of the invention with TNFR2.

Among the difficulties in developing TNFR2 antibodies that are capable of inducing TNFR2 signal transduction stimulating the propagation of T-reg cells has been the elucidation of epitopes within TNFR2 that promote agonistic receptor-binding. Particular, discrete peptide fragments found within the TNFR2 primary structure may bind agonistic antibodies of the invention by virtue of the spatial orientation of these residues in the native conformation of the receptor. Significantly, these residues have been difficult to identify, as many isolated linear TNFR2-derived peptides do not appear to interact with agonistic TNFR2 antibodies due to the different conformations these peptides exhibit when structurally pre-organized within the full-length protein and when isolated in solution. Epitope mapping analysis using linear peptides, as well as constrained cyclic and bicyclic peptides, derived from various regions of TNFR2 indicates that agonistic TNFR2 antibodies of the invention bind epitopes from distinct regions of the TNFR2 amino acid sequence, and may bind these epitopes in a conformation-dependent manner. Particularly important epitopes that bind agonistic TNFR2 antibodies of the invention and promote receptor activation are those that contain one or more, or all, of the residues of the KCSPG motif (SEQ ID NO: 367), located at positions 56-60 of SEQ ID NO: 366 within human TNFR2. One or more of these residues may reside within larger epitopes, such as residues 48-67 of SEQ ID NO: 366, which may interact with agonistic TNFR2 antibodies of the invention. The knowledge of those residues that selectively bind TNFR2 antibodies in a manner that promotes receptor activation, and thus, T-reg cell proliferation, can be used to identify and design a wide array of agonistic TNFR2 antibodies and antigen-binding fragments thereof using library screening techniques, such as those described herein or known in the art. For instance, structurally rigidified peptides containing one or more, or all, of the residues within the KCSPG sequence (e.g., a cyclic or bicyclic peptide that presents the KCSPG motif in a conformation similar to that observed in native human TNFR2) can be used to screen and select for antibodies, antigen-binding fragments, and antibody-like scaffolds that bind these epitopes with high affinity and selectivity.

Several distinct residues within TNFR2 bind agonistic TNFR2 antibodies and antibody fragments of the invention and establish strong intermolecular contacts with these antibodies. Notably, functional agonistic TNFR2 antibodies and antibody fragments of the invention selectively bind an epitope containing one or more, or all, of amino acids 56-60 of SEQ ID NO: 366 within human TNFR2 (KCSPG, SEQ ID NO: 367). The spatial orientation of this epitope is shown in FIG. 4. Agonistic TNFR2 antibodies and antigen-binding fragments thereof of the invention are capable of selectively binding an epitope of TNFR2 that contains one or more, or all, of the residues of the KCSPG motif within TNFR2. For instance, antibodies of the invention may exhibit specific binding to epitopes that include one or more, or all, of residues 48-67 of SEQ ID NO: 366 within human TNFR2 (QTAQMCCSKCSPGQHAKVFC, SEQ ID NO: 346), as well as epitopes that exhibit at least 85% sequence identity (e.g., 85%, 90%, 95%, 97%, 99%, or 100% sequence identity) to this sequence and epitopes that contain conservative amino acid substitutions relative to this sequence (e.g., so long as the amino acids KCSPG are present in the epitope). The KCSPG sequence motif represents an important functional epitope within TNFR2 towards promoting receptor activation and initiating MAPK/NF$_\kappa$B/TRAF2/3 signaling. As such, the ability of a TNFR2 antibody to interact with an epitope including one or more, e.g., all, of residues 56-60 of SEQ ID NO: 366 within TNFR2 characterizes antibodies of the invention that stimulate TNFR2 activity.

In addition to interacting with the KCSPG motif (SEQ ID NO: 367), agonistic TNFR2 antibodies of the invention may also specifically bind an epitope within human TNFR2 that includes at least five continuous or discontinuous residues from positions 96-154 of SEQ ID NO: 366 within human TNFR2 (CGSRCSSDQVETQACTREQNRICTCRPGWY-CALSKQEGCRLCAPIRKCRPGFGVARPGT, SEQ ID NO: 371), as well as epitopes that exhibit at least 85% sequence identity (e.g., 85%, 90%, 95%, 97%, 99%, or 100% sequence identity) to this sequence and epitopes that contain conservative amino acid substitutions relative to this sequence.

Agonistic TNFR2 antibodies of the invention may also specifically bind an epitope containing at least five continuous or discontinuous residues from positions 96-112 of SEQ ID NO: 366 within TNFR2 (CGSRCSSDQVETQACTR, SEQ ID NO: 372), or an epitope that exhibits at least 85% sequence identity (e.g., 85%, 90%, 95%, 97%, 99%, or 100% sequence identity) to this sequence or contains conservative amino acid substitutions relative to this sequence. For example, in certain cases, agonistic TNFR2 antibodies of the invention may specifically bind an epitope that includes one or more residues from positions 101-107 of SEQ ID NO: 366 within TNFR2 (SSDQVET, SEQ ID NO: 368), as well as epitopes that exhibit at least 85% sequence identity (e.g., 85%, 90%, 95%, 97%, 99%, or 100% sequence identity) to this sequence and epitopes that contain conservative amino acid substitutions relative to this sequence.

Additionally, agonistic TNFR2 antibodies of the invention may specifically bind an epitope containing at least five continuous or discontinuous residues from positions 110-147 of SEQ ID NO: 366 within TNFR2 (CTREQNRICT-CRPGWYCALSKQEGCRLCAPLRKCRPGF, SEQ ID NO: 373), or an epitope that exhibits at least 85% sequence identity (e.g., 85%, 90%, 95%, 97%, 99%, or 100% sequence identity) to this sequence or contains conservative amino acid substitutions relative to this sequence. For example, in certain cases, agonistic TNFR2 antibodies of the invention may specifically bind an epitope that includes one or more residues from positions 115-142 of SEQ ID NO: 366 within TNFR2 (NRICTCRPGWYCALSKQEGCRL-CAPLRK, SEQ ID NO: 369), as well as epitopes that exhibit at least 85% sequence identity (e.g., 85%, 90%, 95%, 97%, 99%, or 100% sequence identity) to this sequence and epitopes that contain conservative amino acid substitutions relative to this sequence.

Agonistic TNFR2 antibodies of the invention may also specifically bind an epitope containing at least five continuous or discontinuous residues from positions 106-155 of SEQ ID NO: 366 within TNFR2 (ETQACTREQNRICT-CRPGWYCALSKQEGCRLCAPLRKCRPGFG-VARPGTE, SEQ ID NO: 374), or an epitope that exhibits at least 85% sequence identity (e.g., 85%, 90%, 95%, 97%, 99%, or 100% sequence identity) to this sequence or contains conservative amino acid substitutions relative to this sequence. For example, in certain cases, agonistic TNFR2 antibodies of the invention may specifically bind an epitope that includes one or more residues from positions 111-150 of SEQ ID NO: 366 within TNFR2 (TREQNRICTCRPGWY-CALSKQEGCRLCAPLRKCRPGFGVA, SEQ ID NO: 370), as well as epitopes that exhibit at least 85% sequence identity (e.g., 85%, 90%, 95%, 97%, 99%, or 100% sequence identity) to this sequence and epitopes that contain conservative amino acid substitutions relative to this sequence.

In certain cases, an agonistic TNFR2 antibody of the invention may bind an epitope that includes one or more residues from positions 122-136 of SEQ ID NO: 366 within TNFR2 (PGWYCALSKQEGCRL, SEQ ID NO: 11), as well as epitopes that exhibit at least 85% sequence identity (e.g., 85%, 90%, 95%, 97%, 99%, or 100% sequence identity) to this sequence and epitopes that contain conservative amino acid substitutions relative to this sequence.

In addition to binding epitopes within TNFR2 that contain one or more residues of the KCSPG motif, agonistic TNFR2 antibodies of the invention may also bind epitopes containing one or more residues of the KCRPG motif (positions 142-146 within TNFR2, SEQ ID NO: 375). Preferably, however, agonistic TNFR2 antibodies or antigen-binding fragments thereof bind an epitope containing the KCRPG sequence with a $K_D$ that is substantially higher (e.g., at least 10-fold higher, 15-fold higher, 20-fold higher, 25-fold higher, 50-fold higher, 100-fold higher, 200-fold higher, 300-fold higher, 400-fold higher, 500-fold higher, 600-fold higher, 700-fold higher, 800-fold higher, 900-fold higher, 1,000-fold higher, or 10,000-fold higher) than that of the same antibody or antigen-binding fragment thereof for an epitope containing the KCSPG sequence. For instance, agonistic TNFR2 antibodies of the invention may bind an epitope containing at least five continuous or discontinuous residues from positions 130-149 of SEQ ID NO: 366 (KQEGCRLCAPLRKCRPGFGV, SEQ ID NO: 357), or an epitope that exhibits at least 85% sequence identity (e.g., 85%, 90%, 95%, 97%, 99%, or 100% sequence identity) to this sequence or contains conservative amino acid substitutions relative to this sequence. In certain cases, agonistic TNFR2 antibodies of the invention may bind an epitope containing one or more residues from positions 137-144 of SEQ ID NO: 366 (CAPLRKCR, SEQ ID NO: 376) and/or an epitope containing one or more residues from positions 141-149 of SEQ ID NO: 366 (KCRPGFGV, SEQ ID NO: 377), as well as epitopes that exhibit at least 85% sequence identity (e.g., 85%, 90%, 95%, 97%, 99%, or 100% sequence identity) to these sequences and epitopes that contain conservative amino acid substitutions relative to these sequences. In preferred embodiments, agonistic TNFR2 antibodies or antigen-binding fragments thereof do not exhibit specific binding for an epitope containing the KCRPG sequence.

Agonistic TNFR2 antibodies and antigen-binding fragments thereof of the invention also include those that can discriminate among members of the TNFR superfamily and specifically bind TNFR2 but do not specifically bind other receptors within this family. For instance, in various embodiments, the invention provides agonistic TNFR2 antibodies that are capable of binding and activating TNFR2 while not exhibiting specific binding for a TNFR superfamily member, such as TNFR1, RANK, CD30, CD40, Lymphotoxin beta receptor (LT-βR), OX40, Fas receptor, Decoy receptor 3, CD27, 4-1BB, Death receptor 4, Death receptor 5, Decoy receptor 1, Decoy receptor 2, Osteoprotegrin, TWEAK receptor, TACI, BAFF receptor, Herpesvirus entry mediator, Nerve growth factor receptor, B-cell maturation antigen, Glucocorticoid-induced TNFR-related, TROY, Death receptor 6, Death receptor 3, and Ectodysplasin A2 receptor.

Agonistic TNFR2 antibodies or antigen-binding fragments thereof of the invention include those that are capable of specifically binding an epitope within human TNFR2 containing one or more, or all, or residues 48-67 of SEQ ID NO: 366 (QTAQMCCSKCSPGQHAKVFC, SEQ ID NO: 346), and do not bind any other epitope within TNFR2 or within another TNFR superfamily member. For instance, agonistic TNFR2 antibodies or antigen-binding fragments thereof of the invention may specifically bind an epitope within human TNFR2 containing residues 56-60 of SEQ ID NO: 366 (KCSPG, SEQ ID NO: 367) and may not specifically bind any other epitope within TNFR2 or another TNFR superfamily member (e.g., an epitope containing residues 142-146 of human TNFR2 (KCRPG, SEQ ID NO: 375), or an epitope containing the residues KCPPG (SEQ ID NO: 396) of another TNFR superfamily member).

Agonistic TNFR2 Antibody MR2-1

One example of an agonistic TNFR2 antibody is MR2-1, which binds TNFR2 and potentiates TNFR2-mediated T-reg cell proliferation (FIG. 6A). MR2-1 binds osteoprotegrin, and is not an antibody of the present invention. However, the heavy and/or light chain variable regions of this antibody, or specifically the heavy and/or light chain CDRs of MR2-1, can be modified so as to eliminate the capacity of the resulting antibody or fragment thereof to bind a TNFR superfamily member other than TNFR2 so as to produce an agonistic TNFR2 antibody or antigen-binding fragment thereof of the invention. This can be accomplished using, e.g., genetic engineering and/or antibody library screening techniques described herein (see, e.g., "Negative screens of antibodies of antigen-binding fragments" below).

Agonistic TNFR2 Antibody 8E6.D1

A representative agonistic TNFR2 antibody of the invention is 8E6.D1, which is a murine antibody that binds TNFR2 and potentiates TNFR2-mediated T-reg cell proliferation (FIGS. 6A and 6B). The heavy and light chain CDRs of 8E6.D1, as well as the heavy and light chain variable regions in their entirety, and variants of these regions that exhibit substantially similar specific binding properties of 8E6.D1, can be used to make an agonistic TNFR2 antibody or antigen-binding fragment thereof of the invention, e.g., by replacing the mouse constant region of 8E6. D1 with a non-native constant region (e.g., a constant region from a human antibody). A hybridoma cell line that expresses a humanized version of antibody 8E6.D1 has been deposited in conformity with the requirements of the Budapest Treaty at the American Type Culture Collection (ATCC®) (10801 University Blvd., Manassas, VA 20110) on Dec. 7, 2022. It has been attributed ATCC® Patent Deposit Designation Accession No. PTA-127418.

Agonistic TNFR2 antibodies or antigen-binding fragments thereof of the invention exhibit an affinity for TNFR2 that is the same as or similar to that of 8E6.D1. The high affinity of 8E6.D1 for TNFR2 coupled with the rapid formation and the slow dissociation of the 8E6.D1-TNFR2 complex is consistent with the strong intermolecular contacts that underlie this protein-protein interaction. 8E6.D1 binds to distinct epitopes within the primary structure of TNFR2 that are spatially aligned in the native conformation of the receptor. The KCSPG motif (SEQ ID NO: 367) has been identified as a particularly important functional epitope that establishes strong intermolecular contacts with 8E6.D1 as determined by epitope mapping analysis (FIG. 1B). The interaction of these residues with TNFR2 antibodies of the invention selectively promotes agonistic activity. Agonistic TNFR2 antibody 8E6.D1 does not specifically bind an epitope containing residues 142-146 within TNFR2 (KCRPG, SEQ ID NO: 375). Additionally, 8E6.D1 does not specifically bind any TNFR superfamily member other than TNFR2. 8E6.D1 is capable of inducing T-reg cell proliferation in a dose-dependent fashion, and is also capable of synergizing with the cognate ligand for TNFR2, TNF, in order to promote receptor-mediated T-reg induction (FIGS. 6A and 6B).

Humanized, Primatized, and Chimeric Antibodies

Antibodies of the invention include human, humanized, primatized, and chimeric antibodies that contain one or more of the CDRs of 8E6.D1, or a CDR that exhibits at least 85% sequence identity (e.g., 90%, 95%, 97%, 99%, or 100% sequence identity) to any of these CDRs or sequences that contain conservative mutations relative to these CDRs. Antibodies of the invention also include human, humanized, primatized, and chimeric antibodies that contain one or more CDRs that are identical to those of 8E6.D1 except for conservative amino acid substitutions. For example, agonistic TNFR2 antibodies of the invention can be generated by incorporating any of the CDRs of 8E6.D1 into the framework regions (e.g., FR1, FR2, FR3, and FR4) of a human antibody. Exemplary framework regions that can be used for the development of a humanized TNFR2 antibody containing one or more of the CDRs of 8E6.D1 include, without limitation, those described in U.S. Pat. Nos. 7,732,578, 8,093,068, and WO 2003/105782; the disclosures of which are incorporated herein by reference.

One strategy that can be used to design humanized antibodies of the invention is to align the sequences of the heavy chain variable region and light chain variable region of 8E6.D1 with the heavy chain variable region and light chain variable region of a consensus human antibody. Consensus human antibody heavy chain and light chain sequences are known in the art (see e.g., the "VBASE" human germline sequence database; see also Kabat, et al., Sequences of Proteins of Immunological Interest, Fifth Edition, U.S. Department of Health and Human Services, NIH Publication No. 91-3242 (1991); Tomlinson et al., J. Mol. Biol., 227:776-98 (1992); and Cox et al, Eur. J. Immunol., 24:827-836 (1994); the disclosures of each of which are incorporated herein by reference). In this way, the variable domain framework residues and CDRs can be identified by sequence alignment (see Kabat, supra). One can substitute one or more CDRs of the heavy chain and/or light chain variable domains of a consensus human antibody with one or more corresponding CDRs of an agonistic TNFR2 antibody of the invention in order to produce a humanized TNFR2 antibody. Exemplary variable domains of a consensus human antibody include the heavy chain variable domain EVQLVESGGGLVQPGGSLRLS-CAASGFTFSDYAMSVVVRQAPGKGLEVVVAVISEN-GSDTYYADSVKGRFTIS RDDSKNTLYLQMNSLRAE-DTAVYYCARDRGGAVSYFDVWGQGTLVVVSS (SEQ ID NO: 378) and the light chain variable domain DIQMTQSPSSLSASVGDRVTITCRASQDVSSY-LAWYQQKPGKAPKLLI-YAASSLESGVPSRFSGSGSGTDFT LTISSLQPEDFA-TYYCQQYNSLPYTFGQGTKVEIKRT (SEQ ID NO: 379), identified in U.S. Pat. No. 6,054,297; the disclosure of which is incorporated herein by reference (CDRs are shown in bold were determined according to the method of Chothia, et al., J. Mol. Biol, 196:901-917 (1987), the disclosure of which is incorporated herein by reference). These amino acid substitutions can be made, for example, by recombinant expression of polynucleotides encoding the heavy and light chains of a humanized antibody in a host cell using methods known in the art or described herein. For instance, the heavy chain and light chain CDRs of 8E6.D1 can be inserted into the consensus human antibody heavy and light chain variable domain sequences in place of the CDRs native to these sequences (shown in bold above) in order to produce a humanized agonistic TNFR2 antibody of the invention.

Similarly, this strategy can also be used to produce primatized TNFR2 antibodies, as one can substitute the CDRs of the heavy and/or light chain variable domains of a primate antibody consensus sequence with one or more corresponding CDRs of 8E6.D1. Consensus primate antibody sequences known in the art (see e.g., U.S. Pat. Nos. 5,658,570; 5,681,722; and 5,693,780; the disclosures of each of which are incorporated herein by reference).

In certain cases, it may be desirable to import particular framework residues in addition to CDR sequences from a TNFR2 antibody, such as 8E6.D1, into the heavy and/or light chain variable domains of a human antibody. For instance, U.S. Pat. No. 6,054,297 identifies several instances when it may be advantageous to retain certain framework residues from a particular antibody heavy chain or light chain variable region in the resulting humanized antibody. In certain cases, framework residues may engage in non-covalent interactions with the antigen and thus contribute to the affinity of the antibody for the target antigen. In other cases, individual framework residues may modulate the conformation of a CDR, and thus indirectly influence the interaction of the antibody with the antigen. Alternatively, certain framework residues may form the interface between VH and VL domains, and may therefore contribute to the global antibody structure. In other cases, framework residues may constitute functional glycosylation sites (e.g., Asn-X-Ser/Thr) which may dictate antibody structure and antigen affinity upon attachment to carbohydrate moieties. In cases such as those described above, it may be beneficial to retain certain framework residues of an agonistic TNFR2 antibody (e.g., 8E6.D1) in the resulting humanized or primatized antibodies and antigen-binding fragments thereof of the invention, as various framework residues may promote high epitope affinity and improved biochemical activity of the antibody or antigen-binding fragment thereof.

Antibodies of the invention also include antibody fragments, Fab domains, F(ab')$_2$ molecules, single chain variable fragments (scFvs), tandem scFv fragments, diabodies, triabodies, dual variable domain immunoglobulins, multi-specific antibodies, bispecific antibodies, SMIP proteins, and heterospecific antibodies that contain one or more of the CDRs of 8E6.D1, or a CDR that exhibits at least 85% sequence identity (e.g., 90%, 95%, 97%, 99%, or 100% sequence identity) to any of these CDRs. Antibodies and antigen-binding fragments thereof of the invention include those that also contain CDRs having between one and three amino acid substitutions (e.g., conservative or nonconservative substitutions) relative to the CDR sequences of 8E6.D1. These molecules can be expressed recombinantly, e.g., by incorporating polynucleotides encoding these proteins into expression vectors for transfection in a eukaryotic or prokaryotic cell using techniques described herein or known in the art, or synthesized chemically, e.g., by solid phase peptide synthesis methods described herein or known in the art.

Antibodies of the invention additionally include antibody-like scaffolds that contain one or more of the CDRs of 8E6.D1, or a CDR that exhibits at least 85% sequence identity (e.g., 90%, 95%, 97%, 99%, or 100% sequence identity) to any of these CDRs or sequences that contain between one and three amino acid substitutions (e.g., conservative or nonconservative substitutions) relative to the CDR sequences of 8E6.D1. Examples of antibody-like scaffolds include proteins that contain a tenth fibronectin type III domain ($^{10}$Fn3), which contains BC, DE, and FG structural loops analogous to canonical antibodies. It has been shown that the tertiary structure of the $^{10}$Fn3 domain resembles that of the variable region of the IgG heavy chain, and one of skill in the art can graft, e.g., the CDRs of 8E6.D1 or sequences containing conserved amino acid substitutions relative to these CDRs onto the fibronectin scaffold by replacing residues of the BC, DE, and FG loops of $^{10}$Fn3 with residues of 8E6.D1 CDRs. This can be achieved by recombinant expression of a modified $^{10}$Fn3 domain in a prokaryotic or eukaryotic cell (e.g., using the vectors and techniques described herein). Examples of using the $^{10}$Fn3 domain as an antibody-like scaffold for the grafting of CDRs from antibodies onto the BC, DE, and FG structural loops are reported in WO 2000/034784; WO 2009/142773; WO 2012/088006; and U.S. Pat. No. 8,278,419; the disclosures of each of which are incorporated herein by reference.

Nucleic Acids and Expression Systems

Agonistic TNFR2 antibodies of the invention can be prepared by any of a variety of established techniques. For instance, an agonistic TNFR2 antibody or antigen-binding fragment thereof of the invention can be prepared by recombinant expression of immunoglobulin light and heavy chain genes in a host cell. To express an antibody recombinantly, a host cell can be transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N. Y., 1989), Current Protocols in Molecular Biology (Ausubel et al., eds., Greene Publishing Associates, 1989), and in U.S. Pat. No. 4,816,397; the disclosures of each of which are incorporated herein by reference.

Vectors for Expression of Agonistic TNFR2 Antibodies and Antibody Fragments

Viral genomes provide a rich source of vectors that can be used for the efficient delivery of exogenous genes into the genome of a cell (e.g., a eukaryotic or prokaryotic cell). Viral genomes are particularly useful vectors for gene delivery because the polynucleotides contained within such genomes are typically incorporated into the genome of a target cell by generalized or specialized transduction. These processes occur as part of the natural viral replication cycle, and do not require added proteins or reagents in order to induce gene integration. Examples of viral vectors include a retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpes virus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding antibody light and heavy chains or antibody fragments of the invention include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996, the disclosure of which is incorporated herein by reference). Other examples of viral genomes useful in conjunction with the compositions and methods of the invention include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus, and lentiviruses. Other examples of vectors are described, for example, in U.S. Pat. No. 5,801,030; the disclosure of which is incorporated herein by reference.

Genome Editing Techniques

In addition to viral vectors, a variety of additional methods have been developed for the incorporation of genes, e.g., those encoding antibody light and heavy chains, single chain variable fragments (scFvs), tandem scFvs, Fab domains, F(ab')$_2$ domains, diabodies, and triabodies, among others, into the genomes of target cells for antibody expression. One such method that can be used for incorporating polynucleotides encoding agonistic TNFR2 antibodies or antigen-binding fragments thereof into prokaryotic or eukaryotic cells includes transposons. Transposons are polynucleotides that encode transposase enzymes and contain a polynucleotide sequence or gene of interest flanked by excision sites at the 5' and 3' positions. Once a transposon has been delivered into a cell, expression of the transposase gene commences and results in active enzymes that cleave the gene of interest from the transposon. This activity is mediated by the site-specific recognition of transposon excision sites by the transposase. In certain cases, these excision sites may be terminal repeats or inverted terminal repeats. Once excised from the transposon, the gene of interest can be integrated into the genome of a prokaryotic or eukaryotic cell by transposase-catalyzed cleavage of similar excision sites that exist within nuclear genome of the cell. This allows the gene encoding a TNFR2 antibody or fragment or domain thereof to be inserted into the cleaved nuclear DNA at the excision sites, and subsequent ligation of the phosphodiester bonds that join the gene of interest to the DNA of the prokaryotic or eukaryotic cell genome completes the incorporation process. In certain cases, the transposon may be a retrotransposon, such that the gene encoding the antibody is first transcribed to an RNA product and then reverse-transcribed to DNA before incorporation in the prokaryotic or eukaryotic cell genome. Exemplary transposon systems include the piggybac transposon (described in detail in WO 2010/085699) and the sleeping beauty transposon (described in detail in US20050112764); the disclosures of each of which are incorporated herein by reference.

Another useful method for the integration of nucleic acid molecules encoding agonistic TNFR2 antibodies or antigen-binding fragments thereof into the genome of a prokaryotic or eukaryotic cell utilizes clustered regularly interspaced short palindromic repeats (CRISPR)/Cas technology, which is derived from a system that originally evolved as an adaptive defense mechanism in bacteria and archaea against infection by viruses. The CRISPR/Cas system consists of palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can theoretically design a CRISPR/Cas system to cleave any target DNA molecule of interest. This technique has been exploited in order to edit eukaryotic genomes (Hwang et al., Nat. Biotech., 31:227-229 (2013), the disclosure of which is incorporated herein by reference) and can be used as an efficient means of site-specifically editing eukaryotic or prokaryotic genomes in order to cleave DNA prior to the incorporation of a polynucleotide encoding a TNFR2 antibody or antigen-binding fragment thereof of the invention. The use of CRISPR/Cas to modulate gene expression has been described in U.S. Pat. No. 8,697,359; the disclosure of which is incorporated herein by reference.

Alternative methods for site-specifically cleaving genomic DNA prior to the incorporation of a polynucleotide encoding a TNFR2 antibody or antibody fragment of the invention include the use of zinc finger nucleases and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. Zinc finger nucleases and TALENs for use in genome editing applications are described, e.g., in Urnov et al., Nat. Rev. Genet., 11:636-646 (2010); and in Joung et al., Nat. Rev. Mol. Cell. Bio., 14:49-55 (2013); the disclosures of each of which are incorporated herein by reference. Additional genome editing techniques that can be used to incorporate polynucleotides encoding antibodies of the invention into the genome of a prokaryotic or eukaryotic cell include the use of ARCUS™ meganucleases that can be rationally designed so as to site-specifically cleave genomic DNA. The use of these enzymes for the incorporation of polynucleotides encoding agonistic TNFR2 antibodies or antibody fragments of the invention into the genome of a prokaryotic or eukaryotic cell is particularly advantageous in view of the structure-activity relationships that have been established for these enzymes. Single chain meganucleases can thus be modified at certain amino acid positions in order to create nucleases that selectively cleave DNA at desired locations. These single-chain nucleases have been described extensively, e.g., in U.S. Pat. Nos. 8,021,867 and 8,445,251; the disclosures of each of which are incorporated herein by reference.

Polynucleotide Sequence Elements

To express agonistic TNFR2 antibodies or antibody fragments of the invention, polynucleotides encoding partial or full-length light and heavy chains, e.g., obtained as described above, can be inserted into expression vectors such that the genes are operatively linked to transcriptional and translational control sequences. The expression vector and expression control sequences are chosen to be compatible with the expression host cell used. Polynucleotides encoding the light chain gene and the heavy chain of a TNFR2 antibody can be inserted into separate vectors, or, optionally, both polynucleotides can be incorporated into the same expression vector using established techniques described herein or known in the art.

In addition to polynucleotides encoding the heavy and light chains of an antibody (or a polynucleotide encoding an antibody fragment, such as a scFv molecule), the recombinant expression vectors of the invention may carry regulatory sequences that control the expression of the antibody chain genes in a host cell. The design of the expression vector, including the selection of regulatory sequences, may depend on such factors as the choice of the host cell to be transformed or the level of expression of protein desired. For instance, suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. Nos. 5,168,062; 4,510,245; and 4,968,615; the disclosures of each of which are incorporated herein by reference.

In addition to antibody heavy and light chain genes and regulatory sequences, recombinant expression vectors of the invention may carry additional sequences, such as sequences that regulate replication of the vector in host cells (e.g., origins of replication) and selectable marker genes. A selectable marker gene facilitates selection of host cells into which the vector has been introduced (see e.g., U.S. Pat. Nos. 4,399,216; 4,634,665; and 5,179,017; the disclosures of each of which are incorporated herein by reference). For example, typically the selectable marker gene confers resistance to cytotoxic drugs, such as G418, puromycin, blasticidin, hygromycin or methotrexate, to a host cell into which the vector has been introduced. Suitable selectable marker genes include the dihydrofolate reductase (DHFR) gene (for use in DHFR" host cells with methotrexate selection/amplification) and the neo gene (for G418 selection). In order to express the light and heavy chains of a TNFR2 antibody or a TNFR2 antibody fragment, the expression vector(s) containing polynucleotides encoding the heavy and light chains can be transfected into a host cell by standard techniques known in the art or described herein.

Polynucleotides Encoding Modified Agonistic TNFR2 Antibodies and Antibody Fragments In certain cases, agonistic TNFR2 antibodies or antibody fragments of the invention can be produced that are similar to a particular agonistic TNFR2 antibody but feature differences in the sequence of one or more CDRs. In other cases, the antibodies of the invention may be similar feature differences in one or more framework regions relative to another agonistic TNFR2 antibody. For instance, one or more framework regions of an agonistic TNFR2 antibody derived from a non-human mammal may be substituted with the framework region of a human antibody. Exemplary framework regions include, for example, human framework regions described in U.S. Pat. No. 7,829,086, and primate framework regions as described in EP 1945668; the disclosures of each of which are incorporated herein by reference.

Alternatively, antibodies of the invention may be similar to another agonistic TNFR2 antibody but exhibit differences in the sequence of one or more CDRs and differences in one or more framework regions. To generate nucleic acids encoding such agonistic TNFR2 antibodies, DNA fragments encoding, e.g., at least one, or both, of the light chain variable regions and the heavy chain variable regions can be produced by chemical synthesis (e.g., by solid phase polynucleotide synthesis techniques), in vitro gene amplification (e.g., by polymerase chain reaction techniques), or by replication of the polynucleotide in a host organism. For instance, nucleic acids encoding agonistic TNFR2 antibodies of the invention may be obtained by amplification and modification of germline DNA or cDNA encoding light and heavy chain variable sequences so as to incorporate the CDRs of an agonistic TNFR2 antibody into the framework residues of a consensus antibody. This can be achieved, for example, by performing site-directed mutagenesis of germline DNA or cDNA and amplifying the resulting polynucleotides using the polymerase chain reaction (PCR) according to established procedures. Germline DNA sequences for human heavy and light chain variable region genes are known in the art (see, e.g., the "VBASE" human germline sequence database; see also Kabat et al., Sequences of Proteins of Immunological Interest, Fifth Edition, U.S. Department of Health and Human Services, NIH Publication No. 91-3242 (1991); Tomlinson et al., J. Mol. Biol., 227: 776-798 (1992); and Cox et al., Eur. J. Immunol., 24:827-836 (1994); the disclosures of each of which are incorporated herein by reference). Additionally, a polynucleotide encoding the heavy or light chain variable region of an agonistic TNFR2 antibody can be synthesized and used as a template for mutagenesis to generate a variant as described herein using routine mutagenesis techniques. Alternatively, a DNA fragment encoding the variant can be directly synthesized (e.g., by established solid phase nucleic acid chemical synthesis procedures).

The isolated DNA encoding the $V_H$ region of an agonistic TNFR2 antibody of the invention can be converted to a full-length heavy chain gene (as well as a Fab heavy chain gene) by operatively linking the $V_H$-encoding DNA to another DNA molecule encoding heavy chain constant region domains (CH1, CH2, CH3, and, optionally, CH4). The sequences of human heavy chain constant region genes are known in the art (see e.g., Kabat et al., Sequences of Proteins of Immunological Interest, Fifth Edition, U.S. Department of Health and Human Services, NIH Publication No. 91-3242, 1991, the disclosure of which is incorporated herein by reference) and DNA fragments encompassing these regions can be obtained by standard PCR amplification. The heavy chain constant region can be an IgG1, IgG2, IgG3, IgG4, IgA, IgE, IgM or IgD constant region, but in certain embodiments is an IgG1 constant region. For a Fab fragment heavy chain gene, the VH-encoding DNA can be operatively linked to another DNA molecule encoding only the heavy chain CH1 domain.

The isolated DNA encoding the VL region of an agonistic TNFR2 antibody of the invention can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al., Sequences of Proteins of Immunological Interest, Fifth Edition (U.S. Department of Health and Human Services, NIH Publication No. 91-3242, 1991)) and DNA fragments encompassing these regions can be obtained, e.g., by amplification in a prokaryotic or eukaryotic cell of a polynucleotide encoding these regions, by PCR amplification, or by chemical polynucleotide synthesis. The light chain constant region can be a kappa (κ) or lambda (λ) constant region. To create a scFv gene, the VH and VL-encoding DNA fragments are operatively linked to another fragment encoding a flexible linker, e.g., a polynucleotide encoding a flexible, hydrophilic amino acid sequence, such as the amino acid sequence $(Gly_4Ser)_3$, such that the $V_H$ and $V_L$ sequences can be expressed as a contiguous single-chain protein, with the $V_L$ and $V_H$ regions joined by the linker (see e.g., Bird et al., Science 242:423-426 (1988); Huston et al., Proc. Natl. Acad. Sci. USA 85:5879-5883 (1988); McCafferty et al., Nature 348:552-554 (1990); the disclosures of each of which are incorporated herein by reference).

Recombinant DNA technology can also be used to remove some or all of the DNA encoding either or both of the light and heavy chains that is not necessary for binding to TNFR2. The molecules expressed from such truncated DNA molecules are also encompassed by the antibodies of the invention. In addition, bifunctional antibodies can be produced in which one heavy and one light chain are derived from an agonistic TNFR2 antibody and the other heavy and light chain are specific for an antigen other than TNFR2. Such antibodies can be generated, e.g., by crosslinking a heavy chain and light chain derived from an agonistic TNFR2 antibody to a heavy chain and light chain of a second antibody by standard chemical crosslinking methods (e.g., by disulfide bond formation). Bifunctional antibodies can also be made by expressing a nucleic acid molecule engineered to encode a bifunctional antibody in a prokaryotic or eukaryotic cell.

In certain cases, dual specific antibodies, i.e., antibodies that bind TNFR2 and a different antigen using the same binding site, can be produced by mutating amino acid residues in the light chain and/or heavy chain CDRs. In various embodiments, dual specific antibodies that bind two antigens, such as TNFR2 and a second cell-surface receptor, can be produced by mutating amino acid residues in the periphery of the antigen-binding site. (Bostrom et al., Science 323: 1610-1614 (2009); the disclosure of which is incorporated herein by reference). Dual functional antibodies can be made by expressing a polynucleotide engineered to encode a dual specific antibody.

Modified agonistic TNFR2 antibodies and antibody fragments of the invention can also be produced by chemical synthesis (e.g., by the methods described in Solid Phase Peptide Synthesis, 2nd ed., 1984 The Pierce Chemical Co., Rockford, 111; the disclosure of which is incorporated herein by reference). Variant antibodies can also be generated using a cell-free synthetic platform (see, e.g., Chu et al., Biochemia No. 2, 2001 (Roche Molecular Biologicals); the disclosure of which is incorporated herein by reference).

The above-described methods can be applied to antibody 8E6.D1 so as to produce an agonistic TNFR2 antibody or antigen-binding fragment thereof with altered properties. For instance, agonistic TNFR2 antibodies of the invention can be based on the heavy chain or light chain amino acid sequences or one or more CDRs of 8E6.D1. Using techniques described herein or known in the art, one can modify one or more amino acid sequences of 8E6.D1, e.g., so as to improve the affinity of the resulting antibody for TNFR2. Full-length antibodies and antibody fragments can also be produced using the amino acid sequences of 8E6.D1 as a starting point for the design of other TNFR2 agonistic antibodies or antigen-binding fragments of the invention. For instance, using standard techniques known in the art, one can produce DNA fragments encoding the VH and/or VL segments of 8E6.D1, e.g., by chemical synthesis or by PCR-based methods. These DNA fragments can be further manipulated by standard recombinant DNA techniques, e.g., to convert the variable region genes to full-length antibody chain genes or to fragment genes, such as those that encode a Fab fragment, F(ab')$_2$ fragment, scFv, diabody, triabody, or antibody-like scaffold protein. In these manipulations, a VL- or VH-encoding DNA fragment is operatively linked to another DNA fragment encoding another protein, such as an antibody constant region, a flexible linker, or a scaffold protein (e.g., a $^{10}$Fn3 domain).

Host Cells for Expression of Agonistic TNFR2 Antibodies and Antibody Fragments

Agonistic TNFR2 antibodies and antigen-binding fragments thereof of the invention may be expressed in either prokaryotic or eukaryotic host cells. In certain embodiments, expression of antibodies or antigen-binding fragments thereof is performed in eukaryotic cells, e.g., mammalian host cells, for optimal secretion of a properly folded and immunologically active antibody. Exemplary mammalian host cells for expressing the recombinant antibodies or antigen-binding fragments thereof of the invention include Chinese Hamster Ovary (CHO cells) (including DHFR CHO cells, described in Urlaub and Chasin, Proc. Natl. Acad. Sci. USA, 77:4216-4220 (1980), used with a DHFR selectable marker, e.g., as described in Kaufman and Sharp, Mol. Biol., 159:601-621, (1982), NSO myeloma cells, COS cells, 293 cells, and SP2/0 cells. Additional cell types that may be useful for the expression of antibodies and fragments thereof include bacterial cells, such as BL-21(DE3) E. coli cells, which can be transformed with vectors containing foreign DNA according to established protocols. Additional eukaryotic cells that may be useful for expression of antibodies include yeast cells, such as auxotrophic strains of S. cerevisiae, which can be transformed and selectively grown in incomplete media according to established procedures known in the art. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown.

Antibodies can be recovered from the culture medium using standard protein purification methods. Host cells can also be used to produce portions of intact antibodies, such as Fab fragments or scFv molecules. The invention also includes methods in which the above procedure is varied according to established protocols known in the art. For example, it can be desirable to transfect a host cell with DNA encoding either the light chain or the heavy chain (but not both) of an agonistic TNFR2 antibody of this invention in order to produce an antigen-binding fragment of the antibody.

Once an agonistic TNFR2 antibody or antigen-binding fragments thereof of the invention has been produced by recombinant expression, it can be purified by any method known in the art for purification of an immunoglobulin molecule, for example, by chromatography (e.g., ion exchange, affinity, particularly by affinity for TNFR2 after Protein A or Protein G selection, and sizing column chromatography), centrifugation, differential solubility, or by any other standard technique for the purification of proteins. Further, the agonistic TNFR2 antibodies of the invention or fragments thereof can be fused to heterologous polypeptide sequences described herein or otherwise known in the art to facilitate purification or to produce therapeutic conjugates (see "Antibody conjugates," below).

Once isolated, an agonistic TNFR2 antibody or antigen-binding fragments thereof can, if desired, be further purified, e.g., by high performance liquid chromatography (see, e.g., Fisher, Laboratory Techniques in Biochemistry and Molecular Biology (Work and Burdon, eds., Elsevier, 1980); the disclosure of which is incorporated herein by reference), or by gel filtration chromatography, such as on a Superdex™ 75 column (Pharmacia Biotech AB, Uppsala, Sweden).

Platforms for Generating and Affinity-Maturing Agonistic TNFR2 Antibodies and Antigen-Binding Fragments Mapping Epitopes of TNFR2 that Promote Receptor Activation Agonistic TNFR2 antibodies and antigen-binding fragments thereof of the invention can be produced by screening libraries of antibodies and antigen-binding fragments thereof for functional molecules that are capable of binding epitopes within TNFR2 that selectively promote receptor activation. Linear peptides isolated from the TNFR2 protein may not adopt the same three dimensional conformations as those peptide sequences located within the protein. TNFR2 provides a structurally rigidified framework that biases the conformations of individual peptide fragments and reinforces these spatial orientations by establishing intramolecular contacts (e.g., hydrogen bonds, dipole-dipole interactions, salt bridges) and by differentially positioning various regions for exposure to solvent depending on the relative hydrophilicity and lipophilicity of these areas (Mukai et al., Sci. Signal., 3:ra83-ra83 (2010); the disclosure of which is incorporated herein by reference). The conformational constraint of a peptide fragment within TNFR2 can be achieved by incorporating the amino acid residues of a TNFR2 epitope (e.g., an epitope that promotes receptor activation) into a structurally pre-organized peptide scaffold, such as a cyclic, bicyclic, tricyclic, or tetracyclic peptide. Cyclic and polycyclic peptides such as these confine a peptide fragment to a distinct three-dimensional conformation. This can be achieved, e.g., by synthesizing peptide epitopes isolated from TNFR2 by established chemical synthetic methods (e.g., by solid phase peptide synthesis as described herein) and incorporating cysteine residues into the sequence at the N- and C-terminal positions or at various internal positions within the peptide chain. It may be advantageous to incorporate cysteine residues that are chemically protected at the thiol moiety with a protecting group that can be removed under conditions different from those used to remove other protecting groups within the peptide being synthesized and different from those used to assemble the peptide chain. Exemplary orthogonal protecting groups for the cysteine thiol include the 4-methyltrityl group and 4-methoxtrityl group, each of which can be removed using dilute trifluoracetic acid (examples are described, e.g., in Isidro-Llobet et al., Chem Rev., 109:2455-2504 (2009); the disclosure of which is incorporated herein by reference).

After introducing a cysteine residue into a synthetic peptide fragment derived from an epitope within TNFR2, the peptide can be cyclized by treating the peptide with a multivalent electrophile, such as a bis(bromomethyl) or tris(bromomethyl)arene derivative. Alternative multivalent thiol-reactive electrophiles can be used, e.g., 1,5-difluoro-2,4-dinitrobenzene, acyclic dibromoalkanes, and others (see, e.g., Jo et al., J. Am. Chem. Soc., 134:17704-17713 (2012); the disclosure of which is incorporated herein by reference). In certain cases, it may be advantageous to prevent the participation of a cysteine residue in the synthetic peptide fragment in a cyclization reaction. For instance, it may be desirable to synthesize a polycyclic peptide containing multiple cysteine residues such that only select cysteine thiols participate in the intramolecular crosslinking process. To prevent unwanted participation of these additional Cys thiol groups in the coupling reaction, a simple approach is, for instance, to use Fmoc-Cys(Acm) (Fmoc-acetamidomethyl-L-cysteine) for the introduction of a protected Cys residue during the course of peptide synthesis. Alternatively, Fmoc-Cys(StBu)-OH can be used, and/or the corresponding t-butyloxycarbonyl (Boc)-protected amino acids. The Acm or StBu group is not removed during the course of a normal TFA deprotection-cleavage reaction, and instead requires oxidative treatment (e.g., with iodine, $I_2$) in the case of the Acm group, or reductive treatment (e.g., β-mercaptoethanol or 1,4-dithiothreiotol) in the case of the StBu group to yield the reduced sulfhydryl form of the peptide, which can either be used directly or subsequently oxidized to the corresponding cystinyl peptide. In one embodiment, a peptide is used which contains at least one Cys derivative, such as Cys (Acm) or Cys(StBu), to allow selective deprotection of a Cys-thiol group. Selective deprotection of a Cys-thiol group renders the Cys-thiol group available for reacting at a desired moment, such as following completion of peptide chain assembly and prior to the deprotection of other residues within the peptide (see, e.g., WO 2008/013454; the disclosure of which is incorporated herein by reference).

As an example, libraries of cyclic and polycyclic peptides containing individual fragments isolated from TNFR2 and combinations of fragments from distinct regions of TNFR2 can be synthesized by techniques such as those described above in order to incorporate cysteine residues at various positions within the peptide scaffold and using different electrophilic crosslinking reagents (see, e.g., Example 1 and FIG. 2A, SEQ ID NOs: 1-341). These peptides can be immobilized on a solid surface and screened for molecules that bind MR2-1 using an ELISA-based screening platform using established procedures. Using this assay, peptides that contain residues within epitopes of TNFR2 that promote receptor activation may structurally pre-organize these amino acids such that they resemble the conformations of the corresponding peptide in the native protein. Cyclic and polycyclic peptides thus obtained (e.g., peptides having the sequence of any one of SEQ ID NOs: 1-341, and particularly those that contain the KCSPG motif, as in SEQ ID NOs: 53, 69, 75, 118, and 233) can be used to screen libraries of antibodies and antigen-binding fragments thereof in order to identify TNFR2 antibodies of the invention. Moreover, since these constrained peptides act as surrogates for epitopes within TNFR2 that promote receptor activation, antibodies generated using this screening technique may bind the corresponding epitopes in TNFR2 and are expected to be agonistic of receptor activity.

Screening of Antibody Libraries for Agonistic TNFR2 Antibodies and Antigen-Binding Fragments Methods for high throughput screening of antibody libraries for molecules capable of binding epitopes within TNFR2 (e.g., epitopes presented by peptides having the sequence of any one of SEQ ID NOs: 1-341, such as SEQ ID NOs: 3, 11, 61, or 87, and particularly those that contain the KCSPG motif, as in SEQ ID NOs: 53, 69, 75, 118, and 233) include, without limitation, display techniques including phage display, bacterial display, yeast display, mammalian display, ribosome display, mRNA display, and cDNA display. The use of phage display to isolate ligands that bind biologically relevant molecules has been reviewed, e.g., in Felici et al., Biotechnol. Annual Rev. 1:149-183 (1995); Katz, Annual Rev. Biophys. Biomol. Struct. 26:27-45 (1997); and Hoogenboom et al., Immunotechnology 4:1-20, (1998); the disclosures of each of which are incorporated herein by reference. Several randomized combinatorial peptide libraries have been constructed to select for polypeptides that bind different targets, e.g., cell surface receptors or DNA (reviewed by Kay, Perspect. Drug Discovery Des. 2, 251-268 (1995); and Kay et al., Mol. Divers. 1:139-140 (1996). Proteins and multimeric proteins have been successfully phage-displayed as functional molecules (see EP 0349578A, EP 4527839A, EP 0589877A; Chiswell and McCafferty, Trends Biotechnol. 10, 80-84 (1992)). In addition, functional antibody fragments (e.g. Fab, single chain Fv [scFv]) have been expressed (see, e.g., McCafferty et al., Nature 348: 552-554 (1990); Barbas et al., Proc. Natl. Acad Sci. USA 88:7978-7982 (1991); and Clackson et al., Nature 352:624-628 (1991). These references are hereby incorporated by reference in their entirety.

(i) Phage Display Techniques

As an example, phage display techniques can be used in order to screen libraries of antibodies and antigen-binding fragments thereof for functional molecules capable of binding cyclic or polycyclic peptides containing epitopes within TNFR2 that promote receptor activation (e.g., peptides having the sequence of any one of SEQ ID NOs: 1-341, such as SEQ ID NOs: 3, 11, 61, or 87, and particularly those that contain the KCSPG motif, as in SEQ ID NOs: 53, 69, 75, 118, and 233). For instance, libraries of polynucleotides encoding single chain antibody fragments, such as scFv fragments, that contain randomized hypervariable regions can be obtained using established procedures (e.g., solid phase polynucleotide synthesis or error-prone PCR techniques, see McCullum et al., Meth. Mol. Biol., 634:103-109 (2010); incorporated herein by reference). These randomized polynucleotides can subsequently be incorporated into a viral genome such that the randomized antibody chains encoded by these genes are expressed on the surface of filamentous phage, e.g., by a covalent bond between the antibody chain and a coat protein (e.g., pIII coat protein on the surface of M13 phage). This provides a physical connection between the genotype and phenotype of the antibody chain. In this way, libraries of phage that display diverse antibody chains containing random mutations in hypervariable regions can be screened for the ability of the exterior antibody chains to bind TNFR2 epitopes (e.g., peptides having the sequence of any one of SEQ ID NOs: 1-341) that are immobilized to a surface using established procedures. For instance, cyclic peptides such as those represented by SEQ ID NOs: 53, 69, 75, 118, and 233, which contain the KCSPG motif, can be physically bound to the surface of a microtiter plate by forming a covalent bond between the peptide and an epitope tag (e.g., biotin) and incubating the peptide in wells of a microtiter plate that have been previously coated with a complementary tag (e.g., avidin) that binds the tag attached to the peptide with high affinity. Suitable epitope tags include, without limitation, maltose-binding protein, glutathione-S-transferase, a poly-histidine tag, a FLAG-tag, a myc-tag, human influenza hemagglutinin (HA) tag, biotin, streptavidin. Peptides containing the epitopes presented by these molecules are capable of being immobilized on surfaces containing such complementary molecules as maltose, glutathione, a nickel-containing complex, an anti-FLAG antibody, an anti-myc antibody, an anti-HA antibody, streptavidin, or biotin, respectively. In this way, phage can be incubated with a surface containing an immobilized TNFR2-derived peptide for a time suitable to allow binding of the antibody to the constrained peptide and in the presence of an appropriate buffer system (e.g., one that contains physiological salt concentration, ionic strength, and is maintained at physiological pH by a buffering agent). The surface can then be washed (e.g., with phosphate buffer containing 0.1% Tween-20) so as to remove phage that do not present antibody chains that interact with the TNFR2-derived peptides with an affinity greater than a particular threshold value.

The affinity of the antibodies that remain after this initial panning (i.e., screening) step can be modulated by adjusting the conditions of the washing step (e.g., by including mildly acidic or basic components, or by including other TNFR2-derived peptides at a low concentration in order to compete with immobilized peptides for antigen-binding sites). In this way, the population of phage that remains bound to the surfaces of the microtiter plate following the washing step is enriched for phage that bind TNFR2-derived peptide epitopes that promote receptor activation. The remaining phage can then be amplified by eluting the phage from the surface containing these peptides (e.g., by altering the ambient pH, ionic strength, or temperature) so as to diminish protein-protein interaction strength. The isolated phage can then be amplified, e.g., by infecting bacterial cells, and the resulting phage can optionally be subjected to panning by additional iterations of screening so as to further enrich the population of phage for those harboring higher-affinity TNFR2 antibodies. Following these panning stages, phage that display high-affinity antibodies or antigen-binding fragments thereof can subsequently be isolated and the genomes of these phage can be sequenced in order to identify the polynucleotide and polypeptide sequences of the encoded antibodies. Phage display techniques such as this can be used to generate, e.g., antibody chains, such as scFv fragments, tandem scFv fragments, and other antigen-binding fragments of the invention that can be used as agonists of TNFR2. Exemplary phage display protocols for the identification of antibody chains and antigen-binding fragments thereof that bind a particular antigen with high affinity are well-established and are described, e.g., in U.S. Pat. No. 7,846,892; WO 1997/002342; U.S. Pat. No. 8,846,867; and WO 2007/132917; the disclosures of which are incorporated herein by reference. Similar phage display techniques can be used to generate antibody-like scaffolds (e.g., $^{10}$Fn3 domains) of the invention that bind epitopes within TNFR2 that promote receptor activation (e.g., epitopes presented by peptides with the sequence of any one of SEQ ID NOs: 1-341, such as SEQ ID NOs: 3, 11, 61, or 87, and particularly those that contain the KCSPG motif, as in SEQ ID NOs: 53, 69, 75, 118, and 233). Exemplary phage display protocols for the identification of antibody-like scaffold proteins are described, e.g., in WO 2009/086116; the disclosure of which is incorporated herein by reference.

(ii) Cell-Based Display Techniques

Other in vitro display techniques that exploit the linkage between genotype and phenotype of a solvent-exposed antibody or antigen-binding fragment thereof include yeast and bacterial display. Yeast display techniques are established in the art and are often advantageous in that high quantities of antibodies (often up to 30,000) can be presented on the surface of an individual yeast cell (see, e.g., Boder et al., Nat Biotechnol. 15:553 (1997); the disclosure of which is incorporated herein by reference). The larger size of whole cells (e.g., yeast cells or bacterial cells) over filamentous phage enables an additional screening strategy, as one can use flow cytometry to both analyze and sort libraries of labeled cells. For instance, established procedures can be used to generate libraries of bacterial cells or yeast cells that express antibodies containing randomized hypervariable regions (see, e.g., see U.S. Pat. No. 7,749,501 and US 2013/0085072; the disclosures of each which are incorporated herein by reference). For instance, large libraries of yeast cells that express polynucleotides encoding naïve scFv fragments can be made using established procedures (de Bruin et al., Nat Biotechnol 17:397, (1999); the disclosure of which is incorporated herein by reference). Yeast cells expressing these polynucleotides can then be incubated with two different fluorescent molecules during the panning steps: one dye that binds conserved residues within the antibody and thus reflects the amount of antibody displayed, and another dye that fluoresces at a different wavelength and binds the antigen, thus indicating the amount of antigen bound. In these cases, it is useful to use a cyclic or polycyclic peptide containing the sequence of any one of SEQ ID NOs: 1-341, such as SEQ ID NOs: 3, 11, 61, or 87 (and particularly those that contain the KCSPG motif, as in SEQ ID NOs: 53, 69, 75, 118, and 233) that has been conjugated to an epitope tag (e.g., biotin), optionally at a residue that is not expected to interfere with antibody-antigen-binding. This enables a fluorescent dye labeled with a complementary tag (e.g., avidin) to localize to the antibody-antigen complex. This results in great flexibility and immediate feedback on the progress of a selection. In contrast to phage display, by normalizing to antibody display levels, antibodies with higher affinities, rather than greater expression levels can easily be selected. In fact, it is possible to distinguish and sort antibodies whose affinities differ by only two-fold (see, e.g., VanAntwerp and Wittrup, Biotechnol. Prog., 16:31, (2000); the disclosure of which is incorporated herein by reference).

(iii) Nucleotide Display Techniques

Display techniques that utilize in vitro translation of randomized polynucleotide libraries also provide a powerful approach to generating agonistic TNFR2 antibodies of the invention. For instance, randomized DNA libraries encoding antibodies or antigen-binding fragments thereof that contain mutations within designated hypervariable regions can be obtained, e.g., using established PCR-based mutagenesis techniques as described herein. The polynucleotides of these libraries may contain transcription regulating sequences, such as promoters and transcription terminating sequences, and may additionally encode sequences that increase the rate of translation of the resulting mRNA construct (e.g., IRES sequences, 5' and 3' UTRs, a poly-adenylation tract, and other elements known in the art to promote translation of an RNA transcript). These polynucleotide libraries can be incubated in an appropriately buffered solution containing RNA polymerase and RNA nucleoside triphosphates (NTPs) in order to enable transcription of the DNA sequences to competent mRNA molecules, which can subsequently be translated by large and small ribosomal subunits, aminoacyl tRNA molecules, and translation initiation and elongation factors present in solution (e.g., using the PURExpress® In Vitro Protein Synthesis Kit, New England Biolabs®). Designed mRNA modifications can enable the antibody product to remain covalently bound to the mRNA template by a chemical bond to puromycin (e.g., see Keefe, Curr. Protoc. Mol. Biol., Chapter 24, Unit 24.5 (2001); the disclosure of which is incorporated herein by reference). This genotype-phenotype linkage can thus be used to select for antibodies that bind a TNFR2-derived peptide (e.g., a peptide that has the sequence of any one of SEQ ID NOs: 1-341, such as SEQ ID NOs: 3, 11, 61, or 87, and particularly those that contain the KCRPG motif, as in SEQ ID NOs: 53, 69, 75, 118, and 233) by incubating mRNA:antibody fusion constructs with a peptide immobilized to a surface and panning in a fashion similar to phage display techniques (see, e.g., WO 2006/072773; the disclosure of which is incorporated herein by reference).

Optionally, antibodies of the invention can be generated using a similar technique, except the antibody product may be bound non-covalently to the ribosome-mRNA complex rather than covalently via a puromycin linker. This platform, known as ribosome display, has been described, e.g., in U.S. Pat. No. 7,074,557; the disclosure of which is incorporated herein by reference. Alternatively, antibodies can be generated using cDNA display, a technique that is analogous to mRNA display methodology with the exception that cDNA, rather than mRNA, is covalently bound to an antibody product via a puromycin linker. cDNA display techniques offer the advantage of being able to perform panning steps under increasingly stringent conditions, e.g., under conditions in which the salt concentration, ionic strength, pH, and/or temperature of the environment is adjusted in order to screen for antibodies with particularly high affinity for TNFR2-derived peptides. This is due to the higher natural stability of double-stranded cDNA over single-stranded mRNA. cDNA display screening techniques are described, e.g., in Ueno et al., Methods Mol. Biol., 805:113-135 (2012); the disclosure of which is incorporated herein by reference.

In addition to generating agonistic TNFR2 antibodies of the invention, in vitro display techniques (e.g., those described herein and those known in the art) also provide methods for improving the affinity of a TNFR2 antibody of the invention. For instance, rather than screening libraries of antibodies and fragments thereof containing completely randomized hypervariable regions, one can screen narrower libraries of antibodies and antigen-binding fragments thereof that feature targeted mutations at specific sites within hypervariable regions. This can be accomplished, e.g., by assembling libraries of polynucleotides encoding antibodies or antigen-binding fragments thereof that encode random mutations only at particular sites within hypervariable regions. These polynucleotides can then be expressed in, e.g., filamentous phage, bacterial cells, yeast cells, mammalian cells, or in vitro using, e.g., ribosome display, mRNA display, or cDNA display techniques in order to screen for antibodies or antigen-binding fragments thereof that specifically bind TNFR2 epitopes that promote receptor activation (e.g., peptides containing the sequence of any one of SEQ ID NOs: 1-341, such as SEQ ID NOs: 3, 11, 61, or 87, and particularly those that contain the KCSPG motif, as in SEQ ID NOs: 53, 69, 75, 118, and 233) with improved binding affinity. Yeast display is particularly well-suited for affinity maturation, and has been used previously to improve the affinity of a single chain antibody to a $K_D$ of 48 fM (see Boder et al., Proc Natl Acad Sci USA 97:10701 (2000)); the disclosure of which is incorporated herein by reference.

Additional in vitro techniques that can be used for the generation and affinity maturation of agonistic TNFR2 antibodies of the invention include the screening of combinatorial libraries of antibodies or antigen-binding fragments thereof for functional molecules capable of specifically binding TNFR2-derived peptides (e.g., a peptide having the amino acid sequence of any one of SEQ ID NOs: 1-341, such as SEQ ID NOs: 3, 11, 61, or 87, and particularly a peptide containing the KCSPG motif, such as a peptide having the amino acid sequence of any one of SEQ ID NOs: 53, 69, 75, 118, and 233). Combinatorial antibody libraries can be obtained, e.g., by expression of polynucleotides encoding randomized hypervariable regions of an antibody or antigen-binding fragment thereof in a eukaryotic or prokaryotic cell. This can be achieved, e.g., using gene expression techniques described herein or known in the art. Heterogeneous mixtures of antibodies can be purified, e.g., by Protein A or Protein G selection, sizing column chromatography), centrifugation, differential solubility, and/or by any other standard technique for the purification of proteins. Libraries of combinatorial libraries thus obtained can be screened, e.g., by incubating a heterogeneous mixture of these antibodies with a peptide derived from TNFR2 that has been immobilized to a surface (e.g., a peptide having the amino acid sequence of any one of SEQ ID NOs: 1-341 immobilized to the surface of a solid-phase resin or a well of a microtiter plate) for a period of time sufficient to allow antibody-antigen-binding. Non-binding antibodies or fragments thereof can be removed by washing the surface with an appropriate buffer (e.g., a solution buffered at physiological pH (approximately 7.4) and containing physiological salt concentrations and ionic strength, and optionally containing a detergent, such as TWEEN-20). Antibodies that remain bound can subsequently be detected, e.g., using an ELISA-based detection protocol (see, e.g., U.S. Pat. No. 4,661,445; the disclosure of which is incorporated herein by reference).

Additional techniques for screening combinatorial libraries of antibodies for those that specifically bind TNFR2-derived peptides (e.g., a peptide containing the amino acid sequence of any one of SEQ ID NOs: 1-341, such as SEQ ID NOs: 3, 11, 61, or 87, and particularly a peptide containing the KCSPG motif, such as a peptide having the amino acid sequence of any one of SEQ ID NOs: 53, 69, 75, 118, and 233) include the screening of one-bead-one-compound libraries of antibody fragments. Antibody fragments can be chemically synthesized on a bead (e.g., using established split-and-pool solid phase peptide synthesis protocols) composed of a hydrophilic, water-swellable material such that each bead displays a single antibody fragment. Heterogeneous bead mixtures can then be incubated with a TNFR2-derived peptide that is optionally labeled with a detectable moiety (e.g., a fluorescent dye) or that is conjugated to an epitope tag (e.g., biotin, avidin, FLAG tag, HA tag) that can later be detected by treatment with a complementary tag (e.g., avidin, biotin, anti-FLAG antibody, anti-HA antibody, respectively). Beads containing antibody fragments that specifically bind a TNFR2-derived peptide (e.g., a peptide containing the amino acid sequence of any one of SEQ ID NOs: 1-341, such as SEQ ID NOs: 3, 11, 61, or 87, and particularly a peptide containing the KCSPG motif, such as a peptide having the amino acid sequence of any one of SEQ ID NOs: 53, 69, 75, 118, and 233) can be identified by analyzing the fluorescent properties of the beads following incubation with a fluorescently-labeled antigen or complementary tag (e.g., by confocal fluorescent microscopy or by fluorescence-activated bead sorting; see, e.g., Muller et al., J. Biol. Chem., 16500-16505 (1996); the disclosure of which is incorporated herein by reference). Beads containing antibody fragments that specifically bind TNFR2-derived peptides can thus be separated from those that do not contain high-affinity antibody fragments. The sequence of an antibody fragment that specifically binds a TNFR2-derived peptide can be determined by techniques known in the art, including, e.g., Edman degradation, tandem mass spectrometry, matrix-assisted laser-desorption time-of-flight mass spectrometry (MALDI-TOF MS), nuclear magnetic resonance (NMR), and 2D gel electrophoresis, among others (see, e.g., WO 2004/062553; the disclosure of which is incorporated herein by reference).

Negative Screens of Antibodies or Antigen-Binding Fragments

In addition to the above-described methods for screening for an antibody or antibody fragment that specifically binds to an epitope derived from human TNFR2 containing the KCSPG motif (or an equivalent of this epitope in a non-human mammal TNFR2), one can additionally perform negative screens in order to eliminate antibodies or antibody fragments that may also bind an epitope that contains the KCRPG motif (e.g., a peptide containing residues 130-149 of SEQ ID NO: 366 (KQEGCRLCAPLRKCRPGFGV, SEQ ID NO: 357; or an equivalent of this epitope in a non-human mammal TNFR2).

In addition, antibodies or antibody fragments can also be screened to eliminate antibodies or antigen-binding fragments that specifically bind to a TNFR superfamily member other than TNFR2, such as TNFR1, RANK, CD30, CD40, Lymphotoxin beta receptor (LT-βR), OX40, Fas receptor, Decoy receptor 3, CD27, 4-1BB, Death receptor 4, Death receptor 5, Decoy receptor 1, Decoy receptor 2, Osteoprotegrin, TWEAK receptor, TACI, BAFF receptor, Herpesvirus entry mediator, Nerve growth factor receptor, B-cell maturation antigen, Glucocorticoid-induced TNFR-related, TROY, Death receptor 6, Death receptor 3, or Ectodysplasin A2 receptor. This can be accomplished using any of the above-described methods or variations thereof, e.g., such that the antibodies or antibody fragments being screened are those that were previously identified as being capable of specifically binding a peptide containing one or more residues of the KCSPG sequence (e.g., at least the KCS sequence). Exemplary techniques useful for a negative screen include those described above or known in the art, such as phage display, yeast display, bacterial display, ribosome display, mRNA display, cDNA display, or surface-based combinatorial library screens (e.g., in an ELISA format). This screening technique represents a useful strategy for identifying an agonistic TNFR2 antibody or antibody fragment of the invention that does not bind, e.g., another TNFR superfamily member or an epitope within TNFR2 that contains the KCRPG sequence.

Immunization of a Non-Human Mammal

Another strategy that can be used to produce agonistic TNFR2 antibodies and antigen-binding fragments thereof of the invention includes immunizing a non-human mammal with an antigen that contains the KCSPG motif (or an equivalent of this epitope in a non-human mammal TNFR2). Examples of non-human mammals that can be immunized in order to produce agonistic TNFR2 antibodies and fragments thereof of the invention include rabbits, mice, rats, goats, guinea pigs, hamsters, horses, and sheep, as well as non-human primates. For instance, established procedures for immunizing primates are known in the art (see, e.g., WO 1986/6004782; the disclosure of which is incorporated herein by reference). Immunization represents a robust method of producing monoclonal antibodies by exploiting the antigen specificity of B lymphocytes.

For example, monoclonal antibodies can be prepared by the Kohler-Millstein procedure (described, e.g., in EP 0110716; the disclosure of which is incorporated herein by reference), in which spleen cells from a non-human animal (e.g., a primate) immunized with a peptide that presents a TNFR2-derived antigen that promotes receptor activation (e.g., a peptide containing the amino acid sequence of any one of SEQ ID NOs: 1-341, such as SEQ ID NOs: 3, 11, 61, or 87, and particularly a peptide containing the KCSPG motif, such as a peptide having the amino acid sequence of any one of SEQ ID NOs: 53, 69, 75, 118, and 233). A clonally-expanded B lymphocyte produced by immunization can be isolated from the serum of the animal and subsequently fused with a myeloma cell in order to form a hybridoma. Hybridomas are particularly useful agents for antibody production, as these immortalized cells can provide a lasting supply of an antigen-specific antibody. Antibodies from such hybridomas can subsequently be isolated using techniques known in the art, e.g., by purifying the antibodies from the cell culture medium by affinity chromatography, using reagents such as Protein A or Protein G.

Antibody Conjugates

Prior to administration of agonistic TNFR2 antibodies or fragments thereof of the invention to a mammalian subject (e.g., a human), it may be desirable to conjugate the antibody or fragment thereof to a second molecule, e g., to modulate the activity of the antibody in vivo. Agonistic TNFR2 antibodies and fragments thereof can be conjugated to other molecules at either the N-terminus or C-terminus of a light or heavy chain of the antibody using any one of a variety of established conjugation strategies that are well-known in the art. Examples of pairs of reactive functional groups that can be used to covalently tether an agonistic TNFR2 antibody or fragment thereof to another molecule include, without limitation, thiol pairs, carboxylic acids and amino groups, ketones and amino groups, aldehydes and amino groups, thiols and α,β-unsaturated moieties (such as maleimides or dehydroalanine), thiols and alpha-halo amides, carboxylic acids and hydrazides, aldehydes and hydrazides, and ketones and hydrazides.

Agonistic TNFR2 antibodies and fragments thereof of the invention can be covalently appended directly to another molecule by chemical conjugation as described. Alternatively, fusion proteins containing agonistic TNFR2 antibodies and fragments thereof of the invention can be expressed recombinantly from a cell (e.g., a eukaryotic cell or prokaryotic cell). This can be accomplished, for example, by incorporating a polynucleotide encoding the fusion protein into the nuclear genome of a cell (e.g., using techniques described herein or known in the art). Optionally, antibodies and fragments thereof of the invention can be joined to a second molecule by forming a covalent bond between the antibody and a linker. This linker can then be subsequently conjugated to another molecule, or the linker can be conjugated to another molecule prior to ligation to the TNFR2 antibody or fragment thereof. Examples of linkers that can be used for the formation of a conjugate include polypeptide linkers, such as those that contain naturally occurring or non-naturally occurring amino acids. In certain cases, it may be desirable to include D-amino acids in the linker, as these residues are not present in naturally-occurring proteins and are thus more resistant to degradation by endogenous proteases. Fusion proteins containing polypeptide linkers can be made using chemical synthesis techniques, such as those described herein, or through recombinant expression of a polynucleotide encoding the fusion protein in a cell (e.g., a prokaryotic or eukaryotic cell). Linkers can be prepared using a variety of strategies that are well known in the art, and depending on the reactive components of the linker, can be cleaved by enzymatic hydrolysis, photolysis, hydrolysis under acidic conditions, hydrolysis under basic conditions, oxidation, disulfide reduction, nucleophilic cleavage, or organometallic cleavage (see, e.g., Leriche et al., Bioorg. Med. Chem., 20:571-582 (2012)).

Drug-Antibody Conjugates

An agonistic TNFR2 antibody or antigen-binding fragment thereof of the invention can additionally be conjugated to, admixed with, or administered separately from a therapeutic agent, such as a cytotoxic molecule. Such conjugates of the invention may be applicable to, e.g., the treatment or prevention of a disease associated with autoreactive cytotoxic T-cell activity. In these cases, antibody-drug conjugates of the invention may bind a TNFR2 receptor on the surface of an autoreactive T-cell and induce cell death due to the activity of the conjugated cytotoxic agent. Exemplary cytotoxic agents that can be conjugated to, admixed with, or administered separately from an agonistic TNFR2 antibody include, without limitation, antineoplastic agents such as: acivicin; aclarubicin; acodazole hydrochloride; acronine; adozelesin; adriamycin; aldesleukin; altretamine; ambomycin; a. metantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; camptothecin; caracemide; carbetimer; carboplatin; carmustine; carubicin hydrochloride; carzelesin; cedefingol; chlorambucil; cirolemycin; cisplatin; cladribine; combretestatin a-4; crisnatol mesylate; cyclophosphamide; cytarabine; dacarbazine; daca (n-[2-(dimethyl-amino) ethyl] acridine-4-carboxamide); dactinomycin; daunorubicin hydrochloride; daunomycin; decitabine; dexormaplatin; dezaguanine; dezaguanine mesylate; diaziquone; docetaxel; dolasatins; doxorubicin; doxorubicin hydrochloride; droloxifene; droloxifene citrate; dromostanolone propionate; duazomycin; edatrexate; eflornithine hydrochloride; ellipticine; elsamitrucin; enloplatin; enpromate; epipropidine; epirubicin hydrochloride; erbulozole; esorubicin hydrochloride; estramustine; estramustine phosphate sodium; etanidazole; ethiodized oil i 131; etoposide; etoposide phosphate; etoprine; fadrozole hydrochloride; fazarabine; fenretinide; floxuridine; fludarabine phosphate; fluorouracil; 5-fdump; flurocitabine; fosquidone; fostriecin sodium; gemcitabine; gemcitabine hydrochloride; gold au 198; homocamptothecin; hydroxyurea; idarubicin hydrochloride; ifosfamide; ilmofosine; interferon alfa-2a; interferon alfa-2b; interferon alfa-n1; interferon alfa-n3; interferon beta-i a; interferon gamma-i b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peploycinsulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; rhizoxin; rhizoxin d; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; strontium chloride sr 89; sulofenur; talisomycin; taxane; taxoid; tecogalan sodium; tegafur; teloxantrone hydrochloride; temoporfin; teniposide; teroxirone; testolactone; thiamiprine; thioguanine; thiotepa; thymitaq; tiazofurin; tirapazamine; tomudex; top53; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine; vinblastine sulfate; vincristine; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 2-chlorodeoxyadenosine; 2' deoxyformycin; 9-aminocamptothecin; raltitrexed; N-propargyl-5,8-dideazafolic acid; 2chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N,N'-Bis (2-chloroethyl)-N-nitrosourea (BCNU); N-(2-chloroethyl)-N' cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nitrosourea (fotemustine); streptozotocin; diacarbazine (DTIC); mitozolomide; temozolomide; thiotepa; mitomycin C; AZQ; adozelesin; cisplatin; carboplatin; ormaplatin; oxaliplatin; C1-973; DWA 2114R; JM216; JM335; Bis (platinum); tomudex; azacitidine; cytarabine; gemcitabine; 6-mercaptopurine; 6-thioguanine; hypoxanthine; teniposide 9-amino camptothecin; topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-hydroxyphenyl) retinamide; 13-cis retinoic acid; 3-methyl TTNEB; 9-cis retinoic acid; fludarabine (2-F-ara-AMP); or 2-chlorodeoxyadenosine (2-Cda).

Other cytotoxic agents that can be conjugated to, admixed with, or administered separately from an agonistic TNFR2 antibody or antigen-binding fragment thereof of the invention in order to treat or prevent, e.g., the progression of a disease associated with aberrant cytotoxic T-cell proliferation include, but are not limited to, 20-pi-1, 25 dihydroxyvitamin D3; 5-ethynyluracil; abiraterone; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B;

2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; episteride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; rnerbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Labeled TNFR2 Antibodies or Antigen-Binding Fragments

Agonistic TNFR2 antibodies or antigen-binding fragments thereof may be conjugated to another molecule, such as an epitope tag, e.g., for the purpose of purification or detection. Examples of such molecules that are useful in protein purification include those that present structural epitopes capable of being recognized by a second molecule. This is a common strategy that is employed in protein purification by affinity chromatography, in which a molecule is immobilized on a solid support and exposed to a heterogeneous mixture containing a target protein conjugated to a molecule capable of binding the immobilized compound. Examples of epitope tag molecules that can be conjugated to agonistic TNFR2 antibodies or fragments thereof, e.g., for the purposes of molecular recognition include, without limitation, maltose-binding protein, glutathione-S-transferase, a poly-histidine tag, a FLAG-tag, a myc-tag, human influenza hemagglutinin (HA) tag, biotin, streptavidin. Conjugates containing the epitopes presented by these molecules are capable of being recognized by such complementary molecules as maltose, glutathione, a nickel-containing complex, an anti-FLAG antibody, an anti-myc antibody, an anti-HA antibody, streptavidin, or biotin, respectively. For example, one can purify an agonistic TNFR2 antibody or fragment thereof of the invention that has been conjugated to an epitope tag from a complex mixture of other proteins and biomolecules (e.g., DNA, RNA, carbohydrates, phospholipids, etc) by treating the mixture with a solid phase resin containing a complementary molecule that can selectively recognize and bind the epitope tag of the TNFR2 antibody or fragment thereof. Examples of solid phase resins include agarose beads, which are compatible with purifications in aqueous solution.

A TNFR2 antibody or antigen-binding fragment thereof of the invention can also be covalently appended to a fluorescent molecule, e.g., to detect the antibody or antigen-binding fragment thereof by fluorimetry and/or by direct visualization using fluorescence microscopy. Exemplary fluorescent molecules that can be conjugated to antibodies of the invention include green fluorescent protein, cyan fluorescent protein, yellow fluorescent protein, red fluorescent protein, phycoerythrin, allophycocyanin, hoescht, 4',6-diamidino-2-phenylindole (DAPI), propidium iodide, fluorescein, coumarin, rhodamine, tetramethylrhoadmine, and cyanine. Additional examples of fluorescent molecules suitable for conjugation to antibodies of the invention are well-known in the art and have been described in detail in, e.g., U.S. Pat. Nos. 7,417,131 and 7,413,874; the disclosures of each of which are incorporated by reference herein.

Agonistic TNFR2 antibodies or antigen-binding fragments thereof containing a fluorescent molecule are particularly useful for monitoring the cell-surface localization properties of antibodies and fragments thereof of the invention. For instance, one can expose cultured mammalian cells (e.g., T-reg cells) to agonistic TNFR2 antibodies or fragments thereof of the invention that have been covalently conjugated to a fluorescent molecule and subsequently analyze these cells using conventional fluorescent microscopy techniques known in the art. Confocal fluorescent microscopy is a particularly powerful method for determining cell-surface localization of TNFR2 antibodies or fragments thereof, as individual planes of a cell can be analyzed in order to distinguish antibodies or fragments thereof that have been internalized into a cell's interior, e.g., by receptor-mediated endocytosis, from those that are bound to the external face of the cell membrane. Additionally, cells can be treated with TNFR2 antibodies of the invention conjugated to a fluorescent molecule that emits visible light of a particular wavelength (e.g., fluorescein, which fluoresces at about 535 nm) and an additional fluorescent molecule that is known to localize to a particular site on the T-reg cell surface and that fluoresces at a different wavelength (e.g., a molecule that localizes to CD25 and that fluoresces at about 599 nm). The resulting emission patterns can be visualized by confocal fluorescence microscopy and the images from these two wavelengths can be merged in order to reveal information regarding the location of the TNFR2 antibody or antigen-binding fragment thereof on the T-reg cell surface with respect to other receptors.

Bioluminescent proteins can also be incorporated into a fusion protein for the purposes of detection and visualization of an agonistic TNFR2 antibody or fragment thereof. Bioluminescent proteins, such as Luciferase and aequorin, emit light as part of a chemical reaction with a substrate (e.g., luciferin and coelenterazine). Exemplary bioluminescent proteins suitable for use as a diagnostic sequence and methods for their use are described in, e.g., U.S. Pat. Nos. 5,292,658; 5,670,356; 6,171,809; and 7,183,092; the disclosures of each of which are incorporated herein by reference. Agonistic TNFR2 antibodies or fragments thereof labeled with bioluminescent proteins are a useful tool for the detection of antibodies of the invention following an in vitro assay. For instance, the presence of an agonistic TNFR2 antibody that has been conjugated to a bioluminescent protein can be detected among a complex mixture of additional proteins by separating the components of the mixture using gel electrophoresis methods known in the art (e.g., native gel analysis) and subsequently transferring the separated proteins to a membrane in order to perform a Western blot. Detection of the TNFR2 antibody among the mixture of other proteins can be achieved by treating the membrane with an appropriate Luciferase substrate and subsequently visualizing the mixture of proteins on film using established protocols.

The antibodies and fragments thereof of the invention can also be conjugated to a molecule comprising a radioactive nucleus, such that an antibody or fragment thereof of the invention can be detected by analyzing the radioactive emission pattern of the nucleus. Alternatively, an agonistic TNFR2 antibody or fragment thereof can be modified directly by incorporating a radioactive nucleus within the antibody during the preparation of the protein. Radioactive isotopes of methionine ($^{35}$S), nitrogen ($^{15}$N), or carbon ($^{13}$C) can be incorporated into antibodies or fragments thereof of the invention by, e.g., culturing bacteria in media that has been supplemented with nutrients containing these isotopes. Optionally, tyrosine derivatives containing a radioactive halogen can be incorporated into an agonistic TNFR2 antibody or fragment thereof, e.g., by culturing bacterial cells in media supplemented with radiolabeled tyrosine. It has been shown that tyrosine functionalized with a radioactive halogen at the C2 position of the phenol system are rapidly incorporated into elongating polypeptide chains using the endogenous translation enzymes in vivo (see U.S. Pat. No. 4,925,651; the disclosure of which is incorporated herein by reference). The halogens include fluorine, chlorine, bromine, iodine, and astatine. Additionally, agonistic TNFR2 antibodies or fragments thereof can be modified following isolation and purification from cell culture by functionalizing antibodies or fragments thereof of the invention with a radioactive isotope. The halogens represent a class of isotopes that can be readily incorporated into a purified protein, e.g., by aromatic substitution at tyrosine or tryptophan via reaction of one or more of these residues with an electrophilic halogen species. Examples of radioactive halogen isotopes include $^{18}$F, $^{75}$Br, $^{77}$Br, $^{122}$I, $^{123}$I, $^{124}$I, $^{125}$I, $^{129}$I, $^{131}$I, or $^{211}$At.

An alternative strategy for the incorporation of a radioactive isotope is the covalent attachment of a chelating group to the agonistic TNFR2 antibody or fragment thereof. Chelating groups can be covalently appended to an agonistic TNFR2 antibody or fragment thereof by attachment to a reactive functional group, such as a thiol, amino group, alcohol, or carboxylic acid. The chelating groups can then be modified to contain any of a variety of metallic radioisotopes, including, without limitation, such radioactive nuclides as $^{125}$I, $^{67}$Ga, $^{111}$In, $^{99}$Tc, $^{169}$Yb, $^{186}$Re, $^{123}$I, $^{124}$I, $^{125}$I, $^{131}$I, $^{99m}$Tc, $^{111}$In, $^{64}$Cu, $^{67}$Cu, $^{186}$Re, $^{188}$Re, $^{177}$Lu, $^{90}$Y, $^{77}$As, $^{72}$As, $^{86}$Y, $^{89}$Zr, $^{211}$At, $^{212}$Bi, $^{213}$Bi, or $^{225}$AC.

In certain cases, it may be desirable to covalently conjugate the antibodies or fragments thereof of the invention with a chelating group capable of binding a metal ion from heavy elements or rare earth ions, such as $Gd^{3+}$, $Fe^{3+}$, $Mn^{3+}$, or $Cr^{2+}$. Conjugates containing chelating groups that are coordinated to such paramagnetic metals are useful as in MRI imaging applications. Paramagnetic metals include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). In this way, agonistic TNFR2 antibodies can be detected by MRI spectroscopy. For instance, one can administer agonistic TNFR2 antibodies or fragments thereof conjugated to chelating groups bound to paramagnetic ions to a mammalian subject (e.g., a human patient) in order to monitor the distribution of the antibody following administration. This can be achieved by administration of the antibody to a patient by any of the administration routes described herein, such as intravenously, and subsequently analyzing the location of the administered antibody by recording an MRI of the patient according to established protocols.

Agonistic TNFR2 antibodies or fragments thereof can additionally be conjugated to other molecules for the purpose of improving the solubility and stability of the protein in aqueous solution. Examples of such molecules include PEG, PSA, bovine serum albumin (BSA), and human serum albumin (HSA), among others. For instance, one can conjugate an agonistic TNFR2 antibody or fragment thereof to carbohydrate moieties in order to evade detection of the antibody or fragment thereof by the immune system of the patient receiving treatment. This process of hyperglycosylation reduces the immunogenicity of therapeutic proteins by sterically inhibiting the interaction of the protein with B-cell receptors in circulation. Alternatively, agonistic TNFR2 antibodies or fragments thereof can be conjugated to molecules that prevent clearance from human serum and improve the pharmacokinetic profile of antibodies of the invention. Exemplary molecules that can be conjugated to or inserted within agonistic TNFR2 antibodies or fragments thereof of the invention so as to attenuate clearance and improve the pharmacokinetic profile of these antibodies and fragments include salvage receptor binding epitopes. These epitopes are found within the Fc region of an IgG immunoglobulin and have been shown to bind Fc receptors and prolong antibody half life in human serum. The insertion of salvage receptor binding epitopes into TNFR2 antibodies or fragments thereof can be achieved, e.g., as described in U.S. Pat. No. 5,739,277; the disclosure of which is incorporated herein by reference.

Modified Agonistic TNFR2 Antibodies and Antigen-Binding Fragments Thereof

In addition to conjugation to other therapeutic agents and labels for identification or visualization, agonistic TNFR2 antibodies and fragments thereof of the invention can also be modified so as to improve their pharmacokinetic profile, biophysical stability, or inhibitory capacity. For instance, any cysteine residue not involved in maintaining the bioactive conformation of the agonistic TNFR2 antibody or fragment thereof may be substituted with an isosteric or isoelectronic amino acid (e.g., serine) in order to improve the oxidative stability of the molecule and prevent aberrant crosslinking. Conversely, cystine bond(s) may be added to the antibody or fragment thereof to improve its stability (particularly where the antibody is an antibody fragment, such as an Fv fragment). This can be accomplished, e.g., by altering a polynucleotide encoding the antibody heavy and light chains or a polynucleotide encoding an antibody fragment so as to encode one or more additional pairs of cysteine residues that can form disulfide bonds under oxidative conditions in order to reinforce antibody tertiary structure (see, e.g., U.S. Pat. No. 7,422,899; the disclosure of which is incorporated herein by reference).

Another useful modification that can be made to agonistic TNFR2 antibodies and fragments thereof of the invention includes altering the glycosylation profile of these antibodies and fragments thereof. This can be achieved, e.g., by substituting, inserting, or deleting amino acids in an agonistic TNFR2 antibody so as to insert or remove a glycosylation site. Glycosylation of antibodies typically occurs in N-linked or O-linked fashion. N-linked glycosylation is a process whereby the attachment of a carbohydrate moiety to an antibody occurs at the side chain of an asparagine residue. Consensus amino acid sequences for N-linked glycosylation include the tripeptide sequences asparagine-X-serine (NXS) and asparagine-X-threonine (NXT), where X is any amino acid except proline. The insertion of either of these tripeptide sequences in a polypeptide (e.g., an agonistic TNFR2 antibody) creates a potential glycosylation site. O-linked glycosylation refers to the attachment of one of the sugars N-acetylgalactosamine, galactose, or xylose to a hydroxyamino acid, most commonly serine or threonine, although 5-hydroxyproline and 5-hydroxylysine are also competent substrates for glycoside formation. Addition of glycosylation sites to a TNFR2 antibody can thus be accomplished by altering the amino acid sequence of the antibody (e.g., using recombinant expression techniques as described herein) such that it contains one or more of the above-described tripeptide sequences to promote N-linked glycosylation, or one or more serine or threonine residues to the sequence of the original antibody engender O-linked glycosylation (see, e.g., U.S. Pat. No. 7,422,899; the disclosure of which is incorporated herein by reference).

In alternative cases, it may be desirable to modify the antibody or fragment thereof of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. For instance, cysteine residues may be introduced in the Fc region of an agonistic TNFR2 antibody or fragment thereof (e.g., by recombinant expression techniques as described herein), so as to facilitate additional inter-chain disulfide bond formation in this region. The homodimeric antibody thus generated may have increased conformational constraint, which may foster improved internalization capability and/or increased complement-mediated cell killing and antibody-dependent cellular cytotoxicity (ADCC). Homodimeric antibodies with enhanced anti-tumor activity may also be prepared using heterobifunctional cross-linkers as described, for example, in Wolff et al., Canc. Res., 53:2560-2565 (1993); the disclosure of which is incorporated herein by reference. Alternatively, an antibody can be engineered which has dual Fc regions and may thereby have enhanced complement lysis and ADCC capabilities (see Stevenson et al., Anti-Canc. Drug Des., 3:219-230 (1989); the disclosure of which is incorporated herein by reference).

The serum half life of agonistic TNFR2 antibodies and fragments thereof of the invention can be improved in certain cases by incorporating one more amino acid modifications, such as by altering the CH1 or CL region of the Fab domain to introduce a salvage receptor motif, e.g., that found in the two loops of a CH2 domain of an Fc region of an IgG. Such alterations are described, for instance, in U.S. Pat. Nos. 5,869,046 and 6,121,022; the disclosures of which are incorporated herein by reference.

Methods of Treatment

Agonistic TNFR2 antibodies and antigen-binding fragments thereof of the invention are useful therapeutics for the treatment of a wide array of immunological disorders. Agonistic TNFR2 antibodies and fragments thereof can be administered to a subject, e.g., a mammalian subject, such as a human, in order to treat such conditions as autoimmune diseases, neurological diseases, metabolic diseases (e.g., diabetes), macular diseases (e.g., macular degeneration), muscular atrophy, diseases related to miscarriage, vascular diseases (e.g., atherosclerosis), diseases related to bone loss (e.g., bone loss as a result of menopause or osteoporosis), allergies, asthma, a blood disorder (e.g., hemophilia), a musculoskeletal disorder, a disease related to growth receptor expression or activity, obesity, graft-versus-host disease (GVHD), or an allograft rejection. Agonistic TNFR2 antibodies and antigen-binding fragments thereof of the invention can also be used to treat a patient in need of organ repair or regeneration, e.g., by inducing the proliferation of cells within a damaged tissue or organ. Agonistic TNFR2 antibodies and antigen-binding fragments thereof of the invention can be administered to a mammalian subject, such as a human, to stimulate the proliferation of T-reg cells (e.g., CD4+, CD25+, FOXP3+ T-reg cells). This response can have the effect of reducing populations of cytotoxic T-lymphocytes (e.g., CD8+ T-cells) that are often associated with mounting an inappropriate immune response that can cause an immunological disorder. In addition, antibodies of the invention may synergize with existing T-reg proliferating agents, such as IL-2 and TNFα. For instance, antibodies or antigen-binding fragments thereof of the invention may be capable of stimulating the proliferation of a population of T-reg cells by between 1% and 100% relative to untreated cells (e.g., 1%, 2%, 3%, 4%, 5%, 6%, 7%, 8%, 9%, 10%, 20%, 30%, 40%, 50%, 60%, 70%, 80%, 90%, and 100%) as described in Examples 5 and 6. In certain cases, antibodies of the invention may be capable of reducing the growth of a population of CD8+ T-cells, e.g., by about 50% to about 200% relative to untreated cells (e.g., 50%, 75%, 100%, 125%, 150%, 175%, or 200%).

Agonistic TNFR2 antibodies or antigen-binding fragments thereof of the invention can be administered to a subject, e.g., a mammalian subject, such as a human, suffering from a graft rejection. Agonistic TNFR2 antibodies or antigen-binding fragments thereof of the invention may treat graft rejections, e.g., by binding TNFR2 receptors on the surface of autoreactive CD8+ T-cells that bind antigens presented on the surface of the graft and inducing apoptosis in these CD8+ T-cells, or by inducing the expansion of T-reg cells that may subsequently eliminate autoreactive CD8+ T-cells. Examples of graft rejections that can be treated by administration of agonistic TNFR2 antibodies or antigen-binding fragments thereof of the invention include, without limitation, skin graft rejection, bone graft rejection, vascular tissue graft rejection, ligament graft rejection (e.g., cricothyroid ligament graft rejection, periodontal ligament graft rejection, suspensory ligament of the lens graft rejection, palmar radiocarpal ligament graft rejection, dorsal radiocarpal ligament graft rejection, ulnar collateral ligament graft rejection, radial collateral ligament graft rejection, suspensory ligament of the breast graft rejection, anterior sacroiliac ligament graft rejection, posterior sacroiliac ligament graft rejection, sacrotuberous ligament graft rejection, sacrospinous ligament graft rejection, inferior pubic ligament graft rejection, superior pubic ligament graft rejection, anterior cruciate ligament graft rejection, lateral collateral ligament graft rejection, posterior cruciate ligament graft rejection, medial collateral ligament graft rejection, cranial cruciate ligament graft rejection, caudal cruciate ligament graft rejection, patellar ligament graft rejection) and organ graft rejection (e.g., heart, lung, kidney, liver, pancreas, intestine, and thymus graft rejection, among others).

Agonistic TNFR2 antibodies or antigen-binding fragments thereof of the invention may be administered to a subject, e.g., a mammalian subject, such as a human) suffering from a graft-versus-host disease (GVHD). Exemplary graft-versus-host diseases that can be treated using the compositions and methods of the invention include those that arises from a bone marrow transplant, as well as from the transplantation of blood cells, such as hematopoietic stem cells, common myeloid progenitor cells, common lymphoid progenitor cells, megakaryocytes, monocytes, basophils, eosinophils, neutrophils, macrophages, T-cells, B-cells, natural killer cells, and/or dendritic cells.

Agonistic TNFR2 antibodies of the invention can be administered to a subject, e.g., a mammalian subject, such as a human, suffering from an immunological disease, e.g., in order to bind a TNFR2 receptor on the surface of an autoreactive T-cell and induce apoptosis, and/or to promote T-reg cell growth and thus suppress the activity of inappropriately reactive cytotoxic T-lymphocytes and B-lymphocytes in the patient. Antibodies of the invention can be administered to a subject, e.g., via any of the routes of administration described herein.

Immunological diseases that can be treated by administration of antibodies or antigen-binding fragments thereof of the invention include allergies, such as food allergy, seasonal allergy, pet allergy, hives, hay fever, allergic conjunctivitis, poison ivy allergy oak allergy, mold allergy, drug allergy, dust allergy, cosmetic allergy, and chemical allergy.

Diseases that can be treated by administration of an agonistic TNFR2 antibody or antigen-binding fragment thereof of the invention include autoimmune diseases, such as type I diabetes, alopecia areata, ankylosing spondylitis, antiphospholipid syndrome, autoimmune Addison's Disease, autoimmune hemolytic anemia, autoimmune hepatitis, Behcet's Disease, bullous pemphigoid, cardiomyopathy, celiac sprue-dermatitis, chronic fatigue immune dysfunction syndrome (CFIDS), chronic inflammatory demyelinating polyneuropathy, Churg-Strauss Syndrome, cicatricial pemphigoid, limited scleroderma (CREST Syndrome), cold agglutinin disease, Crohn's Disease, discoid lupus, essential mixed cryoglobulinemia, fibromyalgia-fibromyositis, Graves' Disease, Guillain-Barré Syndrome, Hashimoto's Thyroiditis, hypothyroidism, Inflammatory Bowel Disease, autoimmune lymphoproliferative syndrome (ALPS), idiopathic pulmonary fibrosis, idiopathic thrombocytopenia purpura (ITP), IgA nephropathy, juvenile arthritis, lichen planus, lupus, Ménière's Disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis, dermatomyositis, primary agammaglobulinemia, primary biliary cirrhosis, psoriasis, Raynaud's Phenomenon, Reiter's Syndrome, rheumatic fever, rheumatoid arthritis, sarcoidosis, scleroderma, Sjögren's Syndrome, Stiff-Man syndrome, Takayasu Arteritis, temporal arteritis/giant cell arteritis, ulcerative colitis, uveitis, vasculitis, vitiligo, and Wegener's Granulomatosis.

Agonistic TNFR2 antibodies and antigen-binding fragments thereof of the invention can additionally be used to treat patients in need of organ repair or regeneration. For instance, agonistic TNFR2 antibodies or antigen-binding fragments thereof of the invention may be used to stimulate organ repair or regeneration, e.g., by binding TNFR2 on the surface of cells within damaged tissue so as to induce TRAF2/3- and/or $NF_{\kappa}B$-mediated cell proliferation. Examples of tissues and organs that may be induced to regenerate by administration of an agonistic TNFR2 antibody or antigen-binding fragment thereof of the invention to a subject (e.g., a mammalian subject, such as a human) include the pancreas, salivary gland, pituitary gland, kidney, heart, lung, hematopoietic system, cranial nerves, heart, blood vessels including the aorta, olfactory gland, ear, nerves, structures of the head, eye, thymus, tongue, bone, liver, small intestine, large intestine, gut, lung, brain, skin, peripheral nervous system, central nervous system, spinal cord, breast, embryonic structures, embryos, and testes.

Agonistic TNFR2 antibodies and antigen-binding fragments thereof of the invention can also be administered to a subject (e.g., a mammalian subject, such as a human) in order to treat a neurological disease or condition, such as a brain tumor, a brain metastasis, a spinal cord injury, schizophrenia, epilepsy, Amyotrophic lateral sclerosis (ALS), Parkinson's disease, Alzheimer's disease, Huntington's disease, or stroke.

An agonistic TNFR2 antibody of the invention may also be admixed, conjugated, or administered with, or administered separately from, another agent that promotes T-reg cell proliferation. Additional agents that can be used to promote T-reg cell expansion include, e.g., IL-2 and TNFα, the cognate ligand for TNFR2.

Additionally or alternatively, an agonistic TNFR2 antibody or antigen-binding fragment thereof of the invention may be admixed, conjugated, or administered with, or administered separately from, an immunotherapy agent. Exemplary immunotherapy agents useful in conjunction with the compositions and methods of the invention include an anti-CTLA-4 agent, an anti-PD-1 agent, an anti-PD-L1 agent, an anti-PD-L2 agent, a TNF-α cross-linking agent, a TRAIL cross-linking agent, a CD27 agent, a CD30 agent, a CD40 agent, a 4-1BB agent, a GITR agent, an OX40 agent, a TRAILR1 agent, a TRAILR2 agent, a TWEAKR agent, and, e.g., agents directed toward the immunological targets described in Table 1 of Mahoney et al., Cancer Immunotherapy, 14:561-584 (2015), the disclosure of which is incorporated herein by reference. For example, immunological target 4-1BB ligand may be targeted with an anti-4-1 BB ligand antibody; immunological target OX40L may be targeted with an anti-OX40L antibody; immunological target GITR may be targeted with an anti-GITR antibody; immunological target CD27 may be targeted with an anti-CD27 antibody; immunological target TL1A may be targeted with an anti-TL1A antibody; immunological target CD40L may be targeted with an anti-CD40L antibody; immunological target LIGHT may be targeted with an anti-LIGHT antibody; immunological target BTLA may be targeted with an anti-BTLA antibody; immunological target LAG3 may be targeted with an anti-LAG3 antibody; immunological target TIM3 may be targeted with an anti-TIM3 antibody; immunological target Singlecs may be targeted with an anti-Singlecs antibody; immunological target ICOS ligand may be targeted with an anti-ICOS ligand antibody; immunological target B7-H3 may be targeted with an anti-B7-H3 antibody; immunological target B7-H4 may be targeted with an anti-B7-H4 antibody; immunological target VISTA may be targeted with an anti-VISTA antibody; immunological target TMIGD2 may be targeted with an anti-TMIGD2 antibody; immunological target BTNL2 may be targeted with an anti-BTNL2 antibody; immunological target CD48 may be targeted with an anti-CD48 antibody; immunological target KIR may be targeted with an anti-KIR antibody; immunological target LIR may be targeted with an anti-LIR antibody; immunological target ILT may be targeted with an anti-ILT antibody; immunological target NKG2D may be targeted with an anti-NKG2D antibody; immunological target NKG2A may be targeted with an anti-NKG2A antibody; immunological target MICA may be targeted with an anti-MICA antibody; immunological target MICB may be targeted with an anti-MICB antibody; immunological target CD244 may be targeted with an anti-CD244 antibody; immunological target CSF1R may be targeted with an anti-CSF1R antibody; immunological target IDO may be targeted with an anti-IDO antibody; immunological target TGFβ may be targeted with an anti-TGFβ antibody; immunological target CD39 may be targeted with an anti-CD39 antibody; immunological target CD73 may be targeted with an anti-CD73 antibody; immunological target CXCR4 may be targeted with an anti-CXCR4 antibody; immunological target CXCL12 may be targeted with an anti-CXCL12 antibody; immunological target SIRPA may be targeted with an anti-SIRPA antibody; immunological target CD47 may be targeted with an anti-CD47 antibody; immunological target VEGF may be targeted with an anti-VEGF antibody; and immunological target neuropilin may be targeted with an anti-neuropilin antibody (see, e.g., Table 1 of Mahoney et al.).

A physician of ordinary skill in the art can readily determine an effective amount of an agonistic TNFR2 antibody or antibody fragment for administration to a mammalian subject (e.g., a human) in need thereof. For example, a physician could start prescribing doses of an antibody of the invention at levels lower than that required to achieve the desired therapeutic effect and gradually increase the dosage until the desired effect is achieved. Alternatively, a physician may begin a treatment regimen by administering an agonistic TNFR2 antibody or antibody fragment at a high dose and subsequently administer progressively lower doses until a therapeutic effect is achieved (e.g., a reduction in the proliferation of a population of CD8+ T-cells or a decrease in the peripheral secretion of IFNγ). In general, a suitable daily dose of an antibody or antigen-binding fragment thereof of the invention will be an amount of the antibody which is the lowest dose effective to produce a therapeutic effect. An antibody or antigen-binding fragment thereof of the invention may be administered by injection, e.g., by intravenous, intramuscular, intraperitoneal, or subcutaneous injection, optionally proximal to the site of a target tissue. A daily dose of a therapeutic composition of an antibody or antigen-binding fragment thereof of the invention may be administered as a single dose or as two, three, four, five, six or more doses administered separately at appropriate intervals throughout the day, week, month, or year, optionally, in unit dosage forms. While it is possible for an antibody or fragment thereof of the invention to be administered alone, it may also be administered as a pharmaceutical formulation in combination with excipients, carriers, and optionally, additional therapeutic agents.

Antibodies or fragments thereof of the invention can be monitored for their ability to attenuate the progression of an immunological disease, such as an autoimmune disease, by any of a variety of methods known in the art. For instance, a physician may monitor the response of a mammalian subject (e.g., a human) to treatment with an antibody of the invention by analyzing the quantity of IFNγ secreted by CD8+ T-cells within a particular patient. For example, antibodies of the invention may be capable of reducing IFNγ secretion by between 1% and 100% (e.g., 1%, 5%, 10%, 20%, 30%, 40%, 50%, 60%, 70%, 80%, 90%, 95%, 99%, or 100%). Alternatively, a physician may monitor the responsiveness of a subject (e.g., a human) to treatment with agonisticTNFR2 antibodies or antigen-binding fragments thereof of the invention by analyzing the T-reg cell population in the lymph of a particular subject. For instance, a physician may withdrawn a sample of blood from a mammalian subject (e.g., a human) and determine the quantity or density of a population of T-reg cells (e.g., CD4+ CD25+ FOXP3+ T-reg cells or CD17+ T-reg cells) using established procedures, such as fluorescence activated cell sorting. In these cases, high counts of T-reg cells is indicative of efficacious therapy, while lower T-reg cell counts may indicate that the patient is to be prescribed or administered higher dosages of the TNFR2 antibody of the invention until, e.g., an ideal T-reg cell count is achieved. In addition, a physician of skill in the art may monitor the effect of treatment by administration of agonistic TNFR2 antibodies of antigen-binding fragments thereof to a patient suffering from an immunological disorder, such as an autoimmune disease described herein, by analyzing the quantity of autoreactive CD8+ T-cells within a lymph sample isolated from the patient. Agonistic TNFR2 antibodies and antigen-binding fragments thereof of the invention may attenuate the proliferation of autoreactive T-cells, e.g., by binding TNFR2 at the surface of an autoreactive T-cell and inducing apoptosis, and/or by stimulating the expansion of T-reg cells that subsequently eliminate autoreactive T lymphocytes. Treatment with agonistic TNFR2 antibodies or antigen-binding fragments thereof can lead to reduced quantities of autoreactive T-cells within the lymph isolated from a patient receiving treatment, and a rapid decline in the population of autoreactive T-cells in a lymph sample isolated from such a patient indicates effective treatment. In cases where a lymph sample isolated from a patient exhibits an autoreactive T-cell count that has not declined in response to agonistic TNFR2 antibody therapy, a physician may prescribe the patient higher doses of the antibody or an antigen-binding fragment thereof or may administer the agonistic TNFR2 antibody or antigen-binding fragment thereof with higher frequency, e.g., multiple times per day, week, or month.

Pharmaceutical Compositions

Therapeutic compositions containing an agonistic TNFR2 antibody or antigen-binding fragment thereof of the invention can be prepared using methods known in the art. For example, such compositions can be prepared using, e.g., physiologically acceptable carriers, excipients or stabilizers (Remington's Pharmaceutical Sciences 16th edition, Osol, A. Ed. (1980); incorporated herein by reference), and in a desired form, e.g., in the form of lyophilized formulations or aqueous solutions. The compositions can also be prepared so as to contain the active agent (e.g., an agonistic TNFR2 antibody or fragment thereof) at a desired concentration. For example, a pharmaceutical composition of the invention may contain at least 10% (e.g., 10%, 20%, 30%, 40%, 50%, 60%, 70%, 80%, 90%, 95%, 97%, 98%, 99%, 99.5%, 99.9%, or 100%) active agent by weight (w/w).

Additionally, an active agent (e.g., an agonistic TNFR2 antibody or fragment thereof of the invention) that can be incorporated into a pharmaceutical formulation can itself have a desired level of purity. For example, an antibody or antigen-binding fragment thereof of the invention may be characterized by a certain degree of purity after isolating the antibody from cell culture media or after chemical synthesis, e.g., of a single chain antibody fragment (e.g., scFv) by established solid phase peptide synthesis methods or native chemical ligation as described herein. An agonistic TNFR2 antibody of the invention may be at least 10% pure prior to incorporating the antibody into a pharmaceutical composition (e.g., 10%, 20%, 30%, 40%, 50%, 60%, 70%, 80%, 90%, 95%, 97%, 98%, 99%, 99.5%, 99.9%, 99.99%, or 100% pure).

Pharmaceutical compositions of agonistic TNFR2 antibodies of the invention can be prepared for storage as lyophilized formulations or aqueous solutions by mixing the antibody having the desired degree of purity with optional pharmaceutically acceptable carriers, excipients or stabilizers typically employed in the art, e.g., buffering agents, stabilizing agents, preservatives, isotonifiers, non-ionic detergents, antioxidants, and other miscellaneous additives. See, e.g., Remington's Pharmaceutical Sciences, 16th edition (Osol, ed. 1980; incorporated herein by reference). Such additives must be nontoxic to the recipients at the dosages and concentrations employed.

Buffering Agents

Buffering agents help to maintain the pH in the range which approximates physiological conditions. They can be present at concentration ranging from about 2 mM to about 50 mM. Suitable buffering agents for use with TNFR2 antibodies and antigen-binding fragments thereof of the invention include both organic and inorganic acids and salts thereof such as citrate buffers {e.g., monosodium citrate-disodium citrate mixture, citric acid-trisodium citrate mixture, citric acid-monosodium citrate mixture, etc.), succinate buffers {e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers {e.g., fumaric acid-monosodium fumarate mixture, fumaric acid-disodium fumarate mixture, monosodium fumarate-disodium fumarate mixture, etc.), gluconate buffers {e.g., gluconic acid-sodium glyconate mixture, gluconic acid-sodium hydroxide mixture, gluconic acid-potassium glyuconate mixture, etc.), oxalate buffer {e.g., oxalic acid-sodium oxalate mixture, oxalic acid-sodium hydroxide mixture, oxalic acid-potassium oxalate mixture, etc.), lactate buffers {e.g., lactic acid-sodium lactate mixture, lactic acid-sodium hydroxide mixture, lactic acid-potassium lactate mixture, etc.) and acetate buffers {e.g., acetic acid-sodium acetate mixture, acetic acid-sodium hydroxide mixture, etc.). Additionally, phosphate buffers, histidine buffers and trimethylamine salts such as Tris can be used.

Preservatives

Preservatives can be added to a composition of the invention to retard microbial growth, and can be added in amounts ranging from 0.2%-1% (w/v). Suitable preservatives for use with TNFR2 antibodies and antigen-binding fragments thereof of the invention include phenol, benzyl alcohol, meta-cresol, methyl paraben, propyl paraben, octadecyldimethylbenzyl ammonium chloride, benzalconium halides {e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the invention and include polhydric sugar alcohols, for example trihydric or higher sugar alcohols, such as glycerin, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccharides such as raffinose; and polysaccharides such as dextran. Stabilizers can be present in the range from 0.1 to 10,000 weights per part of weight active protein.

Detergents

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

Other Pharmaceutical Carriers

Alternative pharmaceutically acceptable carriers that can be incorporated into a composition of the invention may include dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. A composition containing a TNFR2 antibody of the invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

Compositions for Combination Therapy

Pharmaceutical compositions of the invention may optionally include more than one active agent. For instance, compositions of the invention may contain an agonistic TNFR2 antibody or fragment thereof conjugated to, admixed with, or administered separately from another pharmaceutically active molecule, e.g., T-reg cell, or an additional agent that is useful for induction of T-reg cell expansion. For instance, an agonistic TNFR2 antibody or antigen-binding fragment thereof may be admixed with one or more additional active agents, such as IL-2 or TNFα, in order to treat an immunological disease, e.g., a disorder described herein. Alternatively, pharmaceutical compositions of the invention may be formulated for co-administration or sequential administration with one or more additional active agents that can be used to attenuate CD8+ T-cell growth. Examples of additional active agents that can be used to attenuate cytotoxic T-cell proliferation and that can be conjugated to, admixed with, or administered separately from an agonistic TNFR2 antibody or antibody fragment of the invention include cytotoxic agents, e.g., those described herein.

Agonistic TNFR2 antibodies or antigen-binding fragments thereof of the invention can also be admixed with, co-administered with, or administered separately from Bacillus Calmette-Guérin (BCG), a bacterial strain that has been used to treat a variety of immunological disorders, such as type I diabetes, multiple sclerosis, scleroderma, Sjogren's disease, systemic lupus erythematosus, Grave's disease, hypothyroidism, Crohn's disease, colititis, an autoimmune skin disease, and rheumatoid arthritis, among others. For instance, a physician of skill in the art may prescribe a patient presenting with an immunological disorder (e.g., one of those described above, such as type I diabetes or rheumatoid arthritis) a therapeutic regimen that includes an agonistic TNFR2 antibody or antigen-binding fragment thereof of the invention in combination with BCG. The agonistic TNFR2 antibody or antigen-binding fragment thereof may be co-administered with BCG, e.g., by an injection route described herein. Alternatively, the agonistic TNFR2 antibody or antigen-binding fragment thereof of the invention may be administered separately from a BCG-containing composition. The use of BCG to treat immunological disorders has been described, e.g., in U.S. Pat. Nos. 6,660,487; and in 6,599,710; the disclosures of each of which are incorporated herein by reference.

Blood-Brain Barrier Penetration

In certain embodiments, agonistic TNFR2 antibodies or antigen-binding fragments thereof of the invention can be formulated to ensure proper distribution in vivo. For example, the blood-brain barrier (BBB) excludes many highly hydrophilic compounds. To ensure that the therapeutic compositions of the invention cross the BBB (if desired), they can be formulated, for example, in liposomes. Methods of manufacturing liposomes have been described, e.g., U.S. Pat. Nos. 4,522,811; 5,374,548; and 5,399,331. The liposomes may comprise one or more moieties that are selectively transported into specific cells or organs, thereby enhancing targeted drug delivery (see, e.g., V. V. Ranade, J. Clin. Pharmacol. 29:685, 1989)). Exemplary targeting moieties include, e.g., folate or biotin (see, e.g., U.S. Pat. No. 5,416,016); mannosides (Umezawa et al. (Biochem. Biophys. Res. Commun. 153:1038, 1988)); antibodies (P. G. Bloeman et al. (FEBS Lett. 357:140, 1995); M. Owais et al. (Antimicrob. Agents Chemother. 39:180, 1995)); surfactant protein A receptor (Briscoe et al. (Am. J. Physiol. 1233:134, 1995)); the disclosures of each of which are incorporated herein by reference.

Routes of Administration and Dosing

Agonistic TNFR2 antibodies and antigen-binding fragments thereof of the invention can be administered to a mammalian subject (e.g., a human) by a variety of routes such as orally, transdermally, subcutaneously, intranasally, intravenously, intramuscularly, intraocularly, intratumorally, parenterally, topically, intrathecally and intracerebroventricularly. The most suitable route for administration in any given case will depend on the particular antibody or antigen-binding fragment administered, the patient, pharmaceutical formulation methods, administration methods (e.g., administration time and administration route), the patient's age, body weight, sex, severity of the diseases being treated, the patient's diet, and the patient's excretion rate.

The effective dose of an agonistic TNFR2 antibody or antigen-binding fragment thereof of the invention can range from about 0.0001 to about 100 mg/kg of body weight per single (e.g., bolus) administration, multiple administrations or continuous administration, or to achieve a serum concentration of 0.0001-5000 µg/mL serum concentration per single (e.g., bolus) administration, multiple administrations or continuous administration, or any effective range or value therein depending on the condition being treated, the route of administration and the age, weight, and condition of the subject. In certain embodiments, e.g., for the treatment of cancer, each dose can range from about 0.0001 mg to about 500 mg/kg of body weight. For instance, a pharmaceutical composition of the invention may be administered in a daily dose in the range of 0.001-100 mg/kg (body weight). The dose may be administered one or more times (e.g., 2-10 times) per day, week, month, or year to a mammalian subject (e.g., a human) in need thereof.

Therapeutic compositions can be administered with medical devices known in the art. For example, in an embodiment, a therapeutic composition of the invention can be administered with a needleless hypodermic injection device, such as the devices disclosed in U.S. Pat. Nos. 5,399,163; 5,383,851; 5,064,413; 4,941,880; 4,790,824; or 4,596,556. Examples of well-known implants and modules useful in the invention include those described in U.S. Pat. No. 4,487,603; which discloses an implantable micro-infusion pump for dispensing medication at a controlled rate; U.S. Pat. No. 4,486,194; which discloses a therapeutic device for administering medicaments through the skin; U.S. Pat. No. 4,447,233; which discloses a medication infusion pump for delivering medication at a precise infusion rate; U.S. Pat. No. 4,447,224; which discloses a variable flow implantable infusion apparatus for continuous drug delivery; U.S. Pat. No. 4,439,196; which discloses an osmotic drug delivery system having multi-chamber compartments; and U.S. Pat. No. 4,475,196; which discloses an osmotic drug delivery system. These patents are incorporated herein by reference. Many other such implants, delivery systems, and modules are known to those skilled in the art.

Kits Containing Aonistic TNFR2 Antibodies and Antigen-Binding Fragments Thereof

This invention also includes kits that contain agonistic TNFR2 antibodies or antigen-binding fragments thereof. The kits provided herein may contain any of the agonistic TNFR2 antibodies and fragments thereof described above, as well as any of the polynucleotides encoding these antibodies, vectors containing these polynucleotides, or cells engineered to express and secrete antibodies of the invention (e.g., prokaryotic or eukaryotic cells). A kit of this invention may include reagents that can be used to produce the compositions of the invention (e.g., agonistic TNFR2 antibodies, conjugates containing agonistic TNFR2 antibodies, polynucleotides encoding agonistic TNFR2 antibodies, and vectors containing these polynucleotides). Optionally, kits of the invention may include reagents that can induce the expression of agonistic TNFR2 antibodies within cells (e.g., mammalian cells), such as doxycycline or tetracycline. In other cases, a kit of the invention may contain a compound capable of binding and detecting a fusion protein that contains an agonistic TNFR2 antibody and an epitope tag. For instance, in such cases a kit of the invention may contain maltose, glutathione, a nickel-containing complex, an anti-FLAG antibody, an anti-myc antibody, an anti-HA antibody, biotin, or streptavidin.

Kits of the invention may also include reagents that are capable of detecting an agonistic TNFR2 antibody or fragment thereof directly. Examples of such reagents include secondary antibodies that selectively recognize and bind particular structural features within the Fc region of an agonistic TNFR2 antibody of the invention. Kits of the invention may contain secondary antibodies that recognize the Fc region of an agonistic TNFR2 antibody and that are conjugated to a fluorescent molecule. These antibody-fluorophore conjugates provide a tool for analyzing the localization of agonistic TNFR2 antibodies, e.g., in a particular tissue or cultured mammalian cell using established immunofluorescence techniques. In certain cases, kits of the invention may include additional fluorescent compounds that exhibit known sub-cellular localization patterns. These reagents can be used in combination with another antibody-fluorophore conjugate, e.g., one that specifically recognizes a different receptor on the cell surface in order to analyze the localization of an agonistic TNFR2 antibody relative to other cell-surface proteins.

Kits of the invention may also contain a reagent that can be used for the analysis of a patient's response to treatment by administration of agonistic TNFR2 antibodies or antigen-binding fragments thereof of the invention. For instance, kits of the invention may include an agonistic TNFR2 antibody and one or more reagents that can be used to determine the quantity of T-reg cells in a blood sample withdrawn from a subject (e.g., a human) that is undergoing treatment with an antibody of the invention. Such a kit may contain, e.g., antibodies that selectively bind cell-surface antigens presented by T-reg cells, such as CD4 and CD25. Optionally, these antibodies may be labeled with a fluorescent dye, such as fluorescein or tetramethylrhodamine, in order to facilitate analysis of a population of T-reg cells by fluorescence-activated cell sorting (FACS) methods known in the art. Kits of the invention may optionally contain one or more reagents that can be used to quantify a population of cytotoxic T-lymphocytes, e.g., in order to determine the effectiveness of an agonistic TNFR2 antibody of the invention in attenuating CD8+ T-cell proliferation. For instance, kits of the invention may contain an antibody that selectively binds cell-surface markers on the surface of a cytotoxic T-cell, such as CD8 or CD3. Optionally, these antibodies may be labeled with fluorescent molecules so as to enable quantitation by FACS analysis.

A kit of the invention may also contain one or more reagents useful for determining the affinity and selectivity of an agonistic TNFR2 antibody or antigen-binding fragment thereof of the invention for one or more peptides derived from TNFR2 (e.g., a peptide containing the sequence of any one of SEQ ID NOs: 1-341, such as SEQ ID NOs: 3, 11, 61, or 87, and particularly those that contain the KCSPG motif, as in SEQ ID NOs: 53, 69, 75, 118, and 233). For instance, a kit may contain an agonistic TNFR2 antibody and one or more reagents that can be used in an ELISA assay to determine the $K_D$ of an antibody of the invention for one or more peptides that present a TNFR2 epitope in a conformation similar to that of the epitope in the native protein. A kit may contain, e.g., a microtiter plate containing wells that have been previously conjugated to avidin, and may contain a library of TNFR2-derived peptides, each of which conjugated to a biotin moiety. Such a kit may optionally contain a secondary antibody that specifically binds to the Fc region of an agonistic TNFR2 antibody of the invention, and the secondary antibody may be conjugated to an enzyme (e.g., horseradish peroxidase) that catalyzes a chemical reaction that results in the emission of luminescent light.

Kits of the invention may also contain agonistic TNFR2 antibodies or antigen-binding fragments thereof of the invention and reagents that can be conjugated to such an antibody, including those previously described (e.g., a cytotoxic agent, a fluorescent molecule, a bioluminescent molecule, a molecule containing a radioactive isotope, a molecule containing a chelating group bound to a paramagnetic ion, etc). These kits may additionally contain instructions for how the conjugation of an agonistic TNFR2 antibody of the invention to a second molecule, such as those described above, can be achieved.

A kit of the invention may also contain a vector containing a polynucleotide that encodes an agonistic TNFR2 antibody or fragment thereof, such as any of the vectors described herein. Alternatively, a kit may include mammalian cells (e.g., CHO cells) that have been genetically altered to express and secrete agonistic TNFR2 antibodies or fragments thereof from the nuclear genome of the cell. Such a kit may also contain instructions describing how expression of the agonistic TNFR2 antibody or fragment thereof from a polynucleotide can be induced, and may additionally include reagents (such as, e.g., doxycycline or tetracycline) that can be used to promote the transcription of these polynucleotides. Such kits may be useful for the manufacture of agonistic TNFR2 antibodies or antigen-binding fragments thereof of the invention.

Other kits of the invention may include tools for engineering a prokaryotic or eukaryotic cell (e.g., a CHO cell or a BL21(DE3) *E. coli* cell) so as to express and secrete an agonistic TNFR2 antibody or fragment thereof of the invention from the nuclear genome of the cell. For example, a kit may contain CHO cells stored in an appropriate media and optionally frozen according to methods known in the art. The kit may also provide a vector containing a polynucleotide that encodes a nuclease (e.g., such as the CRISPER/Cas, zinc finger nuclease, TALEN, ARCUS™ nucleases described herein) as well as reagents for expressing the nuclease in the cell. The kit can additionally provide tools for modifying the polynucleotide that encodes the nuclease so as to enable one to alter the DNA sequence of the nuclease in order to direct the cleavage of a specific target DNA sequence of interest. Examples of such tools include primers for the amplification and site-directed mutagenesis of the polynucleotide encoding the nuclease of interest. The kit may also include restriction enzymes that can be used to selectively excise the nuclease-encoding polynucleotide from the vector and subsequently re-introduce the modified polynucleotide back into the vector once the user has modified the gene. Such a kit may also include a DNA ligase that can be used to catalyze the formation of covalent phosphodiester linkages between the modified nuclease-encoding polynucleotide and the target vector. A kit of the invention may also provide a polynucleotide encoding an agonistic TNFR2 antibody or fragment thereof, as well as a package insert describing the methods one can use to selectively cleave a particular DNA sequence in the genome of the cell in order to incorporate the polynucleotide encoding an agonistic TNFR2 antibody into the genome at this site. Optionally, the kit may provide a polynucleotide encoding a fusion protein that contains an agonistic TNFR2 antibody or fragment thereof and an additional polypeptide, such as, e.g., those described herein.

EXAMPLES

The following examples are put forth so as to provide those of ordinary skill in the art with a description of how the compositions and methods claimed herein may be performed, made, and evaluated, and are intended to be purely exemplary of the invention and are not intended to limit the scope of what the inventor regard as her invention.

Example 1

Mapping the Discrete Epitopes Within TNFR2 that Interact with MR2-1

Libraries of linear, cyclic, and bicyclic peptides derived from human TNFR2 were screened for distinct sequences within the protein that exhibit high affinity for TNFR2 antibody MR2-1. In order to screen conformational epitopes within TNFR2, peptides from distinct regions of the primary protein sequence were conjugated to one another to form chimeric peptides. These peptides contained cysteine residues at strategic positions within their primary sequences (see, e.g., FIG. 2A, SEQ ID NOs: 53, 69, 75, 118, and 233). This facilitated an intramolecular cross-linking strategy that was used to constrain individual peptides to a one of a wide array of three dimensional conformations. Unprotected thiols of cysteine residues were cross-linked via nucleophilic substitution reactions with divalent and trivalent electrophiles, such as 2,6-bis(bromomethyl)pyridine and 1,3,5-tris (bromomethyl)benzene, so as to form conformationally restricted cyclic and bicyclic peptides, respectively. In this way, peptides containing unique combinations of amino acids from disparate regions of the TNFR2 primary sequence were constrained so as to structurally pre-organize epitopes that may resemble those presented in the native TNFR2 tertiary structure. Libraries containing these peptides were screened by immobilizing peptides to distinct regions of a solid surface and treating the surface in turn with MR2-1, secondary antibody conjugated to horseradish peroxidase (HRP), and HRP substrate (2,2'-azino-di-3-ethylbenzthiazoline sulfonate) in the presence of hydrogen peroxide. The solid surface was washed in between treatment with successive reagents so as to remove excess or non-specifically bound materials. The luminescence of each region of each surface was subsequently analyzed using a charge coupled device (CCD)—camera and an image processing system.

The "Constrained Libraries of Peptides on Surfaces" (CLIPS) platform used for this analysis begins with the conversion of the target protein, e.g., TNFR2, into a library of up to 10,000 overlapping peptide constructs, using a combinatorial matrix design (Timmerman et al., J. Mol. Recognit., 20: 283-29 (2007)). On a solid carrier, a matrix of linear peptides is synthesized, which are subsequently shaped into spatially defined CLIPS constructs. Constructs representing multiple parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail.

Peptide Synthesis

To reconstruct epitopes of the target molecule a library of peptides was synthesized. An amino functionalized polypropylene support was obtained by grafting a proprietary hydrophilic polymer formulation via reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS® liquid handling stations (Perkin Elmer). CLIPS technology allows one to structure peptides into single loops, double-loops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the CLIPS template (2,6-bis (bromomethyl)pyridine) is dissolved in ammonium bicarbonate (20 mM, pH 7.8)/acetonitrile (1:3(v/v)). This solution is added to a surface-bound peptide array. The CLIPS template will react with side-chains of two cysteines as present in the solid-phase bound peptides of the peptide-arrays (455 wells plate with 3 μl wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1% beta-mercaptoethanol in PBS (pH 7.2) at 70° C. for 30 minutes, followed by sonication in $H_2O$ for another 45 minutes.

ELISA Screening

The binding of antibody to each of the synthesized peptides was tested in an ELISA format. Surface-immobilized peptide arrays were incubated with primary antibody solution (overnight at 4° C.). After washing, the peptide arrays were incubated with a 1/1000 dilution of an appropriate antibody peroxidase conjugate (SBA) for one hour at 25° C. After washing, the peroxidase substrate 2,2'-azino-di-3-ethylbenzthiazoline sulfonate (ABTS) and 2 μl/ml of 3 percent $H_2O_2$ were added. After one hour, the color development was measured. The color development was quantified with a charge coupled device (CCD)—camera and an image processing system. The values obtained from the CCD camera range from 0 to 3000 mAU, similar to a standard 96-well plate ELISA-reader. The results are quantified and stored into the Peplab database. Occasionally a well contains an air-bubble resulting in a false-positive value, the cards are manually inspected and any values caused by an air-bubble are scored as 0.

Peptides that bound MR2-1 with high affinity are highlighted in FIG. 2A. These peptides therefore contain residues within TNFR2 that are structurally configured into epitopes that are preferentially bound by MR2-1.

Example 2

Agonistic TNFR2 Antibodies Induce T-Reg Cell Proliferation Materials and Methods HUMAN T-REG FLOW™ Kit (BioLegend, Cat. No. 320401)
  Cocktail Anti-human CD4 PE-Cy5/CD25 PE (BioLegend, Part No. 78930)
  ALEXA FLUOR@ 488 Anti-human FOXP3, Clone 259D (BioLegend, Part No. 79467)
  ALEXA FLUOR@ 488 Mouse IgG1, k Isotype Ctrl (ICFC), Clone MOPC-21 (BioLegend, Part No. 79486)
  FOXP3 Fix/Perm Buffer (4×) (BioLegend, Cat. No. 421401)
  FOXP3 Perm Buffer (10×) (BioLegend, Cat. No. 421402)
PE anti-human CD25, Clone: BC96 (BioLegend, Cat. No. 302606)
ALEXA FLUOR@ 488 Anti-human FOXP3, Clone 259D (BioLegend, Cat. No. 320212)
PBS pH 7.4 (1×) (Gibco Cat. No. 10010-023)
HBSS (1×) (Gibco Cat. No. 14175-095)
FBS (heat inactivated)
15 ml tubes
Bench top centrifuge with swing bucket rotor for 15 ml tubes (set speed 1100 rpm or 200 g)

Agonistic TNFR2 antibodies (MR2-1 and 8E6.D1) were tested for the ability to induce the proliferation of T-reg cells. Cultured T-reg cells were treated with varying concentrations of the agonistic TNFR2 antibodies in the presence and absence of stimulatory growth factors (e.g., TNFα) for set periods of time. T-reg cells were also cultured in the presence of MR2-1 at various concentrations ranging, e.g., from 0-250 pg/ml in the presence and absence of TNFα. As controls, T-reg cells were also incubated with TNFα alone at concentrations ranging from 0-100 ng/ml. Additionally, control T-reg cells were cultured in the presence of IL-2 alone.

Following the incubation of T-reg cells under the conditions described above, the cell counts were determined using flow cytometry analysis. T-reg cells at a density of $0.2\text{-}1\times10^6$ cells/100 μl were distributed into a 15-ml conical tube and centrifuged for 5 minutes in order to pellet the cells. The supernatant was discarded and cells were resuspended in 100 μl of wash buffer (1× HBSS containing 2% FBS). 5 μl of PE anti-human CD25 fluorophore-antibody conjugate were added to this mixture, and the cells were subsequently vortexed and incubated in the dark for 25 minutes. The cells were then washed by adding 1 ml of wash buffer and subsequently centrifuging for 5 minutes. The supernatant was then discarded and 1 ml of FoxP3 fixation/permeabilization buffer (1:4 dilution of 4× FOXP3 Fix/Perm buffer in PBS) was added to the cells. The cells were then vortexed and incubated in the dark for 20 minutes. Cells were subsequently centrifuged for 5 minutes and supernatant was discarded. Cells were then resuspended in 1 ml of fresh wash buffer, vortexed, and centrifuged for 5 minutes. Cells were subsequently resuspended in 1 ml of 1× FOXP3 Perm Buffer (1:10 dilution of 10× FOXP3 Perm Buffer in PBS), vortexed, and incubated in the dark for 15 minutes. Following incubation, cells were centrifuged for 5 minutes and supernatant was subsequently discarded. The cell pellet was then resuspended in 100 μl of 1× FOXP3 Perm Buffer. At this point, 5 μl of either ALEXA FLUOR@ 488 anti-human FOXP3 or ALEXA FLUOR@ 488 mouse IgG1, k isotype control were added to the cells. Cells were then vortexed and incubated in the dark for 35 minutes, Following incubation, cells were washed by adding 1 ml of fresh wash buffer to the cells, vortexing the cells and centrifuging for 5 minutes. The supernatant was then discarded and the cell pellet was resuspended in 0.2-0.5 ml of 1× HBSS free of FBS. Cell counts were then determined by flow cytometry analysis.

As seen in FIGS. 5 and 6, incubation of agonistic TNFR2 antibodies MR2-1 and 8E6.D1 induced T-reg cell proliferation in a dose dependent manner. Strikingly, antibody 8E6.D1 is capable of synergizing with TNFα to enhance T-reg cell expansion (FIG. 6B).

Example 3

Generating Agonistic TNFR2 Antibodies by Phage Display

An exemplary method for in vitro protein evolution of agonistic TNFR2 antibodies of the invention is phage display, a technique which is well known in the art. Phage display libraries can be created by making a designed series of mutations or variations within a coding sequence for the CDRs of an antibody or the analogous regions of an antibody-like scaffold (e.g., the BC, CD, and DE loops of $^{10}$Fn3 domains). The template antibody-encoding sequence into which these mutations are introduced may be, e.g., a naive human germline sequence as described herein. These mutations can be performed using standard mutagenesis techniques described herein or known in the art. Each mutant sequence thus encodes an antibody corresponding in overall structure to the template except having one or more amino acid variations in the sequence of the template. Retroviral and phage display vectors can be engineered using standard vector construction techniques as described herein or known in the art. P3 phage display vectors along with compatible protein expression vectors, as is well known in the art, can be used to generate phage display vectors for antibody diversification as described herein.

The mutated DNA provides sequence diversity, and each transformant phage displays one variant of the initial template amino acid sequence encoded by the DNA, leading to a phage population (library) displaying a vast number of different but structurally related amino acid sequences. Due to the well-defined structure of antibody hypervariable regions, the amino acid variations introduced in a phage display screen are expected to alter the binding properties of the binding peptide or domain without significantly altering its structure.

In a typical screen, a phage library is contacted with and allowed to bind a TNFR2-derived peptide (e.g., a peptide having the sequence of any one of SEQ ID NOs: 1-341, such as SEQ ID NOs: 3, 11, 61, or 87, and particularly those that contain the KCSPG motif, as in SEQ ID NOs: 53, 69, 75, 118, and 233), or a particular subcomponent thereof. To facilitate separation of binders and non-binders, it is convenient to immobilize the target on a solid support. Phage bearing a TNFR2-binding moiety can form a complex with the target on the solid support whereas non-binding phage remain in solution and can be washed away with excess buffer. Bound phage can then liberated from the target by changing the buffer to an extreme pH (pH 2 or pH 10), changing the ionic strength of the buffer, adding denaturants, or other known means. To isolate the binding phage exhibiting the polypeptides of the present invention, a protein elution is performed.

The recovered phage can then be amplified through infection of bacterial cells and the screening process can be repeated with the new pool that is now depleted in non-binding antibodies and enriched for antibodies that bind the target peptide. The recovery of even a few binding phage is sufficient to amplify the phage for a subsequent iteration of screening. After a few rounds of selection, the gene sequences encoding the antibodies or antigen-binding fragments thereof derived from selected phage clones in the binding pool are determined by conventional methods, thus revealing the peptide sequence that imparts binding affinity of the phage to the target. During the panning process, the sequence diversity of the population diminishes with each round of selection until desirable peptide-binding antibodies remain. The sequences may converge on a small number of related antibodies or antigen-binding fragments thereof, typically 10-50 out of about $10^9$ to $10^{10}$ original candidates from each library. An increase in the number of phage recovered at each round of selection is a good indication that convergence of the library has occurred in a screen. After a set of binding polypeptides is identified, the sequence information can be used to design other secondary phage libraries, biased for members having additional desired properties (see, e.g., WO 2014/152660; the disclosure of which is incorporated herein by reference).

Example 4

Producing a scFv TNFR2 Agonist

Antibody fragments of the invention include scFv fragments, which consist of the antibody variable regions of the light and heavy chains combined in a single peptide chain. A TNFR2 antibody can be used as a framework for the development of an scFv antibody fragment by recombinantly expressing a polynucleotide encoding the variable region of a light chain of the TNFR2 antibody (e.g., 8E6.D1) operatively linked to the variable region of a heavy chain of that antibody. This can be accomplished using established mutagenesis protocols as described herein or known in the art. This polynucleotide can then be expressed in a cell (e.g., a CHO cell) and the scFv fragment can subsequently be isolated from the cell culture media.

Alternatively, scFv fragments derived from an agonistic TNFR2 antibody can be produced by chemical synthetic methods (e.g., by Fmoc-based solid-phase peptide synthesis, as described herein). One of skill in the art can chemically synthesize a peptide chain consisting of the variable region of a light chain of the TNFR2 antibody (e.g., 8E6.D1) operatively linked to the variable region of a heavy chain of that antibody. Native chemical ligation can be used as a strategy for the synthesis of long peptides (e.g., greater than 50 amino acids). Native chemical ligation protocols are known in the art and have been described, e.g., by Dawson et al., Science, 266:776-779 (1994); the disclosure of which is incorporated herein by reference.

Example 5

Treatment of Type I Diabetes in a Human Patient by Administration of Agonistic TNFR2 Antibodies The agonistic TNFR2 antibodies of the invention (e.g., a humanized version of 8E6-D1 or an antigen-binding fragment thereof) can be administered to a human patient in order to treat type I diabetes. For instance, a human patient suffering from type I diabetes can be treated by administering an agonistic TNFR2 antibody of the invention by an appropriate route (e.g., intravenously) at a particular dosage (e.g., between 0.001 and 100 mg/kg/day) over a course of days, weeks, months, or years. If desired, the agonistic TNFR2 antibody can be co-administered with, admixed with, or administered separately from, another therapeutic effective for treating type I diabetes, such as BCG.

The progression of type I diabetes that is treated with an agonistic TNFR2 antibody of the invention can be monitored by any one or more of several established methods. A physician can monitor the patient by direct observation in order to evaluate how the symptoms exhibited by the patient have changed in response to treatment. A urine sample isolated from the patient may be analyzed in order to determine the content of glucose in the sample, which can indicate the effectiveness of the TNFR2 antibody therapy. For instance, if the content of glucose in the urine sample is high, may indicate that the patient is to be administered higher dosages of an agonistic TNFR2 antibody of the invention until a minimal urine glucose concentration has been maintained.

Example 6

Treatment of Allograft Rejection in a Human Patient by Administration of Agonistic TNFR2 Antibodies The agonistic TNFR2 antibodies of the invention (e.g., a humanized version of 8E6-D1 or an antigen-binding fragment thereof) can be administered to a human patient in order to treat allograft rejection. Administration of these antibodies induces the proliferation of a population of T-reg cells, which attenuates immune responses mounted by self-reactive cytotoxic T-cells that are associated with the rejection of a tissue graft following transplantation. For instance, a human patient presenting with allograft rejection can be treated by administering an agonistic TNFR2 antibody of the invention (e.g., a TNFR2 antibody that specifically binds an epitope containing one or more residues of the KCSPG sequence of TNFR2 (residues 56-60 of SEQ ID NO: 366) by an appropriate route (e.g., intravenously) at a particular dosage (e.g., between 0.001 and 100 mg/kg/day) over a course of days, weeks, months, or years. If desired, the agonistic TNFR2 antibody can be modified, e.g., by hyperglycosylation or by conjugation with PEG, so as to evade immune recognition and/or to improve the pharmacokinetic profile of the antibody.

The progression of the allograft rejection that is treated with an agonistic TNFR2 antibody of the invention can be monitored by any one or more of several established methods. A physician can monitor the patient by direct observation in order to evaluate how the symptoms exhibited by the patient have changed in response to treatment. A blood sample can also be withdrawn from the patient in order to analyze the cell count of one or more CD8+ T-cells in order to determine if the quantity of cells has changed (e.g., decreased) in response to treatment with an agonistic TNFR2 antibody of the invention. A physician may also monitor the fluctuation in the volume of the allograft within the patient during the course of TNFR2 antibody therapy. Based on the results of these analyses, a physician may prescribe higher/lower dosages or more/less frequent dosing of the agonistic TNFR2 antibody in subsequent rounds of treatment in order to preserve the allograft.

Example 7

Treatment of Rheumatoid Arthritis in a Human Patient by Administration of Agonistic TNFR2 Antibodies The agonistic TNFR2 antibodies of the invention (e.g., a humanized version of 8E6-D1 or an antigen-binding fragment thereof) can be administered to a human patient in order to treat rheumatoid arthritis. For instance, a human patient suffering from rheumatoid arthritis can be treated by administering an agonistic TNFR2 antibody of the invention by an appropriate route (e.g., intravenously) at a particular dosage (e.g., between 0.001 and 100 mg/kg/day) over a course of days, weeks, months, or years. If desired, the agonistic TNFR2 antibody can be co-administered with, admixed with, or administered separately from, another therapeutic effective for treating rheumatoid arthritis, such as BCG.

The progression of rheumatoid arthritis that is treated with an agonistic TNFR2 antibody of the invention can be monitored by any one or more of several established methods. A physician can monitor the patient by direct observation in order to evaluate how the symptoms exhibited by the patient have changed in response to treatment. For instance, a physician of skill in the art may monitor the level of joint pain, joint stiffness, or muscle range exhibited by the patient in response to TNFR2 antibody therapy. Additionally, a lymph sample isolated from the patient may be analyzed in order to determine the quantity of autoreactive CD8+ T-cells in the sample, e.g., by FACS analysis, which can indicate the effectiveness of the TNFR2 antibody therapy. For instance, if the count of autoreactive CD8+ T-cells in the lymph sample is high, may indicate that the patient is to be administered higher dosages of an agonistic TNFR2 antibody of the invention, e.g., until the autoreactive T-cell population within the patient has been eliminated.

Example 8

Treatment of Multiple Sclerosis in a Human Patient by Administration of Agonistic TNFR2 Antibodies The agonistic TNFR2 antibodies of the invention (e.g., a humanized version of 8E6-D1 or an antigen-binding fragment thereof) can be administered to a human patient in order to treat multiple sclerosis. For instance, a human patient suffering from multiple sclerosis can be treated by administering an agonistic TNFR2 antibody of the invention by an appropriate route (e.g., intravenously) at a particular dosage (e.g., between 0.001 and 100 mg/kg/day) over a course of days, weeks, months, or years. If desired, the agonistic TNFR2 antibody can be co-administered with, admixed with, or administered separately from, another therapeutic effective for treating multiple sclerosis, such as BCG.

The progression of multiple sclerosis that is treated with an agonistic TNFR2 antibody of the invention can be monitored by any one or more of several established methods. A physician can monitor the patient by direct observation in order to evaluate how the symptoms exhibited by the patient have changed in response to treatment. For instance, a physician of skill in the art may monitor the patient to determine if he or she is exhibiting improved vision and/or coordination, faster reflexes, increased motor activity, and/or improved cognitive performance in response to TNFR2 antibody therapy. If improvements in these traits are not observed, a physician may prescribe the patient higher doses or more frequent administration of the agonistic TNFR antibody or antigen-binding fragment thereof. Additionally, a lymph sample isolated from the patient may be analyzed in order to determine the quantity of autoreactive CD8+ T-cells in the sample, e.g., by FACS analysis, which can indicate the effectiveness of the TNFR2 antibody therapy. For instance, if the count of autoreactive CD8+ T-cells in the lymph sample that recognize myelin sheath-producing cells is high, this may indicate that the patient is to be administered higher dosages of an agonistic TNFR2 antibody of the invention, e.g., until the autoreactive T-cell population within the patient has been eliminated.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

SEQUENCE LISTING

<160> NUMBER OF SEQ ID NOS: 413

<210> SEQ ID NO 1

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 1

Cys Arg Pro His Gln Ile Cys Asn Val Val Ala Ile Pro Gly Asn
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic Construct

<400> SEQUENCE: 2

Cys Arg Pro His Gln Ile Cys Asn Val Val Gly Ala Pro Gly Asn
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct

<400> SEQUENCE: 3

Gln Glu Gly Cys Arg Leu Cys Ala Pro Leu Ala Ala Cys Arg Pro
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Thr Phe Ser Asn Thr Thr Ser Ser Thr Asp Ala Ala Arg Pro His
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic Construct

<400> SEQUENCE: 5

Pro Ser Thr Ser Phe Leu Leu Pro Met Gly Pro Ser Pro Pro Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic Construct

<400> SEQUENCE: 6

Gln Val Glu Thr Gln Ala Cys Thr Arg Glu Gln Asn Arg Ile Cys
1               5                   10                  15

<210> SEQ ID NO 7
<211> LENGTH: 15
```

```
<212> TYPE: PRT
<213> ORGANISM: Artificial Sequence
<220> FEATURE:
<223> OTHER INFORMATION: Synthetic Construct

<400> SEQUENCE: 7

Leu Trp Asn Trp Val Pro Glu Cys Leu Ser Cys Gly Ser Arg Cys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Gln Leu Trp Asn Trp Val Pro Glu Cys Leu Ser Cys Gly Ser Arg
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Construct

<400> SEQUENCE: 9

Gln Ala Cys Thr Arg Glu Gln Asn Arg Ile Cys Thr Cys Arg Pro
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

Thr Phe Ser Asn Thr Thr Ser Ser Thr Asp Ile Cys Arg Pro His
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic Construct

<400> SEQUENCE: 11

Pro Gly Trp Tyr Cys Ala Leu Ser Lys Gln Glu Gly Cys Arg Leu
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Cys Gln Leu Trp Asn Trp Val Pro Glu Ala Leu Ala Gly Gly Ser Arg
1               5                   10                  15

Cys

<210> SEQ ID NO 13
```

```
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 13

Leu Ser Xaa Gly Ser Arg Cys Ser Ser Asp Gln Gly Gly Ser Gly Gly
1               5                   10                  15

Arg Glu Gln Asn Arg Ile Cys Thr Xaa Arg Pro
            20                  25

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Trp Asn Trp Val Pro Glu Cys Leu Ser Cys Ala Ala Arg Cys Ser
1               5                   10                  15

<210> SEQ ID NO 15
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 15

Leu Trp Asn Trp Val Pro Glu Xaa Leu Ser Cys Gly Gly Ser Gly Gly
1               5                   10                  15

Gln Ala Cys Thr Arg Glu Gln Asn Arg Ile Xaa
            20                  25

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Pro Leu Arg Lys Cys Arg Pro Gly Phe Gly Val Ala Arg Pro Gly
1               5                   10                  15

<210> SEQ ID NO 17
<211> LENGTH: 27
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 17

Xaa Gly Ser Arg Cys Ser Ser Asp Gln Val Glu Gly Gly Ser Gly Gly
1               5                   10                  15

Arg Glu Gln Asn Arg Ile Cys Thr Xaa Arg Pro
            20                  25

<210> SEQ ID NO 18
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 18

Pro Glu Xaa Leu Ser Xaa Gly Ser Arg Cys Ser Gly Gly Ser Gly Gly
1               5                   10                  15

Arg Glu Gln Asn Arg Ile Cys Thr Xaa Arg Pro
            20                  25

<210> SEQ ID NO 19
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 19

Leu Trp Asn Trp Val Pro Glu Xaa Leu Ser Cys Gly Gly Ser Gly Gly
1               5                   10                  15

Ala Cys Thr Arg Glu Gln Asn Arg Ile Xaa Thr
            20                  25
```

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Gln Leu Trp Asn Trp Val Pro Glu Cys Leu Ala Ala Gly Ser Arg
1               5                   10                  15

<210> SEQ ID NO 21
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 21

Cys Ser Ser Asp Gln Val Glu Thr Gln Ala Xaa Gly Gly Ser Gly Gly
1               5                   10                  15

Arg Glu Gln Asn Arg Ile Cys Thr Xaa Arg Pro
            20                  25

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Glu Gln Asn Arg Ile Cys Thr Cys Arg Pro Ala Ala Tyr Cys Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic Construct

<400> SEQUENCE: 23

Thr Thr Ser Ser Thr Asp Ile Cys Arg Pro His Gln Ile Cys Asn
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic Construct

<400> SEQUENCE: 24

Ala Cys Thr Arg Glu Gln Asn Arg Ile Cys Thr Cys Arg Pro Gly
1               5                   10                  15

```
<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Cys Gln Leu Trp Asn Trp Val Pro Glu Ala Leu Ser Ala Gly Ser Arg
1               5                   10                  15

Cys

<210> SEQ ID NO 26
<211> LENGTH: 15
<212> TYPE: PRT
<213> ORGANISM: Artificial Sequence
<220> FEATURE:
<223> OTHER INFORMATION: Synthetic Construct

<400> SEQUENCE: 26

Arg Pro His Gln Ile Cys Asn Val Val Ala Ile Pro Gly Asn Ala
1               5                   10                  15

<210> SEQ ID NO 27
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 27

Ser Arg Cys Ser Ser Asp Gln Val Glu Thr Gln Gly Gly Ser Gly Gly
1               5                   10                  15

Arg Glu Gln Asn Arg Ile Cys Thr Xaa Arg Pro
            20                  25

<210> SEQ ID NO 28
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 28

Gly Ser Arg Cys Ser Ser Asp Gln Val Glu Thr Gly Gly Ser Gly Gly
1               5                   10                  15

Arg Glu Gln Asn Arg Ile Cys Thr Xaa Arg Pro
            20                  25

<210> SEQ ID NO 29
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 29

Leu Ser Xaa Gly Ser Arg Cys Ser Ser Asp Gln Gly Gly Ser Gly Gly
1               5                   10                  15

Glu Gln Asn Arg Ile Cys Thr Xaa Arg Pro Gly
            20                  25

<210> SEQ ID NO 30
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group

<400> SEQUENCE: 30

Gln Glu Gly Cys Arg Leu Xaa Ala Pro Leu Arg Gly Gly Ser Gly Gly
1               5                   10                  15

Cys Arg Pro Gly Phe Gly Val Ala Arg Pro Gly
            20                  25

<210> SEQ ID NO 31
<211> LENGTH: 15
<212> TYPE: PRT
<213> ORGANISM: Artificial Sequence
<220> FEATURE:
<223> OTHER INFORMATION: Synthetic Construct

<400> SEQUENCE: 31

Phe Ser Asn Thr Thr Ser Ser Thr Asp Ile Cys Arg Pro His Gln
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic Construct

<400> SEQUENCE: 32

Leu Trp Asn Trp Val Pro Glu Cys Leu Ser Ala Ala Ser Arg Cys
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic Construct

<400> SEQUENCE: 33

Gln Thr Ala Gln Met Cys Cys Ser Lys Cys Ser Pro Gly Gln His
1               5                   10                  15

<210> SEQ ID NO 34

```
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 34

Glu Xaa Leu Ser Xaa Gly Ser Arg Cys Ser Ser Gly Gly Ser Gly Gly
1               5                   10                  15

Arg Glu Gln Asn Arg Ile Cys Thr Xaa Arg Pro
            20                  25

<210> SEQ ID NO 35
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (15)..(15)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 35

Cys Glu Gln Asn Arg Ile Xaa Thr Xaa Arg Pro Gly Trp Tyr Xaa Ala
1               5                   10                  15

Cys Asn Ala Ser Met Asp Ala Val Xaa Thr Ser Thr Ser Pro Thr Arg
            20                  25                  30

Cys

<210> SEQ ID NO 36
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
```

```
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 36

Val Pro Glu Xaa Leu Ser Xaa Gly Ser Arg Cys Gly Gly Ser Gly Gly
1               5                   10                  15

Arg Glu Gln Asn Arg Ile Cys Thr Xaa Arg Pro
            20                  25

<210> SEQ ID NO 37
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 37

Trp Asn Trp Val Pro Glu Xaa Leu Ser Cys Gly Gly Gly Ser Gly Gly
1               5                   10                  15

Gln Ala Cys Thr Arg Glu Gln Asn Arg Ile Xaa
            20                  25

<210> SEQ ID NO 38
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group

<400> SEQUENCE: 38

Leu Trp Asn Trp Val Pro Glu Xaa Leu Ser Cys Gly Gly Ser Gly Gly
1               5                   10                  15

Thr Gln Ala Cys Thr Arg Glu Gln Asn Arg Ile
            20                  25

<210> SEQ ID NO 39
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
```

```
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 39

Val Pro Glu Xaa Leu Ser Xaa Gly Ser Arg Cys Gly Gly Ser Gly Gly
1               5                   10                  15

Gln Ala Xaa Thr Arg Glu Gln Asn Arg Ile Cys
            20                  25

<210> SEQ ID NO 40
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 40

Ser Xaa Gly Ser Arg Cys Ser Ser Asp Gln Val Gly Ser Gly Gly
1               5                   10                  15

Arg Glu Gln Asn Arg Ile Cys Thr Xaa Arg Pro
            20                  25

<210> SEQ ID NO 41
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 41

Xaa Gly Ser Arg Cys Ser Ser Asp Gln Val Glu Gly Gly Ser Gly Gly
1               5                   10                  15

Glu Gln Asn Arg Ile Cys Thr Xaa Arg Pro Gly
            20                  25

<210> SEQ ID NO 42
<211> LENGTH: 15
<212> TYPE: PRT
<213> ORGANISM: Artificial Sequence
<220> FEATURE:
<223> OTHER INFORMATION: Synthetic Construct

<400> SEQUENCE: 42
```

```
Ala Cys Thr Arg Glu Gln Asn Arg Ile Cys Ala Ala Arg Pro Gly
1               5                   10                  15

<210> SEQ ID NO 43
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 43

Ser Xaa Gly Ser Arg Cys Ser Ser Asp Gln Val Gly Gly Ser Gly Gly
1               5                   10                  15

Glu Gln Asn Arg Ile Cys Thr Xaa Arg Pro Gly
            20                  25

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

Pro Leu Arg Lys Cys Arg Pro Gly Phe Gly Ala Gly Arg Pro Gly
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic Construct

<400> SEQUENCE: 45

Ile Cys Arg Pro His Gln Ile Cys Asn Val Ala Gly Ile Pro Gly
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic Construct

<400> SEQUENCE: 46

Gly Trp Tyr Cys Ala Leu Ser Lys Gln Glu Gly Cys Arg Leu Cys
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic Construct

<400> SEQUENCE: 47
```

```
Gln Ala Cys Thr Arg Glu Gln Asn Arg Ile Ala Ala Cys Arg Pro
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic Construct

<400> SEQUENCE: 48

Trp Asn Trp Val Pro Glu Cys Leu Ser Cys Gly Ser Arg Cys Ser
1               5                   10                  15

<210> SEQ ID NO 49
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 49

Xaa Leu Ser Xaa Gly Ser Arg Cys Ser Ser Asp Gly Gly Ser Gly Gly
1               5                   10                  15

Gln Asn Arg Ile Cys Thr Xaa Arg Pro Gly Trp
            20                  25

<210> SEQ ID NO 50
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 50

Val Pro Glu Xaa Leu Ser Cys Gly Ser Arg Xaa Gly Gly Ser Gly Gly
1               5                   10                  15

Gln Ala Cys Thr Arg Glu Gln Asn Arg Ile Xaa
            20                  25
```

```
<210> SEQ ID NO 51
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 51

Xaa Leu Ser Xaa Gly Ser Arg Cys Ser Ser Asp Gly Gly Ser Gly Gly
1               5                   10                  15

Arg Glu Gln Asn Arg Ile Cys Thr Xaa Arg Pro
            20                  25

<210> SEQ ID NO 52
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group

<400> SEQUENCE: 52

Glu Gly Cys Arg Leu Xaa Ala Pro Leu Arg Lys Gly Gly Ser Gly Gly
1               5                   10                  15

Cys Arg Pro Gly Phe Gly Val Ala Arg Pro Gly
            20                  25

<210> SEQ ID NO 53
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
      protecting group

<400> SEQUENCE: 53

Ala Pro Glu Pro Gly Ser Thr Cys Arg Leu Arg Gly Gly Ser Gly Gly
1               5                   10                  15

Met Cys Xaa Ser Lys Xaa Ser Pro Gly Gln His
            20                  25

<210> SEQ ID NO 54
```

```
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 54

Leu Trp Asn Trp Val Pro Glu Xaa Leu Ser Cys Gly Gly Ser Gly Gly
1               5                   10                  15

Cys Thr Arg Glu Gln Asn Arg Ile Xaa Thr Xaa
            20                  25

<210> SEQ ID NO 55
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group

<400> SEQUENCE: 55

Lys Gln Glu Gly Cys Arg Leu Xaa Ala Pro Leu Gly Gly Ser Gly Gly
1               5                   10                  15

Cys Arg Pro Gly Phe Gly Val Ala Arg Pro Gly
            20                  25

<210> SEQ ID NO 56
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group

<400> SEQUENCE: 56

Xaa Ala Leu Ser Lys Gln Glu Gly Cys Arg Leu Gly Gly Ser Gly Gly
1               5                   10                  15

Cys Arg Pro Gly Phe Gly Val Ala Arg Pro Gly
            20                  25

<210> SEQ ID NO 57
<211> LENGTH: 27
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (3)..(3)
<223> OTHER INFORMATION: Xaa is Cys residue protected with ACM
      protecting group

<400> SEQUENCE: 57

Trp Tyr Xaa Ala Leu Ser Lys Gln Glu Gly Cys Gly Gly Ser Gly Gly
1               5                   10                  15

Cys Arg Pro Gly Phe Gly Val Ala Arg Pro Gly
            20                  25

<210> SEQ ID NO 58
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa is Cys residue protected with ACM
      protecting group

<400> SEQUENCE: 58

Leu Ser Lys Gln Glu Gly Cys Arg Leu Xaa Ala Gly Gly Ser Gly Gly
1               5                   10                  15

Cys Arg Pro Gly Phe Gly Val Ala Arg Pro Gly
            20                  25

<210> SEQ ID NO 59
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 59

Gly Ser Arg Cys Ser Ser Asp Gln Val Glu Thr Gly Gly Ser Gly Gly
1               5                   10                  15

Glu Gln Asn Arg Ile Cys Thr Xaa Arg Pro Gly
            20                  25

<210> SEQ ID NO 60
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Cys residue protected with ACM
      protecting group

<400> SEQUENCE: 60

Ala Leu Ser Lys Gln Glu Gly Cys Arg Leu Xaa Gly Gly Ser Gly Gly
1               5                   10                  15

Cys Arg Pro Gly Phe Gly Val Ala Arg Pro Gly
            20                  25

<210> SEQ ID NO 61
<211> LENGTH: 15
```

```
<212> TYPE: PRT
<213> ORGANISM: Artificial Sequence
<220> FEATURE:
<223> OTHER INFORMATION: Synthetic Construct

<400> SEQUENCE: 61

Arg Pro Gly Trp Tyr Cys Ala Leu Ser Lys Gln Glu Gly Cys Arg
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic Construct

<400> SEQUENCE: 62

Ala Phe Thr Pro Tyr Ala Pro Glu Pro Gly Ser Thr Cys Arg Leu
1               5                   10                  15

<210> SEQ ID NO 63
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 63

Arg Cys Ser Ser Asp Gln Val Glu Thr Gln Ala Gly Ser Gly Gly
1               5                   10                  15

Arg Glu Gln Asn Arg Ile Cys Thr Xaa Arg Pro
            20                  25

<210> SEQ ID NO 64
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 64

Trp Asn Trp Val Pro Glu Xaa Leu Ser Cys Gly Gly Gly Ser Gly Gly
1               5                   10                  15

Ala Cys Thr Arg Glu Gln Asn Arg Ile Xaa Thr
            20                  25

<210> SEQ ID NO 65
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (6)..(6)
<223> OTHER INFORMATION: Xaa is Cys residue protected with ACM
      protecting group

<400> SEQUENCE: 65

Thr Ser Asp Val Val Xaa Lys Pro Cys Ala Pro Gly Gly Ser Gly Gly
1               5                   10                  15

Thr Thr Ser Ser Thr Asp Ile Cys Arg Pro His
            20                  25

<210> SEQ ID NO 66
<211> LENGTH: 15
<212> TYPE: PRT
<213> ORGANISM: Artificial Sequence
<220> FEATURE:
<223> OTHER INFORMATION: Synthetic Construct

<400> SEQUENCE: 66

Ile Cys Arg Pro His Gln Ile Cys Asn Val Val Ala Ile Pro Gly
1               5                   10                  15

<210> SEQ ID NO 67
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group

<400> SEQUENCE: 67

Arg Leu Cys Ala Pro Leu Arg Lys Xaa Arg Pro Gly Gly Ser Gly Gly
1               5                   10                  15

Cys Lys Pro Xaa Ala Pro Gly Thr Phe Ser Asn
            20                  25

<210> SEQ ID NO 68
<211> LENGTH: 15
<212> TYPE: PRT
<213> ORGANISM: Artificial Sequence
<220> FEATURE:
<223> OTHER INFORMATION: Synthetic Construct

<400> SEQUENCE: 68

Pro Thr Arg Ser Met Ala Pro Gly Ala Val His Leu Pro Gln Pro
1               5                   10                  15

<210> SEQ ID NO 69
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
```

```
<223> OTHER INFORMATION: Xaa is Cys residue protected with ACM
      protecting group

<400> SEQUENCE: 69

Tyr Ala Pro Glu Pro Gly Ser Thr Cys Arg Leu Gly Gly Ser Gly Gly
1               5                   10                  15

Met Cys Xaa Ser Lys Xaa Ser Pro Gly Gln His
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 70

Trp Val Pro Glu Xaa Leu Ser Cys Gly Ser Arg Gly Gly Ser Gly Gly
1               5                   10                  15

Gln Ala Cys Thr Arg Glu Gln Asn Arg Ile Xaa
            20                  25

<210> SEQ ID NO 71
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 71

Pro Glu Xaa Leu Ser Xaa Gly Ser Arg Cys Ser Gly Gly Ser Gly Gly
1               5                   10                  15

Ala Xaa Thr Arg Glu Gln Asn Arg Ile Cys Thr
            20                  25

<210> SEQ ID NO 72
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
```

```
      protecting group
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 72

Glu Xaa Leu Ser Xaa Gly Ser Arg Cys Ser Ser Gly Gly Ser Gly Gly
1               5                   10                  15

Glu Gln Asn Arg Ile Cys Thr Xaa Arg Pro Gly
            20                  25

<210> SEQ ID NO 73
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (10)..(10)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 73

Pro Glu Xaa Leu Ser Cys Gly Ser Arg Xaa Ser Gly Gly Ser Gly Gly
1               5                   10                  15

Gln Ala Cys Thr Arg Glu Gln Asn Arg Ile Xaa
            20                  25

<210> SEQ ID NO 74
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 74

Trp Val Pro Glu Xaa Leu Ser Cys Gly Ser Arg Gly Gly Ser Gly Gly
1               5                   10                  15

Ala Cys Thr Arg Glu Gln Asn Arg Ile Xaa Thr
            20                  25

<210> SEQ ID NO 75
```

```
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
      protecting group

<400> SEQUENCE: 75

Pro Gly Ser Thr Cys Arg Leu Arg Glu Tyr Tyr Gly Gly Ser Gly Gly
1               5                   10                  15

Met Cys Xaa Ser Lys Xaa Ser Pro Gly Gln His
            20                  25

<210> SEQ ID NO 76
<211> LENGTH: 15
<212> TYPE: PRT
<213> ORGANISM: Artificial Sequence
<220> FEATURE:
<223> OTHER INFORMATION: Synthetic Construct

<400> SEQUENCE: 76

Pro Ser Thr Ala Pro Ser Thr Ser Phe Leu Leu Pro Met Gly Pro
1               5                   10                  15

<210> SEQ ID NO 77
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 77

Arg Cys Ser Ser Asp Gln Val Glu Thr Gln Ala Gly Gly Ser Gly Gly
1               5                   10                  15

Gln Asn Arg Ile Cys Thr Xaa Arg Pro Gly Trp
            20                  25

<210> SEQ ID NO 78
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
```

```
        protecting group

<400> SEQUENCE: 78

Pro Glu Xaa Leu Ser Xaa Gly Ser Arg Cys Ser Gly Gly Ser Gly Gly
1               5                   10                  15

Gln Asn Arg Ile Cys Thr Xaa Arg Pro Gly Trp
            20                  25

<210> SEQ ID NO 79
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 79

Cys Ser Ser Asp Gln Val Glu Thr Gln Ala Xaa Gly Gly Ser Gly Gly
1               5                   10                  15

Glu Gln Asn Arg Ile Cys Thr Xaa Arg Pro Gly
            20                  25

<210> SEQ ID NO 80
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
      protecting group

<400> SEQUENCE: 80

Pro Tyr Ala Pro Glu Pro Gly Ser Thr Cys Arg Gly Gly Ser Gly Gly
1               5                   10                  15

Met Cys Xaa Ser Lys Xaa Ser Pro Gly Gln His
            20                  25

<210> SEQ ID NO 81
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (7)..(7)
<223> OTHER INFORMATION: Xaa is Cys residue protected with ACM
      protecting group
```

```
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 81

Val Pro Glu Xaa Leu Ser Xaa Gly Ser Arg Cys Gly Gly Ser Gly Gly
1               5                   10                  15

Ala Xaa Thr Arg Glu Gln Asn Arg Ile Cys Thr
            20                  25

<210> SEQ ID NO 82
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (21)..(21)
<223> OTHER INFORMATION: Xaa is Cys residue protected with ACM
      protecting group

<400> SEQUENCE: 82

Cys Ser Ser Asp Gln Val Glu Thr Gln Ala Xaa Thr Arg Glu Gln Asn
1               5                   10                  15

Arg Ile Cys Thr Xaa Arg
            20

<210> SEQ ID NO 83
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 83

Glu Xaa Leu Ser Xaa Gly Ser Arg Cys Ser Ser Gly Gly Ser Gly Gly
1               5                   10                  15

Gln Ala Xaa Thr Arg Glu Gln Asn Arg Ile Cys
            20                  25

<210> SEQ ID NO 84
<211> LENGTH: 27
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 84

Leu Ser Xaa Gly Ser Arg Cys Ser Ser Asp Gln Gly Gly Ser Gly Gly
1               5                   10                  15

Gln Asn Arg Ile Cys Thr Xaa Arg Pro Gly Trp
            20                  25

<210> SEQ ID NO 85
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 85

Xaa Ala Leu Ser Lys Gln Glu Gly Cys Arg Leu Gly Gly Ser Gly Gly
1               5                   10                  15

Leu Xaa Ala Pro Leu Arg Lys Cys Arg Pro Gly
            20                  25

<210> SEQ ID NO 86
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
      protecting group

<400> SEQUENCE: 86

Pro Glu Pro Gly Ser Thr Cys Arg Leu Arg Glu Gly Gly Ser Gly Gly
1               5                   10                  15

Met Cys Xaa Ser Lys Xaa Ser Pro Gly Gln His
            20                  25

<210> SEQ ID NO 87
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group

<400> SEQUENCE: 87

Asn Arg Ile Xaa Thr Cys Arg Pro Gly Trp Tyr Cys Ala Leu Ser Lys
1               5                   10                  15

Gln Glu Gly Xaa Arg Leu
            20

<210> SEQ ID NO 88
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 88

Val Pro Glu Xaa Leu Ser Xaa Gly Ser Arg Cys Gly Gly Ser Gly Gly
1               5                   10                  15

Glu Gln Asn Arg Ile Cys Thr Xaa Arg Pro Gly
            20                  25

<210> SEQ ID NO 89
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
      protecting group

<400> SEQUENCE: 89

Glu Pro Gly Ser Thr Cys Arg Leu Arg Glu Tyr Gly Gly Ser Gly Gly
1               5                   10                  15

Met Cys Xaa Ser Lys Xaa Ser Pro Gly Gln His
            20                  25

<210> SEQ ID NO 90
<211> LENGTH: 27
<212> TYPE: PRT
<213> ORGANISM: Artificial Sequence
```

```
<220> FEATURE:
<223> OTHER INFORMATION: Synthetic Construct

<400> SEQUENCE: 90

Lys Pro Cys Ala Pro Gly Thr Phe Ser Asn Thr Gly Ser Gly Gly
1               5                   10                  15

Thr Thr Ser Ser Thr Asp Ile Cys Arg Pro His
            20                  25

<210> SEQ ID NO 91
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 91

Ser Arg Cys Ser Ser Asp Gln Val Glu Thr Gln Gly Gly Ser Gly Gly
1               5                   10                  15

Glu Gln Asn Arg Ile Cys Thr Xaa Arg Pro Gly
            20                  25

<210> SEQ ID NO 92
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group

<400> SEQUENCE: 92

Cys Ala Pro Leu Arg Lys Xaa Arg Pro Gly Phe Gly Gly Ser Gly Gly
1               5                   10                  15

Cys Lys Pro Xaa Ala Pro Gly Thr Phe Ser Asn
            20                  25

<210> SEQ ID NO 93
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
``` protecting group

<400> SEQUENCE: 93

Val Pro Glu Xaa Leu Ser Cys Gly Ser Arg Xaa Gly Gly Ser Gly Gly
1               5                   10                  15

Ala Cys Thr Arg Glu Gln Asn Arg Ile Xaa Thr
            20                  25

<210> SEQ ID NO 94
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group

<400> SEQUENCE: 94

Trp Asn Trp Val Pro Glu Xaa Leu Ser Cys Gly Gly Gly Ser Gly Gly
1               5                   10                  15

Thr Gln Ala Cys Thr Arg Glu Gln Asn Arg Ile
            20                  25

<210> SEQ ID NO 95
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 95

Xaa Leu Ser Xaa Gly Ser Arg Cys Ser Ser Asp Gly Gly Ser Gly Gly
1               5                   10                  15

Gln Ala Xaa Thr Arg Glu Gln Asn Arg Ile Cys
            20                  25

<210> SEQ ID NO 96
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group

<400> SEQUENCE: 96

Ser Lys Gln Glu Gly Cys Arg Leu Xaa Ala Pro Gly Gly Ser Gly Gly
1               5                   10                  15

```
Cys Arg Pro Gly Phe Gly Val Ala Arg Pro Gly
            20                  25

<210> SEQ ID NO 97
<211> LENGTH: 15
<212> TYPE: PRT
<213> ORGANISM: Artificial Sequence
<220> FEATURE:
<223> OTHER INFORMATION: Synthetic Construct

<400> SEQUENCE: 97

Leu Arg Lys Cys Arg Pro Gly Phe Gly Val Ala Arg Pro Gly Thr
1               5                   10                  15

<210> SEQ ID NO 98
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 98

Trp Val Pro Glu Xaa Leu Ser Cys Gly Ser Arg Gly Gly Ser Gly Gly
1               5                   10                  15

Cys Thr Arg Glu Gln Asn Arg Ile Xaa Thr Xaa
            20                  25

<210> SEQ ID NO 99
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 99

Trp Tyr Xaa Ala Leu Ser Lys Gln Glu Gly Cys Gly Ser Gly Gly
1               5                   10                  15

Leu Xaa Ala Pro Leu Arg Lys Cys Arg Pro Gly
            20                  25

<210> SEQ ID NO 100
<211> LENGTH: 33
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 100

Cys Gly Xaa Arg Leu Xaa Ala Pro Leu Arg Lys Xaa Arg Pro Gly Phe
1               5                   10                  15

Cys Asn Ala Ser Met Asp Ala Val Xaa Thr Ser Thr Ser Pro Thr Arg
            20                  25                  30

Cys

<210> SEQ ID NO 101
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 101

Cys Gln Ile Xaa Asn Val Val Ala Ile Pro Gly Asn Ala Ser Met Asp
1               5                   10                  15

Cys Ala Pro Leu Arg Lys Xaa Arg Pro Gly Phe Gly Val Ala Arg Pro
            20                  25                  30

Cys

<210> SEQ ID NO 102
<211> LENGTH: 15
<212> TYPE: PRT
<213> ORGANISM: Artificial Sequence
<220> FEATURE:
<223> OTHER INFORMATION: Synthetic Construct

<400> SEQUENCE: 102

Val Glu Thr Gln Ala Cys Thr Arg Glu Gln Asn Arg Ile Cys Thr
1               5                   10                  15

<210> SEQ ID NO 103
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 103

Asn Trp Val Pro Glu Xaa Leu Ser Cys Gly Ser Gly Gly Ser Gly Gly
1               5                   10                  15

Ala Cys Thr Arg Glu Gln Asn Arg Ile Xaa Thr
            20                  25

<210> SEQ ID NO 104
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
      protecting group

<400> SEQUENCE: 104

Thr Cys Arg Leu Arg Glu Tyr Tyr Asp Gln Thr Gly Gly Ser Gly Gly
1               5                   10                  15

Met Cys Xaa Ser Lys Xaa Ser Pro Gly Gln His
            20                  25

<210> SEQ ID NO 105
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 105

Pro Glu Xaa Leu Ser Xaa Gly Ser Arg Cys Ser Gly Gly Ser Gly Gly
1               5                   10                  15

Glu Gln Asn Arg Ile Cys Thr Xaa Arg Pro Gly
            20                  25
```

```
<210> SEQ ID NO 106
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 106

Gly Ser Arg Cys Ser Ser Asp Gln Val Glu Thr Gly Gly Ser Gly Gly
1               5                   10                  15

Gln Asn Arg Ile Cys Thr Xaa Arg Pro Gly Trp
            20                  25

<210> SEQ ID NO 107
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (10)..(10)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 107

Pro Glu Xaa Leu Ser Cys Gly Ser Arg Xaa Ser Gly Gly Ser Gly Gly
1               5                   10                  15

Ala Cys Thr Arg Glu Gln Asn Arg Ile Xaa Thr
            20                  25

<210> SEQ ID NO 108
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 108

Leu Ser Cys Gly Ser Arg Xaa Ser Ser Asp Gln Gly Gly Ser Gly Gly
1               5                   10                  15

Gln Ala Cys Thr Arg Glu Gln Asn Arg Ile Xaa
            20                  25

<210> SEQ ID NO 109
```

```
<211> LENGTH: 27
<212> TYPE: PRT
<213> ORGANISM: Artificial Sequence
<220> FEATURE:
<223> OTHER INFORMATION: Synthetic Construct

<400> SEQUENCE: 109

Pro Cys Ala Pro Gly Thr Phe Ser Asn Thr Thr Gly Gly Ser Gly Gly
1               5                   10                  15

Thr Thr Ser Ser Thr Asp Ile Cys Arg Pro His
            20                  25

<210> SEQ ID NO 110
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 110

Cys Gln Ala Xaa Thr Arg Glu Gln Asn Arg Ile Xaa Thr Xaa Arg Pro
1               5                   10                  15

Cys Asn Ala Ser Met Asp Ala Val Xaa Thr Ser Thr Ser Pro Thr Arg
            20                  25                  30

Cys

<210> SEQ ID NO 111
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 111

Ser Arg Cys Ser Ser Asp Gln Val Glu Thr Gln Gly Gly Ser Gly Gly
1               5                   10                  15

Gln Asn Arg Ile Cys Thr Xaa Arg Pro Gly Trp
            20                  25

<210> SEQ ID NO 112
<211> LENGTH: 17
<212> TYPE: PRT
<213> ORGANISM: Artificial Sequence
<220> FEATURE:
```

```
<223> OTHER INFORMATION: Synthetic Construct

<400> SEQUENCE: 112

Cys Gln Ala Ala Thr Arg Glu Gln Asn Arg Ile Gly Ala Ala Arg Pro
1               5                   10                  15

Cys

<210> SEQ ID NO 113
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 113

Cys Ser Ser Asp Gln Val Glu Thr Gln Ala Xaa Gly Gly Ser Gly Gly
1               5                   10                  15

Gln Asn Arg Ile Cys Thr Xaa Arg Pro Gly Trp
            20                  25

<210> SEQ ID NO 114
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 114

Cys Ala Phe Thr Pro Tyr Ala Pro Glu Pro Gly Ser Thr Xaa Arg Leu
1               5                   10                  15

Cys Asn Ala Ser Met Asp Ala Val Xaa Thr Ser Thr Ser Pro Thr Arg
            20                  25                  30

Cys

<210> SEQ ID NO 115
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
```

```
                              protecting group

<400> SEQUENCE: 115

Cys Arg Leu Arg Glu Tyr Tyr Asp Gln Thr Ala Gly Gly Ser Gly Gly
1               5                   10                  15

Met Cys Xaa Ser Lys Xaa Ser Pro Gly Gln His
            20                  25

<210> SEQ ID NO 116
<211> LENGTH: 15
<212> TYPE: PRT
<213> ORGANISM: Artificial Sequence
<220> FEATURE:
<223> OTHER INFORMATION: Synthetic Construct

<400> SEQUENCE: 116

Glu Gly Cys Arg Leu Cys Ala Pro Leu Arg Lys Cys Arg Pro Gly
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic Construct

<400> SEQUENCE: 117

Ala Phe Thr Pro Tyr Ala Pro Glu Pro Gly Ala Ala Cys Arg Leu
1               5                   10                  15

<210> SEQ ID NO 118
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 118

Cys Xaa Glu Asp Ser Thr Tyr Thr Gln Leu Trp Asn Trp Val Pro Glu
1               5                   10                  15

Cys Gln Thr Ala Gln Met Xaa Xaa Ser Lys Xaa Ser Pro Gly Gln His
            20                  25                  30

Cys

<210> SEQ ID NO 119
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 119

Glu Xaa Leu Ser Cys Gly Ser Arg Xaa Ser Ser Gly Gly Ser Gly Gly
1               5                   10                  15

Gln Ala Cys Thr Arg Glu Gln Asn Arg Ile Xaa
            20                  25

<210> SEQ ID NO 120
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (17)..(17)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 120

Pro Glu Xaa Leu Ser Xaa Gly Ser Arg Cys Ser Gly Gly Ser Gly Gly
1               5                   10                  15

Xaa Thr Arg Glu Gln Asn Arg Ile Cys Thr Xaa
            20                  25

<210> SEQ ID NO 121
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
```

```
<400> SEQUENCE: 121

Leu Cys Ala Pro Leu Arg Lys Xaa Arg Pro Gly Gly Gly Ser Gly Gly
1               5                   10                  15

Cys Lys Pro Xaa Ala Pro Gly Thr Phe Ser Asn
            20                  25

<210> SEQ ID NO 122
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group

<400> SEQUENCE: 122

Leu Trp Asn Trp Val Pro Glu Xaa Leu Ser Cys Gly Gly Ser Gly Gly
1               5                   10                  15

Glu Thr Gln Ala Cys Thr Arg Glu Gln Asn Arg
            20                  25

<210> SEQ ID NO 123
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 123

Asn Trp Val Pro Glu Xaa Leu Ser Cys Gly Ser Gly Gly Ser Gly Gly
1               5                   10                  15

Gln Ala Cys Thr Arg Glu Gln Asn Arg Ile Xaa
            20                  25

<210> SEQ ID NO 124
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 124

Arg Cys Ser Ser Asp Gln Val Glu Thr Gln Ala Gly Gly Ser Gly Gly
1               5                   10                  15

Glu Gln Asn Arg Ile Cys Thr Xaa Arg Pro Gly
            20                  25

<210> SEQ ID NO 125
```

```
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group

<400> SEQUENCE: 125

Tyr Xaa Ala Leu Ser Lys Gln Glu Gly Cys Arg Gly Gly Ser Gly Gly
1               5                   10                  15

Cys Arg Pro Gly Phe Gly Val Ala Arg Pro Gly
            20                  25

<210> SEQ ID NO 126
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 126

Leu Ser Lys Gln Glu Gly Cys Arg Leu Xaa Ala Gly Gly Ser Gly Gly
1               5                   10                  15

Leu Xaa Ala Pro Leu Arg Lys Cys Arg Pro Gly
            20                  25

<210> SEQ ID NO 127
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group

<400> SEQUENCE: 127

Trp Tyr Xaa Ala Leu Ser Lys Gln Glu Gly Cys Gly Gly Ser Gly Gly
1               5                   10                  15

Lys Cys Arg Pro Gly Phe Gly Val Ala Arg Pro
            20                  25

<210> SEQ ID NO 128
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
```

```
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 128

Cys Gly Xaa Arg Leu Xaa Ala Pro Leu Arg Lys Xaa Arg Pro Gly Phe
1               5                   10                  15

Cys Ala Phe Thr Pro Tyr Ala Pro Glu Pro Gly Ser Thr Xaa Arg Leu
            20                  25                  30

Cys

<210> SEQ ID NO 129
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 129

Xaa Leu Ser Cys Gly Ser Arg Xaa Ser Ser Asp Gly Gly Ser Gly Gly
1               5                   10                  15

Gln Ala Cys Thr Arg Glu Gln Asn Arg Ile Xaa
            20                  25

<210> SEQ ID NO 130
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 130

Cys Asp Gln Val Glu Thr Gln Ala Xaa Thr Arg Glu Gln Asn Arg Ile
1               5                   10                  15
```

```
Cys Asn Ala Ser Met Asp Ala Val Xaa Thr Ser Thr Ser Pro Thr Arg
             20                  25                  30

Cys

<210> SEQ ID NO 131
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 131

Ala Leu Ser Lys Gln Glu Gly Cys Arg Leu Xaa Gly Gly Ser Gly Gly
1               5                   10                  15

Leu Xaa Ala Pro Leu Arg Lys Cys Arg Pro Gly
             20                  25

<210> SEQ ID NO 132
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 132

Trp Asn Trp Val Pro Glu Xaa Leu Ser Cys Gly Gly Ser Gly Gly
1               5                   10                  15

Cys Thr Arg Glu Gln Asn Arg Ile Xaa Thr Xaa
             20                  25

<210> SEQ ID NO 133
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
```

<400> SEQUENCE: 133

Leu Ser Lys Gln Glu Gly Xaa Arg Leu Cys Ala Gly Gly Ser Gly Gly
1               5                   10                  15

Cys Lys Pro Xaa Ala Pro Gly Thr Phe Ser Asn
            20                  25

<210> SEQ ID NO 134
<211> LENGTH: 15
<212> TYPE: PRT
<213> ORGANISM: Artificial Sequence
<220> FEATURE:
<223> OTHER INFORMATION: Synthetic Construct

<400> SEQUENCE: 134

Cys Thr Arg Glu Gln Asn Arg Ile Cys Thr Ala Ala Pro Gly Trp
1               5                   10                  15

<210> SEQ ID NO 135
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 135

Tyr Xaa Ala Leu Ser Lys Gln Glu Gly Cys Arg Gly Gly Ser Gly Gly
1               5                   10                  15

Leu Xaa Ala Pro Leu Arg Lys Cys Arg Pro Gly
            20                  25

<210> SEQ ID NO 136
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (10)..(10)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group

<400> SEQUENCE: 136

Xaa Arg Leu Cys Ala Pro Leu Arg Lys Xaa Arg Gly Gly Ser Gly Gly
1               5                   10                  15

Cys Lys Pro Xaa Ala Pro Gly Thr Phe Ser Asn
            20                  25

<210> SEQ ID NO 137
<211> LENGTH: 15
<212> TYPE: PRT
<213> ORGANISM: Artificial Sequence
<220> FEATURE:
<223> OTHER INFORMATION: Synthetic Construct

<400> SEQUENCE: 137

Gln Asn Arg Ile Cys Thr Cys Arg Pro Gly Ala Ala Cys Ala Leu
1               5                   10                  15

<210> SEQ ID NO 138
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 138

Cys Gly Xaa Arg Leu Xaa Ala Pro Leu Arg Lys Xaa Arg Pro Gly Phe
1               5                   10                  15

Cys Gln Ala Xaa Thr Arg Glu Gln Asn Arg Ile Xaa Thr Xaa Arg Pro
                20                  25                  30

Cys

<210> SEQ ID NO 139
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group

<400> SEQUENCE: 139

Asp Val Val Xaa Lys Pro Cys Ala Pro Gly Thr Gly Gly Ser Gly Gly
1               5                   10                  15

```
Thr Thr Ser Ser Thr Asp Ile Cys Arg Pro His
            20                  25
```

<210> SEQ ID NO 140
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 140

```
Gln Asn Arg Ile Xaa Thr Cys Arg Pro Gly Trp Gly Gly Ser Gly Gly
1               5                   10                  15

Tyr Cys Ala Leu Ser Lys Gln Glu Gly Xaa Arg
            20                  25
```

<210> SEQ ID NO 141
<211> LENGTH: 15
<212> TYPE: PRT
<213> ORGANISM: Artificial Sequence
<220> FEATURE:
<223> OTHER INFORMATION: Synthetic Construct

<400> SEQUENCE: 141

```
Pro Ser Thr Ser Phe Leu Leu Pro Met Gly Ala Ala Pro Pro Ala
1               5                   10                  15
```

<210> SEQ ID NO 142
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group

<400> SEQUENCE: 142

```
Glu Gly Cys Arg Leu Xaa Ala Pro Leu Arg Lys Cys Arg Pro Gly Phe
1               5                   10                  15

Gly Val Ala Arg Pro Gly
            20
```

<210> SEQ ID NO 143
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (5)..(5)
<223> OTHER INFORMATION: Xaa is Cys residue protected with ACM

```
             protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 143

Glu Xaa Leu Ser Xaa Gly Ser Arg Cys Ser Ser Gly Gly Ser Gly Gly
1               5                   10                  15

Ala Xaa Thr Arg Glu Gln Asn Arg Ile Cys Thr
            20                  25

<210> SEQ ID NO 144
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 144

Glu Xaa Leu Ser Xaa Gly Ser Arg Cys Ser Ser Gly Gly Ser Gly Gly
1               5                   10                  15

Gln Asn Arg Ile Cys Thr Xaa Arg Pro Gly Trp
            20                  25

<210> SEQ ID NO 145
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 145

Leu Ser Xaa Gly Ser Arg Cys Ser Ser Asp Gln Gly Gly Ser Gly Gly
1               5                   10                  15

Gln Ala Xaa Thr Arg Glu Gln Asn Arg Ile Cys
            20                  25

<210> SEQ ID NO 146
<211> LENGTH: 27
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
      protecting group

<400> SEQUENCE: 146

Gly Ser Thr Cys Arg Leu Arg Glu Tyr Tyr Asp Gly Gly Ser Gly Gly
1               5                   10                  15

Met Cys Xaa Ser Lys Xaa Ser Pro Gly Gln His
            20                  25

<210> SEQ ID NO 147
<211> LENGTH: 15
<212> TYPE: PRT
<213> ORGANISM: Artificial Sequence
<220> FEATURE:
<223> OTHER INFORMATION: Synthetic Construct

<400> SEQUENCE: 147

Ala Pro Ser Thr Ser Phe Leu Leu Pro Met Gly Pro Ser Pro Pro
1               5                   10                  15

<210> SEQ ID NO 148
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group

<400> SEQUENCE: 148

Asn Trp Val Pro Glu Xaa Leu Ser Cys Gly Ser Gly Gly Ser Gly Gly
1               5                   10                  15

Thr Gln Ala Cys Thr Arg Glu Gln Asn Arg Ile
            20                  25

<210> SEQ ID NO 149
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 149

Asn Arg Ile Xaa Thr Cys Arg Pro Gly Trp Tyr Gly Gly Ser Gly Gly
1               5                   10                  15

Tyr Cys Ala Leu Ser Lys Gln Glu Gly Xaa Arg
            20                  25
```

```
<210> SEQ ID NO 150
<211> LENGTH: 27
<212> TYPE: PRT
<213> ORGANISM: Artificial Sequence
<220> FEATURE:
<223> OTHER INFORMATION: Synthetic Construct

<400> SEQUENCE: 150

Lys Pro Cys Ala Pro Gly Thr Phe Ser Asn Thr Gly Gly Ser Gly Gly
1               5                   10                  15

Thr Ser Ser Thr Asp Ile Cys Arg Pro His Gln
            20                  25

<210> SEQ ID NO 151
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 151

Cys Ala Pro Leu Arg Lys Xaa Arg Pro Gly Phe Gly Val Ala Arg Pro
1               5                   10                  15

Cys Ala Phe Thr Pro Tyr Ala Pro Glu Pro Gly Ser Thr Xaa Arg Leu
            20                  25                  30

Cys

<210> SEQ ID NO 152
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
      protecting group

<400> SEQUENCE: 152

Thr Pro Tyr Ala Pro Glu Pro Gly Ser Thr Cys Gly Gly Ser Gly Gly
1               5                   10                  15

Met Cys Xaa Ser Lys Xaa Ser Pro Gly Gln His
            20                  25

<210> SEQ ID NO 153
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 153

Leu Ser Cys Gly Ser Arg Xaa Ser Ser Asp Gln Gly Gly Ser Gly Gly
1               5                   10                  15

Cys Thr Arg Glu Gln Asn Arg Ile Xaa Thr Xaa
            20                  25

<210> SEQ ID NO 154
<211> LENGTH: 15
<212> TYPE: PRT
<213> ORGANISM: Artificial Sequence
<220> FEATURE:
<223> OTHER INFORMATION: Synthetic Construct

<400> SEQUENCE: 154

Thr Ala Pro Ser Thr Ser Phe Leu Leu Pro Met Gly Pro Ser Pro
1               5                   10                  15

<210> SEQ ID NO 155
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 155

Glu Xaa Leu Ser Cys Gly Ser Arg Xaa Ser Ser Gly Gly Ser Gly Gly
1               5                   10                  15

Ala Cys Thr Arg Glu Gln Asn Arg Ile Xaa Thr
            20                  25

<210> SEQ ID NO 156
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
```

```
<221> NAME/KEY: MISC_FEATURE
<222> LOCATION: (26)..(26)
<223> OTHER INFORMATION: Xaa is Cys residue protected with ACM
      protecting group

<400> SEQUENCE: 156

Cys Ser Ser Asp Gln Val Glu Thr Gln Ala Xaa Gly Gly Ser Gly Gly
1               5                   10                  15

Thr Arg Glu Gln Asn Arg Ile Cys Thr Xaa Arg
            20                  25

<210> SEQ ID NO 157
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 157

Pro Glu Xaa Leu Ser Xaa Gly Ser Arg Cys Ser Gly Gly Ser Gly Gly
1               5                   10                  15

Gln Ala Xaa Thr Arg Glu Gln Asn Arg Ile Cys
            20                  25

<210> SEQ ID NO 158
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 158

Xaa Gly Ser Arg Cys Ser Ser Asp Gln Val Glu Gly Gly Ser Gly Gly
1               5                   10                  15

Gln Asn Arg Ile Cys Thr Xaa Arg Pro Gly Trp
            20                  25

<210> SEQ ID NO 159
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 159

Ser Lys Gln Glu Gly Cys Arg Leu Xaa Ala Pro Gly Gly Ser Gly Gly
1               5                   10                  15

Leu Xaa Ala Pro Leu Arg Lys Cys Arg Pro Gly
            20                  25

<210> SEQ ID NO 160
<211> LENGTH: 27
<212> TYPE: PRT
<213> ORGANISM: Artificial Sequence
<220> FEATURE:
<223> OTHER INFORMATION: Synthetic Construct

<400> SEQUENCE: 160

Cys Ala Pro Gly Thr Phe Ser Asn Thr Thr Ser Gly Gly Ser Gly Gly
1               5                   10                  15

Thr Thr Ser Ser Thr Asp Ile Cys Arg Pro His
            20                  25

<210> SEQ ID NO 161
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 161

Xaa Gly Ser Arg Cys Ser Ser Asp Gln Val Glu Gly Gly Ser Gly Gly
1               5                   10                  15

Thr Arg Glu Gln Asn Arg Ile Cys Thr Xaa Arg
            20                  25

<210> SEQ ID NO 162
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 162
```

```
Cys Ala Pro Leu Arg Lys Xaa Arg Pro Gly Phe Gly Val Ala Arg Pro
1               5                   10                  15

Cys Ala Pro Leu Arg Lys Xaa Arg Pro Gly Phe Gly Val Ala Arg Pro
            20                  25                  30

Cys

<210> SEQ ID NO 163
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 163

Val Pro Glu Xaa Leu Ser Xaa Gly Ser Arg Cys Gly Gly Ser Gly Gly
1               5                   10                  15

Gln Asn Arg Ile Cys Thr Xaa Arg Pro Gly Trp
            20                  25

<210> SEQ ID NO 164
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group

<400> SEQUENCE: 164

Val Xaa Lys Pro Cys Ala Pro Gly Thr Phe Ser Gly Gly Ser Gly Gly
1               5                   10                  15

Thr Thr Ser Ser Thr Asp Ile Cys Arg Pro His
            20                  25

<210> SEQ ID NO 165
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group

<400> SEQUENCE: 165

Trp Asn Trp Val Pro Glu Xaa Leu Ser Cys Gly Gly Gly Ser Gly Gly
1               5                   10                  15

Glu Thr Gln Ala Cys Thr Arg Glu Gln Asn Arg
            20                  25
```

20                  25

<210> SEQ ID NO 166
<211> LENGTH: 15
<212> TYPE: PRT
<213> ORGANISM: Artificial Sequence
<220> FEATURE:
<223> OTHER INFORMATION: Synthetic Construct

<400> SEQUENCE: 166

Asp Gln Val Glu Thr Gln Ala Cys Thr Arg Glu Gln Asn Arg Ile
1               5                   10                  15

<210> SEQ ID NO 167
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 167

Cys Ala Pro Leu Arg Lys Xaa Arg Pro Gly Phe Gly Val Ala Arg Pro
1               5                   10                  15

Cys Gln Ala Xaa Thr Arg Glu Gln Asn Arg Ile Xaa Thr Xaa Arg Pro
            20                  25                  30

Cys

<210> SEQ ID NO 168
<211> LENGTH: 15
<212> TYPE: PRT
<213> ORGANISM: Artificial Sequence
<220> FEATURE:
<223> OTHER INFORMATION: Synthetic Construct

<400> SEQUENCE: 168

Asn Trp Val Pro Glu Cys Leu Ser Cys Gly Ser Arg Cys Ser Ser
1               5                   10                  15

<210> SEQ ID NO 169
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:

```
<221> NAME/KEY: MISC_FEATURE
<222> LOCATION: (26)..(26)
<223> OTHER INFORMATION: Xaa is Cys residue protected with ACM
      protecting group

<400> SEQUENCE: 169

Leu Ser Xaa Gly Ser Arg Cys Ser Ser Asp Gln Gly Gly Ser Gly Gly
1               5                   10                  15

Thr Arg Glu Gln Asn Arg Ile Cys Thr Xaa Arg
            20                  25

<210> SEQ ID NO 170
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 170

Cys Gly Xaa Arg Leu Xaa Ala Pro Leu Arg Lys Xaa Arg Pro Gly Phe
1               5                   10                  15

Cys Gln Ala Xaa Thr Arg Glu Gln Asn Arg Ile Xaa Thr Xaa Arg Pro
            20                  25                  30

Cys

<210> SEQ ID NO 171
<211> LENGTH: 15
<212> TYPE: PRT
<213> ORGANISM: Artificial Sequence
<220> FEATURE:
<223> OTHER INFORMATION: Synthetic Construct

<400> SEQUENCE: 171

Ser Asn Thr Thr Ser Ser Thr Asp Ile Cys Arg Pro His Gln Ile
1               5                   10                  15

<210> SEQ ID NO 172
<211> LENGTH: 15
<212> TYPE: PRT
<213> ORGANISM: Artificial Sequence
```

```
<220> FEATURE:
<223> OTHER INFORMATION: Synthetic Construct

<400> SEQUENCE: 172

Glu Gly Cys Arg Leu Cys Ala Pro Leu Arg Ala Ala Arg Pro Gly
1               5                   10                  15

<210> SEQ ID NO 173
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 173

Cys Ala Pro Glu Pro Gly Ser Thr Xaa Arg Leu Arg Glu Tyr Tyr Asp
1               5                   10                  15

Cys Asn Ala Ser Met Asp Ala Val Xaa Thr Ser Thr Ser Pro Thr Arg
            20                  25                  30

Cys

<210> SEQ ID NO 174
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 174

Arg Glu Gln Asn Arg Ile Xaa Thr Cys Arg Pro Gly Gly Ser Gly Gly
1               5                   10                  15

Tyr Cys Ala Leu Ser Lys Gln Glu Gly Xaa Arg
            20                  25

<210> SEQ ID NO 175
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM
      protecting group
```

```
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 175

Cys Ser Arg Xaa Ser Ser Asp Gln Val Glu Thr Gln Ala Xaa Thr Arg
1               5                   10                  15

Cys Ala Pro Leu Arg Lys Xaa Arg Pro Gly Phe Gly Val Ala Arg Pro
            20                  25                  30

Cys

<210> SEQ ID NO 176
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group

<400> SEQUENCE: 176

Val Val Xaa Lys Pro Cys Ala Pro Gly Thr Phe Gly Gly Ser Gly Gly
1               5                   10                  15

Thr Ser Ser Thr Asp Ile Cys Arg Pro His Gln
            20                  25

<210> SEQ ID NO 177
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group

<400> SEQUENCE: 177

Xaa Lys Pro Cys Ala Pro Gly Thr Phe Ser Asn Thr Thr Ser Ser Thr
1               5                   10                  15

Asp Ile Cys Arg Pro His
            20

<210> SEQ ID NO 178
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group

<400> SEQUENCE: 178

Thr Glu Thr Ser Asp Val Val Xaa Lys Pro Cys Gly Gly Ser Gly Gly
1               5                   10                  15

Thr Thr Ser Ser Thr Asp Ile Cys Arg Pro His
            20                  25
```

<210> SEQ ID NO 179
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 179

Arg Cys Ser Ser Asp Gln Val Glu Thr Gln Ala Gly Gly Ser Gly Gly
1               5                   10                  15

Gln Ala Xaa Thr Arg Glu Gln Asn Arg Ile Cys
            20                  25

<210> SEQ ID NO 180
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 180

Cys Ser Ser Asp Gln Val Glu Thr Gln Ala Xaa Gly Gly Ser Gly Gly
1               5                   10                  15

Gln Ala Xaa Thr Arg Glu Gln Asn Arg Ile Cys
            20                  25

<210> SEQ ID NO 181
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (17)..(17)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 181

Val Pro Glu Xaa Leu Ser Xaa Gly Ser Arg Cys Gly Gly Ser Gly Gly
1               5                   10                  15

```
Xaa Thr Arg Glu Gln Asn Arg Ile Cys Thr Xaa
            20                  25

<210> SEQ ID NO 182
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 182

Thr Arg Glu Gln Asn Arg Ile Xaa Thr Cys Arg Gly Gly Ser Gly Gly
1               5                   10                  15

Cys Ala Leu Ser Lys Gln Glu Gly Xaa Arg Leu
            20                  25

<210> SEQ ID NO 183
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 183

Thr Arg Glu Gln Asn Arg Ile Xaa Thr Cys Arg Gly Gly Ser Gly Gly
1               5                   10                  15

Tyr Cys Ala Leu Ser Lys Gln Glu Gly Xaa Arg
            20                  25

<210> SEQ ID NO 184
<211> LENGTH: 15
<212> TYPE: PRT
<213> ORGANISM: Artificial Sequence
<220> FEATURE:
<223> OTHER INFORMATION: Synthetic Construct

<400> SEQUENCE: 184

Val Cys Thr Ser Thr Ser Pro Thr Arg Ser Ala Gly Pro Gly Ala
1               5                   10                  15

<210> SEQ ID NO 185
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
```

```
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 185

Cys Gln Ala Xaa Thr Arg Glu Gln Asn Arg Ile Xaa Thr Xaa Arg Pro
1               5                   10                  15

Cys Ala Pro Leu Arg Lys Xaa Arg Pro Gly Phe Gly Val Ala Arg Pro
                20                  25                  30

Cys

<210> SEQ ID NO 186
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group

<400> SEQUENCE: 186

Ser Asp Val Val Xaa Lys Pro Cys Ala Pro Gly Gly Ser Gly Gly
1               5                   10                  15

Thr Thr Ser Ser Thr Asp Ile Cys Arg Pro His
                20                  25

<210> SEQ ID NO 187
<211> LENGTH: 17
<212> TYPE: PRT
<213> ORGANISM: Artificial Sequence
<220> FEATURE:
<223> OTHER INFORMATION: Synthetic Construct

<400> SEQUENCE: 187

Cys Ala Ala Thr Arg Glu Gln Asn Arg Ile Ala Ala Gly Arg Pro Gly
1               5                   10                  15

Cys

<210> SEQ ID NO 188
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (22)..(22)
```

```
<223> OTHER INFORMATION: Xaa is Cys residue protected with ACM
      protecting group
<220> FEATURE:
<221> NAME/KEY: misc_feature
<222> LOCATION: (23)..(23)
<223> OTHER INFORMATION: Xaa can be any naturally occurring amino acid

<400> SEQUENCE: 188

Cys Asp Gln Val Glu Thr Gln Ala Xaa Thr Arg Glu Gln Asn Arg Ile
1               5                   10                  15

Cys Ala Pro Leu Arg Lys Xaa Arg Pro Gly Phe Gly Val Ala Arg Pro
            20                  25                  30

Cys

<210> SEQ ID NO 189
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 189

Ser Arg Cys Ser Ser Asp Gln Val Glu Thr Gln Gly Gly Ser Gly Gly
1               5                   10                  15

Thr Arg Glu Gln Asn Arg Ile Cys Thr Xaa Arg
            20                  25

<210> SEQ ID NO 190
<211> LENGTH: 15
<212> TYPE: PRT
<213> ORGANISM: Artificial Sequence
<220> FEATURE:
<223> OTHER INFORMATION: Synthetic Construct

<400> SEQUENCE: 190

Ser Thr Ala Pro Ser Thr Ser Phe Leu Leu Pro Met Gly Pro Ser
1               5                   10                  15

<210> SEQ ID NO 191
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 191

Leu Ser Xaa Gly Ser Arg Cys Ser Ser Asp Gln Gly Gly Ser Gly Gly
1               5                   10                  15

Ala Xaa Thr Arg Glu Gln Asn Arg Ile Cys Thr
            20                  25

<210> SEQ ID NO 192
```

```
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 192

Cys Leu Ser Lys Gln Glu Gly Xaa Arg Leu Xaa Ala Pro Leu Arg Lys
 1               5                  10                  15

Cys Ala Phe Thr Pro Tyr Ala Pro Glu Pro Gly Ser Thr Xaa Arg Leu
                20                  25                  30

Cys

<210> SEQ ID NO 193
<211> LENGTH: 24
<212> TYPE: PRT
<213> ORGANISM: Artificial Sequence
<220> FEATURE:
<223> OTHER INFORMATION: Synthetic Construct

<400> SEQUENCE: 193

Cys Asn Trp Val Pro Glu Ala Leu Ser Ala Gly Pro Gly Ala Ser Ser
 1               5                  10                  15

Asp Gln Val Glu Thr Gln Ala Cys
                20

<210> SEQ ID NO 194
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group

<400> SEQUENCE: 194

Glu Thr Ser Asp Val Val Xaa Lys Pro Cys Ala Gly Gly Ser Gly Gly
 1               5                  10                  15

Thr Thr Ser Ser Thr Asp Ile Cys Arg Pro His
                20                  25

<210> SEQ ID NO 195
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
``` protecting group

<400> SEQUENCE: 195

Val Xaa Lys Pro Cys Ala Pro Gly Thr Phe Ser Gly Gly Ser Gly Gly
1               5                   10                  15

Thr Ser Ser Thr Asp Ile Cys Arg Pro His Gln
            20                  25

<210> SEQ ID NO 196
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 196

Cys Val Ala Ile Pro Gly Asn Ala Ser Met Asp Ala Val Xaa Thr Ser
1               5                   10                  15

Cys Ala Pro Leu Arg Lys Xaa Arg Pro Gly Phe Gly Val Ala Arg Pro
            20                  25                  30

Cys

<210> SEQ ID NO 197
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group

<400> SEQUENCE: 197

Ser Asp Val Val Xaa Lys Pro Cys Ala Pro Gly Gly Gly Ser Gly Gly
1               5                   10                  15

Thr Ser Ser Thr Asp Ile Cys Arg Pro His Gln
            20                  25

<210> SEQ ID NO 198
<211> LENGTH: 27
<212> TYPE: PRT
<213> ORGANISM: Artificial Sequence
<220> FEATURE:
<223> OTHER INFORMATION: Synthetic Construct

<400> SEQUENCE: 198

Gln Ile Cys Asn Val Val Ala Ile Pro Gly Asn Gly Gly Ser Gly Gly
1               5                   10                  15

Cys Thr Ser Thr Ser Pro Thr Arg Ser Met Ala
            20                  25

<210> SEQ ID NO 199
<211> LENGTH: 15
<212> TYPE: PRT

```
<213> ORGANISM: Artificial Sequence
<220> FEATURE:
<223> OTHER INFORMATION: Synthetic Construct

<400> SEQUENCE: 199

Asp Ile Cys Arg Pro His Gln Ile Cys Asn Val Val Ala Ile Pro
1               5                   10                  15

<210> SEQ ID NO 200
<211> LENGTH: 17
<212> TYPE: PRT
<213> ORGANISM: Artificial Sequence
<220> FEATURE:
<223> OTHER INFORMATION: Synthetic Construct

<400> SEQUENCE: 200

Cys Leu Trp Asn Trp Val Pro Glu Ala Leu Ser Ala Gly Ser Arg Ala
1               5                   10                  15

Cys

<210> SEQ ID NO 201
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 201

Cys Ala Pro Glu Pro Gly Ser Thr Xaa Arg Leu Arg Glu Tyr Tyr Asp
1               5                   10                  15

Cys Ala Pro Leu Arg Lys Xaa Arg Pro Gly Phe Gly Val Ala Arg Pro
            20                  25                  30

Cys

<210> SEQ ID NO 202
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group
<220> FEATURE:
<221> NAME/KEY: MISC_FEATURE
<222> LOCATION: (22)..(22)
<223> OTHER INFORMATION: Xaa is Cys residue protected with ACM
      protecting group

<400> SEQUENCE: 202

Ser Thr Cys Arg Leu Arg Glu Tyr Tyr Asp Gln Gly Gly Ser Gly Gly
1               5                   10                  15

Met Cys Xaa Ser Lys Xaa Ser Pro Gly Gln His
            20                  25
```

```
<210> SEQ ID NO 203
<211> LENGTH: 27
<212> TYPE: PRT
<213> ORGANISM: Artificial Sequence
<220> FE

```
<210> SEQ ID NO 206
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 206

Ser Cys Gly Ser Arg Xaa Ser Ser Asp Gln Val Gly Gly Ser Gly Gly
1               5                   10                  15

Gln Ala Cys Thr Arg Glu Gln Asn Arg Ile Xaa
            20                  25

<210> SEQ ID NO 207
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 207

Ser Arg Cys Ser Ser Asp Gln Val Glu Thr Gln Gly Gly Ser Gly Gly
1               5                   10                  15

Gln Ala Xaa Thr Arg Glu Gln Asn Arg Ile Cys
            20                  25

<210> SEQ ID NO 208
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 208

Cys Thr Ser Pro Thr Arg Ser Met Ala Pro Gly Ala Val His Leu Pro
1               5                   10                  15

Cys Ala Pro Leu Arg Lys Xaa Arg Pro Gly Phe Gly Val Ala Arg Pro
            20                  25                  30

Cys

<210> SEQ ID NO 209
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 209

Ser Xaa Gly Ser Arg Cys Ser Ser Asp Gln Val Gly Gly Ser Gly Gly
1               5                   10                  15

Gln Ala Xaa Thr Arg Glu Gln Asn Arg Ile Cys
            20                  25

<210> SEQ ID NO 210
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 210

Lys Gln Glu Gly Cys Arg Leu Xaa Ala Pro Leu Gly Gly Ser Gly Gly
1               5                   10                  15

Leu Xaa Ala Pro Leu Arg Lys Cys Arg Pro Gly
            20                  25

<210> SEQ ID NO 211
<211> LENGTH: 17
<212> TYPE: PRT
<213> ORGANISM: Artificial Sequence
<220> FEATURE:
<223> OTHER INFORMATION: Synthetic Construct

<400> SEQUENCE: 211

Cys Ala Ala Thr Arg Glu Gln Asn Arg Ile Ala Thr Ala Arg Pro Gly
1               5                   10                  15

Cys

<210> SEQ ID NO 212
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
```

```
                        protecting group
<220> FEATURE:
<221> NAME/KEY: MISC_FEATURE
<222> LOCATION: (16)..(16)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 212

Cys Xaa Xaa Ser Lys Xaa Ser Pro Gly Gln His Ala Lys Val Phe Xaa
1               5                   10                  15

Cys Ala Pro Leu Arg Lys Xaa Arg Pro Gly Phe Gly Val Ala Arg Pro
            20                  25                  30

Cys

<210> SEQ ID NO 213
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 213

Cys Asp Val Val Xaa Lys Pro Xaa Ala Pro Gly Thr Phe Ser Asn Thr
1               5                   10                  15

Cys Asn Ala Ser Met Asp Ala Val Xaa Thr Ser Thr Ser Pro Thr Arg
            20                  25                  30

Cys

<210> SEQ ID NO 214
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 214
```

```
Xaa Leu Ser Xaa Gly Ser Arg Cys Ser Ser Asp Gly Gly Ser Gly Gly
1               5                   10                  15

Ala Xaa Thr Arg Glu Gln Asn Arg Ile Cys Thr
            20                  25

<210> SEQ ID NO 215
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (9)..(9)
<223> OTHER INFORMATION: Xaa is Cys residue protected with ACM
      protecting group

<400> SEQUENCE: 215

Glu Xaa Leu Ser Cys Gly Ser Arg Xaa Ser Ser Gly Gly Ser Gly Gly
1               5                   10                  15

Thr Gln Ala Cys Thr Arg Glu Gln Asn Arg Ile
            20                  25

<210> SEQ ID NO 216
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (15)..(15)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 216

Cys Tyr Thr Gln Leu Trp Asn Trp Val Pro Glu Xaa Leu Ser Xaa Gly
1               5                   10                  15

Cys Asn Ala Ser Met Asp Ala Val Xaa Thr Ser Thr Ser Pro Thr Arg
            20                  25                  30

Cys

<210> SEQ ID NO 217
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
```

```
<221> NAME/KEY: MISC_FEATURE
<222> LOCATION: (17)..(17)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 217

Leu Ser Xaa Gly Ser Arg Cys Ser Ser Asp Gln Gly Gly Ser Gly Gly
1               5                   10                  15

Xaa Thr Arg Glu Gln Asn Arg Ile Cys Thr Xaa
            20                  25

<210> SEQ ID NO 218
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 218

Cys Xaa Leu Ser Xaa Gly Ser Arg Xaa Ser Ser Asp Gln Val Glu Thr
1               5                   10                  15

Cys Ala Pro Leu Arg Lys Xaa Arg Pro Gly Phe Gly Val Ala Arg Pro
            20                  25                  30

Cys

<210> SEQ ID NO 219
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group

<400> SEQUENCE: 219

Trp Val Pro Glu Xaa Leu Ser Cys Gly Ser Arg Gly Gly Ser Gly Gly
1               5                   10                  15

Thr Gln Ala Cys Thr Arg Glu Gln Asn Arg Ile
            20                  25

<210> SEQ ID NO 220
```

```
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 220

Xaa Thr Arg Glu Gln Asn Arg Ile Xaa Thr Cys Gly Gly Ser Gly Gly
1               5                   10                  15

Cys Ala Leu Ser Lys Gln Glu Gly Xaa Arg Leu
            20                  25

<210> SEQ ID NO 221
<211> LENGTH: 15
<212> TYPE: PRT
<213> ORGANISM: Artificial Sequence
<220> FEATURE:
<223> OTHER INFORMATION: Synthetic Construct

<400> SEQUENCE: 221

Ser Asp Gln Val Glu Thr Gln Ala Cys Thr Arg Glu Gln Asn Arg
1               5                   10                  15

<210> SEQ ID NO 222
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (19)..(19)
<223> OTHER INFORMATION: Xaa is Cys residue protected with ACM
      protecting group

<400> SEQUENCE: 222

Xaa Gly Ser Arg Cys Ser Ser Asp Gln Val Glu Gly Gly Ser Gly Gly
1               5                   10                  15

Gln Ala Xaa Thr Arg Glu Gln Asn Arg Ile Cys
            20                  25

<210> SEQ ID NO 223
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
```

```
            protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 223

Asn Arg Ile Xaa Thr Cys Arg Pro Gly Trp Tyr Gly Gly Ser Gly Gly
1               5                   10                  15

Cys Ala Leu Ser Lys Gln Glu Gly Xaa Arg Leu
            20                  25

<210> SEQ ID NO 224
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (29)..(29)
<223> OTHER INFORMATION: Xaa is Cys residue protected with ACM
      protecting group
<220> FEATURE:
<221> NAME/KEY: MISC_FEATURE
<222> LOCATION: (32)..(32)
<223> OTHER INFORMATION: Xaa is Cys residue protected with ACM
      protecting group

<400> SEQUENCE: 224

Cys Gly Xaa Arg Leu Xaa Ala Pro Leu Arg Lys Xaa Arg Pro Gly Phe
1               5                   10                  15

Cys Arg Glu Tyr Tyr Asp Gln Thr Ala Gln Met Xaa Xaa Ser Lys Xaa
            20                  25                  30

Cys

<210> SEQ ID NO 225
<211> LENGTH: 15
<212> TYPE: PRT
<213> ORGANISM: Artificial Sequence
<220> FEATURE:
<223> OTHER INFORMATION: Synthetic Construct

<400> SEQUENCE: 225

Gly Thr Phe Ser Asn Thr Thr Ser Ser Thr Ala Ala Cys Arg Pro
1               5                   10                  15

<210> SEQ ID NO 226
<211> LENGTH: 33
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 226

Cys Thr Val Xaa Asp Ser Xaa Glu Asp Ser Thr Tyr Thr Gln Leu Trp
1               5                   10                  15

Cys Asn Ala Ser Met Asp Ala Val Xaa Thr Ser Thr Ser Pro Thr Arg
            20                  25                  30

Cys

<210> SEQ ID NO 227
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 227

Pro Gly Ser Thr Cys Arg Leu Arg Glu Tyr Tyr Gly Gly Ser Gly Gly
1               5                   10                  15

Gln Met Cys Xaa Ser Lys Xaa Ser Pro Gly Gln
            20                  25

<210> SEQ ID NO 228
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group

<400> SEQUENCE: 228

Trp Val Pro Glu Xaa Leu Ser Cys Gly Ser Arg Gly Gly Ser Gly Gly
1               5                   10                  15

Glu Thr Gln Ala Cys Thr Arg Glu Gln Asn Arg
            20                  25

<210> SEQ ID NO 229
```

```
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group

<400> SEQUENCE: 229

Leu Ser Cys Gly Ser Arg Xaa Ser Ser Asp Gln Gly Gly Ser Gly Gly
1               5                   10                  15

Thr Gln Ala Cys Thr Arg Glu Gln Asn Arg Ile
            20                  25

<210> SEQ ID NO 230
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (17)..(17)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 230

Glu Xaa Leu Ser Xaa Gly Ser Arg Cys Ser Ser Gly Gly Ser Gly Gly
1               5                   10                  15

Xaa Thr Arg Glu Gln Asn Arg Ile Cys Thr Xaa
            20                  25

<210> SEQ ID NO 231
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 231
```

```
Xaa Leu Ser Xaa Gly Ser Arg Cys Ser Ser Asp Gly Gly Ser Gly Gly
1               5                   10                  15

Thr Arg Glu Gln Asn Arg Ile Cys Thr Xaa Arg
            20                  25

<210> SEQ ID NO 232
<211> LENGTH: 15
<212> TYPE: PRT
<213> ORGANISM: Artificial Sequence
<220> FEATURE:
<223> OTHER INFORMATION: Synthetic Construct

<400> SEQUENCE: 232

Pro Tyr Ala Pro Glu Pro Gly Ser Thr Cys Arg Leu Arg Glu Tyr
1               5                   10                  15

<210> SEQ ID NO 233
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (16)..(16)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 233

Cys Xaa Xaa Ser Lys Xaa Ser Pro Gly Gln His Ala Lys Val Phe Xaa
1               5                   10                  15

Cys Asn Ala Ser Met Asp Ala Val Xaa Thr Ser Thr Ser Pro Thr Arg
            20                  25                  30

Cys

<210> SEQ ID NO 234
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM
```

```
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 234

Cys Thr Ser Ser Thr Asp Ile Xaa Arg Pro His Gln Ile Xaa Asn Val
1               5                   10                  15

Cys Asn Ala Ser Met Asp Ala Val Xaa Thr Ser Thr Ser Pro Thr Arg
            20                  25                  30

Cys

<210> SEQ ID NO 235
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (16)..(16)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group

<400> SEQUENCE: 235

Cys Xaa Xaa Ser Lys Xaa Ser Pro Gly Gln His Ala Lys Val Phe Xaa
1               5                   10                  15

Cys Ala Val Xaa Thr Ser Thr Ser Pro Thr Arg Ser Met Ala Pro Gly
            20                  25                  30

Cys

<210> SEQ ID NO 236
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (10)..(10)
<223> OTHER INFORMATION: Xaa is Cys residue protected with ACM
      protecting group

<400> SEQUENCE: 236
```

```
Pro Glu Xaa Leu Ser Cys Gly Ser Arg Xaa Ser Gly Gly Ser Gly Gly
1               5                   10                  15

Thr Gln Ala Cys Thr Arg Glu Gln Asn Arg Ile
            20                  25

<210> SEQ ID NO 237
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 237

Gly Ser Arg Cys Ser Ser Asp Gln Val Glu Thr Gly Ser Gly Gly
1               5                   10                  15

Thr Arg Glu Gln Asn Arg Ile Cys Thr Xaa Arg
            20                  25

<210> SEQ ID NO 238
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group

<400> SEQUENCE: 238

Lys Gln Glu Gly Xaa Arg Leu Cys Ala Pro Leu Gly Gly Ser Gly Gly
1               5                   10                  15

Cys Lys Pro Xaa Ala Pro Gly Thr Phe Ser Asn
            20                  25

<210> SEQ ID NO 239
<211> LENGTH: 27
<212> TYPE: PRT
<213> ORGANISM: Artificial Sequence
<220> FEATURE:
<223> OTHER INFORMATION: Synthetic Construct

<400> SEQUENCE: 239

Pro His Gln Ile Cys Asn Val Val Ala Ile Pro Gly Gly Ser Gly Gly
1               5                   10                  15

Cys Thr Ser Thr Ser Pro Thr Arg Ser Met Ala
            20                  25

<210> SEQ ID NO 240
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (23)..(23)
<223> OTHER INFORMATION: Xaa is Cys residue protected with ACM
      protecting group

<400> SEQUENCE: 240

Cys Leu Pro Met Gly Pro Ser Pro Pro Ala Glu Gly Ser Thr Gly Asp
1               5                   10                  15

Cys Ala Pro Leu Arg Lys Xaa Arg Pro Gly Phe Gly Val Ala Arg Pro
            20                  25                  30

Cys

<210> SEQ ID NO 241
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 241

Xaa Leu Ser Cys Gly Ser Arg Xaa Ser Ser Asp Gly Gly Ser Gly Gly
1               5                   10                  15

Cys Thr Arg Glu Gln Asn Arg Ile Xaa Thr Xaa
            20                  25

<210> SEQ ID NO 242
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group

<400> SEQUENCE: 242

Xaa Lys Pro Cys Ala Pro Gly Thr Phe Ser Asn Gly Gly Ser Gly Gly
1               5                   10                  15

Thr Thr Ser Ser Thr Asp Ile Cys Arg Pro His
            20                  25

<210> SEQ ID NO 243
<211> LENGTH: 33
<212> TYPE: PRT
<213> ORGANISM: Artificial Sequence
<220> FEATURE:
<223> OTHER INFORMATION: Synthetic Construct
<220> FEATURE:
```

<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 243

Cys Gln Thr Ala Gln Met Xaa Xaa Ser Lys Xaa Ser Pro Gly Gln His
1               5                   10                  15

Cys Ala Phe Thr Pro Tyr Ala Pro Glu Pro Gly Ser Thr Xaa Arg Leu
            20                  25                  30

Cys

<210> SEQ ID NO 244
<211> LENGTH: 15
<212> TYPE: PRT
<213> ORGANISM: Artificial Sequence
<220> FEATURE:
<223> OTHER INFORMATION: Synthetic Construct

<400> SEQUENCE: 244

Thr Ser Ser Thr Asp Ile Cys Arg Pro His Gln Ile Cys Asn Val
1               5                   10                  15

<210> SEQ ID NO 245
<211> LENGTH: 17
<212> TYPE: PRT
<213> ORGANISM: Artificial Sequence
<220> FEATURE:
<223> OTHER INFORMATION: Synthetic Construct

<400> SEQUENCE: 245

Cys Glu Gly Ala Arg Leu Ala Ala Pro Leu Arg Ala Gly Arg Pro Gly
1               5                   10                  15

Cys

<210> SEQ ID NO 246
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM

```
        protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 246

Cys Gln Ala Xaa Thr Arg Glu Gln Asn Arg Ile Xaa Thr Xaa Arg Pro
1               5                   10                  15

Cys Ala Phe Thr Pro Tyr Ala Pro Glu Pro Gly Ser Thr Xaa Arg Leu
            20                  25                  30

Cys

<210> SEQ ID NO 247
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 247

Ser Xaa Gly Ser Arg Cys Ser Ser Asp Gln Val Gly Gly Ser Gly Gly
1               5                   10                  15

Gln Asn Arg Ile Cys Thr Xaa Arg Pro Gly Trp
            20                  25

<210> SEQ ID NO 248
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 248

Val Xaa Lys Pro Cys Ala Pro Gly Thr Phe Ser Gly Ser Gly Gly
1               5                   10                  15

Asp Ile Cys Arg Pro His Gln Ile Xaa Asn Val
            20                  25

<210> SEQ ID NO 249
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
```

<223> OTHER INFORMATION: Xaa is Cys residue protected with ACM
     protecting group
<220> FEATURE:
<221> NAME/KEY: MISC_FEATURE
<222> LOCATION: (8)..(8)
<223> OTHER INFORMATION: Xaa is Cys residue protected with ACM
     protecting group
<220> FEATURE:
<221> NAME/KEY: MISC_FEATURE
<222> LOCATION: (26)..(26)
<223> OTHER INFORMATION: Xaa is Cys residue protected with ACM
     protecting group

<400> SEQUENCE: 249

Xaa Leu Ser Cys Gly Ser Arg Xaa Ser Ser Asp Gly Gly Ser Gly Gly
1               5                   10                  15

Ala Cys Thr Arg Glu Gln Asn Arg Ile Xaa Thr
            20                  25

<210> SEQ ID NO 250
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (19)..(19)
<223> OTHER INFORMATION: Xaa is Cys residue protected with ACM
     protecting group

<400> SEQUENCE: 250

Gly Ser Arg Cys Ser Ser Asp Gln Val Glu Thr Gly Gly Ser Gly Gly
1               5                   10                  15

Gln Ala Xaa Thr Arg Glu Gln Asn Arg Ile Cys
            20                  25

<210> SEQ ID NO 251
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
     protecting group
<220> FEATURE:
<221> NAME/KEY: MISC_FEATURE
<222> LOCATION: (8)..(8)
<223> OTHER INFORMATION: Xaa is Cys residue protected with ACM
     protecting group
<220> FEATURE:
<221> NAME/KEY: MISC_FEATURE
<222> LOCATION: (11)..(11)
<223> OTHER INFORMATION: Xaa is Cys residue protected with ACM
     protecting group
<220> FEATURE:
<221> NAME/KEY: MISC_FEATURE
<222> LOCATION: (20)..(20)
<223> OTHER INFORMATION: Xaa is Cys residue protected with ACM
     protecting group
<220> FEATURE:
<221> NAME/KEY: MISC_FEATURE
<222> LOCATION: (28)..(28)
<223> OTHER INFORMATION: Xaa is Cys residue protected with ACM
     protecting group
<220> FEATURE:
<221> NAME/KEY: MISC_FEATURE
<222> LOCATION: (30)..(30)
<223> OTHER INFORMATION: Xaa is Cys residue protected with ACM
     protecting group

```
<400> SEQUENCE: 251

Cys Gln Thr Ala Gln Met Xaa Xaa Ser Lys Xaa Ser Pro Gly Gln His
1               5                   10                  15

Cys Gln Ala Xaa Thr Arg Glu Gln Asn Arg Ile Xaa Thr Xaa Arg Pro
            20                  25                  30

Cys

<210> SEQ ID NO 252
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group

<400> SEQUENCE: 252

Tyr Xaa Ala Leu Ser Lys Gln Glu Gly Cys Arg Gly Gly Ser Gly Gly
1               5                   10                  15

Lys Cys Arg Pro Gly Phe Gly Val Ala Arg Pro
            20                  25

<210> SEQ ID NO 253
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 253

Pro Cys Ala Pro Gly Thr Phe Ser Asn Thr Thr Gly Gly Ser Gly Gly
1               5                   10                  15

Thr Asp Ile Cys Arg Pro His Gln Ile Xaa Asn
            20                  25

<210> SEQ ID NO 254
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group

<400> SEQUENCE: 254

Asp Ile Xaa Arg Pro His Gln Ile Cys Asn Val Gly Gly Ser Gly Gly
1               5                   10                  15

Val Cys Thr Ser Thr Ser Pro Thr Arg Ser Met
            20                  25

<210> SEQ ID NO 255
<211> LENGTH: 17
<212> TYPE: PRT
<213> ORGANISM: Artificial Sequence
```

```
<220> FEATURE:
<223> OTHER INFORMATION: Synthetic Construct

<400> SEQUENCE: 255

Cys Tyr Thr Gln Leu Trp Asn Trp Val Pro Glu Gly Ala Ser Ala Gly
1               5                   10                  15

Cys

<210> SEQ ID NO 256
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 256

Gly Ser Thr Cys Arg Leu Arg Glu Tyr Tyr Asp Gly Ser Gly Gly
1               5                   10                  15

Gln Met Cys Xaa Ser Lys Xaa Ser Pro Gly Gln
                20                  25

<210> SEQ ID NO 257
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group

<400> SEQUENCE: 257

Gln Glu Gly Cys Arg Leu Xaa Ala Pro Leu Arg Gly Ser Gly Gly
1               5                   10                  15

Lys Cys Arg Pro Gly Phe Gly Val Ala Arg Pro
                20                  25

<210> SEQ ID NO 258
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 258

Cys Asn Ala Ser Met Asp Ala Val Xaa Thr Ser Thr Ser Pro Thr Arg
1               5                   10                  15
```

Cys Ala Pro Leu Arg Lys Xaa Arg Pro Gly Phe Gly Val Ala Arg Pro
            20                  25                  30

Cys

<210> SEQ ID NO 259
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (13)..(13)
<223> OTHER INFORMATION: Xaa is Cys residue protected with ACM
      protecting group
<220> FEATURE:
<221> NAME/KEY: MISC_FEATURE
<222> LOCATION: (16)..(16)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 259

Cys Arg Glu Tyr Tyr Asp Gln Thr Ala Gln Met Xaa Xaa Ser Lys Xaa
1               5                   10                  15

Cys Asn Ala Ser Met Asp Ala Val Xaa Thr Ser Thr Ser Pro Thr Arg
            20                  25                  30

Cys

<210> SEQ ID NO 260
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 260

Cys Gly Ser Arg Xaa Ser Ser Asp Gln Val Glu Gly Gly Ser Gly Gly
1               5                   10                  15

Gln Ala Cys Thr Arg Glu Gln Asn Arg Ile Xaa
            20                  25

<210> SEQ ID NO 261
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE

```
<222> LOCATION: (25)..(25)
<223> OTHER INFORMATION: Xaa is Cys residue protected with ACM
      protecting group

<400> SEQUENCE: 261

Cys Leu Pro Ala Gln Val Ala Phe Thr Pro Tyr Ala Pro Glu Pro Gly
1               5                   10                  15

Cys Asn Ala Ser Met Asp Ala Val Xaa Thr Ser Thr Ser Pro Thr Arg
            20                  25                  30

Cys

<210> SEQ ID NO 262
<211> LENGTH: 24
<212> TYPE: PRT
<213> ORGANISM: Artificial Sequence
<220> FEATURE:
<223> OTHER INFORMATION: Synthetic Construct

<400> SEQUENCE: 262

Cys Leu Trp Asn Trp Val Pro Glu Ala Leu Ser Pro Gly Ser Arg Ala
1               5                   10                  15

Ser Ser Asp Gln Val Glu Thr Cys
            20

<210> SEQ ID NO 263
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 263

Ser Xaa Gly Ser Arg Cys Ser Ser Asp Gln Val Gly Gly Ser Gly Gly
1               5                   10                  15

Ala Xaa Thr Arg Glu Gln Asn Arg Ile Cys Thr
            20                  25

<210> SEQ ID NO 264
<211> LENGTH: 17
<212> TYPE: PRT
<213> ORGANISM: Artificial Sequence
<220> FEATURE:
<223> OTHER INFORMATION: Synthetic Construct

<400> SEQUENCE: 264

Cys Ser Thr Ala Pro Ser Thr Ser Phe Leu Leu Pro Met Gly Pro Ser
1               5                   10                  15

Cys

<210> SEQ ID NO 265
<211> LENGTH: 33
<212> TYPE: PRT
<213> ORGANISM: Artificial Sequence
<220> FEATURE:
<223> OTHER INFORMATION: Synthetic Construct
<220> FEATURE:
```

<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 265

Cys Gln Ala Xaa Thr Arg Glu Gln Asn Arg Ile Xaa Thr Xaa Arg Pro
1               5                   10                  15

Cys Ala Phe Thr Pro Tyr Ala Pro Glu Pro Gly Ser Thr Xaa Arg Leu
            20                  25                  30

Cys

<210> SEQ ID NO 266
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 266

Cys Ala Val Xaa Thr Ser Thr Ser Pro Thr Arg Ser Met Ala Pro Gly
1               5                   10                  15

Cys Ala Pro Leu Arg Lys Xaa Arg Pro Gly Phe Gly Val Ala Arg Pro
            20                  25                  30

Cys

<210> SEQ ID NO 267
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (21)..(21)
<223> OTHER INFORMATION: Xaa is Cys residue protected with ACM
      protecting group

<400> SEQUENCE: 267

Gln Asn Arg Ile Xaa Thr Cys Arg Pro Gly Trp Tyr Cys Ala Leu Ser

```
1               5                  10                  15
Lys Gln Glu Gly Xaa Arg
                20
```

<210> SEQ ID NO 268
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 268

```
Val Pro Glu Xaa Leu Ser Xaa Gly Ser Arg Cys Gly Gly Ser Gly Gly
1               5                  10                  15
Thr Arg Glu Gln Asn Arg Ile Cys Thr Xaa Arg
                20                  25
```

<210> SEQ ID NO 269
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group

<400> SEQUENCE: 269

```
Xaa Lys Pro Cys Ala Pro Gly Thr Phe Ser Asn Gly Gly Ser Gly Gly
1               5                  10                  15
Thr Ser Ser Thr Asp Ile Cys Arg Pro His Gln
                20                  25
```

<210> SEQ ID NO 270
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group -continued

<400> SEQUENCE: 270

Asn Trp Val Pro Glu Xaa Leu Ser Cys Gly Ser Gly Gly Ser Gly Gly
1               5                   10                  15

Cys Thr Arg Glu Gln Asn Arg Ile Xaa Thr Xaa
            20                  25

<210> SEQ ID NO 271
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (13)..(13)
<223> OTHER INFORMATION: Xaa is Cys residue protected with ACM
      protecting group
<220> FEATURE:
<221> NAME/KEY: MISC_FEATURE
<222> LOCATION: (16)..(16)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 271

Cys Arg Glu Tyr Tyr Asp Gln Thr Ala Gln Met Xaa Xaa Ser Lys Xaa
1               5                   10                  15

Cys Ala Pro Leu Arg Lys Xaa Arg Pro Gly Phe Gly Val Ala Arg Pro
            20                  25                  30

Cys

<210> SEQ ID NO 272
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (17)..(17)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 272

Xaa Leu Ser Xaa Gly Ser Arg Cys Ser Ser Asp Gly Gly Ser Gly Gly
1               5                   10                  15

```
Xaa Thr Arg Glu Gln Asn Arg Ile Cys Thr Xaa
            20                  25
```

<210> SEQ ID NO 273
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group

<400> SEQUENCE: 273

```
Gln Glu Gly Xaa Arg Leu Cys Ala Pro Leu Arg Gly Gly Ser Gly Gly
1               5                   10                  15

Cys Lys Pro Xaa Ala Pro Gly Thr Phe Ser Asn
            20                  25
```

<210> SEQ ID NO 274
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 274

```
Cys Ala Pro Leu Arg Lys Xaa Arg Pro Gly Phe Gly Val Ala Arg Pro
1               5                   10                  15

Cys Asn Ala Ser Met Asp Ala Val Xaa Thr Ser Thr Ser Pro Thr Arg
            20                  25                  30

Cys
```

<210> SEQ ID NO 275
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group

<400> SEQUENCE: 275

```
Asp Ile Xaa Arg Pro His Gln Ile Cys Asn Val Gly Ser Gly Gly
1               5                   10                  15

Cys Thr Ser Thr Ser Pro Thr Arg Ser Met Ala
            20                  25
```

```
<210> SEQ ID NO 276
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 276

Cys Gln Ala Xaa Thr Arg Glu Gln Asn Arg Ile Xaa Thr Xaa Arg Pro
1               5                   10                  15

Cys Gln Ala Xaa Thr Arg Glu Gln Asn Arg Ile Xaa Thr Xaa Arg Pro
            20                  25                  30

Cys

<210> SEQ ID NO 277
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
``` protecting group

<400> SEQUENCE: 277

Cys Thr Ser Ser Thr Asp Ile Xaa Arg Pro His Gln Ile Xaa Asn Val
1               5                   10                  15

Cys Gln Ala Xaa Thr Arg Glu Gln Asn Arg Ile Xaa Thr Xaa Arg Pro
            20                  25                  30

Cys

<210> SEQ ID NO 278
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 278

Cys Leu Pro Ala Gln Val Ala Phe Thr Pro Tyr Ala Pro Glu Pro Gly
1               5                   10                  15

Cys Ala Pro Leu Arg Lys Xaa Arg Pro Gly Phe Gly Val Ala Arg Pro
            20                  25                  30

Cys

<210> SEQ ID NO 279
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (11)..(11)
<223> OTHER INFORMATION: Xaa is Cys residue protected with ACM
      protecting group

<400> SEQUENCE: 279

Val Pro Glu Xaa Leu Ser Cys Gly Ser Arg Xaa Gly Gly Ser Gly Gly
1               5                   10                  15

Glu Thr Gln Ala Cys Thr Arg Glu Gln Asn Arg
            20                  25

<210> SEQ ID NO 280
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 280

Cys Ala Phe Thr Pro Tyr Ala Pro Glu Pro Gly Ser Thr Xaa Arg Leu
1               5                   10                  15

Cys Ala Pro Leu Arg Lys Xaa Arg Pro Gly Phe Gly Val Ala Arg Pro
            20                  25                  30

Cys

<210> SEQ ID NO 281
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 281

Cys Ile Xaa Arg Pro His Gln Ile Xaa Asn Val Val Ala Ile Pro Gly
1               5                   10                  15

Cys Ala Pro Leu Arg Lys Xaa Arg Pro Gly Phe Gly Val Ala Arg Pro
            20                  25                  30

Cys

<210> SEQ ID NO 282
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 282

Cys Ser Thr Ser Phe Leu Leu Pro Met Gly Pro Ser Pro Pro Ala Glu
1               5                   10                  15

Cys Ala Pro Leu Arg Lys Xaa Arg Pro Gly Phe Gly Val Ala Arg Pro
            20                  25                  30

Cys

<210> SEQ ID NO 283
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:

```
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 283

Xaa Thr Arg Glu Gln Asn Arg Ile Xaa Thr Cys Gly Gly Ser Gly Gly
1               5                   10                  15

Tyr Cys Ala Leu Ser Lys Gln Glu Gly Xaa Arg
            20                  25

<210> SEQ ID NO 284
<211> LENGTH: 27
<212> TYPE: PRT
<213> ORGANISM: Artificial Sequence
<220> FEATURE:
<223> OTHER INFORMATION: Synthetic Construct

<400> SEQUENCE: 284

Cys Ala Pro Gly Thr Phe Ser Asn Thr Thr Ser Gly Gly Ser Gly Gly
1               5                   10                  15

Thr Ser Ser Thr Asp Ile Cys Arg Pro His Gln
            20                  25

<210> SEQ ID NO 285
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 285

Cys Gln Thr Ala Gln Met Xaa Xaa Ser Lys Xaa Ser Pro Gly Gln His
1               5                   10                  15

Cys Asn Ala Ser Met Asp Ala Val Xaa Thr Ser Thr Ser Pro Thr Arg
            20                  25                  30

Cys

<210> SEQ ID NO 286
<211> LENGTH: 33
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 286

Cys Asn Ala Ser Met Asp Ala Val Xaa Thr Ser Thr Ser Pro Thr Arg
1               5                   10                  15

Cys Asn Ala Ser Met Asp Ala Val Xaa Thr Ser Thr Ser Pro Thr Arg
            20                  25                  30

Cys

<210> SEQ ID NO 287
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (15)..(15)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 287

Cys Tyr Thr Gln Leu Trp Asn Trp Val Pro Glu Xaa Leu Ser Xaa Gly
1               5                   10                  15

Cys Leu Ser Lys Gln Glu Gly Xaa Arg Leu Xaa Ala Pro Leu Arg Lys
            20                  25                  30

Cys

<210> SEQ ID NO 288
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 288
```

```
Cys Arg Leu Arg Glu Tyr Tyr Asp Gln Thr Ala Gly Gly Ser Gly Gly
1               5                   10                  15

Gln Met Cys Xaa Ser Lys Xaa Ser Pro Gly Gln
            20                  25
```

<210> SEQ ID NO 289
<211> LENGTH: 15
<212> TYPE: PRT
<213> ORGANISM: Artificial Sequence
<220> FEATURE:
<223> OTHER INFORMATION: Synthetic Construct

<400> SEQUENCE: 289

```
Met Asp Ala Val Cys Thr Ser Thr Ser Pro Thr Arg Ser Met Ala
1               5                   10                  15
```

<210> SEQ ID NO 290
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 290

```
Cys Ala Val His Leu Pro Gln Pro Val Ser Thr Arg Ser Gln His Thr
1               5                   10                  15

Cys Gln Ala Xaa Thr Arg Glu Gln Asn Arg Ile Xaa Thr Xaa Arg Pro
                20                  25                  30

Cys
```

<210> SEQ ID NO 291
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 291

```
Pro Glu Xaa Leu Ser Xaa Gly Ser Arg Cys Ser Gly Gly Ser Gly Gly
1               5                   10                  15
```

```
Thr Arg Glu Gln Asn Arg Ile Cys Thr Xaa Arg
            20                  25

<210> SEQ ID NO 292
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (24)..(24)
<223> OTHER INFORMATION: Xaa is Cys residue protected with ACM
      protecting group

<400> SEQUENCE: 292

Xaa Leu Ser Xaa Gly Ser Arg Cys Ser Ser Asp Gly Gly Ser Gly Gly
1               5                   10                  15

Glu Gln Asn Arg Ile Cys Thr Xaa Arg Pro Gly
            20                  25

<210> SEQ ID NO 293
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 293

Arg Glu Gln Asn Arg Ile Xaa Thr Cys Arg Pro Gly Ser Gly Gly
1               5                   10                  15

Cys Ala Leu Ser Lys Gln Glu Gly Xaa Arg Leu
            20                  25

<210> SEQ ID NO 294
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
```

```
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 294

Cys Gln Thr Ala Gln Met Xaa Xaa Ser Lys Xaa Ser Pro Gly Gln His
1               5                   10                  15

Cys Ala Pro Leu Arg Lys Xaa Arg Pro Gly Phe Gly Val Ala Arg Pro
            20                  25                  30

Cys

<210> SEQ ID NO 295
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (4)..(4)
<223> OTHER INFORMATION: Xaa is Cys residue protected with ACM
      protecting group
<220> FEATURE:
<221> NAME/KEY: MISC_FEATURE
<222> LOCATION: (10)..(10)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 295

Cys Xaa Thr Xaa Arg Pro Gly Trp Tyr Xaa Ala Leu Ser Lys Gln Glu
1               5                   10                  15

Cys Ala Pro Leu Arg Lys Xaa Arg Pro Gly Phe Gly Val Ala Arg Pro
            20                  25                  30

Cys

<210> SEQ ID NO 296
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is Cys residue protected with ACM
      protecting group
<220> FEATURE:
<221> NAME/KEY: MISC_FEATURE
<222> LOCATION: (10)..(10)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM
```

```
            protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 296

Cys Asn Trp Val Pro Glu Xaa Leu Ser Xaa Gly Ser Arg Xaa Ser Ser
1               5                   10                  15

Cys Asn Ala Ser Met Asp Ala Val Xaa Thr Ser Thr Ser Pro Thr Arg
            20                  25                  30

Cys

<210> SEQ ID NO 297
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (26)..(26)
<223> OTHER INFORMATION: Xaa is Cys residue protected with ACM
      protecting group

<400> SEQUENCE: 297

Arg Cys Ser Ser Asp Gln Val Glu Thr Gln Ala Gly Gly Ser Gly Gly
1               5                   10                  15

Thr Arg Glu Gln Asn Arg Ile Cys Thr Xaa Arg
            20                  25

<210> SEQ ID NO 298
<211> LENGTH: 15
<212> TYPE: PRT
<213> ORGANISM: Artificial Sequence
<220> FEATURE:
<223> OTHER INFORMATION: Synthetic Construct

<400> SEQUENCE: 298

Tyr Asp Gln Thr Ala Gln Met Cys Cys Ser Lys Cys Ser Pro Gly
1               5                   10                  15

<210> SEQ ID NO 299
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 299

Cys Ser Pro Gly Gln His Ala Lys Val Phe Xaa Thr Lys Thr Ser Asp
1               5                   10                  15

Cys Ala Pro Leu Arg Lys Xaa Arg Pro Gly Phe Gly Val Ala Arg Pro
            20                  25                  30

Cys
```

-continued

```
<210> SEQ ID NO 300
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 300

Cys Leu Ser Lys Gln Glu Gly Xaa Arg Leu Xaa Ala Pro Leu Arg Lys
1               5                   10                  15

Cys Asp Gln Val Glu Thr Gln Ala Xaa Thr Arg Glu Gln Asn Arg Ile
            20                  25                  30

Cys

<210> SEQ ID NO 301
<211> LENGTH: 18
<212> TYPE: PRT
<213> ORGANISM: Artificial Sequence
<220> FEATURE:
<223> OTHER INFORMATION: Synthetic Construct

<400> SEQUENCE: 301

Cys Ser Asp Gln Val Glu Thr Gln Pro Gly Thr Arg Glu Gln Asn Arg
1               5                   10                  15

Ile Cys

<210> SEQ ID NO 302
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 302

Glu Gln Asn Arg Ile Xaa Thr Cys Arg Pro Gly Gly Gly Ser Gly Gly
1               5                   10                  15

Cys Ala Leu Ser Lys Gln Glu Gly Xaa Arg Leu
            20                  25

<210> SEQ ID NO 303
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Cys residue protected with ACM
      protecting group

<400> SEQUENCE: 303

Asp Val Val Xaa Lys Pro Cys Ala Pro Gly Thr Gly Ser Gly Gly
1               5                   10                  15

Thr Ser Ser Thr Asp Ile Cys Arg Pro His Gln
                20                  25

<210> SEQ ID NO 304
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group

<400> SEQUENCE: 304

Ser Thr Asp Ile Xaa Arg Pro His Gln Ile Cys Gly Gly Ser Gly Gly
1               5                   10                  15

Cys Thr Ser Thr Ser Pro Thr Arg Ser Met Ala
                20                  25

<210> SEQ ID NO 305
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 305

Cys Pro Ser Thr Ala Pro Ser Thr Ser Phe Leu Leu Pro Met Gly Pro
1               5                   10                  15

Cys Asn Ala Ser Met Asp Ala Val Xaa Thr Ser Thr Ser Pro Thr Arg
                20                  25                  30

Cys

<210> SEQ ID NO 306
<211> LENGTH: 15
<212> TYPE: PRT
<213> ORGANISM: Artificial Sequence
<220> FEATURE:
<223> OTHER INFORMATION: Synthetic Construct

<400> SEQUENCE: 306

Gly Ala Val His Leu Pro Gln Pro Val Ser Thr Arg Ser Gln His
1               5                   10                  15

<210> SEQ ID NO 307
<211> LENGTH: 33
<212> TYPE: PRT
<213> ORGANISM: Artificial Sequence
<220> FEATURE:
```

<223> OTHER INFORMATION: Synthetic Construct
<220> FEATURE:
<221> NAME/KEY: MISC_FEATURE
<222> LOCATION: (12)..(12)
<223> OTHER INFORMATION: Xaa is Cys residue protected with ACM
      protecting group
<220> FEATURE:
<221> NAME/KEY: MISC_FEATURE
<222> LOCATION: (13)..(13)
<223> OTHER INFORMATION: Xaa is Cys residue protected with ACM
      protecting group
<220> FEATURE:
<221> NAME/KEY: MISC_FEATURE
<222> LOCATION: (16)..(16)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 307

Cys Arg Glu Tyr Tyr Asp Gln Thr Ala Gln Met Xaa Xaa Ser Lys Xaa
1               5                   10                  15

Cys Gln Ala Xaa Thr Arg Glu Gln Asn Arg Ile Xaa Thr Xaa Arg Pro
            20                  25                  30

Cys

<210> SEQ ID NO 308
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (3)..(3)
<223> OTHER INFORMATION: Xaa is Cys residue protected with ACM
      protecting group
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (16)..(16)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group

```
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 308

Cys Xaa Xaa Ser Lys Xaa Ser Pro Gly Gln His Ala Lys Val Phe Xaa
1               5                   10                  15

Cys Gln Ala Xaa Thr Arg Glu Gln Asn Arg Ile Xaa Thr Xaa Arg Pro
            20                  25                  30

Cys

<210> SEQ ID NO 309
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (13)..(13)
<223> OTHER INFORMATION: Xaa is Cys residue protected with ACM
      protecting group
<220> FEATURE:
<221> NAME/KEY: MISC_FEATURE
<222> LOCATION: (16)..(16)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 309

Cys Gly Trp Tyr Xaa Ala Leu Ser Lys Gln Glu Gly Xaa Arg Leu Xaa
1               5                   10                  15

Cys Gln Ala Xaa Thr Arg Glu Gln Asn Arg Ile Xaa Thr Xaa Arg Pro
            20                  25                  30

Cys

<210> SEQ ID NO 310
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (11)..(11)
```

```
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 310

Cys Leu Ser Lys Gln Glu Gly Xaa Arg Leu Xaa Ala Pro Leu Arg Lys
1               5                   10                  15

Cys Gln Ala Xaa Thr Arg Glu Gln Asn Arg Ile Xaa Thr Xaa Arg Pro
            20                  25                  30

Cys

<210> SEQ ID NO 311
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 311

Cys Thr Ser Ser Thr Asp Ile Xaa Arg Pro His Gln Ile Xaa Asn Val
1               5                   10                  15

Cys Ala Pro Leu Arg Lys Xaa Arg Pro Gly Phe Gly Val Ala Arg Pro
            20                  25                  30

Cys

<210> SEQ ID NO 312
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Cys residue protected with ACM
      protecting group
<220> FEATURE:
<221> NAME/KEY: MISC_FEATURE
<222> LOCATION: (8)..(8)
<223> OTHER INFORMATION: Xaa is Cys residue protected with ACM
      protecting group
```

-continued

```
<400> SEQUENCE: 312

Xaa Leu Ser Cys Gly Ser Arg Xaa Ser Ser Asp Gly Ser Gly Gly
1               5                   10                  15

Thr Gln Ala Cys Thr Arg Glu Gln Asn Arg Ile
                20                  25

<210> SEQ ID NO 313
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 313

Cys Asp Gln Val Glu Thr Gln Ala Xaa Thr Arg Glu Gln Asn Arg Ile
1               5                   10                  15

Cys Ala Phe Thr Pro Tyr Ala Pro Glu Pro Gly Ser Thr Xaa Arg Leu
                20                  25                  30

Cys

<210> SEQ ID NO 314
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 314

Cys Asn Ala Ser Met Asp Ala Val Xaa Thr Ser Thr Ser Pro Thr Arg
1               5                   10                  15

Cys Gln Ala Xaa Thr Arg Glu Gln Asn Arg Ile Xaa Thr Xaa Arg Pro
                20                  25                  30

Cys

<210> SEQ ID NO 315
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 315

Pro Glu Pro Gly Ser Thr Cys Arg Leu Arg Glu Gly Gly Ser Gly Gly
1               5                   10                  15

Gln Met Cys Xaa Ser Lys Xaa Ser Pro Gly Gln
            20                  25

<210> SEQ ID NO 316
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 316

Ser Thr Cys Arg Leu Arg Glu Tyr Tyr Asp Gln Gly Gly Ser Gly Gly
1               5                   10                  15

Gln Met Cys Xaa Ser Lys Xaa Ser Pro Gly Gln
            20                  25

<210> SEQ ID NO 317
<211> LENGTH: 15
<212> TYPE: PRT
<213> ORGANISM: Artificial Sequence
<220> FEATURE:
<223> OTHER INFORMATION: Synthetic Construct

<400> SEQUENCE: 317

Leu Arg Lys Cys Arg Pro Gly Phe Gly Val Gly Ala Pro Gly Thr
1               5                   10                  15

<210> SEQ ID NO 318
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (11)..(11)
<223> OTHER INFORMATION: Xaa is Cys residue protected with ACM
      protecting group
<220> FEATURE:
<221> NAME/KEY: MISC_FEATURE
```

<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (29)..(29)
<223> OTHER INFORMATION: Xaa is Cys residue protected with ACM
      protecting group
<220> FEATURE:
<221> NAME/KEY: MISC_FEATURE
<222> LOCATION: (32)..(32)
<223> OTHER INFORMATION: Xaa is Cys residue protected with ACM
      protecting group

<400> SEQUENCE: 318

Cys Leu Ser Lys Gln Glu Gly Xaa Arg Leu Xaa Ala Pro Leu Arg Lys
1               5                   10                  15

Cys Arg Glu Tyr Tyr Asp Gln Thr Ala Gln Met Xaa Xaa Ser Lys Xaa
            20                  25                  30

Cys

<210> SEQ ID NO 319
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (13)..(13)
<223> OTHER INFORMATION: Xaa is Cys residue protected with ACM
      protecting group
<220> FEATURE:
<221> NAME/KEY: MISC_FEATURE
<222> LOCATION: (16)..(16)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 319

Cys Gly Trp Tyr Xaa Ala Leu Ser Lys Gln Glu Gly Xaa Arg Leu Xaa
1               5                   10                  15

Cys Asn Ala Ser Met Asp Ala Val Xaa Thr Ser Thr Ser Pro Thr Arg
            20                  25                  30

Cys

<210> SEQ ID NO 320
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (13)..(13)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 320

Cys Thr Phe Ser Asn Thr Thr Ser Ser Thr Asp Ile Xaa Arg Pro His
1               5                   10                  15

Cys Asn Ala Ser Met Asp Ala Val Xaa Thr Ser Thr Ser Pro Thr Arg
            20                  25                  30

Cys

<210> SEQ ID NO 321
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group

<400> SEQUENCE: 321

Ser Cys Gly Ser Arg Xaa Ser Ser Asp Gln Val Gly Ser Gly Gly
1               5                   10                  15

Thr Gln Ala Cys Thr Arg Glu Gln Asn Arg Ile
            20                  25

<210> SEQ ID NO 322
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Cys residue protected with ACM
      protecting group
<220> FEATURE:
<221> NAME/KEY: MISC_FEATURE
<222> LOCATION: (18)..(18)
<223> OTHER INFORMATION: Xaa is Cys residue protected with ACM
      protecting group

<400> SEQUENCE: 322

Glu Gly Cys Arg Leu Xaa Ala Pro Leu Arg Lys Gly Gly Ser Gly Gly
1               5                   10                  15

Leu Xaa Ala Pro Leu Arg Lys Cys Arg Pro Gly
            20                  25

<210> SEQ ID NO 323
<211> LENGTH: 15
<212> TYPE: PRT
<213> ORGANISM: Artificial Sequence
<220> FEATURE:
<223> OTHER INFORMATION: Synthetic Construct

<400> SEQUENCE: 323

Thr Ser Ser Thr Asp Ile Cys Arg Pro His Ala Ala Cys Asn Val
1               5                   10                  15

<210> SEQ ID NO 324
<211> LENGTH: 33
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (23)..(23)
<223> OTHER INFORMATION: Xaa is Cys residue protected with ACM
      protecting group

<400> SEQUENCE: 324

Cys Arg Ser Gln His Thr Gln Pro Thr Pro Glu Pro Ser Thr Ala Pro
1               5                   10                  15

Cys Ala Pro Leu Arg Lys Xaa Arg Pro Gly Phe Gly Val Ala Arg Pro
            20                  25                  30

Cys

<210> SEQ ID NO 325
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 325

Cys Asp Gln Val Glu Thr Gln Ala Xaa Thr Arg Glu Gln Asn Arg Ile
1               5                   10                  15

Cys Gln Ala Xaa Thr Arg Glu Gln Asn Arg Ile Xaa Thr Xaa Arg Pro
            20                  25                  30

Cys

<210> SEQ ID NO 326
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 326

Cys Thr Ser Pro Thr Arg Ser Met Ala Pro Gly Ala Val His Leu Pro
1               5                   10                  15

Cys Asn Ala Ser Met Asp Ala Val Xaa Thr Ser Thr Ser Pro Thr Arg
            20                  25                  30

Cys

<210> SEQ ID NO 327
<211> LENGTH: 22
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group

<400> SEQUENCE: 327

Cys Gly Ser Arg Xaa Ser Ser Asp Gln Val Glu Thr Gln Ala Cys Thr
1               5                   10                  15

Arg Glu Gln Asn Arg Ile
            20

<210> SEQ ID NO 328
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 328

Ala Pro Glu Pro Gly Ser Thr Cys Arg Leu Arg Gly Gly Ser Gly Gly
1               5                   10                  15

Gln Met Cys Xaa Ser Lys Xaa Ser Pro Gly Gln
            20                  25

<210> SEQ ID NO 329
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Cys residue protected with ACM
      protecting group
<220> FEATURE:
<221> NAME/KEY: MISC_FEATURE
<222> LOCATION: (9)..(9)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group
<220> FEATURE:
<221> NAME/KEY: MISC_FEATURE
<222> LOCATION: (27)..(27)
<223> OTHER INFORMATION: Xaa is Cys residue protected with ACM
      protecting group

<400> SEQUENCE: 329

Glu Xaa Leu Ser Cys Gly Ser Arg Xaa Ser Ser Gly Gly Ser Gly Gly
1               5                   10                  15

Cys Thr Arg Glu Gln Asn Arg Ile Xaa Thr Xaa
            20                  25
```

<210> SEQ ID NO 330
<211> LENGTH: 27
<212> TYPE: PRT
<213> ORGANISM: Artificial Sequence
<220> FEATURE:
<223> OTHER INFORMATION: Synthetic Construct

<400> SEQUENCE: 330

Ile Cys Asn Val Val Ala Ile Pro Gly Asn Ala Gly Gly Ser Gly Gly
1               5                   10                  15

Asp Ala Val Cys Thr Ser Thr Ser Pro Thr Arg
            20                  25

<210> SEQ ID NO 331
<211> LENGTH: 15
<212> TYPE: PRT
<213> ORGANISM: Artificial Sequence
<220> FEATURE:
<223> OTHER INFORMATION: Synthetic Construct

<400> SEQUENCE: 331

Ala Pro Ser Thr Ser Phe Leu Leu Pro Met Ala Ala Ser Pro Pro
1               5                   10                  15

<210> SEQ ID NO 332
<211> LENGTH: 17
<212> TYPE: PRT
<213> ORGANISM: Artificial Sequence
<220> FEATURE:
<223> OTHER INFORMATION: Synthetic Construct

<400> SEQUENCE: 332

Cys Glu Gln Asn Arg Ile Ala Thr Ala Arg Pro Ala Ala Tyr Ala Ala
1               5                   10                  15

Cys

<210> SEQ ID NO 333
<211> LENGTH: 18
<212> TYPE: PRT
<213> ORGANISM: Artificial Sequence
<220> FEATURE:
<223> OTHER INFORMATION: Synthetic Construct

<400> SEQUENCE: 333

Cys Gln Val Ala Phe Thr Pro Tyr Pro Gly Glu Pro Gly Ser Thr Ala
1               5                   10                  15

Arg Cys

<210> SEQ ID NO 334
<211> LENGTH: 27
<212> TYPE: PRT
<213> ORGANISM: Artificial Sequence
<220> FEATURE:
<223> OTHER INFORMATION: Synthetic Construct

<400> SEQUENCE: 334

Arg Pro His Gln Ile Cys Asn Val Val Ala Ile Gly Gly Ser Gly Gly
1               5                   10                  15

Cys Thr Ser Thr Ser Pro Thr Arg Ser Met Ala
            20                  25

<210> SEQ ID NO 335
<211> LENGTH: 15

```
<212> TYPE: PRT
<213> ORGANISM: Artificial Sequence
<220> FEATURE:
<223> OTHER INFORMATION: Synthetic Construct

<400> SEQUENCE: 335

Thr Arg Ser Met Ala Pro Gly Ala Val His Leu Pro Gln Pro Val
1               5                   10                  15

<210> SEQ ID NO 336
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Cys residue protected with ACM
      protecting group
<220> FEATURE:
<221> NAME/KEY: MISC_FEATURE
<222> LOCATION: (25)..(25)
<223> OTHER INFORMATION: Xaa is Cys residue protected with ACM
      protecting group

<400> SEQUENCE: 336

Gln Asn Arg Ile Xaa Thr Cys Arg Pro Gly Trp Gly Gly Ser Gly Gly
1               5                   10                  15

Cys Ala Leu Ser Lys Gln Glu Gly Xaa Arg Leu
            20                  25

<210> SEQ ID NO 337
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group

<400> SEQUENCE: 337

Ala Leu Ser Lys Gln Glu Gly Xaa Arg Leu Cys Gly Gly Ser Gly Gly
1               5                   10                  15

Cys Lys Pro Xaa Ala Pro Gly Thr Phe Ser Asn
            20                  25

<210> SEQ ID NO 338
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (15)..(15)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group
```

<400> SEQUENCE: 338

Cys Gly Val Ala Arg Pro Gly Thr Glu Thr Ser Asp Val Val Xaa Lys
1               5                   10                  15

Cys Ala Pro Leu Arg Lys Xaa Arg Pro Gly Phe Gly Val Ala Arg Pro
            20                  25                  30

Cys

<210> SEQ ID NO 339
<211> LENGTH: 27
<212> TYPE: PRT
<213> ORGANISM: Artificial Sequence
<220> FEATURE:
<223> OTHER INFORMATION: Synthetic Construct

<400> SEQUENCE: 339

Pro Cys Ala Pro Gly Thr Phe Ser Asn Thr Thr Gly Gly Ser Gly Gly
1               5                   10                  15

Thr Ser Ser Thr Asp Ile Cys Arg Pro His Gln
            20                  25

<210> SEQ ID NO 340
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa is Cys residue protected with ACM
      protecting group
<220> FEATURE:
<221> NAME/KEY: MISC_FEATURE
<222> LOCATION: (20)..(20)
<223> OTHER INFORMATION: Xaa is Cys residue protected with ACM
      protecting group
<220> FEATURE:
<221> NAME/KEY: MISC_FEATURE
<222> LOCATION: (28)..(28)
<223> OTHER INFORMATION: Xaa is Cys residue protected with ACM
      protecting group
<220> FEATURE:
<221> NAME/KEY: MISC_FEATURE
<222> LOCATION: (30)..(30)
<223> OTHER INFORMATION: Xaa is Cys residue protected with ACM
      protecting group

<400> SEQUENCE: 340

Cys Ala Phe Thr Pro Tyr Ala Pro Glu Pro Gly Ser Thr Xaa Arg Leu
1               5                   10                  15

Cys Gln Ala Xaa Thr Arg Glu Gln Asn Arg Ile Xaa Thr Xaa Arg Pro
            20                  25                  30

Cys

<210> SEQ ID NO 341
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa is Cys residue protected with ACM
      protecting group
<220> FEATURE:
<221> NAME/KEY: MISC_FEATURE

```
<222> LOCATION: (13)..(13)
<223> OTHER INFORMATION: Xaa is Cys residue protected with ACM
      protecting group
<220> FEATURE:
<221> NAME/KEY: MISC_FEATURE
<222> LOCATION: (23)..(23)
<223> OTHER INFORMATION: Xaa is Cys residue protected with ACM
      protecting group

<400> SEQUENCE: 341

Cys Gly Thr Glu Thr Ser Asp Val Val Xaa Lys Pro Xaa Ala Pro Gly
1               5                   10                  15

Cys Ala Pro Leu Arg Lys Xaa Arg Pro Gly Phe Gly Val Ala Arg Pro
            20                  25                  30

Cys

<210> SEQ ID NO 342
<211> LENGTH: 185
<212> TYPE: PRT
<213> ORGANISM: Artificial Sequence
<220> FEATURE:
<223> OTHER INFORMATION: Synthetic Construct

<400> SEQUENCE: 342

Tyr Tyr Asp Gln Thr Ala Gln Met Cys Cys Ser Lys Cys Ser Pro Gly
1               5                   10                  15

Gln His Ala Lys Val Phe Cys Thr Lys Thr Ser Asp Thr Val Cys Asp
            20                  25                  30

Ser Cys Glu Asp Ser Thr Tyr Thr Gln Leu Trp Asn Trp Val Pro Glu
        35                  40                  45

Cys Leu Ser Cys Gly Ser Arg Cys Ser Ser Asp Gln Val Glu Thr Gln
    50                  55                  60

Ala Cys Thr Arg Glu Gln Asn Arg Ile Cys Thr Cys Arg Pro Gly Trp
65                  70                  75                  80

Tyr Cys Ala Leu Ser Lys Gln Glu Gly Cys Arg Leu Cys Ala Pro Leu
                85                  90                  95

Arg Lys Cys Arg Pro Gly Phe Gly Val Ala Arg Pro Gly Thr Glu Thr
            100                 105                 110

Ser Asp Val Val Cys Lys Pro Cys Ala Pro Gly Thr Phe Ser Asn Thr
        115                 120                 125

Thr Ser Ser Thr Asp Ile Cys Arg Pro His Gln Ile Cys Asn Val Val
    130                 135                 140

Ala Ile Pro Gly Asn Ala Ser Met Asp Ala Val Cys Thr Ser Thr Ser
145                 150                 155                 160

Pro Thr Arg Ser Met Ala Pro Gly Ala Val His Leu Pro Gln Pro Val
                165                 170                 175

Ser Thr Arg Ser Gln His Thr Gln Pro
            180                 185

<210> SEQ ID NO 343
<211> LENGTH: 20
<212> TYPE: PRT
<213> ORGANISM: Artificial Sequence
<220> FEATURE:
<223> OTHER INFORMATION: Synthetic Construct

<400> SEQUENCE: 343

Leu Pro Ala Gln Val Ala Phe Thr Pro Tyr Ala Pro Glu Pro Gly Ser
1               5                   10                  15

Thr Cys Arg Leu
```

20

<210> SEQ ID NO 344
<211> LENGTH: 20
<212> TYPE: PRT
<213> ORGANISM: Artificial Sequence
<220> FEATURE:
<223> OTHER INFORMATION: Synthetic Construct

<400> SEQUENCE: 344

Pro Tyr Ala Pro Glu Pro Gly Ser Thr Cys Arg Leu Arg Glu Tyr Tyr
1               5                   10                  15

Asp Gln Thr Ala
            20

<210> SEQ ID NO 345
<211> LENGTH: 20
<212> TYPE: PRT
<213> ORGANISM: Artificial Sequence
<220> FEATURE:
<223> OTHER INFORMATION: Synthetic Construct

<400> SEQUENCE: 345

Thr Cys Arg Leu Arg Glu Tyr Tyr Asp Gln Thr Ala Gln Met Cys Cys
1               5                   10                  15

Ser Lys Cys Ser
            20

<210> SEQ ID NO 346
<211> LENGTH: 20
<212> TYPE: PRT
<213> ORGANISM: Artificial Sequence
<220> FEATURE:
<223> OTHER INFORMATION: Synthetic Construct

<400> SEQUENCE: 346

Gln Thr Ala Gln Met Cys Cys Ser Lys Cys Ser Pro Gly Gln His Ala
1               5                   10                  15

Lys Val Phe Cys
            20

<210> SEQ ID NO 347
<211> LENGTH: 20
<212> TYPE: PRT
<213> ORGANISM: Artificial Sequence
<220> FEATURE:
<223> OTHER INFORMATION: Synthetic Construct

<400> SEQUENCE: 347

Lys Cys Ser Pro Gly Gln His Ala Lys Val Phe Cys Thr Lys Thr Ser
1               5                   10                  15

Asp Thr Val Cys
            20

<210> SEQ ID NO 348
<211> LENGTH: 20
<212> TYPE: PRT
<213> ORGANISM: Artificial Sequence
<220> FEATURE:
<223> OTHER INFORMATION: Synthetic Construct

<400> SEQUENCE: 348

Lys Val Phe Cys Thr Lys Thr Ser Asp Thr Val Cys Asp Ser Cys Glu
1               5                   10                  15

```
Asp Ser Thr Tyr
        20

<210> SEQ ID NO 349
<211> LENGTH: 20
<212> TYPE: PRT
<213> ORGANISM: Artificial Sequence
<220> FEATURE:
<223> OTHER INFORMATION: Synthetic Construct

<400> SEQUENCE: 349

Asp Thr Val Cys Asp Ser Cys Glu Asp Ser Thr Tyr Thr Gln Leu Trp
1               5                   10                  15

Asn Trp Val Pro
        20

<210> SEQ ID NO 350
<211> LENGTH: 20
<212> TYPE: PRT
<213> ORGANISM: Artificial Sequence
<220> FEATURE:
<223> OTHER INFORMATION: Synthetic Construct

<400> SEQUENCE: 350

Asp Ser Thr Tyr Thr Gln Leu Trp Asn Trp Val Pro Glu Cys Leu Ser
1               5                   10                  15

Cys Gly Ser Arg
        20

<210> SEQ ID NO 351
<211> LENGTH: 20
<212> TYPE: PRT
<213> ORGANISM: Artificial Sequence
<220> FEATURE:
<223> OTHER INFORMATION: Synthetic Construct

<400> SEQUENCE: 351

Asn Trp Val Pro Glu Cys Leu Ser Cys Gly Ser Arg Cys Ser Ser Asp
1               5                   10                  15

Gln Val Glu Thr
        20

<210> SEQ ID NO 352
<211> LENGTH: 20
<212> TYPE: PRT
<213> ORGANISM: Artificial Sequence
<220> FEATURE:
<223> OTHER INFORMATION: Synthetic Construct

<400> SEQUENCE: 352

Cys Gly Ser Arg Cys Ser Ser Asp Gln Val Glu Thr Gln Ala Cys Thr
1               5                   10                  15

Arg Glu Gln Asn
        20

<210> SEQ ID NO 353
<211> LENGTH: 20
<212> TYPE: PRT
<213> ORGANISM: Artificial Sequence
<220> FEATURE:
<223> OTHER INFORMATION: Synthetic Construct

<400> SEQUENCE: 353

Gln Val Glu Thr Gln Ala Cys Thr Arg Glu Gln Asn Arg Ile Cys Thr
1               5                   10                  15
```

```
Cys Arg Pro Gly
            20

<210> SEQ ID NO 354
<211> LENGTH: 20
<212> TYPE: PRT
<213> ORGANISM: Artificial Sequence
<220> FEATURE:
<223> OTHER INFORMATION: Synthetic Construct

<400> SEQUENCE: 354

Arg Glu Gln Asn Arg Ile Cys Thr Cys Arg Pro Gly Trp Tyr Cys Ala
1               5                   10                  15

Leu Ser Lys Gln
            20

<210> SEQ ID NO 355
<211> LENGTH: 20
<212> TYPE: PRT
<213> ORGANISM: Artificial Sequence
<220> FEATURE:
<223> OTHER INFORMATION: Synthetic Construct

<400> SEQUENCE: 355

Cys Arg Pro Gly Trp Tyr Cys Ala Leu Ser Lys Gln Glu Gly Cys Arg
1               5                   10                  15

Leu Cys Ala Pro
            20

<210> SEQ ID NO 356
<211> LENGTH: 20
<212> TYPE: PRT
<213> ORGANISM: Artificial Sequence
<220> FEATURE:
<223> OTHER INFORMATION: Synthetic Construct

<400> SEQUENCE: 356

Leu Ser Lys Gln Glu Gly Cys Arg Leu Cys Ala Pro Leu Arg Lys Cys
1               5                   10                  15

Arg Pro Gly Phe
            20

<210> SEQ ID NO 357
<211> LENGTH: 20
<212> TYPE: PRT
<213> ORGANISM: Artificial Sequence
<220> FEATURE:
<223> OTHER INFORMATION: Synthetic Construct

<400> SEQUENCE: 357

Lys Gln Glu Gly Cys Arg Leu Cys Ala Pro Leu Arg Lys Cys Arg Pro
1               5                   10                  15

Gly Phe Gly Val
            20

<210> SEQ ID NO 358
<211> LENGTH: 20
<212> TYPE: PRT
<213> ORGANISM: Artificial Sequence
<220> FEATURE:
<223> OTHER INFORMATION: Synthetic Construct

<400> SEQUENCE: 358

Leu Cys Ala Pro Leu Arg Lys Cys Arg Pro Gly Phe Gly Val Ala Arg
```

```
1               5                  10                 15
Pro Gly Thr Glu
            20

<210> SEQ ID NO 359
<211> LENGTH: 20
<212> TYPE: PRT
<213> ORGANISM: Artificial Sequence
<220> FEATURE:
<223> OTHER INFORMATION: Synthetic Construct

<400> SEQUENCE: 359

Arg Pro Gly Phe Gly Val Ala Arg Pro Gly Thr Glu Thr Ser Asp Val
1               5                  10                 15

Val Cys Lys Pro
            20

<210> SEQ ID NO 360
<211> LENGTH: 20
<212> TYPE: PRT
<213> ORGANISM: Artificial Sequence
<220> FEATURE:
<223> OTHER INFORMATION: Synthetic Construct

<400> SEQUENCE: 360

Pro Gly Thr Glu Thr Ser Asp Val Val Cys Lys Pro Cys Ala Pro Gly
1               5                  10                 15

Thr Phe Ser Asn
            20

<210> SEQ ID NO 361
<211> LENGTH: 20
<212> TYPE: PRT
<213> ORGANISM: Artificial Sequence
<220> FEATURE:
<223> OTHER INFORMATION: Synthetic Construct

<400> SEQUENCE: 361

Val Cys Lys Pro Cys Ala Pro Gly Thr Phe Ser Asn Thr Thr Ser Ser
1               5                  10                 15

Thr Asp Ile Cys
            20

<210> SEQ ID NO 362
<211> LENGTH: 20
<212> TYPE: PRT
<213> ORGANISM: Artificial Sequence
<220> FEATURE:
<223> OTHER INFORMATION: Synthetic Construct

<400> SEQUENCE: 362

Thr Phe Ser Asn Thr Thr Ser Ser Thr Asp Ile Cys Arg Pro His Gln
1               5                  10                 15

Ile Cys Asn Val
            20

<210> SEQ ID NO 363
<211> LENGTH: 20
<212> TYPE: PRT
<213> ORGANISM: Artificial Sequence
<220> FEATURE:
<223> OTHER INFORMATION: Synthetic Construct

<400> SEQUENCE: 363
```

-continued

Thr Asp Ile Cys Arg Pro His Gln Ile Cys Asn Val Val Ala Ile Pro
1               5                   10                  15

Gly Asn Ala Ser
            20

<210> SEQ ID NO 364
<211> LENGTH: 20
<212> TYPE: PRT
<213> ORGANISM: Artificial Sequence
<220> FEATURE:
<223> OTHER INFORMATION: Synthetic Construct

<400> SEQUENCE: 364

Ile Cys Asn Val Val Ala Ile Pro Gly Asn Ala Ser Met Asp Ala Val
1               5                   10                  15

Cys Thr Ser Thr
            20

<210> SEQ ID NO 365
<211> LENGTH: 20
<212> TYPE: PRT
<213> ORGANISM: Artificial Sequence
<220> FEATURE:
<223> OTHER INFORMATION: Synthetic Construct

<400> SEQUENCE: 365

Gly Asn Ala Ser Met Asp Ala Val Cys Thr Ser Thr Pro Thr Arg
1               5                   10                  15

Ser Met Ala Pro
            20

<210> SEQ ID NO 366
<211> LENGTH: 461
<212> TYPE: PRT
<213> ORGANISM: Homo sapiens

<400> SEQUENCE: 366

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

-continued

Asp Ile Cys Arg Pro His Gln Ile Cys Asn Val Val Ala Ile Pro Gly
              180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
        290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
450                 455                 460

<210> SEQ ID NO 367
<211> LENGTH: 5
<212> TYPE: PRT
<213> ORGANISM: Homo sapiens

<400> SEQUENCE: 367

Lys Cys Ser Pro Gly
1               5

<210> SEQ ID NO 368
<211> LENGTH: 7
<212> TYPE: PRT
<213> ORGANISM: Homo sapiens

<400> SEQUENCE: 368

Ser Ser Asp Gln Val Glu Thr
1               5

<210> SEQ ID NO 369
<211> LENGTH: 28

```
<212> TYPE: PRT
<213> ORGANISM: Homo sapiens

<400> SEQUENCE: 369

Asn Arg Ile Cys Thr Cys Arg Pro Gly Trp Tyr Cys Ala Leu Ser Lys
1               5                   10                  15

Gln Glu Gly Cys Arg Leu Cys Ala Pro Leu Arg Lys
            20                  25

<210> SEQ ID NO 370
<211> LENGTH: 40
<212> TYPE: PRT
<213> ORGANISM: Homo sapiens

<400> SEQUENCE: 370

Thr Arg Glu Gln Asn Arg Ile Cys Thr Cys Arg Pro Gly Trp Tyr Cys
1               5                   10                  15

Ala Leu Ser Lys Gln Glu Gly Cys Arg Leu Cys Ala Pro Leu Arg Lys
            20                  25                  30

Cys Arg Pro Gly Phe Gly Val Ala
            35                  40

<210> SEQ ID NO 371
<211> LENGTH: 59
<212> TYPE: PRT
<213> ORGANISM: Homo sapiens

<400> SEQUENCE: 371

Cys Gly Ser Arg Cys Ser Ser Asp Gln Val Glu Thr Gln Ala Cys Thr
1               5                   10                  15

Arg Glu Gln Asn Arg Ile Cys Thr Cys Arg Pro Gly Trp Tyr Cys Ala
            20                  25                  30

Leu Ser Lys Gln Glu Gly Cys Arg Leu Cys Ala Pro Leu Arg Lys Cys
            35                  40                  45

Arg Pro Gly Phe Gly Val Ala Arg Pro Gly Thr
        50                  55

<210> SEQ ID NO 372
<211> LENGTH: 17
<212> TYPE: PRT
<213> ORGANISM: Homo sapiens

<400> SEQUENCE: 372

Cys Gly Ser Arg Cys Ser Ser Asp Gln Val Glu Thr Gln Ala Cys Thr
1               5                   10                  15

Arg

<210> SEQ ID NO 373
<211> LENGTH: 39
<212> TYPE: PRT
<213> ORGANISM: Homo sapiens

<400> SEQUENCE: 373

Cys Thr Arg Glu Gln Asn Arg Ile Cys Thr Cys Arg Pro Gly Trp Tyr
1               5                   10                  15

Cys Ala Leu Ser Lys Gln Glu Gly Cys Arg Leu Cys Ala Pro Leu Arg
            20                  25                  30

Lys Cys Arg Pro Ser Gly Phe
            35
```

```
<210> SEQ ID NO 374
<211> LENGTH: 50
<212> TYPE: PRT
<213> ORGANISM: Homo sapiens

<400> SEQUENCE: 374

Glu Thr Gln Ala Cys Thr Arg Glu Gln Asn Arg Ile Cys Thr Cys Arg
1               5                   10                  15

Pro Gly Trp Tyr Cys Ala Leu Ser Lys Gln Glu Gly Cys Arg Leu Cys
            20                  25                  30

Ala Pro Leu Arg Lys Cys Arg Pro Gly Phe Gly Val Ala Arg Pro Gly
        35                  40                  45

Thr Glu
    50

<210> SEQ ID NO 375
<211> LENGTH: 5
<212> TYPE: PRT
<213> ORGANISM: Homo sapiens

<400> SEQUENCE: 375

Lys Cys Arg Pro Gly
1               5

<210> SEQ ID NO 376
<211> LENGTH: 8
<212> TYPE: PRT
<213> ORGANISM: Homo sapiens

<400> SEQUENCE: 376

Cys Ala Pro Leu Arg Lys Cys Arg
1               5

<210> SEQ ID NO 377
<211> LENGTH: 8
<212> TYPE: PRT
<213> ORGANISM: Homo sapiens

<400> SEQUENCE: 377

Lys Cys Arg Pro Gly Phe Gly Val
1               5

<210> SEQ ID NO 378
<211> LENGTH: 120
<212> TYPE: PRT
<213> ORGANISM: Homo sapiens

<400> SEQUENCE: 378

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Val Ile Ser Glu Asn Gly Ser Asp Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
```

```
                100                 105                 110

Gly Thr Leu Val Thr Val Ser Ser
        115                 120

<210> SEQ ID NO 379
<211> LENGTH: 109
<212> TYPE: PRT
<213> ORGANISM: Homo sapiens

<400> SEQUENCE: 379

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Tyr
                85                  90                  95

Thr Phe Gly Gln Gly Thr Lys Val Glu Ile Lys Arg Thr
            100                 105

<210> SEQ ID NO 380
<211> LENGTH: 5
<212> TYPE: PRT
<213> ORGANISM: Mus musculus

<400> SEQUENCE: 380

Ala Asp Ala Ala Pro
1               5

<210> SEQ ID NO 381
<211> LENGTH: 5
<212> TYPE: PRT
<213> ORGANISM: Homo sapiens

<400> SEQUENCE: 381

Thr Val Ala Ala Pro
1               5

<210> SEQ ID NO 382
<211> LENGTH: 11
<212> TYPE: PRT
<213> ORGANISM: Mus musculus

<400> SEQUENCE: 382

Ala Asp Ala Ala Pro Thr Val Ser Ile Phe Pro
1               5                   10

<210> SEQ ID NO 383
<211> LENGTH: 12
<212> TYPE: PRT
<213> ORGANISM: Homo sapiens

<400> SEQUENCE: 383

Thr Val Ala Ala Pro Ser Val Phe Ile Phe Pro Pro
1               5                   10
```

```
<210> SEQ ID NO 384
<211> LENGTH: 6
<212> TYPE: PRT
<213> ORGANISM: Homo sapiens

<400> SEQUENCE: 384

Gln Pro Lys Ala Ala Pro
1               5

<210> SEQ ID NO 385
<211> LENGTH: 13
<212> TYPE: PRT
<213> ORGANISM: Homo sapiens

<400> SEQUENCE: 385

Gln Pro Lys Ala Ala Pro Ser Val Thr Leu Phe Pro Pro
1               5                   10

<210> SEQ ID NO 386
<211> LENGTH: 5
<212> TYPE: PRT
<213> ORGANISM: Artificial Sequence
<220> FEATURE:
<223> OTHER INFORMATION: Synthetic Construct

<400> SEQUENCE: 386

Gly Gly Ser Gly Gly
1               5

<210> SEQ ID NO 387
<211> LENGTH: 9
<212> TYPE: PRT
<213> ORGANISM: Artificial Sequence
<220> FEATURE:
<223> OTHER INFORMATION: Synthetic Construct

<400> SEQUENCE: 387

Gly Gly Ser Gly Gly Gly Gly Ser Gly
1               5

<210> SEQ ID NO 388
<211> LENGTH: 13
<212> TYPE: PRT
<213> ORGANISM: Artificial Sequence
<220> FEATURE:
<223> OTHER INFORMATION: Synthetic Construct

<400> SEQUENCE: 388

Gly Gly Ser Gly Gly Gly Ser Gly Gly Gly Gly Ser
1               5                   10

<210> SEQ ID NO 389
<211> LENGTH: 6
<212> TYPE: PRT
<213> ORGANISM: Mus musculus

<400> SEQUENCE: 389

Ala Lys Thr Thr Ala Pro
1               5

<210> SEQ ID NO 390
<211> LENGTH: 6
<212> TYPE: PRT
<213> ORGANISM: Homo sapiens

<400> SEQUENCE: 390
```

```
Ala Ser Thr Lys Gly Pro
1               5

<210> SEQ ID NO 391
<211> LENGTH: 13
<212> TYPE: PRT
<213> ORGANISM: Mus musculus

<400> SEQUENCE: 391

Ala Lys Thr Thr Ala Pro Ser Val Tyr Pro Leu Ala Pro
1               5                   10

<210> SEQ ID NO 392
<211> LENGTH: 13
<212> TYPE: PRT
<213> ORGANISM: Homo sapiens

<400> SEQUENCE: 392

Ala Ser Thr Lys Gly Pro Ser Val Phe Pro Leu Ala Pro
1               5                   10

<210> SEQ ID NO 393
<211> LENGTH: 6
<212> TYPE: PRT
<213> ORGANISM: Artificial Sequence
<220> FEATURE:
<223> OTHER INFORMATION: Synthetic Construct

<400> SEQUENCE: 393

Gly Gly Gly Gly Ser Gly
1               5

<210> SEQ ID NO 394
<211> LENGTH: 10
<212> TYPE: PRT
<213> ORGANISM: Artificial Sequence
<220> FEATURE:
<223> OTHER INFORMATION: Synthetic Construct

<400> SEQUENCE: 394

Gly Gly Gly Gly Ser Gly Gly Gly Gly Ser
1               5                   10

<210> SEQ ID NO 395
<211> LENGTH: 14
<212> TYPE: PRT
<213> ORGANISM: Artificial Sequence
<220> FEATURE:
<223> OTHER INFORMATION: Synthetic Construct

<400> SEQUENCE: 395

Gly Gly Gly Gly Ser Gly Gly Gly Ser Gly Gly Gly Gly
1               5                   10

<210> SEQ ID NO 396
<211> LENGTH: 5
<212> TYPE: PRT
<213> ORGANISM: Bos taurus

<400> SEQUENCE: 396

Lys Cys Pro Pro Gly
1               5

<210> SEQ ID NO 397
<211> LENGTH: 459
<212> TYPE: PRT
```

<213> ORGANISM: Bos taurus

<400> SEQUENCE: 397

Met Ala Pro Thr Ala Phe Trp Ala Ala Leu Ala Val Gly Leu Gln Phe
1               5                   10                  15

Trp Ala Ala Gly Arg Ala Val Pro Ala Gln Ala Val Phe Thr Pro Tyr
                20                  25                  30

Ile Pro Glu Pro Gly Ser Ser Cys Arg Gln Gln Glu Tyr Tyr Asn Gln
            35                  40                  45

Lys Ile Gln Met Cys Cys Ser Lys Cys Pro Pro Gly Tyr Arg Val Gln
        50                  55                  60

Ser Leu Cys Asn Met Thr Leu Asp Thr Ile Cys Ala Ser Cys Glu Ser
65                  70                  75                  80

Ser Thr Tyr Thr Gln Leu Trp Asn Leu Val Thr Ala Cys Phe Ser Cys
                85                  90                  95

Asn Ser Arg Cys Ser Ser Asp Gln Val Glu Thr Gln Ala Cys Thr Thr
            100                 105                 110

Lys Gln Asn Arg Ile Cys Thr Cys Lys Pro Gly Trp Tyr Cys Thr Leu
        115                 120                 125

Gly Arg Gln Glu Gly Cys Arg Leu Cys Val Ala Leu Arg Lys Cys Gly
130                 135                 140

Pro Gly Phe Gly Val Ala Lys Pro Gly Thr Ala Thr Thr Asn Val Ile
145                 150                 155                 160

Cys Ala Pro Cys Gly Pro Gly Thr Phe Ser Asp Thr Thr Ser Tyr Thr
                165                 170                 175

Asp Thr Cys Lys Pro His Arg Asn Cys Ser Ser Val Ala Ile Pro Gly
            180                 185                 190

Thr Ala Ser Thr Asp Ala Val Cys Thr Ser Val Leu Pro Thr Arg Lys
        195                 200                 205

Val Ala Arg Gly Pro Ala Thr Thr Arg Ser Gln His Met Glu Pro Thr
210                 215                 220

Leu Gly Pro Ser Thr Ala Pro Ser Thr Phe Phe Leu Leu Pro Lys Val
225                 230                 235                 240

Pro Ser Pro Pro Ser Ser Pro Val Glu Gln Pro Asn Thr Gly Asn Ile
                245                 250                 255

Ser Leu Pro Ile Glu Leu Ile Val Gly Val Thr Ala Leu Gly Leu Leu
            260                 265                 270

Leu Ile Val Val Val Asn Cys Val Ile Met Thr Gln Lys Lys Lys Lys
        275                 280                 285

Pro Phe Cys Leu Gln Gly Asp Ala Lys Val Pro His Leu Pro Ala Asn
290                 295                 300

Lys Ala Gln Gly Ala Pro Gly Pro Glu Gln Gln His Leu Leu Thr Thr
305                 310                 315                 320

Ala Pro Ser Ser Ser Ser Ser Leu Glu Ser Ser Thr Ser Ser Thr
                325                 330                 335

Asp Lys Arg Ala Pro Thr Arg Ser Gln Leu Gln Ser Pro Gly Val Glu
            340                 345                 350

Lys Ala Ser Thr Ser Gly Glu Ala Gln Thr Gly Cys Ser Ser Ser Glu
        355                 360                 365

Ala Ser Ser Gly Gly His Gly Thr Gln Val Asn Val Thr Cys Ile Val
370                 375                 380

Asn Val Cys Ser Gly Pro Asp His Ser Ser Gln Cys Pro Ser Gln Ala
385                 390                 395                 400

```
Gly Ser Thr Arg Asp Thr Asp Ala Ser Thr Pro Asn Ser Pro Lys Glu
                405                 410                 415

Glu Gln Val Pro Phe Ser Lys Glu Glu Arg Pro Phe Gln Ser Gln Pro
            420                 425                 430

Gly Ala Pro Glu Thr Leu Leu Gln Gly Leu Glu Glu Lys Pro Leu Pro
            435                 440                 445

Leu Gly Val Pro Asp Ala Gly Met Lys Pro Ser
    450                 455

<210> SEQ ID NO 398
<211> LENGTH: 458
<212> TYPE: PRT
<213> ORGANISM: Bison bison

<400> SEQUENCE: 398

Met Ala Pro Thr Ala Phe Trp Ala Ala Leu Ala Val Gly Leu Gln Phe
1               5                   10                  15

Trp Ala Ala Gly Arg Ala Val Pro Ala Gln Ala Val Phe Thr Pro Tyr
                20                  25                  30

Ile Pro Glu Pro Gly Ser Ser Cys Arg Gln Gln Glu Tyr Tyr Asn His
            35                  40                  45

Lys Ile Gln Met Cys Cys Ser Lys Cys Pro Pro Gly Tyr Arg Val Gln
    50                  55                  60

Ser Leu Cys Asn Thr Thr Leu Asp Thr Ile Cys Ala Ser Cys Glu Ser
65                  70                  75                  80

Ser Thr Tyr Thr Gln Leu Trp Asn Leu Val Thr Ala Cys Phe Ser Cys
                85                  90                  95

Asn Ser Arg Cys Ser Ser Asp Gln Val Glu Thr Gln Ala Cys Thr Thr
            100                 105                 110

Lys Gln Asn Arg Ile Cys Thr Cys Lys Pro Gly Trp Tyr Cys Thr Leu
        115                 120                 125

Gly Arg Gln Glu Gly Cys Arg Leu Cys Val Ala Leu Arg Lys Cys Gly
    130                 135                 140

Pro Gly Phe Gly Val Ala Lys Pro Gly Thr Ala Thr Thr Asn Val Ile
145                 150                 155                 160

Cys Ala Pro Cys Gly Pro Gly Thr Phe Ser Asp Thr Thr Ser Tyr Thr
                165                 170                 175

Asp Thr Cys Lys Pro His Arg Asn Cys Ser Ser Val Ala Ile Pro Gly
            180                 185                 190

Thr Ala Ser Thr Asp Ala Val Cys Thr Ser Val Leu Pro Thr Arg Lys
        195                 200                 205

Val Ala Arg Gly Pro Ala Thr Thr Arg Ser Gln His Met Glu Pro Thr
    210                 215                 220

Leu Gly Pro Ser Thr Ala Pro Ser Thr Phe Phe Leu Leu Pro Lys Val
225                 230                 235                 240

Pro Ser Pro Pro Ser Ser Pro Val Glu Gln Pro Asn Ala Gly Asn Ile
                245                 250                 255

Ser Leu Pro Ile Glu Leu Ile Val Gly Val Thr Ala Leu Gly Leu Leu
            260                 265                 270

Leu Ile Val Val Val Asn Cys Val Ile Met Thr Gln Lys Lys Lys Lys
        275                 280                 285

Pro Phe Cys Leu Gln Gly Asp Ala Lys Val Pro His Leu Pro Ala Asn
    290                 295                 300

Lys Ala Gln Gly Ala Pro Gly Pro Glu Gln Gln His Leu Leu Thr Thr
305                 310                 315                 320
```

```
Ala Pro Ser Ser Ser Ser Ser Leu Glu Ser Ser Thr Ser Ser Thr
            325                 330                 335

Asp Lys Arg Ala Pro Thr Arg Ser Gln Leu Gln Ser Pro Gly Val Glu
            340                 345                 350

Ala Asn Thr Ser Gly Glu Ala Gln Thr Gly Cys Ser Ser Ser Glu Ala
            355                 360                 365

Ser Ser Gly Gly His Gly Thr Gln Val Asn Val Thr Cys Ile Val Asn
            370                 375                 380

Val Cys Ser Gly Pro Asp His Ser Ser Gln Cys Pro Ser Gln Ala Gly
385                 390                 395                 400

Ser Thr Arg Asp Thr Asp Ala Ser Thr Pro Asn Ser Pro Lys Glu Glu
            405                 410                 415

Gln Val Pro Phe Ser Lys Glu Arg Pro Phe Gln Ser Gln Pro Gly
            420                 425                 430

Ala Pro Glu Thr Leu Leu Gln Gly Leu Glu Glu Lys Pro Leu Pro Leu
            435                 440                 445

Gly Val Pro Asp Ala Gly Met Lys Pro Ser
        450                 455

<210> SEQ ID NO 399
<211> LENGTH: 461
<212> TYPE: PRT
<213> ORGANISM: Sus scrofa

<400> SEQUENCE: 399

Met Ala Pro Ala Ala Val Trp Ala Ala Leu Thr Val Gly Leu Gln Leu
1               5                   10                  15

Trp Ala Ala Gly Arg Ala Val Pro Ser Gln Ala Val Phe Met Pro Tyr
            20                  25                  30

Ala Pro Glu Leu Gly Ser Ser Cys Arg Leu Pro Leu Lys Glu Tyr Tyr
            35                  40                  45

Asp Thr Lys Ala Gln Met Cys Cys Ser Lys Cys Pro Pro Gly Phe Arg
        50                  55                  60

Ile Gln Thr Ser Cys Asn Arg Thr Ser Asp Thr Val Cys Gly Ser Cys
65                  70                  75                  80

Glu Ser Ser Thr Tyr Thr Gln Leu Trp Asn Ser Val Ser Ala Cys Phe
                85                  90                  95

Ser Cys Asn Ser Arg Cys Ser Ser Asp Gln Val Glu Thr Gln Ala Cys
                100                 105                 110

Thr Pro Lys Gln Asn Arg Ile Cys Ser Cys Lys Pro Gly Trp Tyr Cys
            115                 120                 125

Thr Leu Gly Arg Gln Glu Gly Cys Arg Leu Cys Met Ala Leu Arg Lys
        130                 135                 140

Cys Ser Pro Gly Phe Gly Val Thr Lys Pro Gly Thr Ala Thr Ser Asp
145                 150                 155                 160

Val Val Cys Ala Pro Cys Ala Pro Gly Thr Phe Ser Ser Thr Leu Ser
                165                 170                 175

Ser Thr Asp Thr Cys Arg Pro His Arg Ile Cys Ser Ser Val Ala Ile
            180                 185                 190

Pro Gly Thr Ala Arg Met Asp Ala Val Cys Thr Ser Glu Ser Pro Thr
        195                 200                 205

Leu Asn Val Ala Gln Gly Pro Ala Pro Thr Arg Ser Gln Arg Met Glu
    210                 215                 220

Pro Thr Pro Gly Pro Ser Val Ala Pro Ser Thr Ala Pro Leu Pro Pro
```

```
           225                 230                 235                 240
       Met Thr Pro Ser Pro Pro Ser Pro Val Glu Gly Leu Asn Thr Gly
                       245                 250                 255

Asn Ile Ser Leu Pro Ile Gly Leu Ile Val Gly Val Thr Ala Met Gly
                       260                 265                 270

Leu Leu Ile Ile Val Leu Val Asn Cys Val Ile Met Thr Gln Lys Lys
                       275                 280                 285

Lys Lys Pro Phe Cys Leu Gln Gly Asp Ala Lys Val Pro His Leu Pro
                       290                 295                 300

Ala Lys Lys Ala Arg Ser Val Pro Gly Pro Glu Gln Gln His Leu Leu
       305                 310                 315                 320

Thr Thr Ala Pro Ser Ser Ser Ser Ser Leu Glu Ser Ser Ala Ser
                       325                 330                 335

Ala Pro Asp Arg Arg Ala Pro Thr Pro Ser Gln Leu Gln Ala Pro Gly
                       340                 345                 350

Ala Asp Lys Thr Ser Gly Ser Gly Glu Ala Arg Ala Ser Ser Ser Ser
                       355                 360                 365

Ser Glu Ser Ser Ser Gly Ser His Gly Thr Gln Val Asn Val Thr Cys
                       370                 375                 380

Ile Val Asn Val Cys Ser Ser Asp His Ser Ser Gln Cys Pro Ser
       385                 390                 395                 400

Gln Ala Ser Ser Thr Arg Asp Thr Asp Ala Ser Pro Ser Ser Ser Pro
                       405                 410                 415

Lys Asp Glu Gln Val Pro Phe Ser Lys Glu Glu Arg Pro Phe Gln Pro
                       420                 425                 430

Gln Pro Gly Ala Pro Glu Thr Leu Leu Gln Ser Pro Glu Glu Lys Pro
                       435                 440                 445

Leu Pro Leu Gly Val Pro Asp Ala Gly Met Lys Pro Ser
                       450                 455                 460

<210> SEQ ID NO 400
<211> LENGTH: 474
<212> TYPE: PRT
<213> ORGANISM: Mus musculus

<400> SEQUENCE: 400

Met Ala Pro Ala Ala Leu Trp Val Ala Leu Val Phe Glu Leu Gln Leu
       1               5                   10                  15

Trp Ala Thr Gly His Thr Val Pro Ala Gln Val Val Leu Thr Pro Tyr
                       20                  25                  30

Lys Pro Glu Pro Gly Tyr Glu Cys Gln Ile Ser Gln Glu Tyr Tyr Asp
                       35                  40                  45

Arg Lys Ala Gln Met Cys Cys Ala Lys Cys Pro Pro Gly Gln Tyr Val
       50                  55                  60

Lys His Phe Cys Asn Lys Thr Ser Asp Thr Val Cys Ala Asp Cys Glu
       65                  70                  75                  80

Ala Ser Met Tyr Thr Gln Val Trp Asn Gln Phe Arg Thr Cys Leu Ser
                       85                  90                  95

Cys Ser Ser Ser Cys Thr Thr Asp Gln Val Glu Ile Arg Ala Cys Thr
                       100                 105                 110

Lys Gln Gln Asn Arg Val Cys Ala Cys Glu Ala Gly Arg Tyr Cys Ala
                       115                 120                 125

Leu Lys Thr His Ser Gly Ser Cys Arg Gln Cys Met Arg Leu Ser Lys
                       130                 135                 140
```

```
Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
            165                 170                 175

Ser Thr Asp Val Cys Arg Pro His Arg Ile Cys Ser Ile Leu Ala Ile
        180                 185                 190

Pro Gly Asn Ala Ser Thr Asp Ala Val Cys Ala Pro Glu Ser Pro Thr
    195                 200                 205

Leu Ser Ala Ile Pro Arg Thr Leu Tyr Val Ser Gln Pro Glu Pro Thr
210                 215                 220

Arg Ser Gln Pro Leu Asp Gln Glu Pro Gly Pro Ser Gln Thr Pro Ser
225                 230                 235                 240

Ile Leu Thr Ser Leu Gly Ser Thr Pro Ile Ile Glu Gln Ser Thr Lys
            245                 250                 255

Gly Gly Ile Ser Leu Pro Ile Gly Leu Ile Val Gly Val Thr Ser Leu
            260                 265                 270

Gly Leu Leu Met Leu Gly Leu Val Asn Cys Ile Ile Leu Val Gln Arg
            275                 280                 285

Lys Lys Lys Pro Ser Cys Leu Gln Arg Asp Ala Lys Val Pro His Val
290                 295                 300

Pro Asp Glu Lys Ser Gln Asp Ala Val Gly Leu Glu Gln Gln His Leu
305                 310                 315                 320

Leu Thr Thr Ala Pro Ser Ser Ser Ser Ser Leu Glu Ser Ser Ala
                325                 330                 335

Ser Ala Gly Asp Arg Arg Ala Pro Pro Gly Gly His Pro Gln Ala Arg
            340                 345                 350

Val Met Ala Glu Ala Gln Gly Phe Gln Glu Ala Arg Ala Ser Ser Arg
            355                 360                 365

Ile Ser Asp Ser Ser His Gly Ser His Gly Thr His Val Asn Val Thr
            370                 375                 380

Cys Ile Val Asn Val Cys Ser Ser Asp His Ser Ser Gln Cys Ser
385                 390                 395                 400

Ser Gln Ala Ser Ala Thr Val Gly Asp Pro Asp Ala Lys Pro Ser Ala
            405                 410                 415

Ser Pro Lys Asp Glu Gln Val Pro Phe Ser Gln Glu Glu Cys Pro Ser
            420                 425                 430

Gln Ser Pro Cys Glu Thr Thr Glu Thr Leu Gln Ser His Glu Lys Pro
            435                 440                 445

Leu Pro Leu Gly Val Pro Asp Met Gly Met Lys Pro Ser Gln Ala Gly
            450                 455                 460

Trp Phe Asp Gln Ile Ala Val Lys Val Ala
465                 470

<210> SEQ ID NO 401
<211> LENGTH: 474
<212> TYPE: PRT
<213> ORGANISM: Rattus rattus

<400> SEQUENCE: 401

Met Ala Pro Ala Ala Leu Trp Val Ala Leu Val Val Glu Leu Gln Leu
1               5                   10                  15

Trp Ala Thr Gly His Thr Val Pro Ala Lys Val Val Leu Thr Pro Tyr
            20                  25                  30

Lys Pro Glu Pro Gly Asn Gln Cys Gln Ile Ser Gln Glu Tyr Tyr Asp
        35                  40                  45
```

-continued

```
Lys Lys Ala Gln Met Cys Cys Ala Lys Cys Pro Gly Gln Tyr Ala
 50              55              60
Lys His Phe Cys Asn Lys Thr Ser Asp Thr Val Cys Ala Asp Cys Ala
 65              70              75              80
Ala Gly Met Phe Thr Gln Val Trp Asn His Leu His Thr Cys Leu Ser
                 85              90              95
Cys Ser Ser Ser Cys Ser Asp Asp Gln Val Glu Thr His Asn Cys Thr
             100             105             110
Lys Lys Gln Asn Arg Val Cys Ala Cys Asn Ala Asp Ser Tyr Cys Ala
         115             120             125
Leu Lys Leu His Ser Gly Asn Cys Arg Gln Cys Met Lys Leu Ser Lys
     130             135             140
Cys Gly Pro Gly Phe Gly Val Ala Arg Ser Arg Thr Ser Asn Gly Asn
145             150             155             160
Val Ile Cys Ser Ala Cys Ala Pro Gly Thr Phe Ser Asp Thr Thr Ser
                 165             170             175
Ser Thr Asp Val Cys Arg Pro His Arg Ile Cys Ser Ile Leu Ala Ile
             180             185             190
Pro Gly Asn Ala Ser Thr Asp Ala Val Cys Ala Ser Glu Ser Pro Thr
         195             200             205
Pro Ser Ala Val Pro Arg Thr Ile Tyr Val Ser Gln Pro Glu Pro Thr
     210             215             220
Arg Ser Gln Pro Met Asp Gln Glu Pro Gly Pro Ser Gln Thr Pro His
225             230             235             240
Ile Pro Val Ser Leu Gly Ser Thr Pro Ile Ile Glu Pro Ser Ile Thr
                 245             250             255
Gly Gly Ile Ser Leu Pro Ile Gly Leu Ile Val Gly Leu Thr Thr Leu
             260             265             270
Gly Leu Leu Met Leu Gly Leu Ala Asn Cys Phe Ile Leu Val Gln Arg
         275             280             285
Lys Lys Lys Pro Ser Cys Leu Gln Arg Glu Thr Met Val Pro His Leu
     290             295             300
Pro Asp Asp Lys Ser Gln Asp Ala Ile Gly Leu Glu Gln Gln His Leu
305             310             315             320
Leu Thr Thr Ala Pro Ser Ser Ser Ser Ser Leu Glu Ser Ser Ala
                 325             330             335
Ser Ala Gly Asp Arg Arg Ala Pro Pro Gly Gly His Pro Gln Ala Arg
             340             345             350
Val Thr Ala Glu Ala Gln Gly Ser Gln Glu Ala Cys Ala Gly Ser Arg
         355             360             365
Ser Ser Asp Ser Ser His Gly Ser His Gly Thr His Val Asn Val Thr
     370             375             380
Cys Ile Val Asn Val Cys Ser Ser Ser Asp His Ser Ser Gln Cys Ser
385             390             395             400
Ser Gln Ala Ser Thr Thr Val Gly Asp Pro Asp Ala Asn Pro Ser Gly
                 405             410             415
Ser Pro Lys Asp Glu Gln Val Pro Phe Ser Gln Glu Glu Cys Pro Ser
             420             425             430
Gln Ser Gln Trp Glu Thr Thr Glu Thr Leu Gln Asn His Asp Lys Pro
         435             440             445
Phe Pro Leu Gly Val Pro Asp Val Gly Met Lys Pro Asn Gln Pro Gly
     450             455             460
```

```
Trp Tyr Asp Gln Ile Ala Val Lys Val Pro
465                 470

<210> SEQ ID NO 402
<211> LENGTH: 20
<212> TYPE: PRT
<213> ORGANISM: Bos taurus

<400> SEQUENCE: 402

Gln Lys Ile Gln Met Cys Cys Ser Lys Cys Pro Pro Gly Tyr Arg Val
1               5                   10                  15

Gln Ser Leu Cys
            20

<210> SEQ ID NO 403
<211> LENGTH: 20
<212> TYPE: PRT
<213> ORGANISM: Bison bison

<400> SEQUENCE: 403

His Lys Ile Gln Met Cys Cys Ser Lys Cys Pro Pro Gly Tyr Arg Val
1               5                   10                  15

Gln Ser Leu Cys
            20

<210> SEQ ID NO 404
<211> LENGTH: 20
<212> TYPE: PRT
<213> ORGANISM: Sus scrofa

<400> SEQUENCE: 404

Thr Lys Ala Gln Met Cys Cys Ser Lys Cys Pro Pro Gly Phe Arg Ile
1               5                   10                  15

Gln Thr Ser Cys
            20

<210> SEQ ID NO 405
<211> LENGTH: 20
<212> TYPE: PRT
<213> ORGANISM: Mus musculus

<400> SEQUENCE: 405

Arg Lys Ala Gln Met Cys Cys Ala Lys Cys Pro Pro Gly Gln Tyr Val
1               5                   10                  15

Lys His Phe Cys
            20

<210> SEQ ID NO 406
<211> LENGTH: 20
<212> TYPE: PRT
<213> ORGANISM: Rattus rattus

<400> SEQUENCE: 406

Lys Lys Ala Gln Met Cys Cys Ala Lys Cys Pro Pro Gly Gln Tyr Ala
1               5                   10                  15

Lys His Phe Cys
            20

<210> SEQ ID NO 407
<211> LENGTH: 7
<212> TYPE: PRT
<213> ORGANISM: Mus musculus
```

-continued

<400> SEQUENCE: 407

Thr Thr Asp Gln Val Glu Ile
1               5

<210> SEQ ID NO 408
<211> LENGTH: 7
<212> TYPE: PRT
<213> ORGANISM: Rattus rattus

<400> SEQUENCE: 408

Ser Asp Asp Gln Val Glu Thr
1               5

<210> SEQ ID NO 409
<211> LENGTH: 40
<212> TYPE: PRT
<213> ORGANISM: Bos taurus

<400> SEQUENCE: 409

Thr Thr Lys Gln Asn Arg Ile Cys Thr Cys Lys Pro Gly Trp Tyr Cys
1               5                   10                  15

Thr Leu Gly Arg Gln Glu Gly Cys Arg Leu Cys Val Ala Leu Arg Lys
            20                  25                  30

Cys Gly Pro Gly Phe Gly Val Ala
        35                  40

<210> SEQ ID NO 410
<211> LENGTH: 40
<212> TYPE: PRT
<213> ORGANISM: Sus scrofa

<400> SEQUENCE: 410

Thr Pro Lys Gln Asn Arg Ile Cys Ser Cys Lys Pro Gly Trp Tyr Cys
1               5                   10                  15

Thr Leu Gly Arg Gln Glu Gly Cys Arg Leu Cys Met Ala Leu Arg Lys
            20                  25                  30

Cys Ser Pro Gly Phe Gly Val Thr
        35                  40

<210> SEQ ID NO 411
<211> LENGTH: 41
<212> TYPE: PRT
<213> ORGANISM: Mus musculus

<400> SEQUENCE: 411

Thr Lys Gln Gln Asn Arg Val Cys Ala Cys Glu Ala Gly Arg Tyr Cys
1               5                   10                  15

Ala Leu Lys Thr His Ser Gly Ser Cys Arg Gln Cys Met Arg Leu Ser
            20                  25                  30

Lys Cys Gly Pro Gly Phe Gly Val Ala
        35                  40

<210> SEQ ID NO 412
<211> LENGTH: 41
<212> TYPE: PRT
<213> ORGANISM: Rattus rattus

<400> SEQUENCE: 412

Thr Lys Lys Gln Asn Arg Val Cys Ala Cys Asn Ala Asp Ser Tyr Cys
1               5                   10                  15

Ala Leu Lys Leu His Ser Gly Asn Cys Arg Gln Cys Met Lys Leu Ser

```
              20                  25                  30
Lys Cys Gly Pro Gly Phe Gly Val Ala
            35                  40

<210> SEQ ID NO 413
<211> LENGTH: 5
<212> TYPE: PRT
<213> ORGANISM: Bos taurus

<400> SEQUENCE: 413

Lys Cys Gly Pro Gly
1               5
```

The invention claimed is:

1. An antibody or antigen-binding fragment thereof that specifically binds human tumor necrosis factor receptor 2 (TNFR2) comprising:
   (a) means for binding an epitope within human TNFR2 bound by antibody 8E6.D1 (ATCC® accession number PTA-127418); and
   (b) an Fc region,
   wherein the antibody or antigen-binding fragment thereof does not bind an epitope within human TNFR2 comprising amino acids 142-146 of SEQ ID NO: 366.

2. The antibody or antigen-binding fragment thereof of claim 1, wherein the antibody or antigen-binding fragment thereof specifically binds an epitope within human TNFR2 comprising amino acids 56-60 of SEQ ID NO: 366.

3. The antibody or antigen-binding fragment thereof of claim 2, wherein the antibody or antigen-binding fragment thereof specifically binds:
   (a) an epitope within amino acids 48-67 of SEQ ID NO: 366; and/or
   (b) an epitope within human TNFR2 comprising amino acids 56-60 of SEQ ID NO: 366 with a $K_D$ of less than about 10 nM.

4. The antibody or antigen-binding fragment thereof of claim 1, wherein the antibody or antigen-binding fragment thereof does not bind another tumor necrosis factor receptor (TNFR) superfamily member.

5. The antibody or antigen-binding fragment thereof of claim 1, wherein the antibody or antigen-binding fragment thereof specifically binds a polypeptide having the amino acid sequence of SEQ ID NO: 346 or 367.

6. The antibody or antigen-binding fragment thereof of claim 1, wherein the antibody or antigen-binding fragment thereof is a monoclonal antibody or antigen-binding fragment thereof.

7. The antibody or antigen-binding fragment thereof of claim 1, wherein the antibody comprises an immunoglobulin of subtype IgG.

8. The antibody or antigen-binding fragment thereof of claim 1, wherein the antibody or antigen-binding fragment thereof is antibody 8E6.D1 (ATCC® accession number PTA-127418).

9. A pharmaceutical composition comprising the antibody or antigen-binding fragment thereof of claim 1 and a pharmaceutically acceptable carrier or excipient.

10. The pharmaceutical composition of claim 9, wherein the pharmaceutical composition further comprises a therapeutic agent.

11. The pharmaceutical composition of claim 10, wherein the therapeutic agent is TNFα or Bacillus Calmette-Guérin (BCG).

12. A kit comprising the antibody or antigen-binding fragment thereof of claim 1.

13. An antibody or antigen-binding fragment thereof that specifically binds human TNFR2, wherein the antibody or antigen-binding fragment thereof is antibody 8E6.D1 (ATCC® accession number PTA-127418), wherein the antibody or antigen-binding fragment thereof specifically binds:
   (a) an epitope within human TNFR2 comprising amino acids 56-60 of SEQ ID NO: 366; and/or
   (b) a polypeptide having the amino acid sequence of SEQ ID NO: 346 or 367;
   and wherein the antibody or antigen-binding fragment thereof does not bind an epitope within human TNFR2 comprising amino acids 142-146 of SEQ ID NO: 366.

* * * * *